(12) United States Patent
Spear et al.

(10) Patent No.: US 11,534,566 B2
(45) Date of Patent: Dec. 27, 2022

(54) NASAL SEAL AND RESPIRATORY INTERFACE

(71) Applicant: Fisher & Paykel Healthcare Limited, Auckland (NZ)

(72) Inventors: Tony William Spear, Auckland (NZ); Melissa Catherine Bornholdt, Auckland (NZ); Jake Baker Hocking, Auckland (NZ); Jonathan Tong Lok Sng, Auckland (NZ); Jeremy Owen Young, Auckland (NZ); Arvin San Jose Gardiola, Auckland (NZ); Stephen Francis Heffernan, Auckland (NZ); Christine Marie Lynch, Auckland (NZ); Wen Dong Huang, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 194 days.

(21) Appl. No.: 16/307,842

(22) PCT Filed: Jun. 13, 2017

(86) PCT No.: PCT/IB2017/053480
§ 371 (c)(1),
(2) Date: Dec. 6, 2018

(87) PCT Pub. No.: WO2017/216708
PCT Pub. Date: Dec. 21, 2017

(65) Prior Publication Data

US 2019/0217036 A1   Jul. 18, 2019

Related U.S. Application Data

(60) Provisional application No. 62/349,293, filed on Jun. 13, 2016.

(51) Int. Cl.
*A61M 16/06* (2006.01)

(52) U.S. Cl.
CPC ........ *A61M 16/0616* (2014.02); *A61M 16/06* (2013.01); *A61M 16/0633* (2014.02);
(Continued)

(58) Field of Classification Search
CPC .......... A61M 16/0616; A61M 16/0605; A61M 16/0611; A61M 16/0622; A61M 16/0633;
(Continued)

(56) References Cited

U.S. PATENT DOCUMENTS

| 2,353,643 | A |   | 7/1944 | Bulbulian |
| 2,415,846 | A | * | 2/1947 | Randall ................ A62B 18/025 128/206.24 |

(Continued)

FOREIGN PATENT DOCUMENTS

| AU | 2012331716 A1 | 5/2013 |
| AU | 2013206439 A1 | 7/2013 |

(Continued)

OTHER PUBLICATIONS

European Patent Office, Extended European Search Report, Application No. PCT/IB2017053480, dated Jan. 3, 2020, in 6 pages.
(Continued)

*Primary Examiner* — Bradley H Philips
*Assistant Examiner* — Savannah L Gabriel
(74) *Attorney, Agent, or Firm* — Knobbe Martens Olson & Bear LLP

(57) ABSTRACT

A nasal mask having a seal housing and a flexible nasal seal connected or connectable to the seal housing to define a mask cavity. The nasal seal extends between a face-contacting side and an outer side. The nasal seal has a contacting surface having an edge that defines a nose-receiving opening into the mask cavity and which is configured to seal about
(Continued)

the user's nose. The nasal seal also has an under-nose support fixedly connected into the seal and which is configured to extend within the mask cavity and having a contact surface that is oriented to contact at least a portion of the under-nose surface of the user.

27 Claims, 110 Drawing Sheets

(52) U.S. Cl.
CPC ............... *A61M 16/0683* (2013.01); *A61M 2202/0225* (2013.01); *A61M 2205/42* (2013.01); *A61M 2210/0618* (2013.01)

(58) Field of Classification Search
CPC .......... A61M 16/0638; A61M 16/0644; A61M 16/065; A61M 16/0655; A61M 16/0683; A61M 2016/0661; A61M 2202/0225; A61M 2202/0085; A61M 2205/42; A61M 2210/0618
See application file for complete search history.

(56) References Cited

U.S. PATENT DOCUMENTS

| | | | | |
|---|---|---|---|---|
| 5,018,519 | A * | 5/1991 | Brown .................. | A61M 16/06 128/203.29 |
| 2006/0124131 | A1 * | 6/2006 | Chandran ............. | A61M 16/06 128/206.28 |
| 2007/0089749 | A1 | 4/2007 | Ho et al. | |
| 2009/0120442 | A1 * | 5/2009 | Ho ...................... | A61M 16/0611 128/206.24 |
| 2009/0126739 | A1 * | 5/2009 | Ng ...................... | A61M 16/065 128/205.25 |
| 2011/0146685 | A1 * | 6/2011 | Allan ................. | A61M 16/0605 128/205.25 |
| 2013/0008447 | A1 * | 1/2013 | Gunaratnam ..... | A61M 16/0644 128/205.25 |
| 2014/0158136 | A1 * | 6/2014 | Romagnoli ....... | A61M 16/0875 128/206.24 |
| 2014/0261432 | A1 | 9/2014 | Eves et al. | |
| 2016/0082214 | A1 * | 3/2016 | Barlow ............. | A61M 16/0622 128/206.24 |
| 2016/0287828 | A1 * | 10/2016 | Harrison ........... | A61M 16/0816 |
| 2017/0196512 | A1 * | 7/2017 | Inoue ....................... | A62B 9/04 |

FOREIGN PATENT DOCUMENTS

| | | |
|---|---|---|
| AU | 2013206439 B2 | 5/2015 |
| AU | 2015202783 A1 * | 6/2015 |
| CN | 102892450 A | 1/2013 |
| CN | 103945890 A | 7/2014 |
| CN | 105283211 A | 1/2016 |
| EP | 2737921 A2 | 6/2014 |
| EP | 3936179 | 1/2022 |
| JP | 2008-518718 | 6/2008 |
| WO | WO 2010/066004 | 6/2010 |
| WO | WO 2010/131189 | 11/2010 |
| WO | WO 2010/131189 A1 | 11/2010 |
| WO | WO-2010131189 A1 * | 11/2010 ........ A61M 16/0875 |
| WO | WO 2014/025267 | 2/2014 |
| WO | WO 2014/077708 A1 | 5/2014 |
| WO | WO 2014/175752 | 10/2014 |
| WO | WO 2015/070289 | 5/2015 |
| WO | WO 2015/151019 | 10/2015 |

OTHER PUBLICATIONS

International Search Report in PCT/IB2017/053480 dated Sep. 11, 2017 in 9 pages.
First Office Action for Chinese Application No. 201780036673.4, dated Jan. 12, 2021, with translation, in 15 pages.

* cited by examiner

NASAL SEAL AND RESPIRATORY INTERFACE

FIELD OF THE INVENTION

This disclosure generally relates to a nasal seal for a respiratory interface, and to a nasal mask interface or interface assembly including the nasal seal.

BACKGROUND TO THE INVENTION

Respiratory interfaces are used to provide respiratory gas or gases, such as air in CPAP therapy, to a user under positive pressure. A nasal interface delivers gas to the nose.

The seal of an indirect nasal interface or nasal mask contacts the upper lip, the face on either side of the nose, and the bridge of the nose, and substantially encloses the nose. Such nasal interfaces are often secured to the head of the user with headgear. Often the nasal mask assembly comprises a T-piece frame for connecting to headgear that include a pair of upper side straps and lower side straps that extend generally substantially horizontally across the side of the users head. The upper straps extend above the user's ears and connect to an upper part of the T-piece frame in the user's forehead region, and the lower straps extend under the user's ears and connect to a lower part of the T-piece frame at or toward the nasal interface, or from the nasal interface itself. While such headgear tends to provide a relative stable securement of the nasal interface to the user, it can be obstructive or uncomfortable in use. Single side strap headgears are known that are less bulky, but also tend to be less stable in securing the nasal interface in a sealing engagement during use.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

It is an object of at least some embodiments of the invention to provide a nasal seal and/or nasal mask interface including the nasal seal and/or respiratory interface assembly which is improved in at least one or more respects, or to at least provide the public or medical profession with a useful choice.

In one aspect, the invention broadly relates to a nasal mask interface comprising: a seal housing; a flexible nasal seal connected or connectable to the seal housing to define a mask cavity, the nasal seal extending between a face-contacting side and an outer side, and comprising: a contacting surface comprising an edge that defines a nose-receiving opening into the mask cavity and which is configured to seal about the user's nose; and an under-nose support fixedly connected into the nasal seal and which is configured to extend within the mask cavity and having a contact surface that is oriented to contact at least a portion of the under-nose surface of the user.

In an embodiment, the seal housing is rigid relative to the flexible nasal seal.

In an embodiment, the contacting surface seals about the user's nose including across a portion at or proximal to the nasal bridge region.

In an embodiment, the under-nose support at least extends laterally across the nasal seal within the mask cavity between opposing sides of the nasal seal at locations that are isolated or displaced from edge of the contacting surface of the nasal seal.

In an embodiment, the under-nose support at least extends laterally across the nasal seal within the mask cavity between opposing sides of the nasal seal at locations displaced from the contacting surface of the nasal seal.

In an embodiment, the under-nose support comprises one or more extension portions that extend from within the mask cavity and connect to the edge of the contacting surface of the nasal seal in an upper lip region of the nasal seal.

In an embodiment, the under-nose support comprises at least a main lateral portion that extends laterally across the mask cavity between opposing sides of the nasal seal.

In an embodiment, the main lateral portion of the under-nose support is integrally connected to the seal at locations that are isolated or displaced from at least the edge of the contacting surface of the nasal seal.

In an embodiment, the nasal seal comprises a sidewall that extends rearwardly from the contacting surface of the nasal seal, and wherein the main lateral portion of the under-nose support is integrally or fixedly connected to opposing sidewall portions of the nasal seal.

In an embodiment, the under-nose support further comprises one or more extension portions that extend from the main lateral portion toward and connecting to the nasal seal at an upper lip region of the nasal seal.

In an embodiment, the extension portion or portions connect to the upper lip region of the nasal seal at locations in the upper lip region of the nasal seal that are isolated or displaced from at least the edge of the contacting surface of the nasal seal.

In an embodiment, the extension portion or portions of the under-nose support are connected to the edge of the contacting surface in the upper lip region of the nasal seal.

In an embodiment, the under-nose support comprises a central extension portion having a contacting surface that is primarily configured to contact with at least a portion of the columella of the nasal septum of the under-nose surface of the nose of a user.

In an embodiment, the under-nose support comprises left and right side extension portions that extend on opposite sides of the nasal seal and which comprise contacting surfaces that are configured to primarily contact at least portions of respective left and right alar rims of the under-nose surface of the nose of a user.

In an embodiment, at any location along the under-nose support, the under-nose support is substantially thinner in the transverse direction relative to its contact surface than the corresponding width of the contact surface at that location.

In an embodiment, the flexible nasal seal is formed of silicone.

In an embodiment, the seal housing is rigid and formed from plastic.

In an embodiment, the nasal seal is removably connectable to the seal housing.

In an embodiment, the outer side of the nasal seal comprises a peripheral channel that is configured to receive a complimentary peripheral ridge of the seal housing to connect thei nasal seal to the seal housing.

In an embodiment, a peripheral edge of the outer side of the nasal seal is overmolded to a complimentary rigid clip, and wherein the rigid clip is connectable to the seal housing.

In an embodiment, the nasal seal is permanently or semi-permanently coupled to the seal housing.

In an embodiment, a peripheral edge of the outer side of the nasal seal is overmolded to a complimentary shaped opening edge of the seal housing.

In another aspect, the invention broadly relates to a nasal seal for a nasal mask or interface, the seal formed of a flexible material and extending between a face-contacting side and an outer side, comprising: a contacting surface comprising an edge that defines a nose-receiving opening and which is configured to seal about the user's nose; and an under-nose support fixedly connected into the seal and which is configured to extend rearward of the nose-receiving opening and having a contact surface that is oriented to contact at least a portion of the under-nose surface of the user.

In another aspect, the invention broadly relates to a nasal mask interface assembly comprising: a seal housing; a flexible nasal seal connected or connectable to the seal housing to define a mask cavity, the nasal seal extending between a face-contacting side and an outer side, and comprising: a contacting surface comprising an edge that defines a nose-receiving opening into the mask cavity and which is configured to seal about the user's nose; and an under-nose support fixedly connected to the nasal seal and which is configured to extend within the mask cavity and having a contact surface that is oriented to contact at least a portion of the under-nose surface of the user; and headgear comprising single left and right side straps configured to extend over the user's ears and which connect to the seal housing.

In an embodiment, the left and right side straps connect to respective attachment locations at or toward respective sides of the seal housing.

In another aspect, the invention broadly relates to a nasal mask interface assembly comprising: a seal housing; a flexible nasal seal connected or connectable to the seal housing to define a mask cavity, the nasal seal extending between a face-contacting side and an outer side, and comprising: a contacting surface comprising an edge that defines a nose-receiving opening into the mask cavity and which is configured to seal about the user's nose; and an under-nose support fixedly connected into the nasal seal and which is configured to extend within the mask cavity and having a contact surface that is oriented to contact at least a portion of the under-nose surface of the user.

In an embodiment, the seal housing is rigid relative to the flexible nasal seal.

In an embodiment, the contacting surface seals about the user's nose including across a portion at or proximal to the user's nasal bridge.

In an embodiment, the contacting surface seals about the user's nose including across a portion of the nasal bridge in an area extending between the tip of the user's nose and the center of their nasal bridge.

In an embodiment, the under-nose support at least extends laterally across the nasal seal within the mask cavity between connecting locations at opposing sides or upper lateral regions within the nasal seal.

In an embodiment, the connecting locations at the opposing sides or upper lateral regions within nasal seal are isolated or displaced from the edge of the contacting surface of the nasal seal.

In an embodiment, the connecting locations at the opposing sides or the upper lateral regions within the nasal seal are displaced from the contacting surface of the nasal seal.

In an embodiment, the under-nose support comprises one or more extension or connecting portions that extend from within the mask cavity and connect to the edge of the contacting surface of the nasal seal in an upper lip region of the nasal seal.

In an embodiment, the under-nose support comprises at least a main lateral portion with two ends that extend laterally across at least a portion of the mask cavity between connecting locations at opposing sides or upper lateral regions within the nasal seal.

In an embodiment, the under-nose support further comprises one or more extension or connecting portions that extend from the main lateral portion toward and connect to the nasal seal at an upper lip region of the nasal seal.

In an embodiment, the under-nose support further comprises a central connecting portion that extends between the main lateral portion and a portion of the edge of the contacting surface in an upper lip region of the nasal seal.

In an embodiment, the central connecting portion of the under-nose support has a contacting surface that is primarily configured to contact with at least a portion of the columella of the nasal septum of the under-nose surface of the nose of a user.

In an embodiment, the central connecting portion of the under-nose support varies in thickness across is length from a thicker region at the end connecting to the main lateral portion and a thinner region at or toward the end connecting to the edge of the contacting surface.

In an embodiment, the central connecting portion of the under-nose support comprises a central region of reduced width relative to the width at its ends.

In an embodiment, the width of the central connecting portion progressively varies along its length such that it is substantially hour-glass in shape or profile.

In an embodiment, the main lateral portion of the under-nose support is integrally connected at its ends to within the nasal seal at connecting locations that are isolated or displaced from at least the edge of the contacting surface of the nasal seal.

In an embodiment, the nasal seal comprises a sidewall that extends rearwardly from the contacting surface of the nasal seal to the outer side of the nasal seal, and wherein the main lateral portion of the under-nose support is integrally or fixedly connected at its ends to at least opposing sidewall portions within the nasal seal.

In an embodiment, the main lateral portion of the under-nose support is integrally or fixedly connected at each end directly to inner surfaces of the nasal seal.

In an embodiment, the main lateral portion of the under-nose support is integrally or fixedly connected at each end indirectly to inner surfaces of the nasal seal via a respective rib that extends from the inner surfaces of the nasal seal.

In an embodiment, each rib comprises a panel of flexible material having a first connecting edge portion that is connected to a portion of the inner surface of the nasal seal and a second connecting edge portion that is connected to a respective end of the main lateral portion of the under-nose support at another portion of its peripheral edge.

In an embodiment, the first connecting edge portion of each rib is connected to a portion of the inner surface of the nasal seal that extends between a thinner front region of the nasal seal located toward the face-contacting side and which comprises the contacting surface and a thicker rear region of the nasal seal located toward the outer side of the nasal seal.

In an embodiment, the first connecting edge portion of each rib terminates at or toward a thinned edge region of the front region of the nasal seal that is located about the periphery of the edge of the contacting surface, the edge region being thinner than the remaining portion of the front region.

In an embodiment, each rib is shaped or configured with a buckling axis or zone that allows the rib feature to buckle or bend under compression applied to the contacting surface of the nasal seal.

In an embodiment, the buckling axis of zone of each rib is formed by a recessed region or zone of the rib.

In an embodiment, each rib has a substantially vertical orientation within the nasal seal.

In an embodiment, the ribs extend from respective upper lateral regions of the inner surface of the nasal seal, one from each side of the nasal bridge region of the nasal seal.

In an embodiment, the nasal seal is formed of a material having varying thickness across regions of the nasal seal, the nasal seal defined by a front region extending toward the face contacting side of the nasal seal from an intermediate boundary and which comprises the contacting surface, and a rear region extending toward the outer side of the nasal seal from the intermediate boundary, the rear region being thicker on average than the front region.

In an embodiment, the front region comprises a thinned edge region that extends about the periphery of the edge of the contacting surface, the thinned edge region being thinner than the remaining portion of the front region.

In an embodiment, the contact surface of at least a central portion of the under-nose support is oriented at an angle relative to a seal axis that extends tangentially between outermost upper and lower contact points in a central region of the contacting surface of the nasal seal.

In an embodiment, the contact surface of the central portion of the under-nose support is oriented at an angle in the range of approximately 40° to approximately 80° relative to the seal axis.

In an embodiment, the contact surface of the central portion of the under-nose support is oriented at an angle in the range of approximately 55° to approximately 65° relative to the seal axis.

In an embodiment, the ratio of the overall height to overall depth of the seal housing and nasal seal when assembled together is in the range of approximately 1:0.8 to approximately 1:1.2.

In an embodiment, the ratio of the overall height to overall depth of the seal housing and nasal seal when assembled together is approximately 1:1.

In an embodiment, the ratio of the overall height to overall depth to overall lateral width of the seal housing and nasal seal when assembled together is in the range of approximately 1:0.8:1 to approximately 1:1.2:1.4.

In an embodiment, the ratio of the overall height to overall depth to overall lateral width of the seal housing and nasal seal when assembled together is approximately 1:1:1.2.

In an embodiment, the assembly further comprises: a yoke connected or connectable to the seal housing, headgear connected or connectable to the yoke, and an inlet opening in the seal housing for connecting to a gases supply conduit.

In an embodiment, the seal housing comprises a yoke channel extending lateral across the exterior surface of the seal housing that is configured to releasable receive and retain the yoke.

In an embodiment, the yoke is curved along its length between its ends, having a concave inner engagement surface with the yoke channel and a convex outer surface.

In an embodiment, the headgear comprises at least a pair of side straps, each one of the pair of side straps extending along the sides or cheeks of the user's face and over the user's ears, and wherein each side strap connects or extends from a respective end of the yoke.

In an embodiment, a central portion of the yoke is received in the yoke channel of the seal housing and the lateral portions of the yoke on either side of the central portion extend outwardly away from the sides of the nasal seal.

In an embodiment, the lateral portions of the yoke are thicker in height and/or width relative to the central portion of the yoke.

In an embodiment, the headgear is automatically adjusting headgear and the yoke comprises one or more directional locks that interact with core elements extending from side straps of the automatically adjusting headgear.

In an embodiment, a conduit frame that is releasably received and retained in the inlet opening of the seal housing, the conduit frame being connected or connectable to an end of the gases supply conduit.

In an embodiment, the conduit frame is a hollow body that is ovular in shape, and wherein the conduit frame is symmetrical such that is can be releasably received and retained in the inlet opening of the seal housing in either of two orientations that are 180 degrees apart.

In an embodiment, at any location along the under-nose support, the under-nose support is substantially thinner in the transverse direction relative to its contact surface than the corresponding width of the contact surface at that location.

In an embodiment, the flexible nasal seal is formed of silicone.

In an embodiment, the seal housing is rigid and formed from plastic.

In an embodiment, the nasal seal is removably connectable to the seal housing.

In an embodiment, the outer side of the nasal seal comprises a peripheral channel that is configured to receive a complimentary peripheral ridge of the seal housing to connect the nasal seal to the seal housing.

In an embodiment, a peripheral edge of the outer side of the nasal seal is overmolded to a complimentary rigid clip, and wherein the rigid clip is connectable to the seal housing.

In an embodiment, the nasal seal is permanently or semi-permanently coupled to the seal housing.

In an embodiment, a peripheral edge of the outer side of the nasal seal is secured to a complimentary shaped connecting edge of the seal housing.

In an embodiment, the peripheral edge of the outer side of the nasal seal is overmolded to a complimentary shaped opening edge of the seal housing.

In another aspect, the invention broadly relates to a nasal seal for a nasal mask or interface, the seal formed of a flexible material and extending between a face-contacting side and an outer side, comprising: a contacting surface comprising an edge that defines a nose-receiving opening and which is configured to seal about the user's nose; and an under-nose support fixedly connected within the seal and which is located rearward of the nose-receiving opening and having a contact surface that is oriented to contact at least a portion of the under-nose surface of the user.

In another aspect, the invention broadly relates to a nasal mask interface assembly comprising: a seal housing; a flexible nasal seal connected or connectable to the seal housing to define a mask cavity, the nasal seal extending between a face-contacting side and an outer side, and comprising: a contacting surface comprising an edge that defines a nose-receiving opening into the mask cavity and which is configured to seal about the user's nose; and an under-nose support fixedly connected within the nasal seal and which is configured to extend within the mask cavity and having a contact surface that is oriented to contact at least a portion of the under-nose surface of the user; and headgear comprising single left and right side straps configured to extend over the user's ears and which connect to the seal housing.

In an embodiment, the left and right side straps connect to respective attachment locations at or toward respective sides of the seal housing.

In another aspect, the invention broadly relates to a nasal seal for a nasal mask or interface, the seal formed of a flexible material and extending between a face-contacting side and an outer side, comprising: a contacting surface comprising an edge that defines a nose-receiving opening and which is configured to seal about the user's nose; and an under-nose support fixedly connected to extend within the nasal seal.

In an embodiment, the under-nose support at least extends laterally across the nasal seal within the mask cavity between connecting locations at opposing sides or upper lateral regions within the nasal seal.

In an embodiment, the under-nose support comprises one or more extension or connecting portions that extend from within the mask cavity and connect to the edge of the contacting surface of the nasal seal in an upper lip region of the nasal seal.

In an embodiment, the contact surface of at least a central portion of the under-nose support is oriented at an angle relative to a seal axis that extends tangentially between outermost upper and lower contact points in a central region of the contacting surface of the nasal seal.

In an embodiment, the contact surface of the central portion of the under-nose support is oriented at an angle in the range of approximately 40° to approximately 80° relative to the seal axis.

In an embodiment, the nasal seal is defined by the contact surface at the face-contacting side and a sidewall portion that extends rearwardly from the contact surface to the outer side of the nasal seal and which terminates in an opening or connecting edge for coupling or connected to a complimentary seal housing.

In another aspect, the invention broadly relates to a nasal mask interface assembly comprising: a seal housing comprising; a flexible nasal seal connected or connectable to the seal housing to define a mask cavity, the nasal seal extending between a face-contacting side and an outer side, and comprising: a contacting surface comprising an edge that defines a nose-receiving opening into the mask cavity and which is configured to seal about the user's nose; and an arrangement of bias vent holes in the seal housing, wherein the arrangement of bias vent holes comprises at least one upper array of bias vent holes extending laterally across an upper region of the seal housing, and at least one lateral array of bias vent holes extending down portions of the sides of the seal housing.

In an embodiment, each array of bias vent holes is a line array of spaced-part apertures or holes extending into the housing.

In another aspect, the invention broadly relates to a nasal mask interface assembly comprising: a seal housing comprising an inlet opening; a flexible nasal seal connected or connectable to the seal housing to define a mask cavity, the nasal seal extending between a face-contacting side and an outer side, and comprising: a contacting surface comprising an edge that defines a nose-receiving opening into the mask cavity and which is configured to seal about the user's nose; and a conduit frame that is releasably received and retained in the inlet opening of the seal housing, the conduit frame being connected or connectable to an end of the gases supply conduit, wherein the conduit frame is symmetrical such that is can be releasably received and retained in the inlet opening of the seal housing in either of two orientations that are 180 degrees apart.

In an embodiment, the conduit frame is a hollow body that is ovular in shape.

In another aspect, the invention broadly relates to a nasal seal for a nasal mask or interface, the seal formed of a flexible material and extending between a face-contacting side and an outer side, comprising: a contacting surface comprising an edge that defines a nose-receiving opening and which is configured to seal about the user's nose; and wherein the ratio of overall height to overall lateral width of the nasal seal is in the range of approximately 1:1 to approximately 1:1.4.

In an embodiment, the ratio of the overall height to overall lateral width of the nasal seal is approximately 1:1.2.

In an embodiment, the ratio of the overall height to overall lateral width to overall depth of the nasal seal is in the range of approximately 1:1:0.6 to approximately 1:1.4:1.

In an embodiment, the ratio of the overall height to overall lateral width to overall depth of the nasal seal is approximately 1:1.2:0.8.

Each aspect of the invention above may have any one or more features mentioned in respect of any one or more of the other aspects of the invention above.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

Number Ranges

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "and/or" means "and" or "or", or both.

As used herein "(s)" following a noun means the plural and/or singular forms of the noun.

The invention consists in the foregoing and also envisages constructions of which the following gives examples only.

BRIEF DESCRIPTION OF THE DRAWINGS

Preferred embodiments of the invention will be described by way of example only and with reference to the drawings, in which:

FIG. 121 is a front or face-contacting side view of the second form nasal mask interface of FIG. 118;

FIG. 122 is an outer side view of the seal housing of the second form nasal mask interface of FIG. 118;

FIG. 123 is a side elevation view of the seal housing of the second form nasal mask interface of FIG. 118;

FIGS. 124, 125 and 126 show a front perspective view, outer side view and top views of the yoke of the second form nasal mask interface of FIG. 118;

FIG. 127 is a cross-sectional view of the second form nasal mask interface of FIG. 118 through line BC of FIG. 120;

FIG. 128 is a close-up cross-sectional view of area BD of FIG. 127;

FIG. 129 is an outer side perspective view of a third form of the fifth embodiment nasal mask interface;

FIG. 130 is a side elevation view of the third form nasal mask interface of FIG. 129;

FIG. 131 is an outer side view of the third form nasal mask interface of FIG. 129;

FIG. 132 is a front or face-contacting side view of the third form nasal mask interface of FIG. 129;

FIG. 133 is an outer side view of the seal housing of the third form nasal mask interface of FIG. 129;

FIG. 134 is a side elevation view of the seal housing of FIG. 133;

Figure 129:
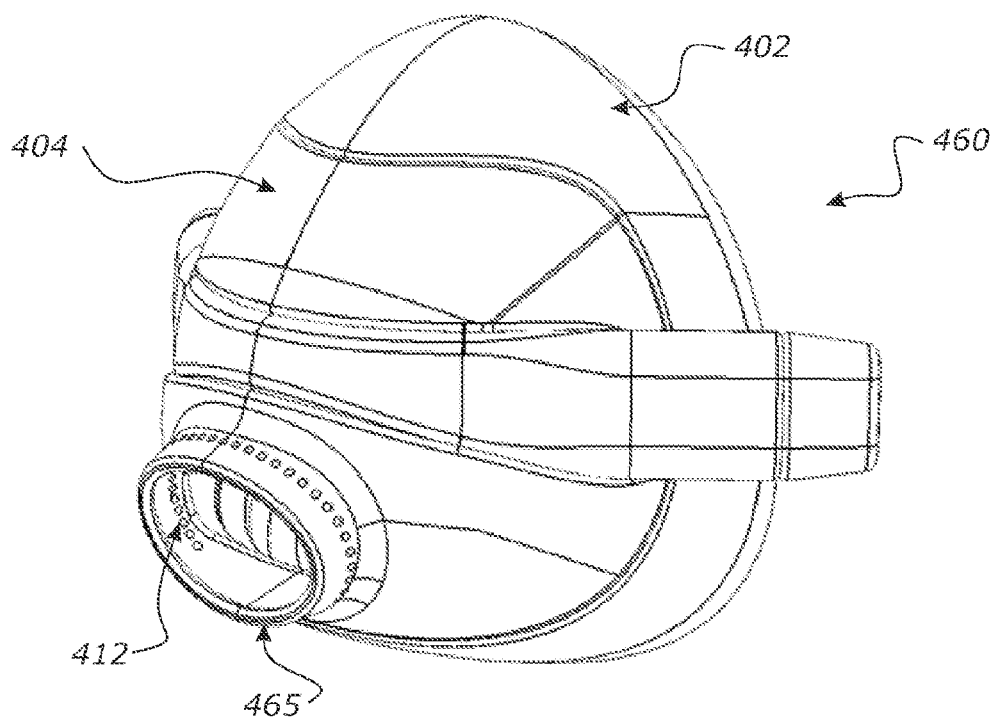
Figure 135:
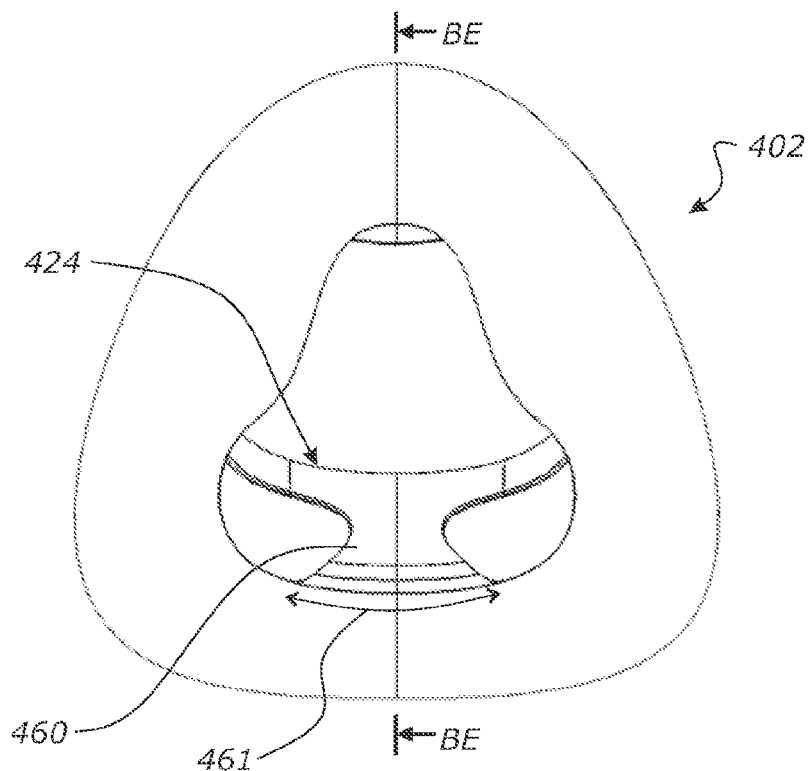
Figure 136:
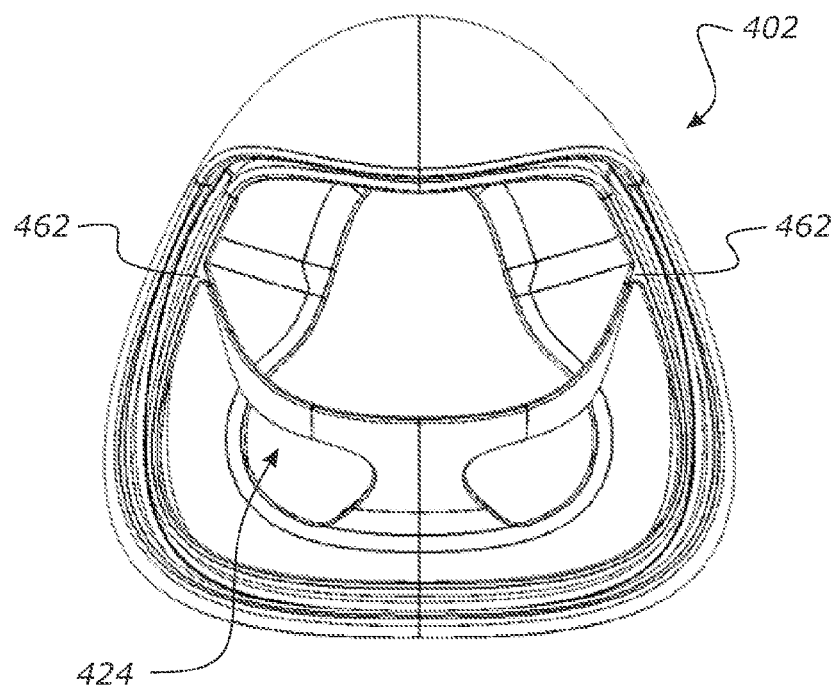
Figure 137:
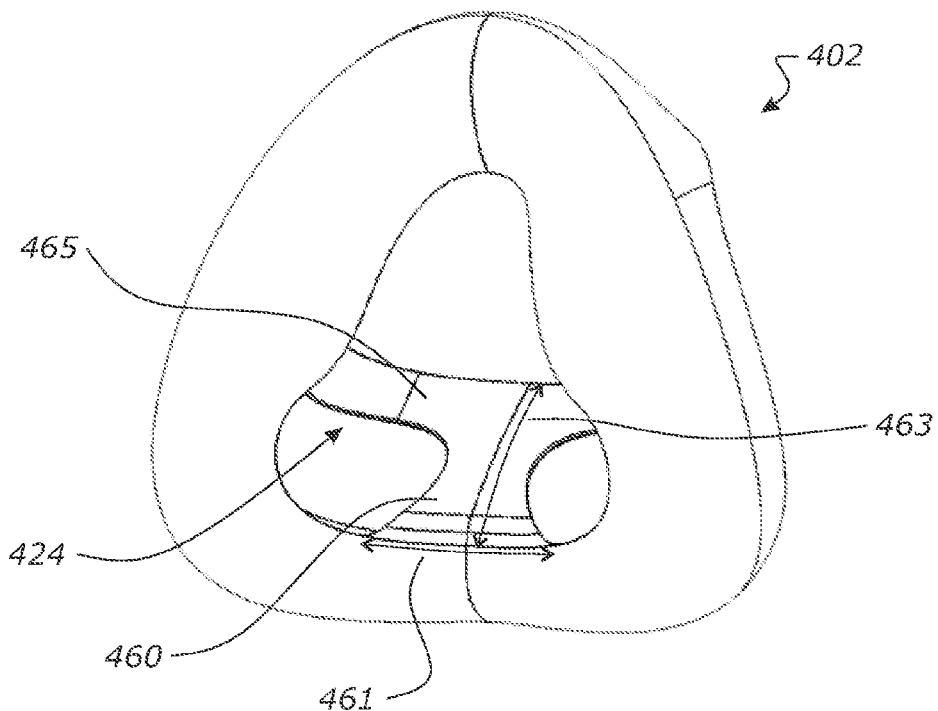
Figure 138:
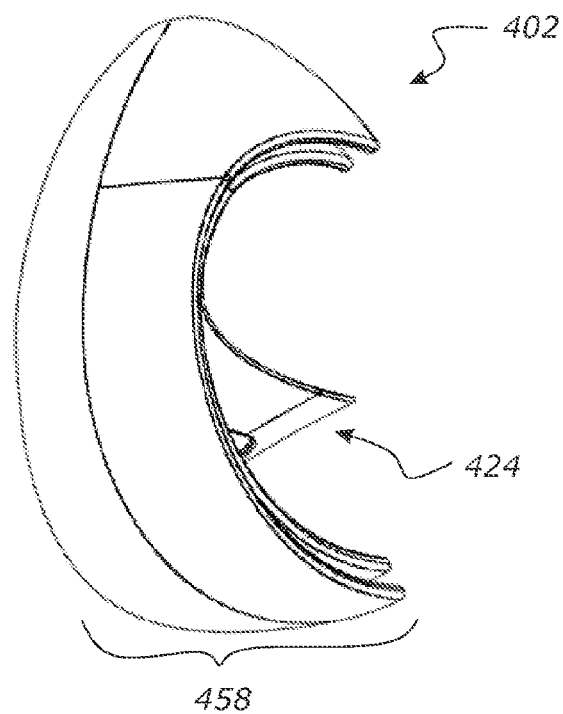
Figure 139:
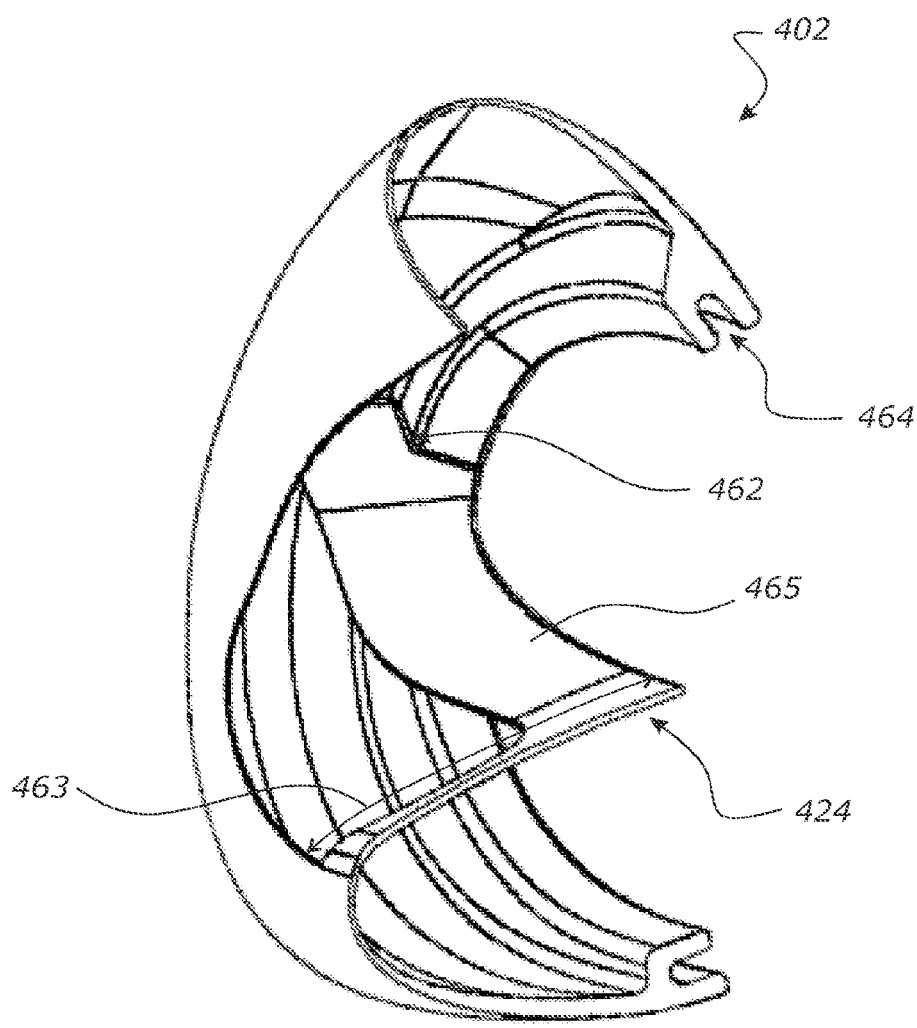
Figure 140:
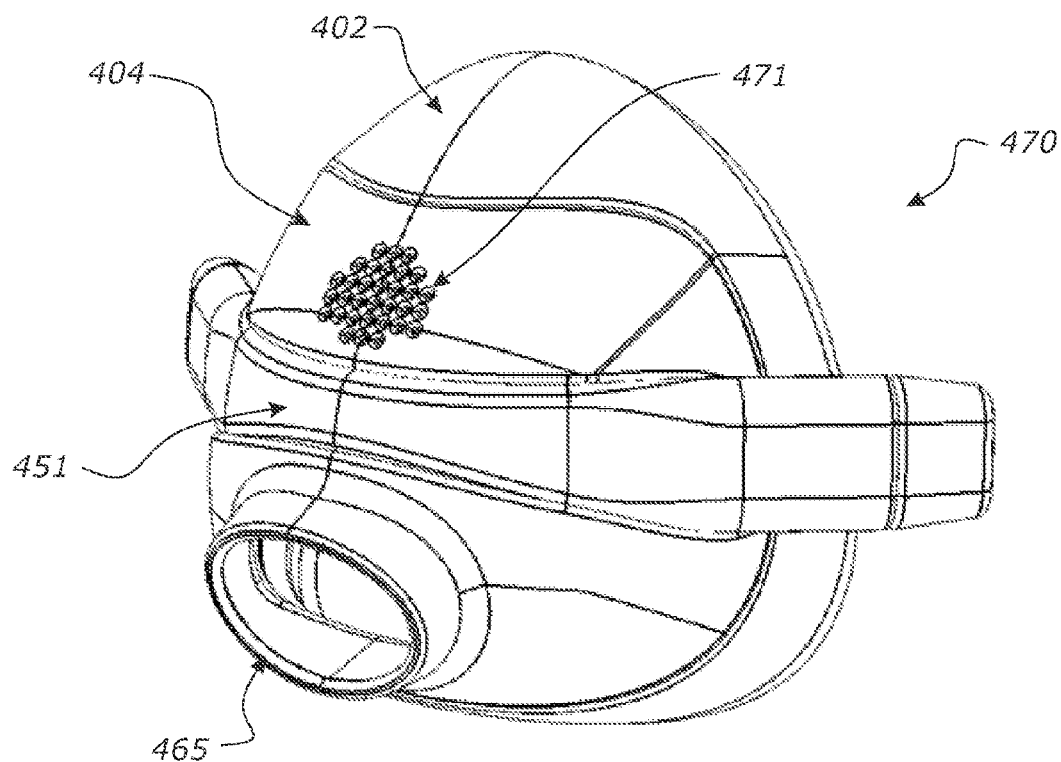
Figure 141:
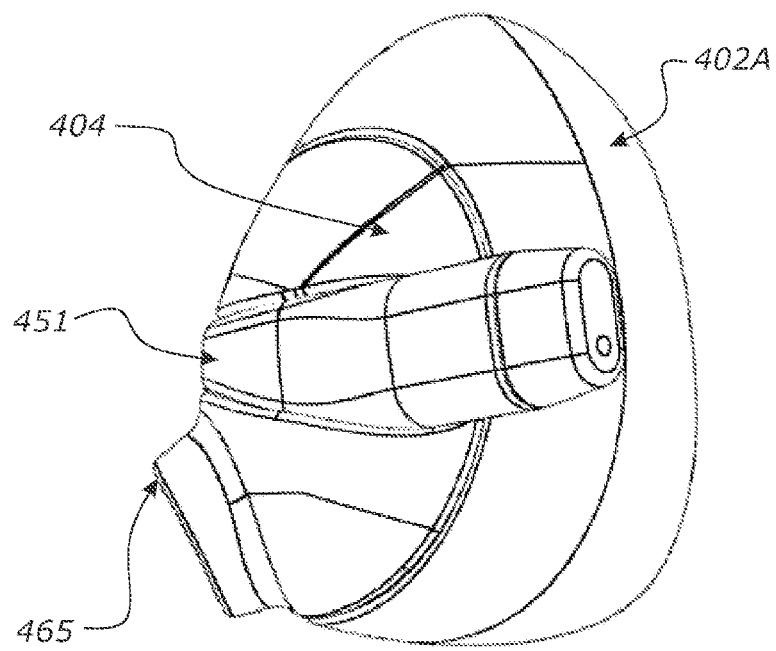
Figure 142:
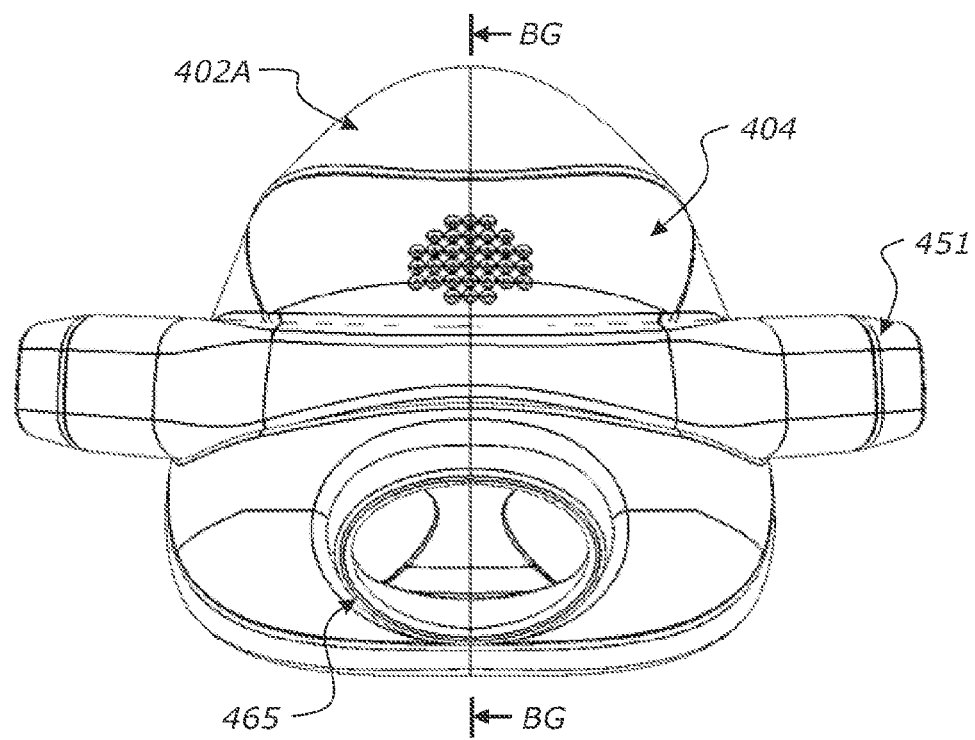
Figure 143:
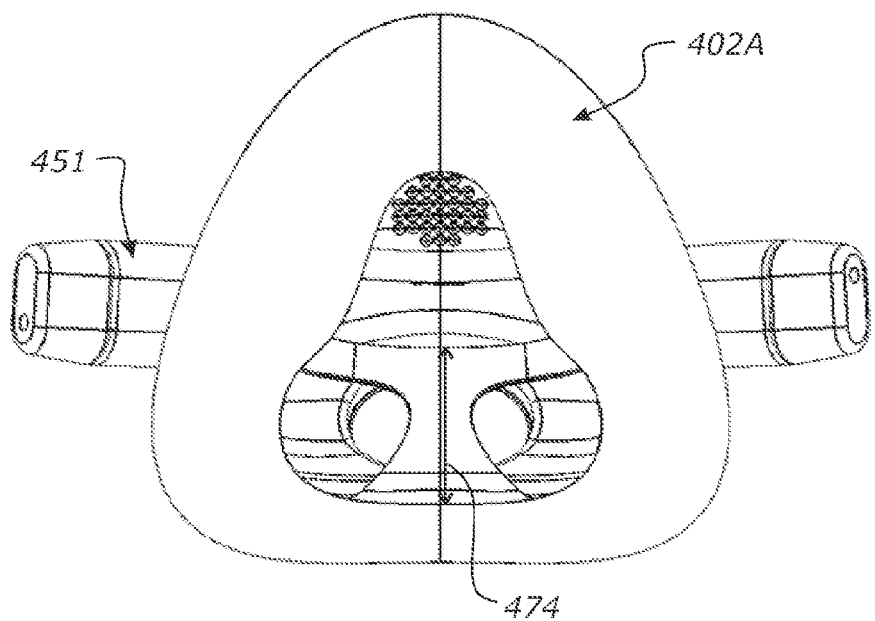
Figure 144:
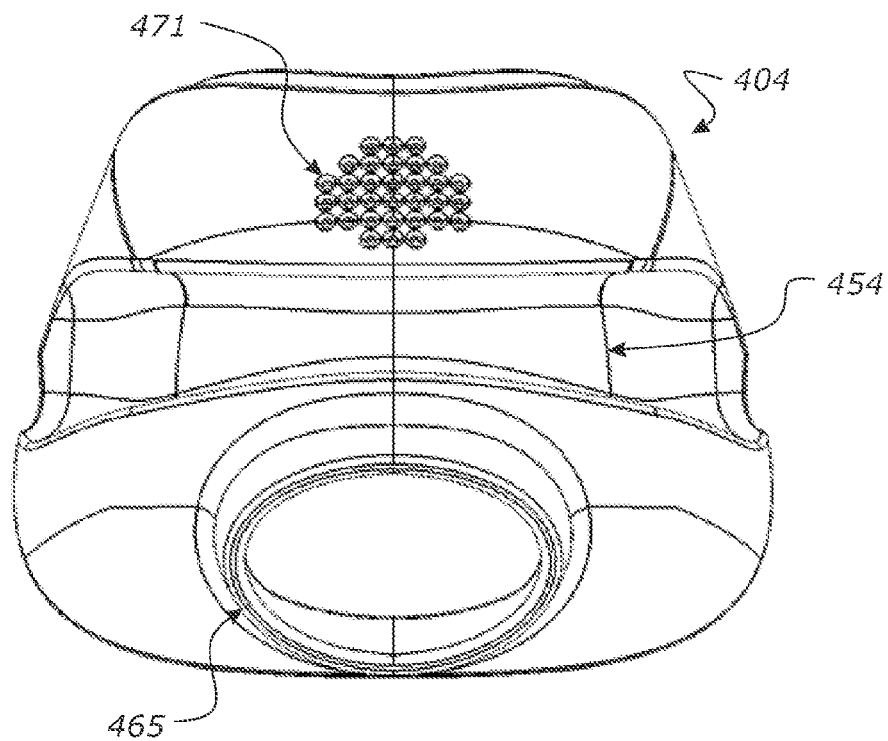
Figure 145:
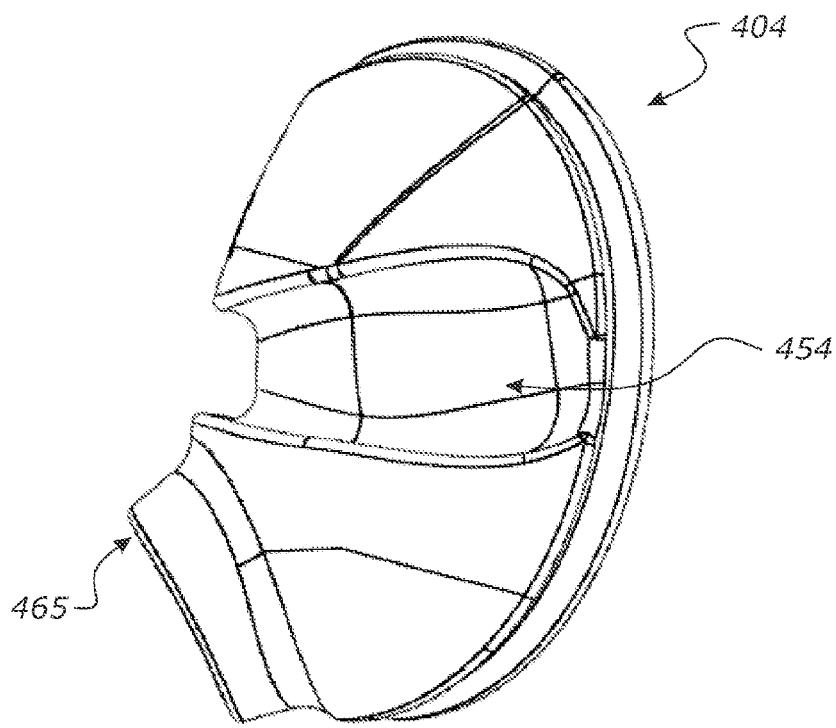
Figure 146:
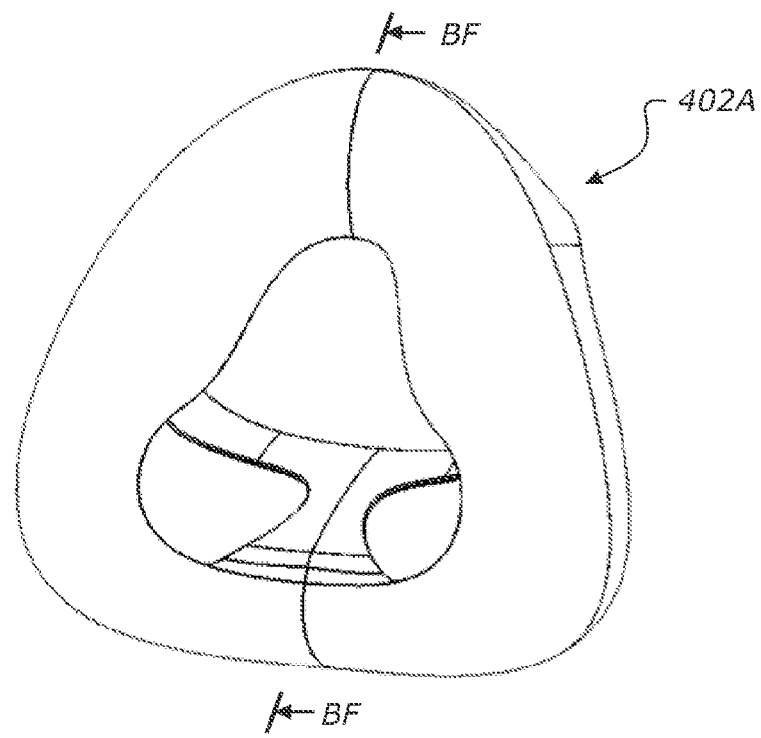
Figure 147:
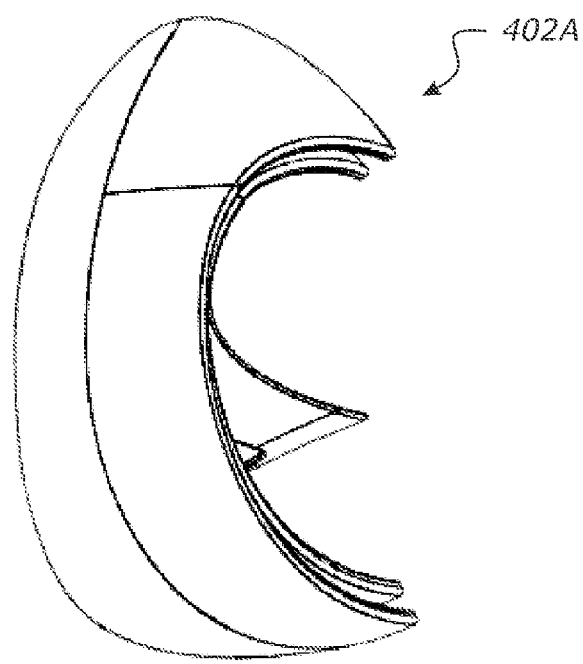
Figure 148:
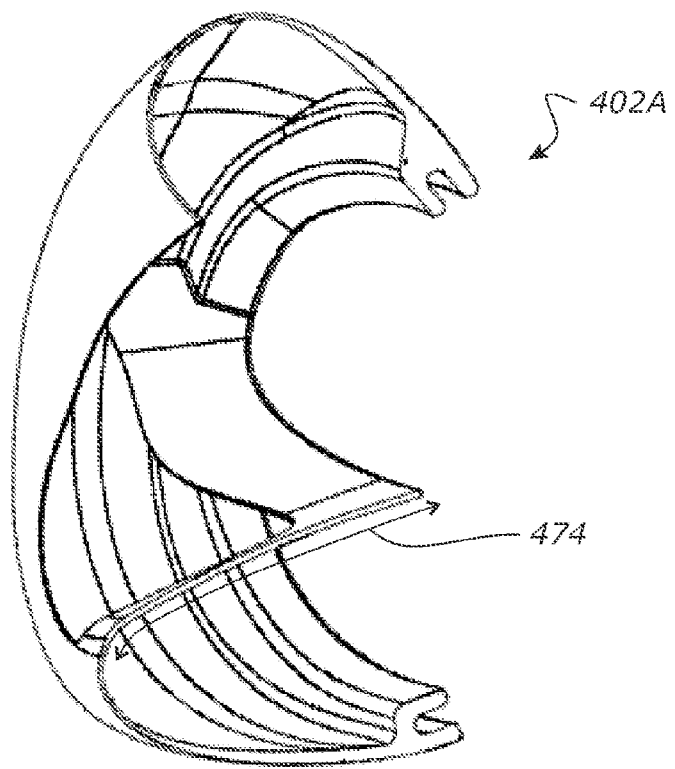
Figure 149:
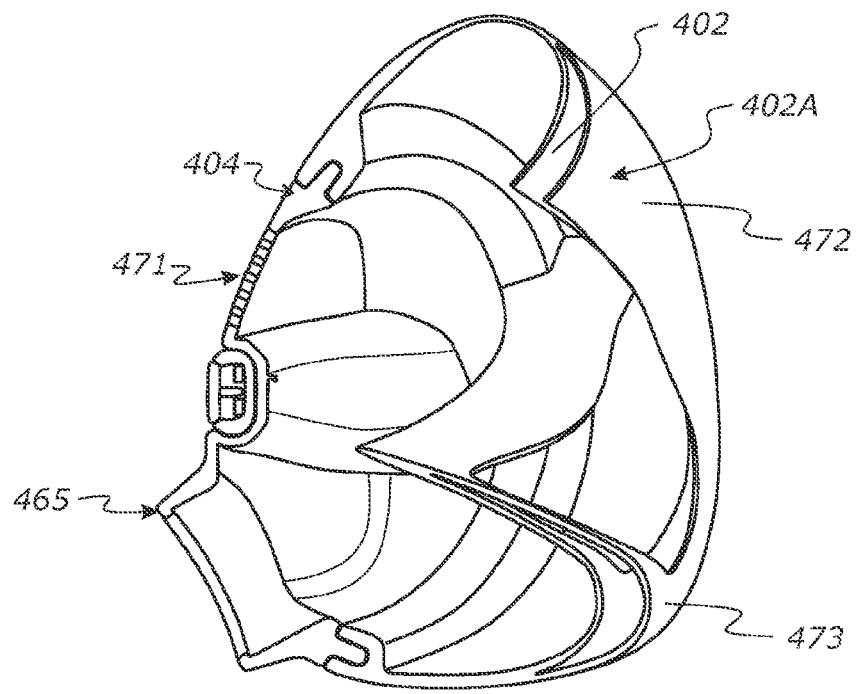
Figure 150:
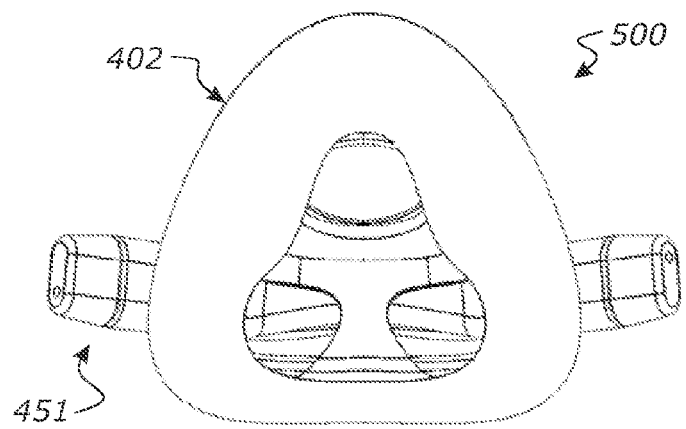
Figure 151:
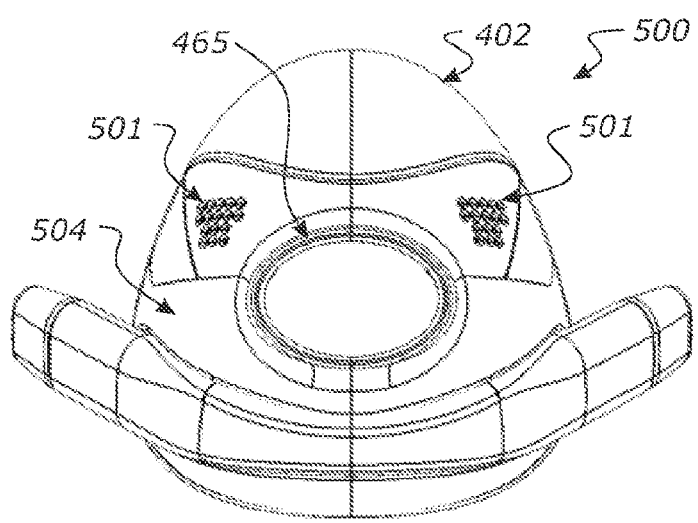
Figure 152:
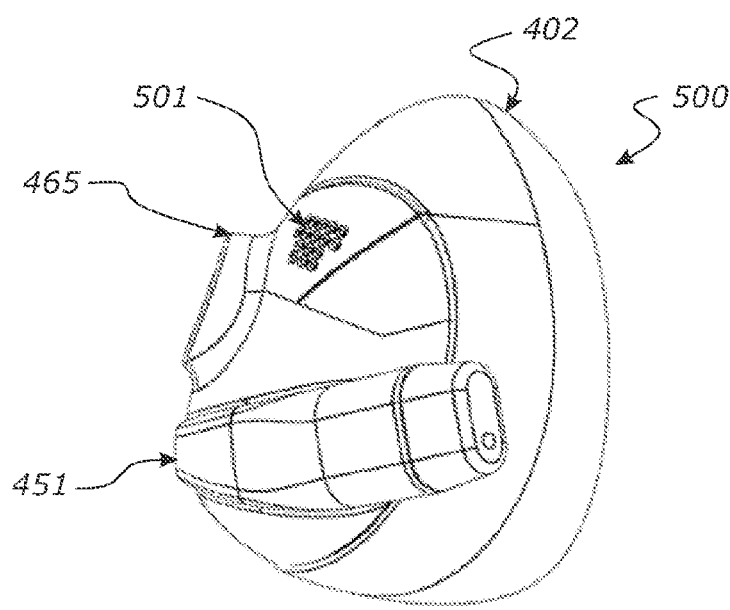
Figure 153:
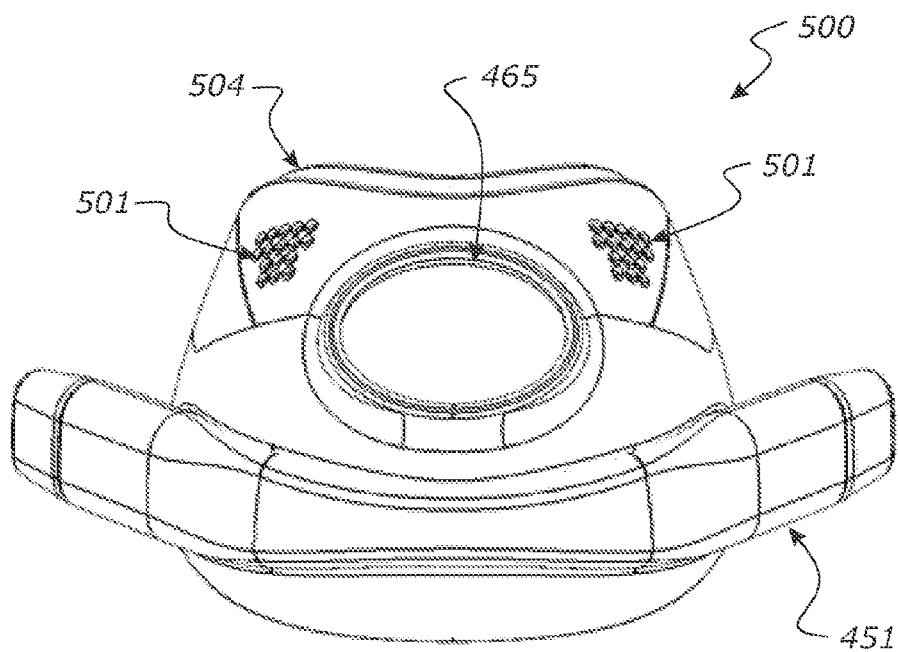
Figure 154:
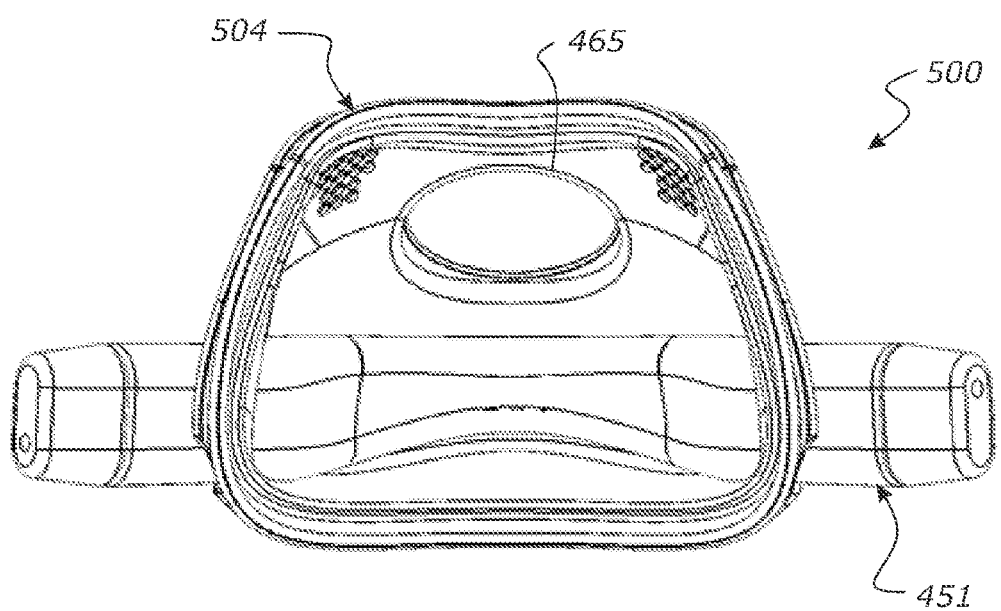
Figure 155:
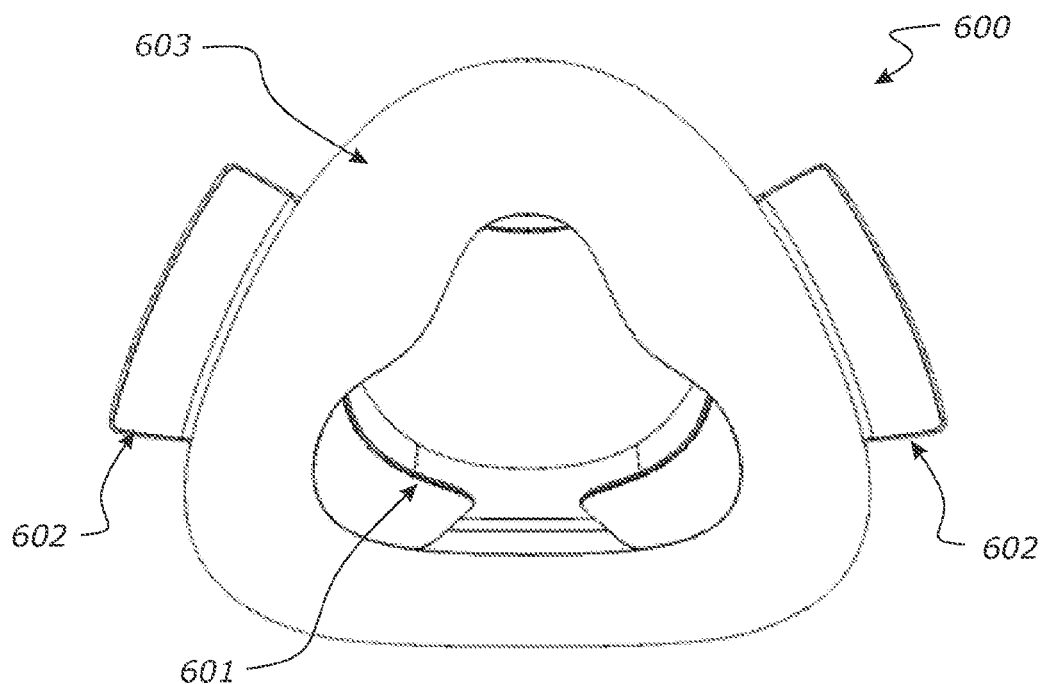
Figure 156:
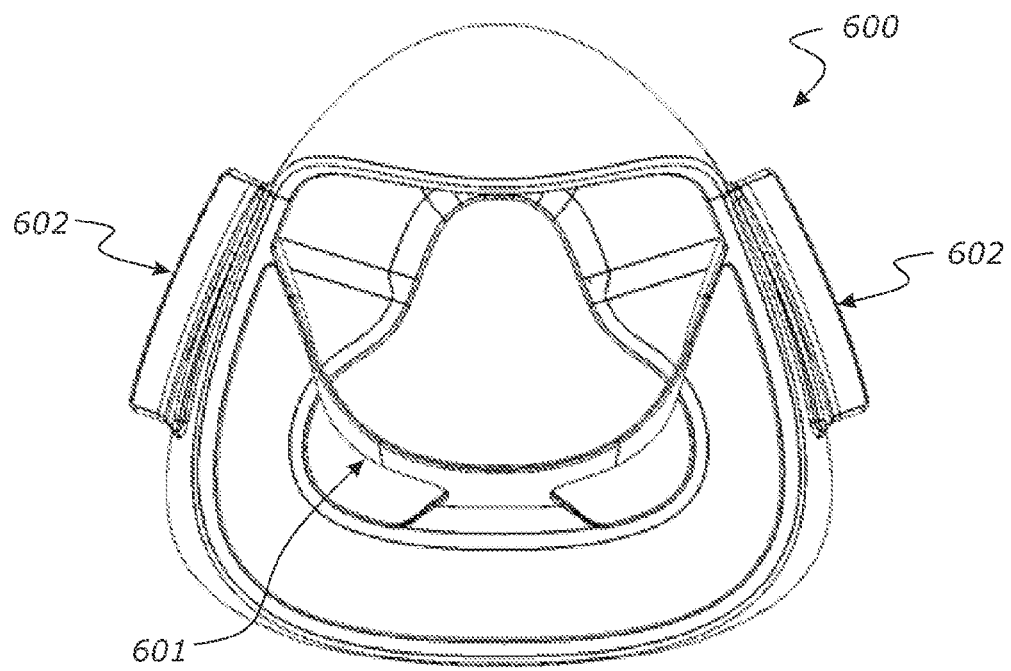
Figure 157:
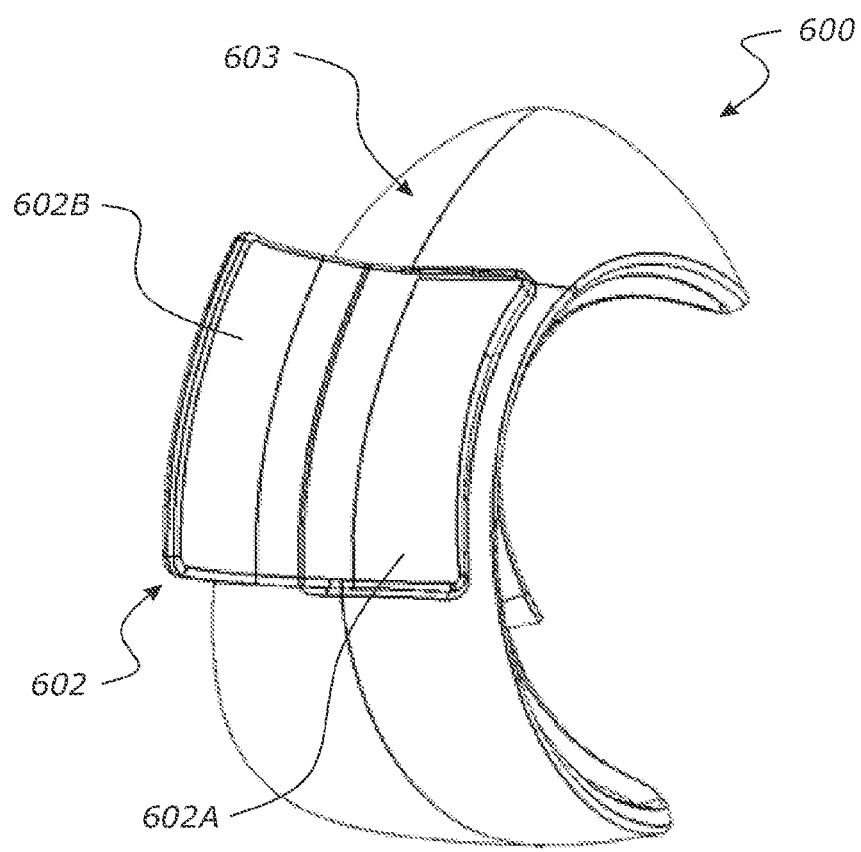
Figure 158:
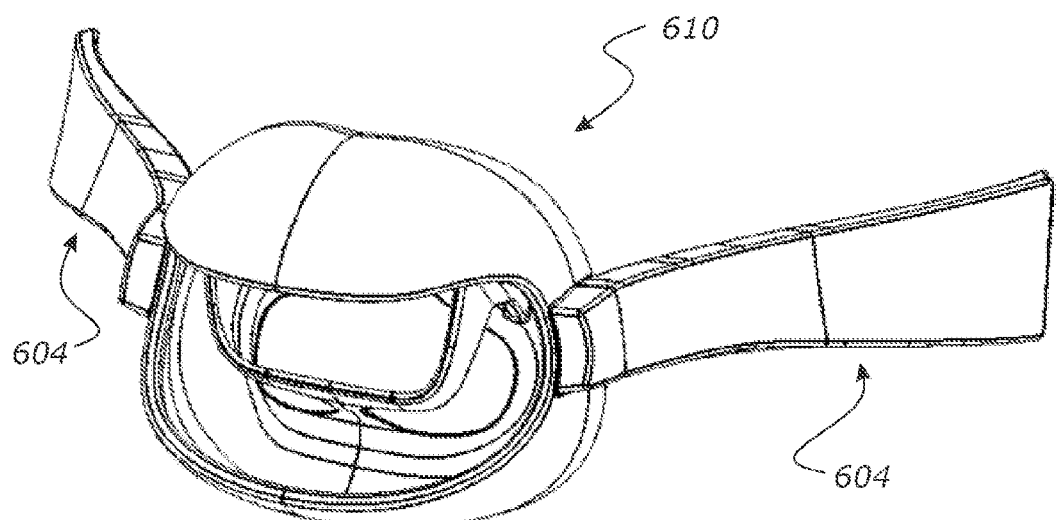
Figure 159:
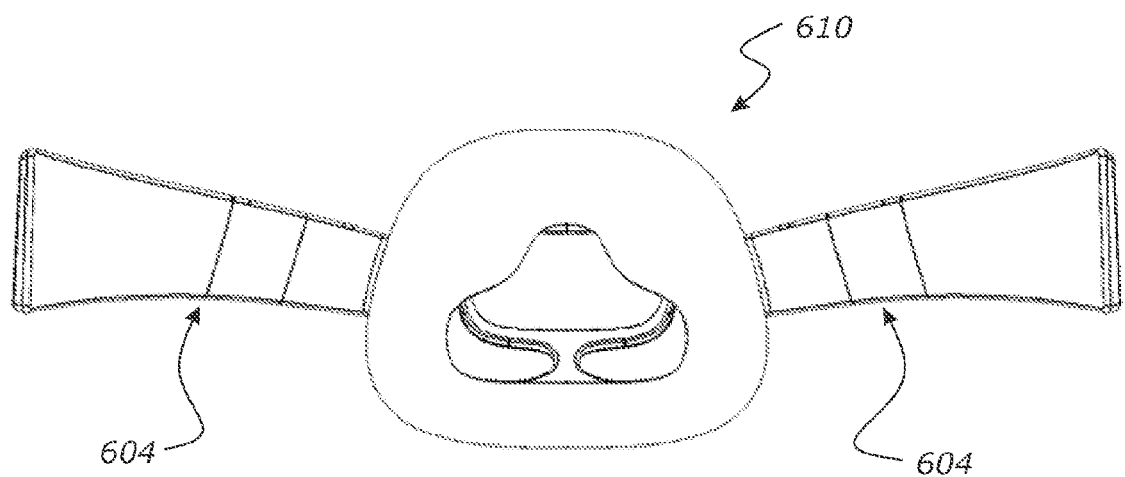
Figure 160:
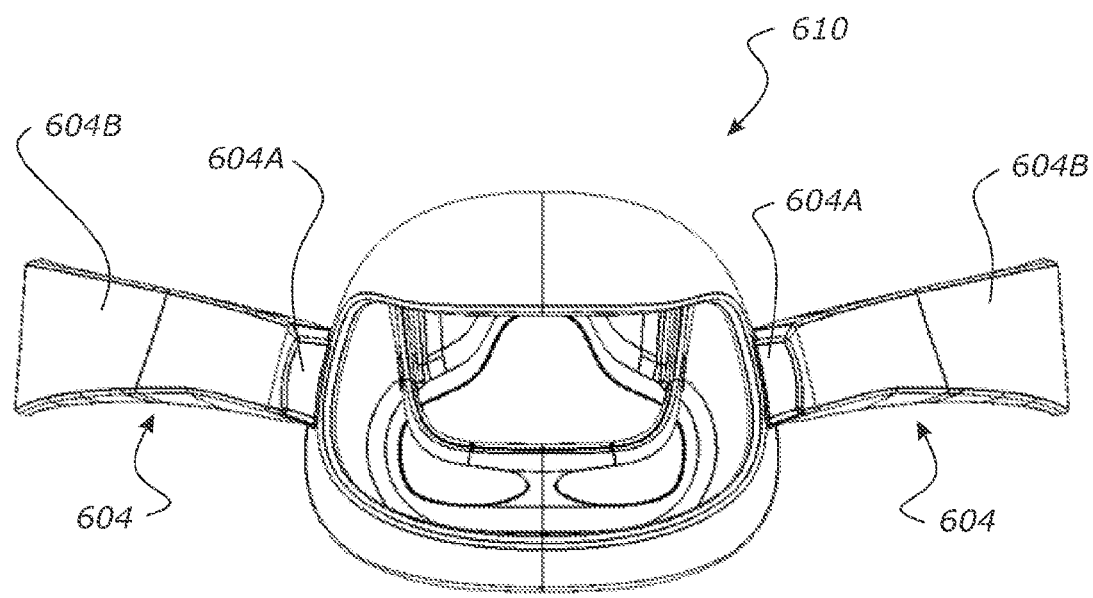
Figure 161:
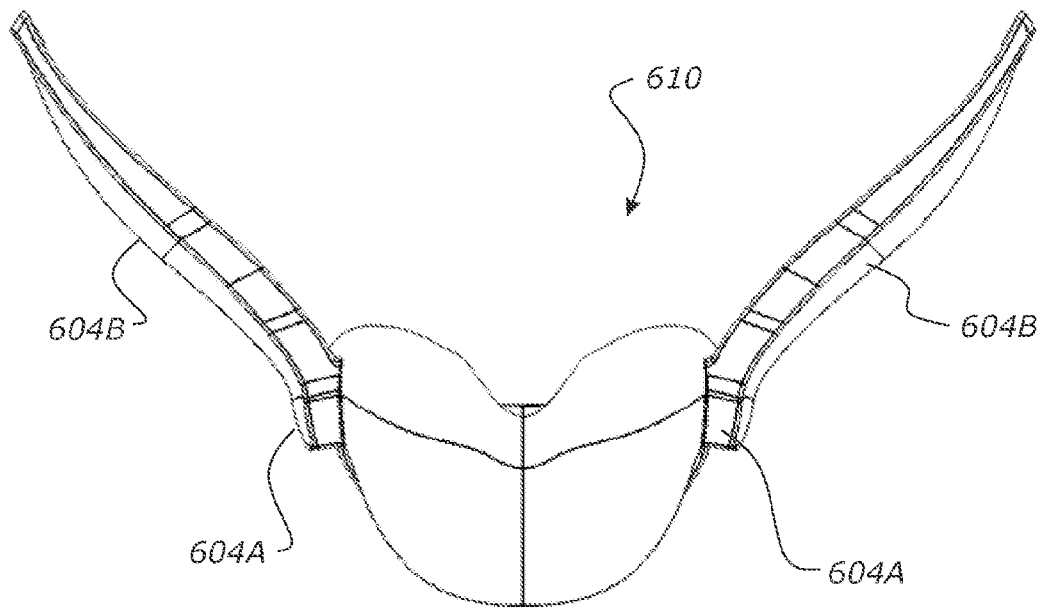
Figure 162:
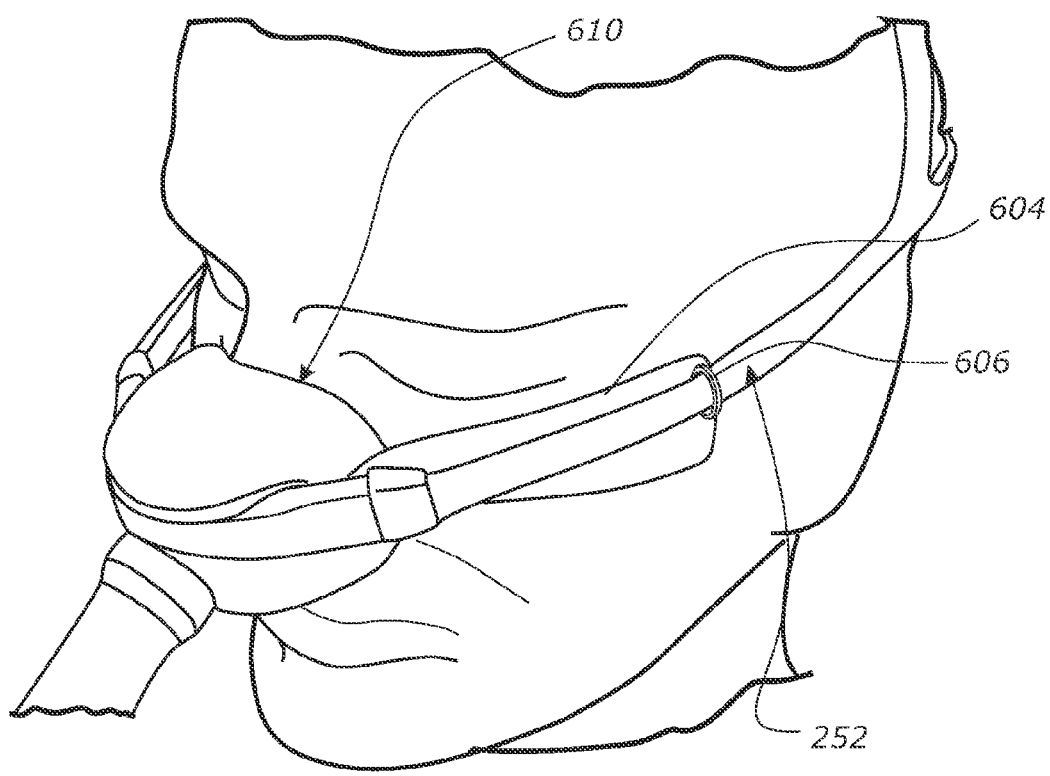
Figure 163:
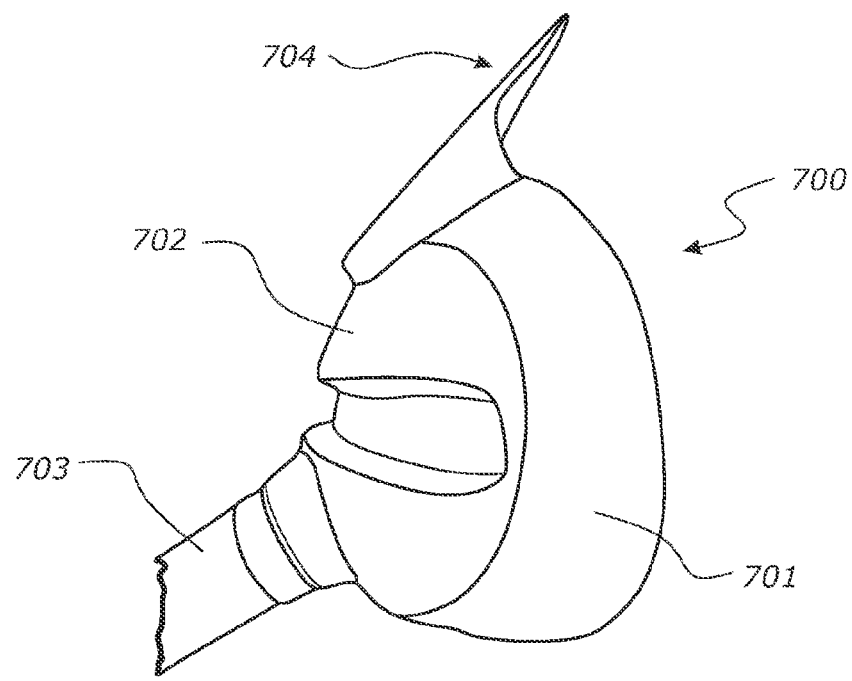
Figure 164:
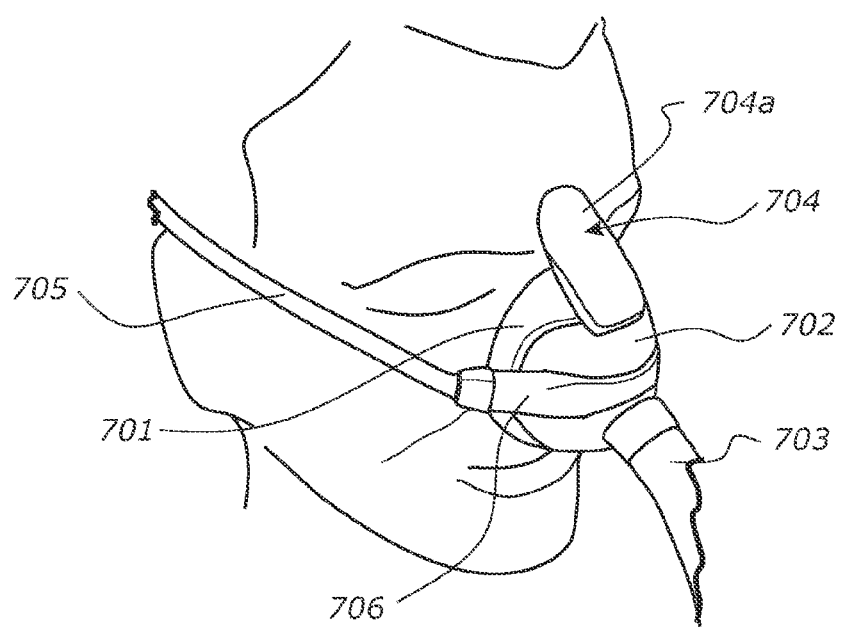
Figure 165:
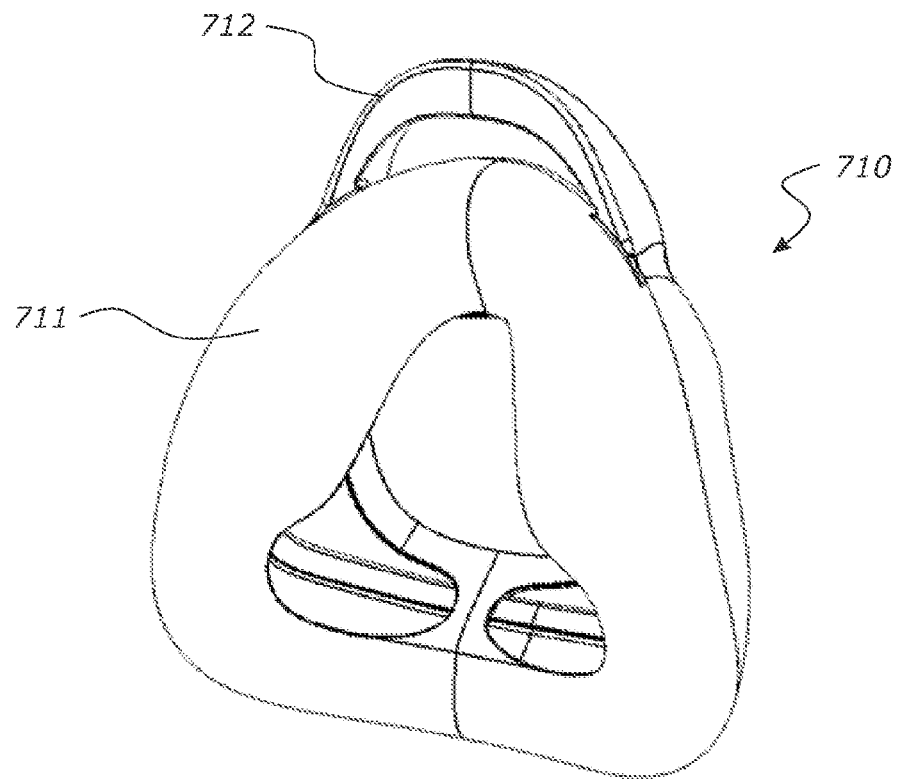
Figure 166:
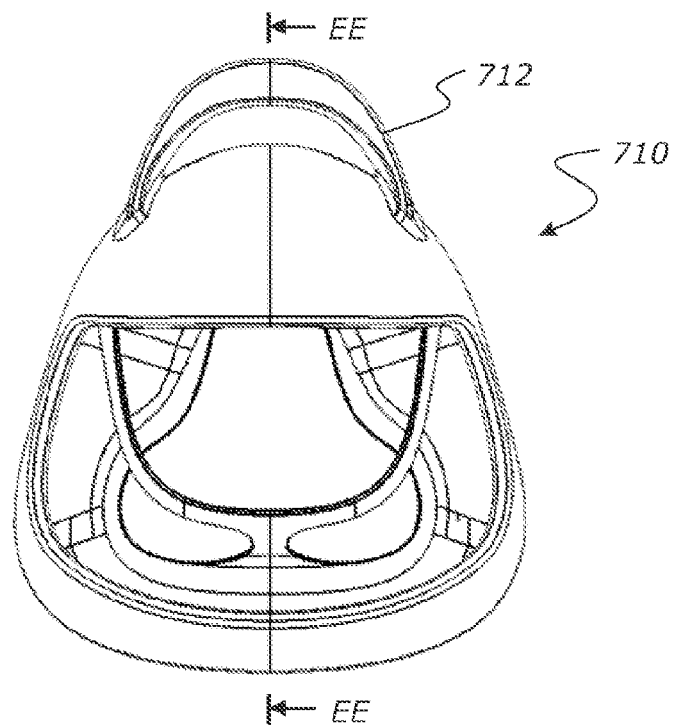
Figure 167:
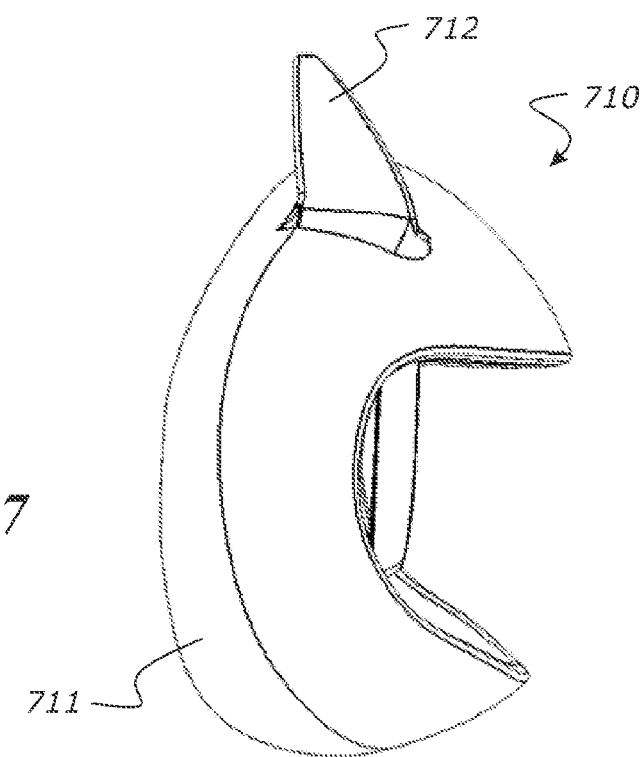
Figure 168:
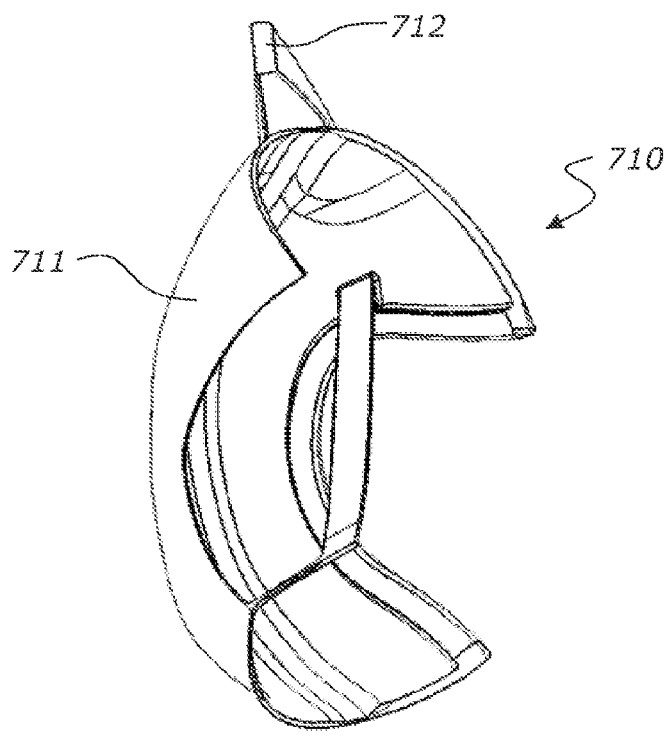
Figure 169:
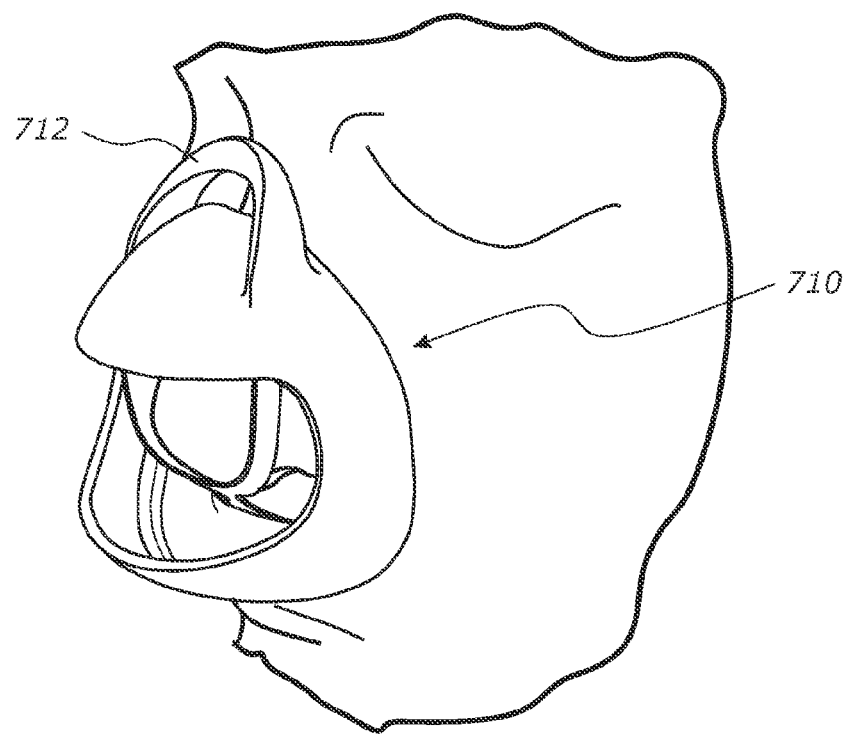
Figure 170:
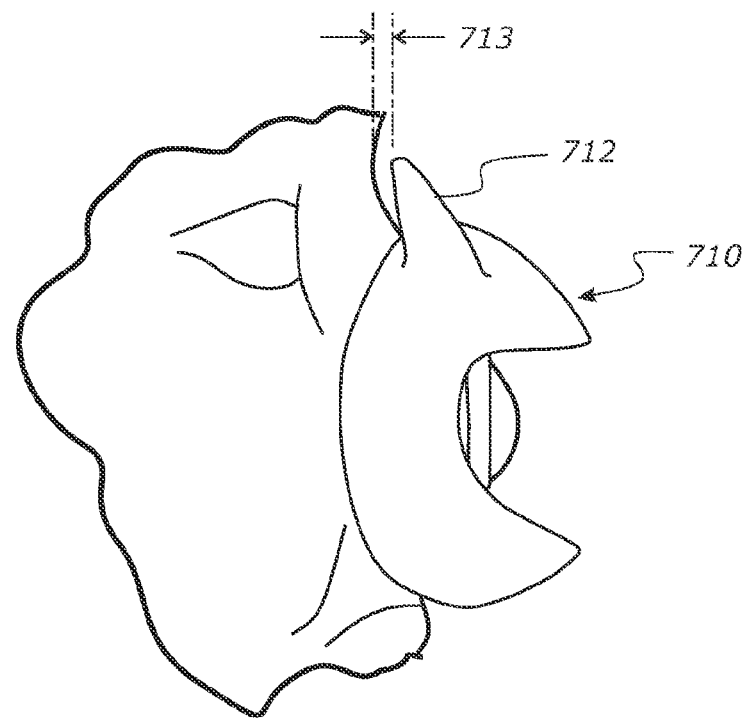
Figure 171:
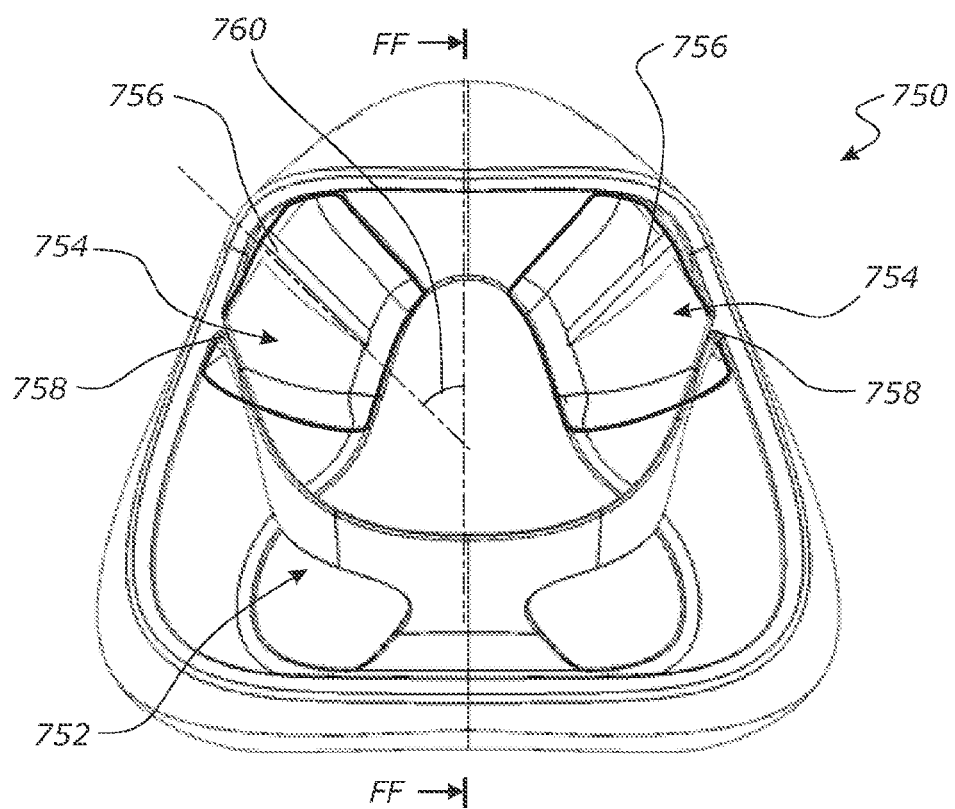
Figure 172:
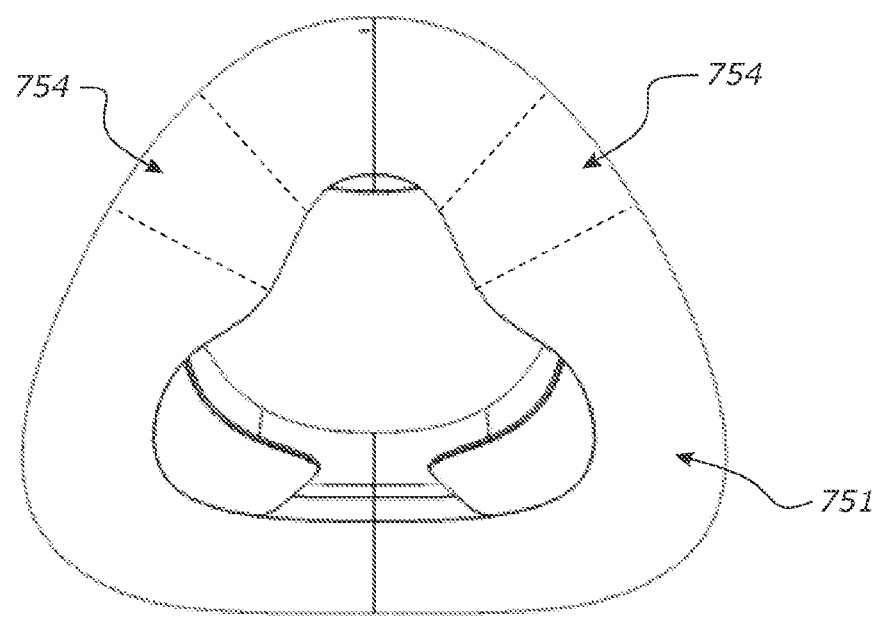
Figure 173:
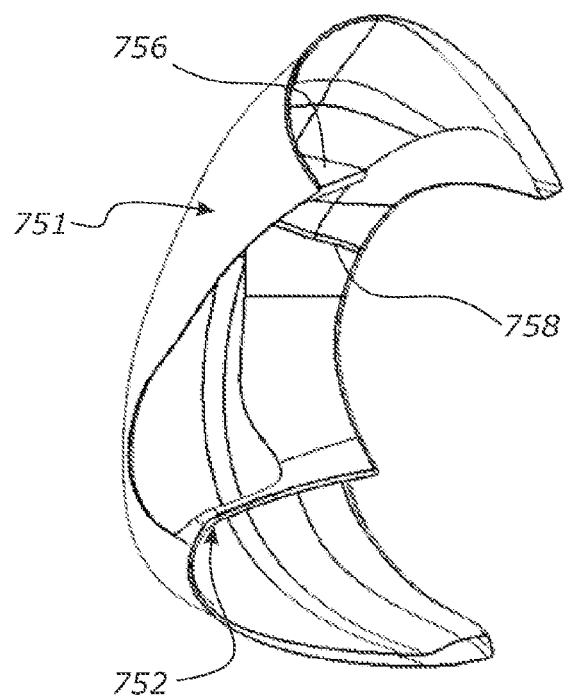
Figure 174:
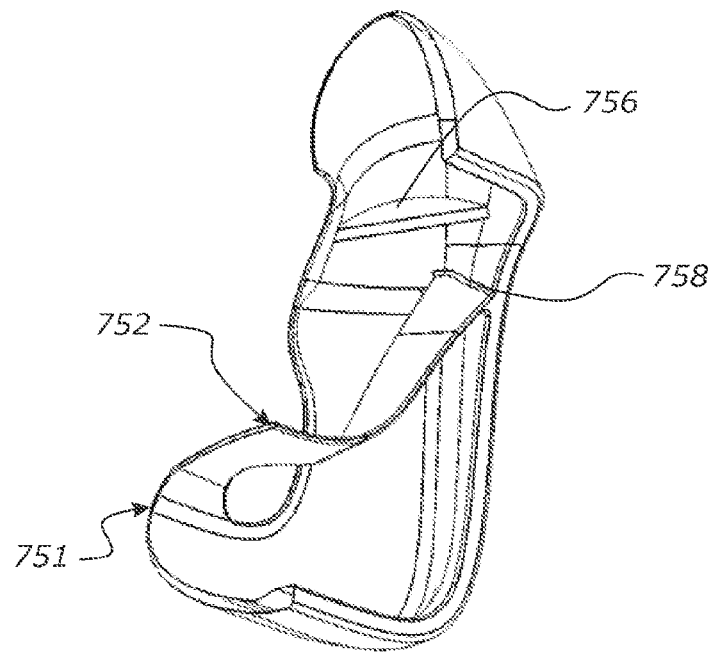
Figure 175:
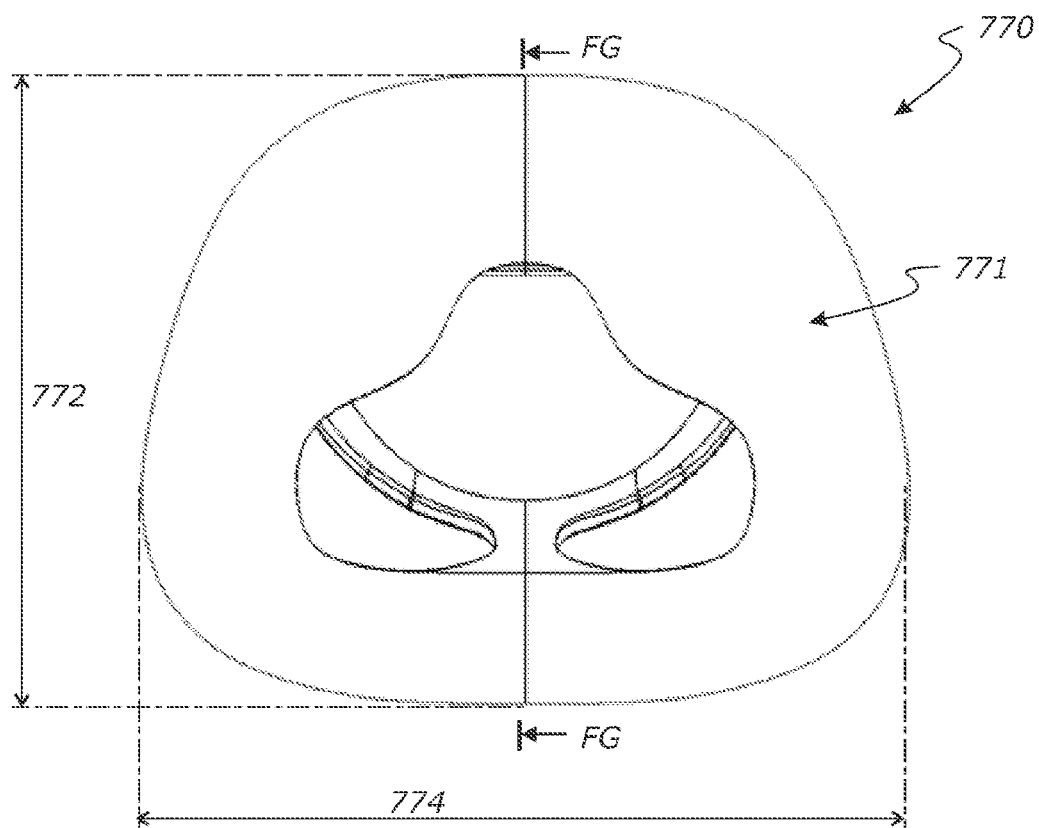
Figure 176:
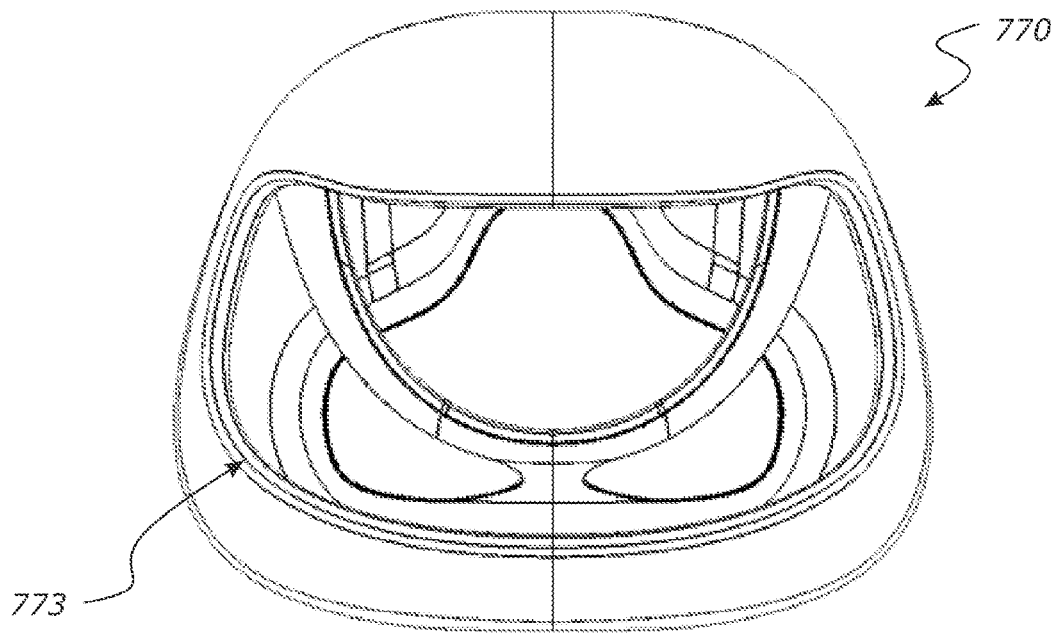
Figure 177:
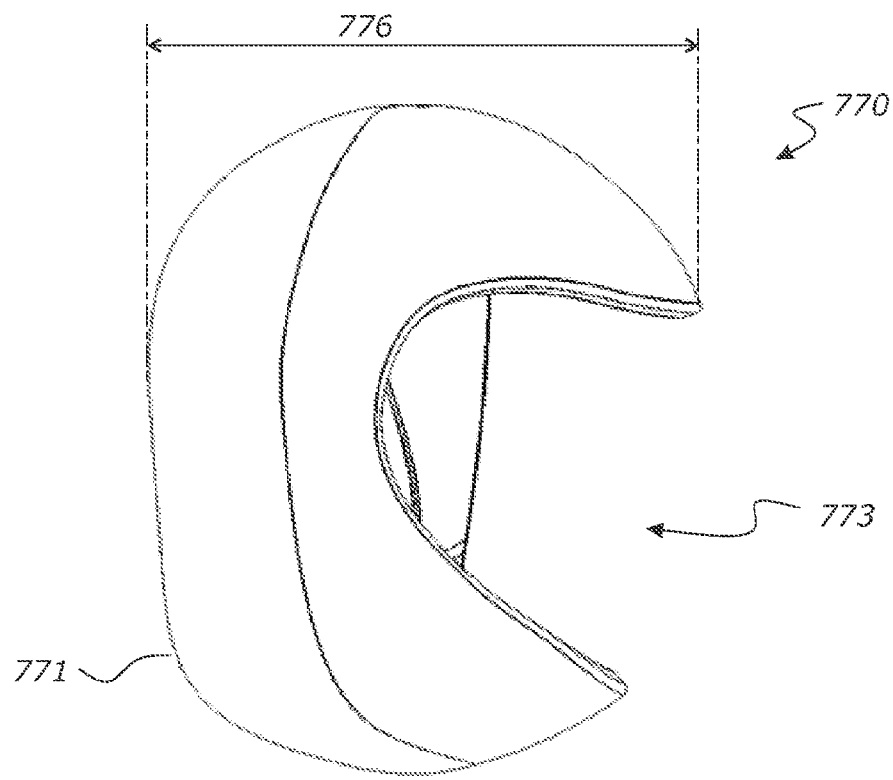
Figure 178:
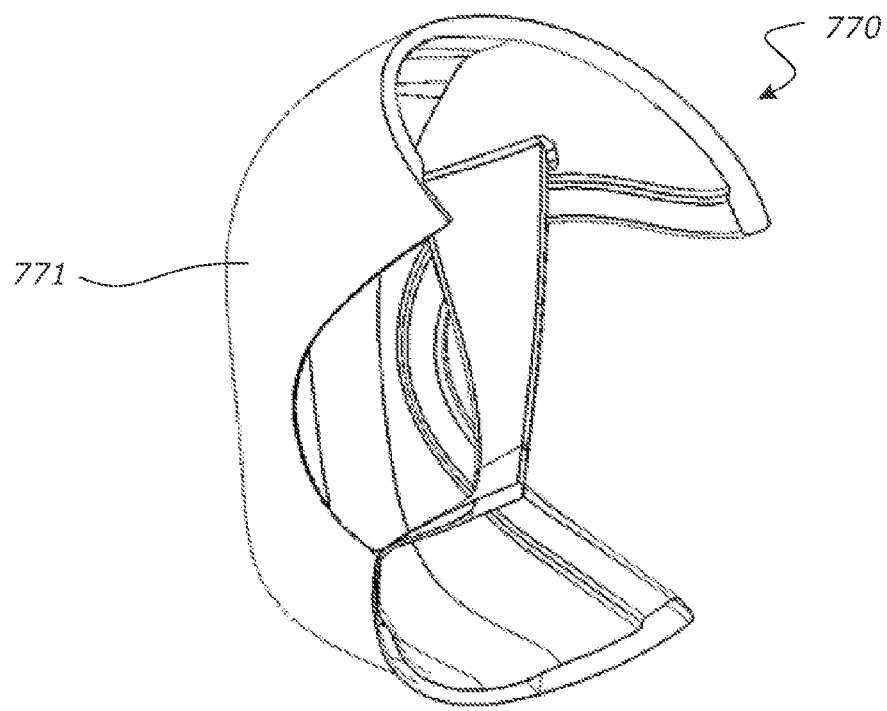
Figure 179:
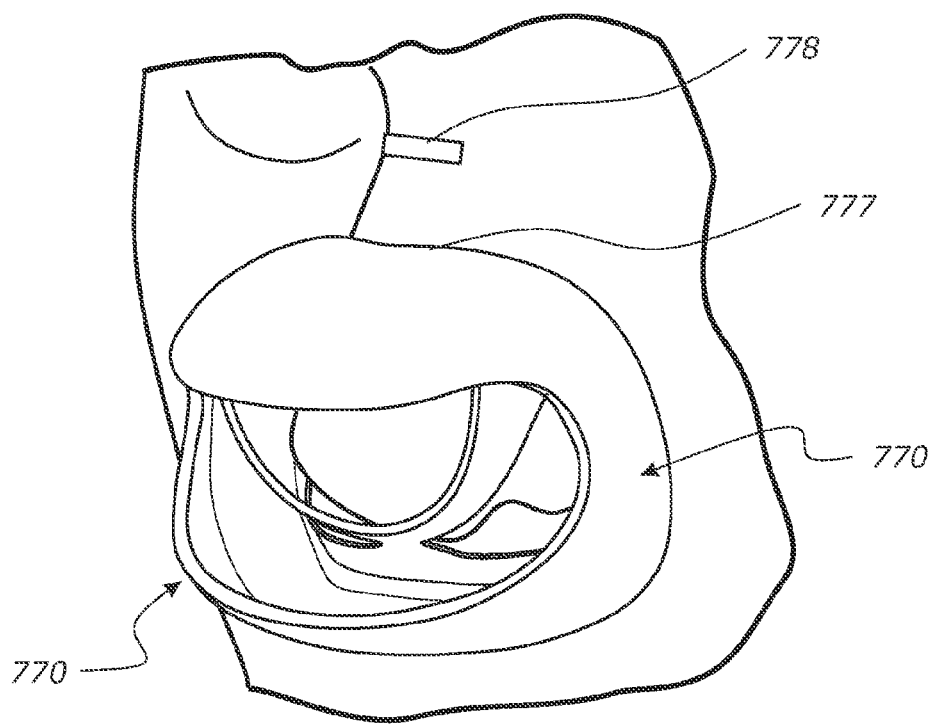
Figure 180:
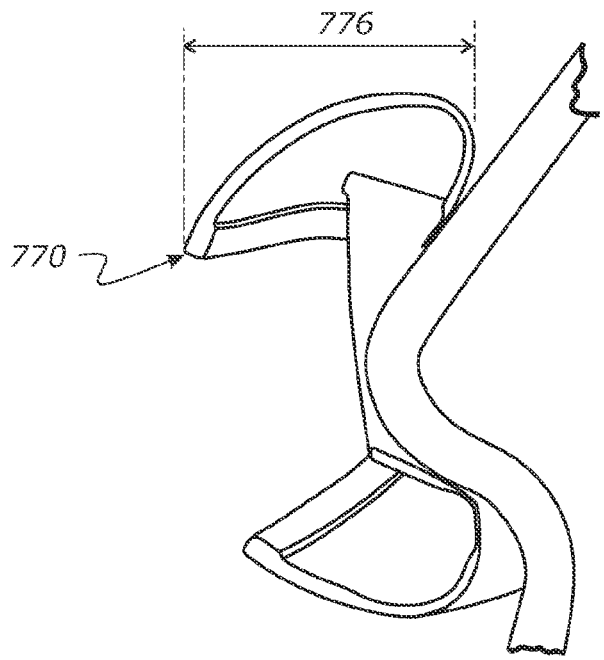
Figure 181:
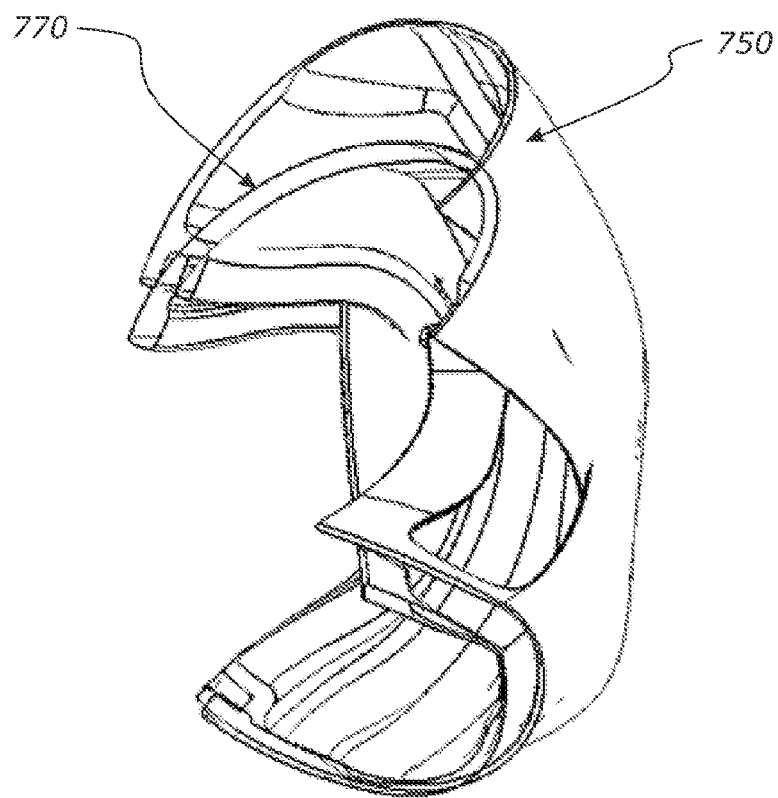
Figure 182:
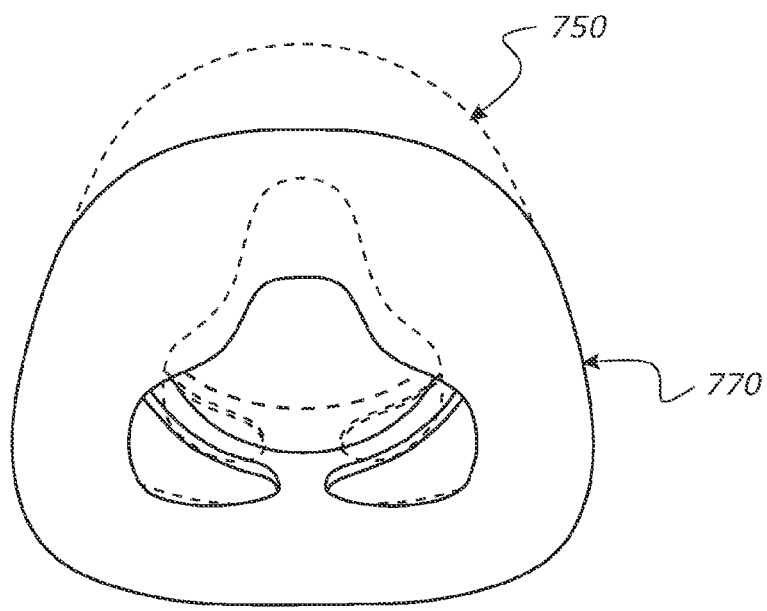
Figure 183:
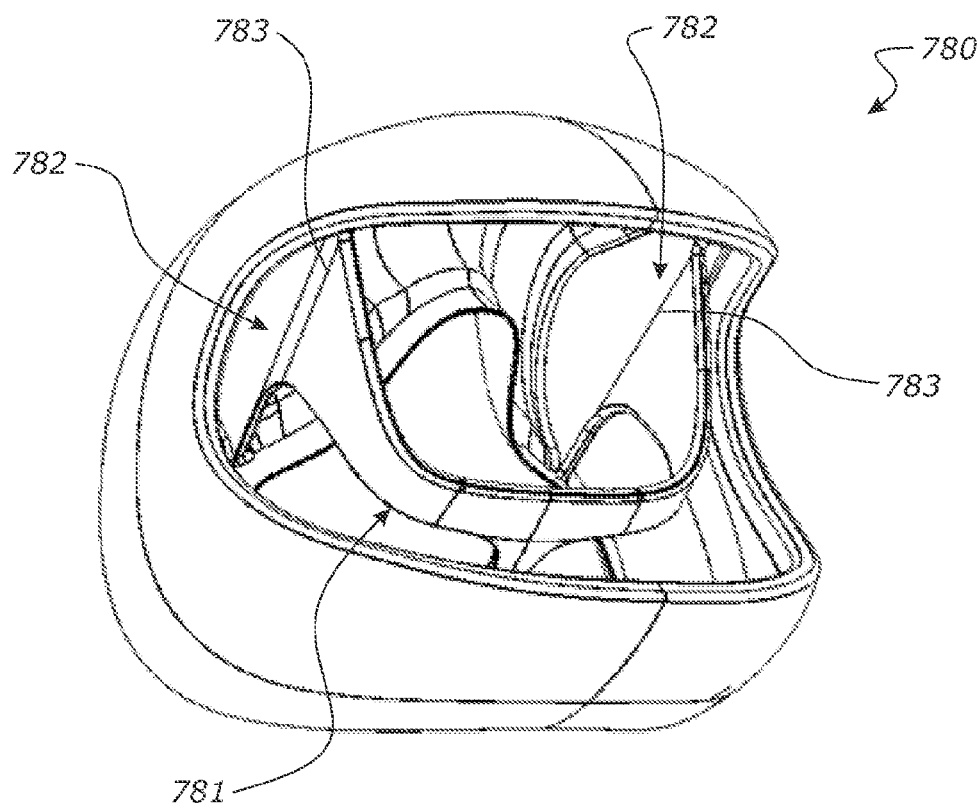
Figure 184:
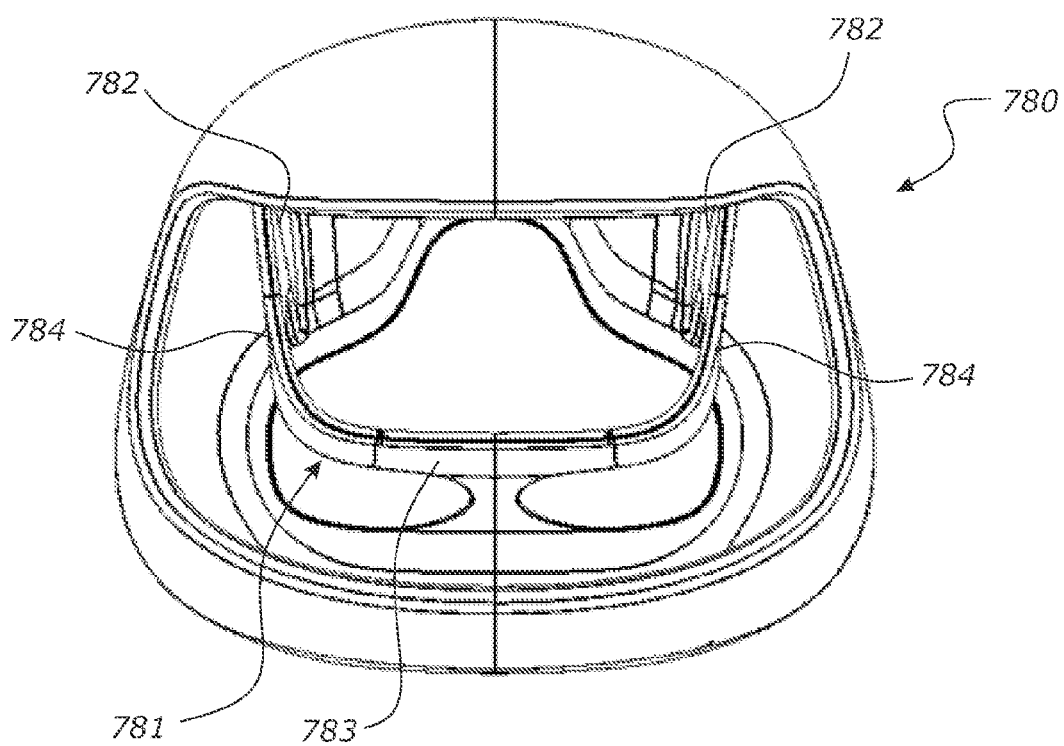
Figure 185:
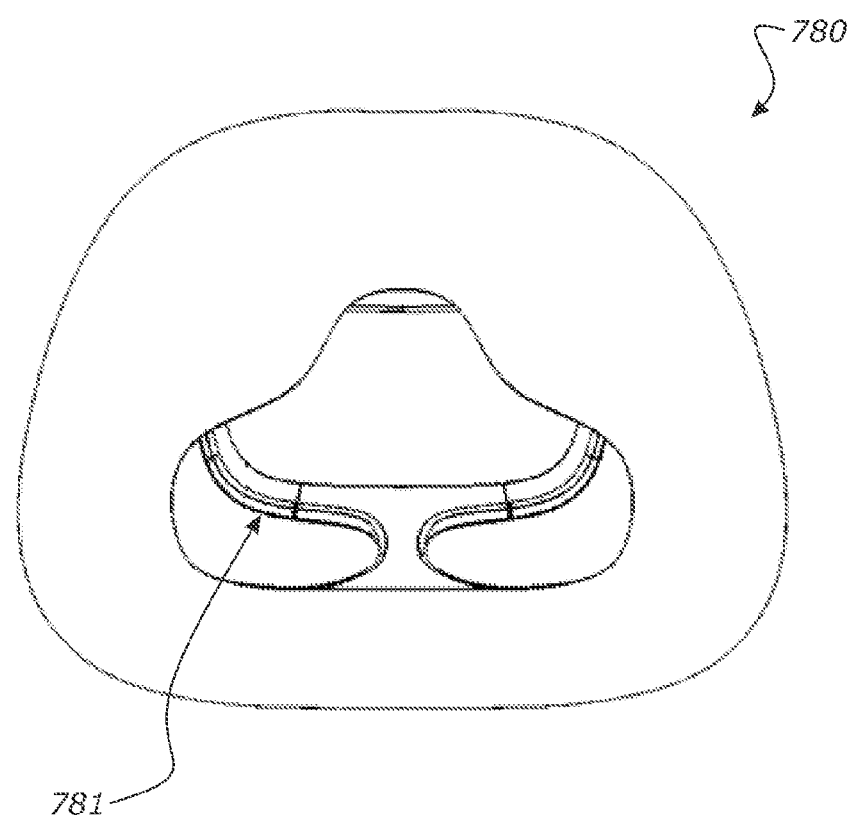
Figure 186:
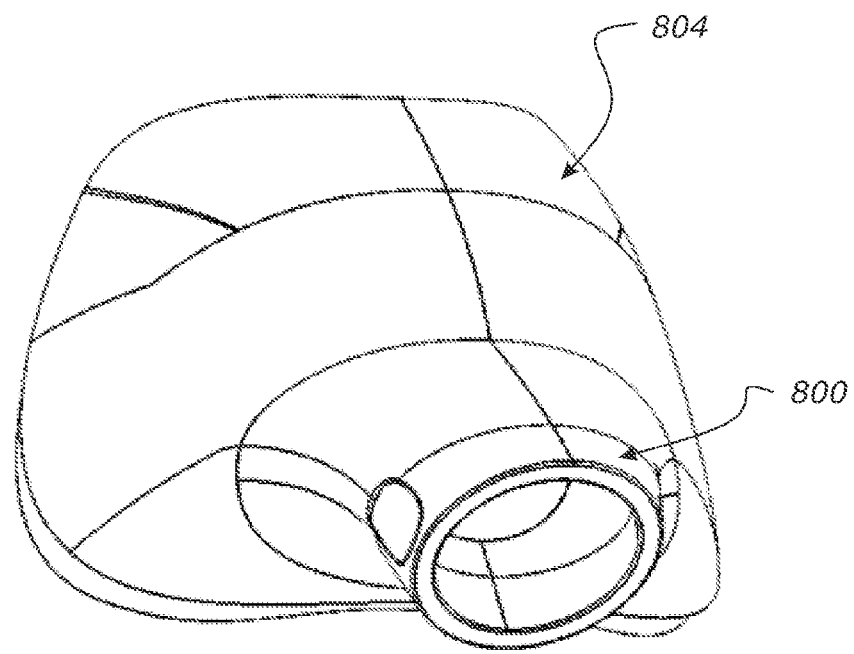
Figure 187:
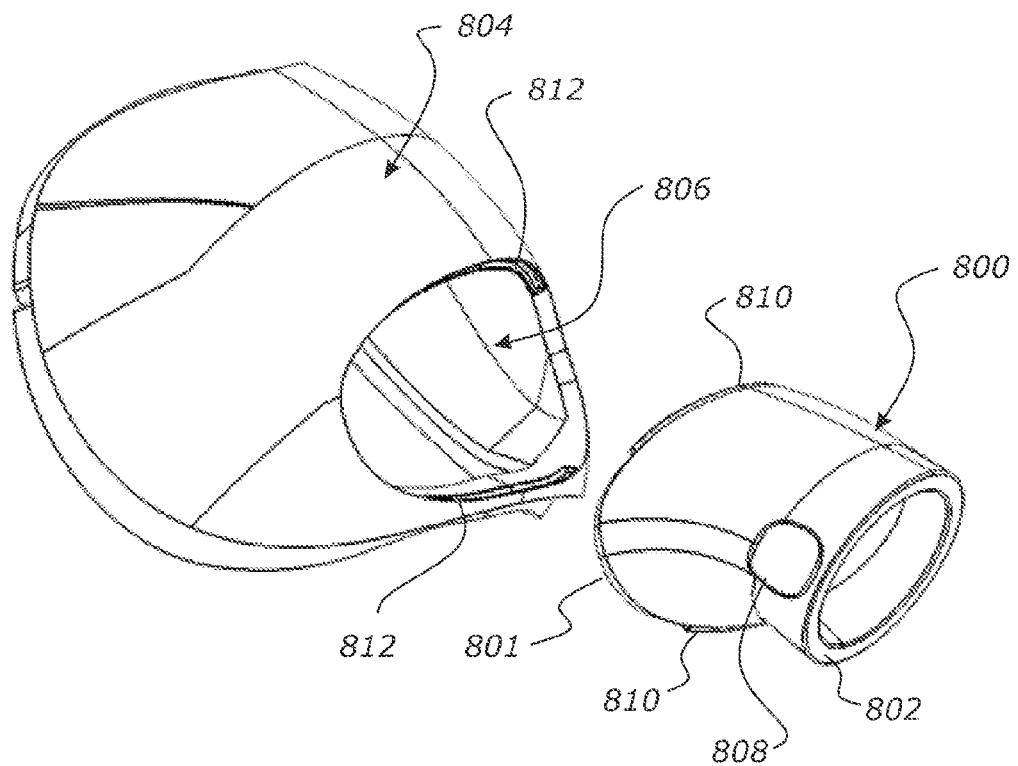
Figure 188:
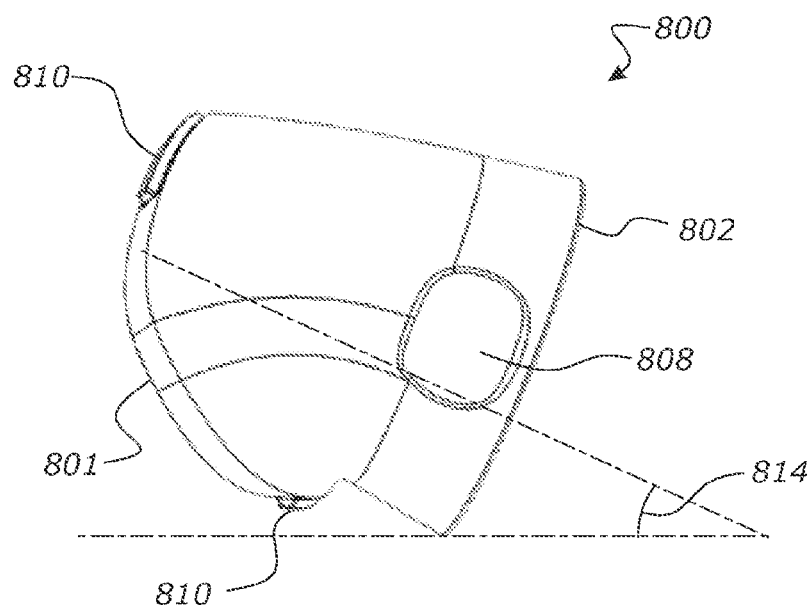
Figure 189:
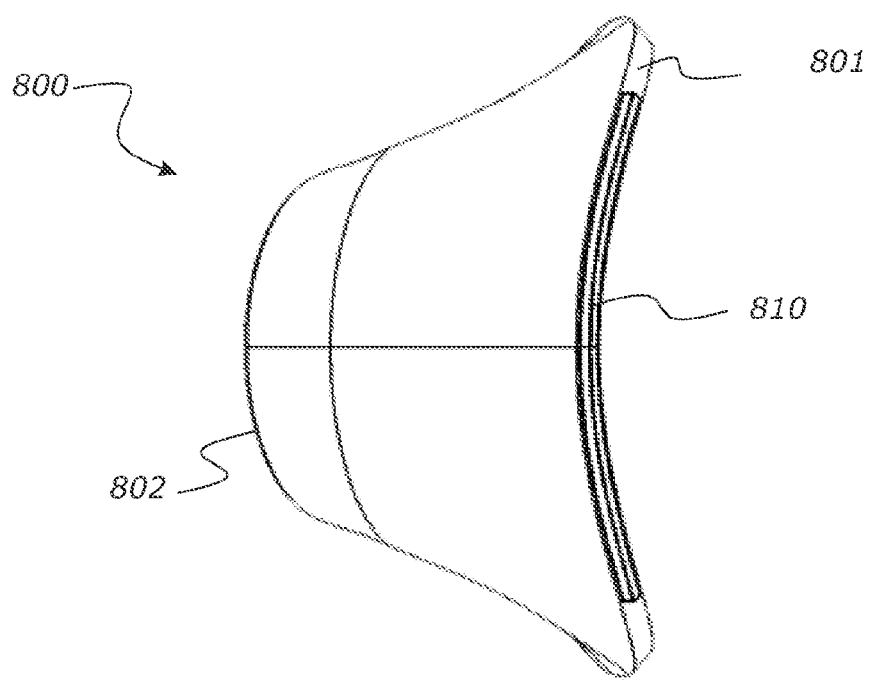
Figure 190:
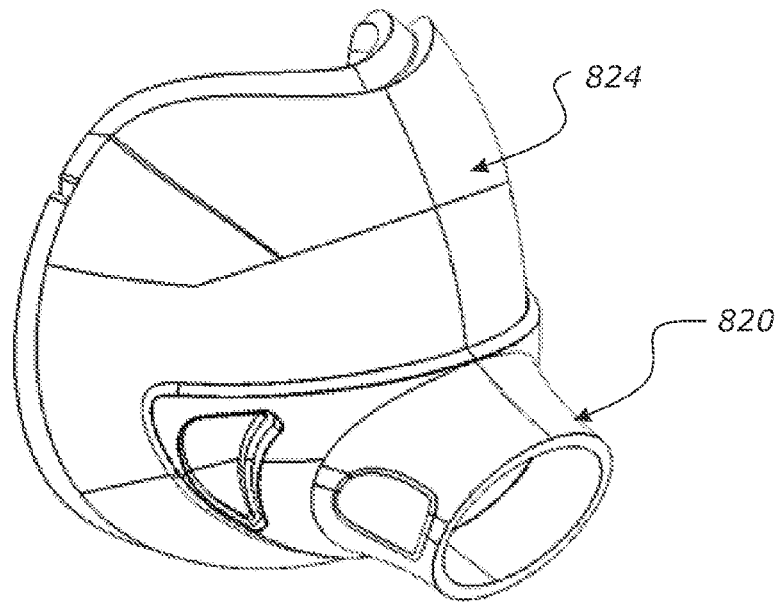
Figure 191:
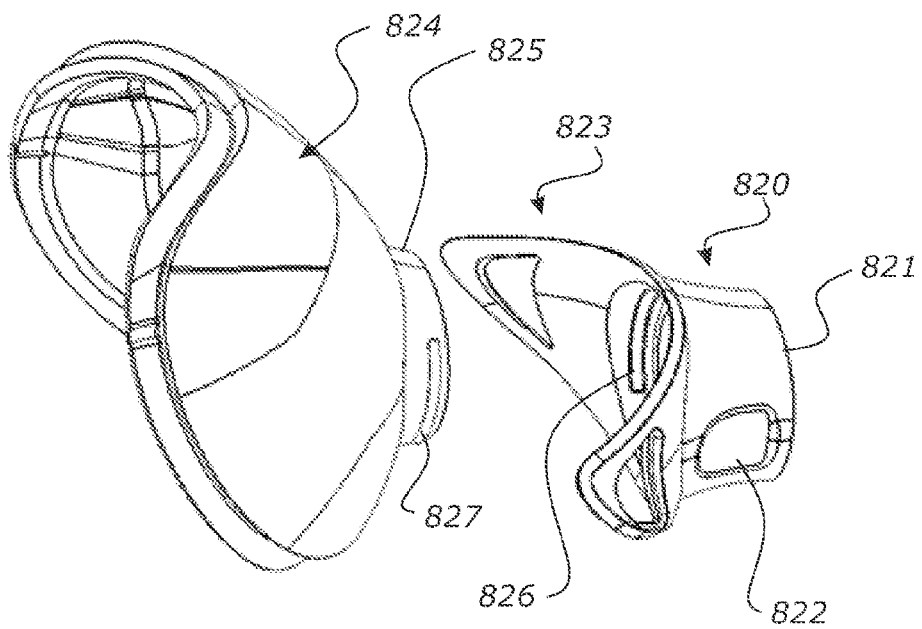
Figure 192:
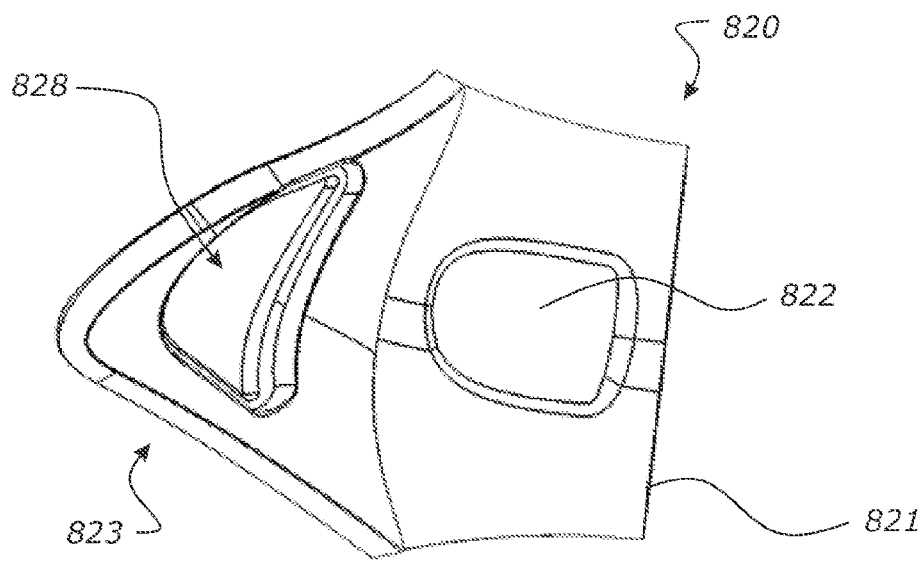
Figure 193:
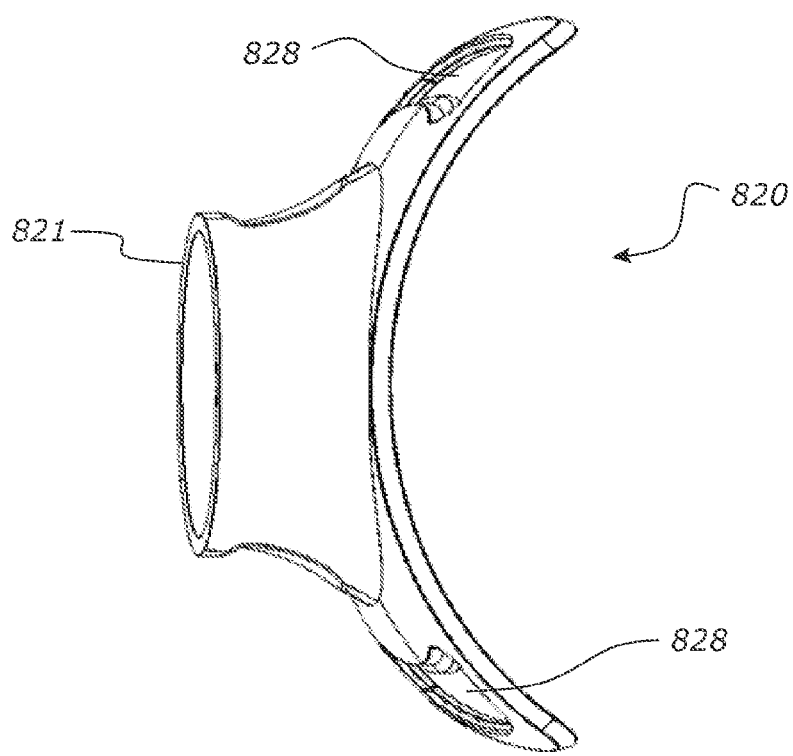
Figure 194:
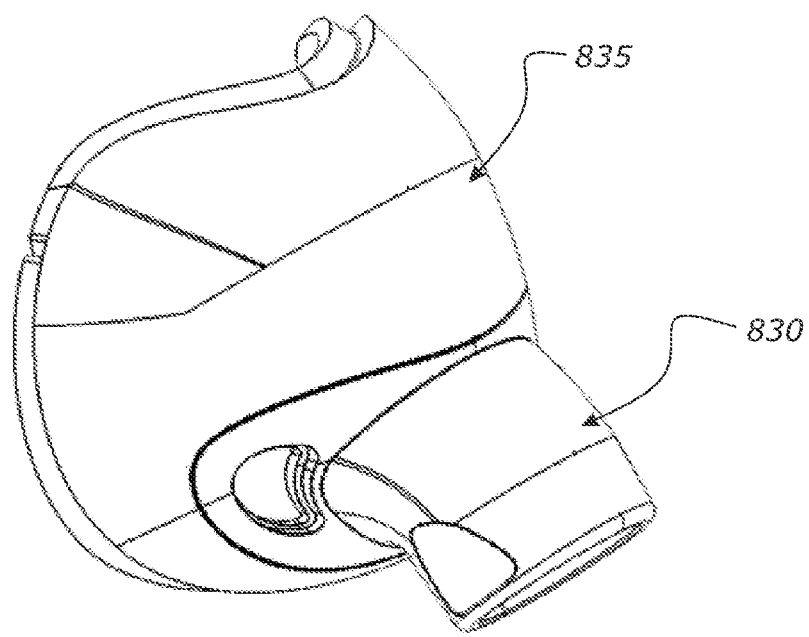
Figure 195:
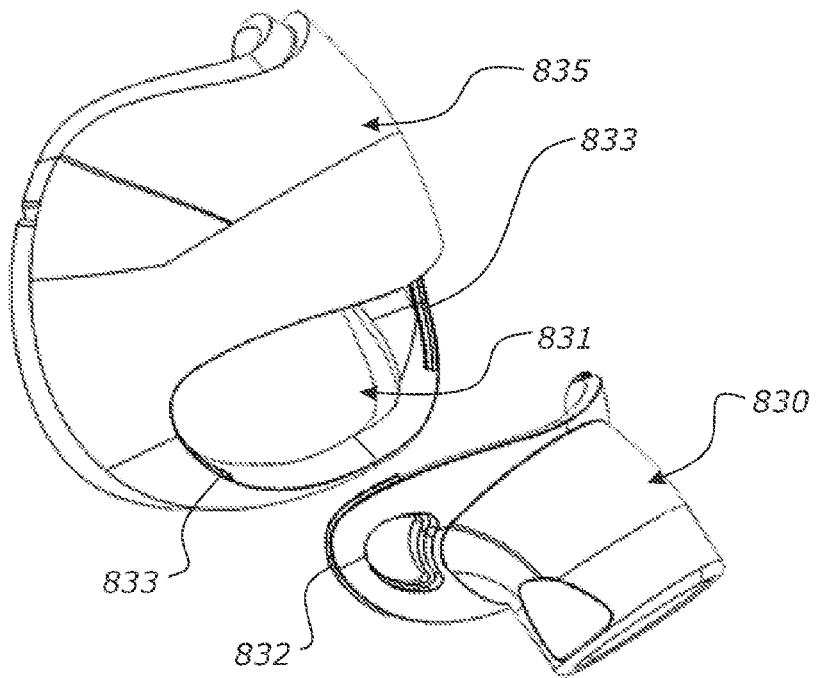
Figure 196:
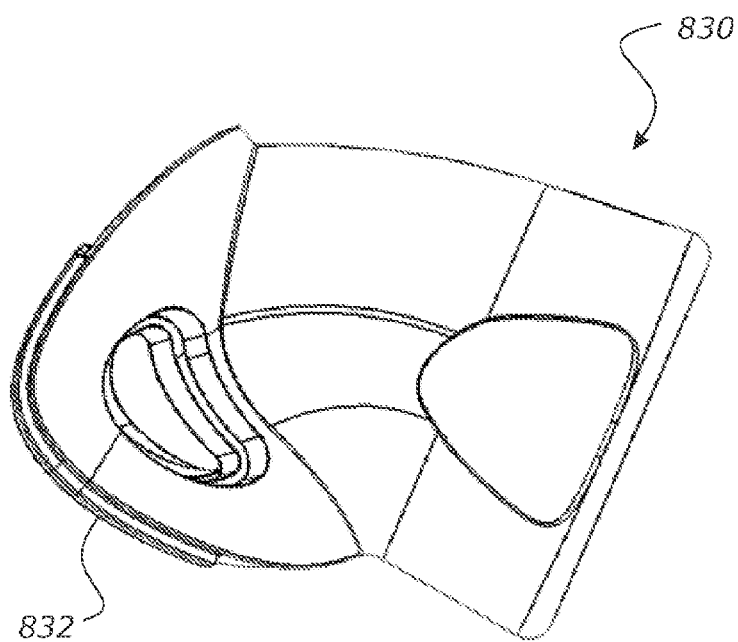
Figure 197:
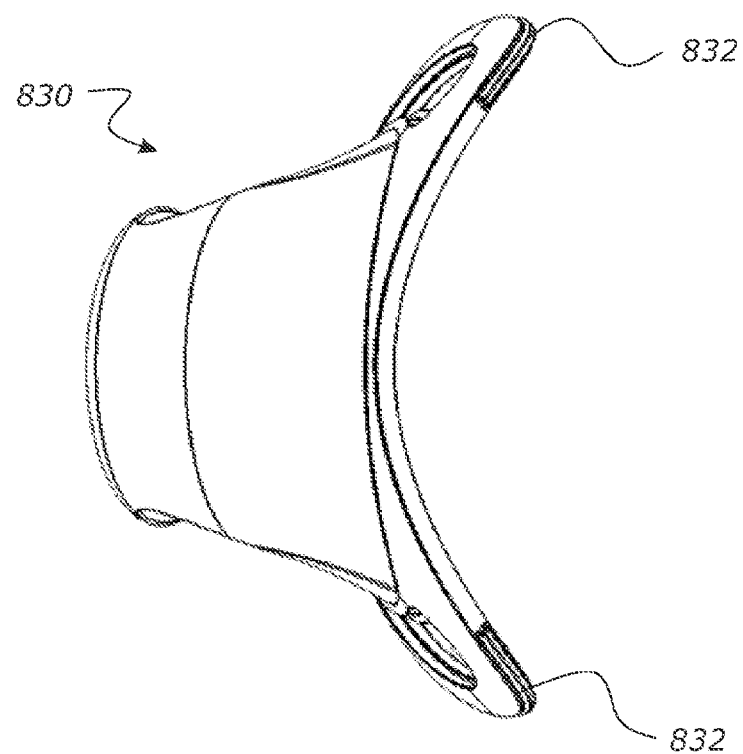
Figure 198:
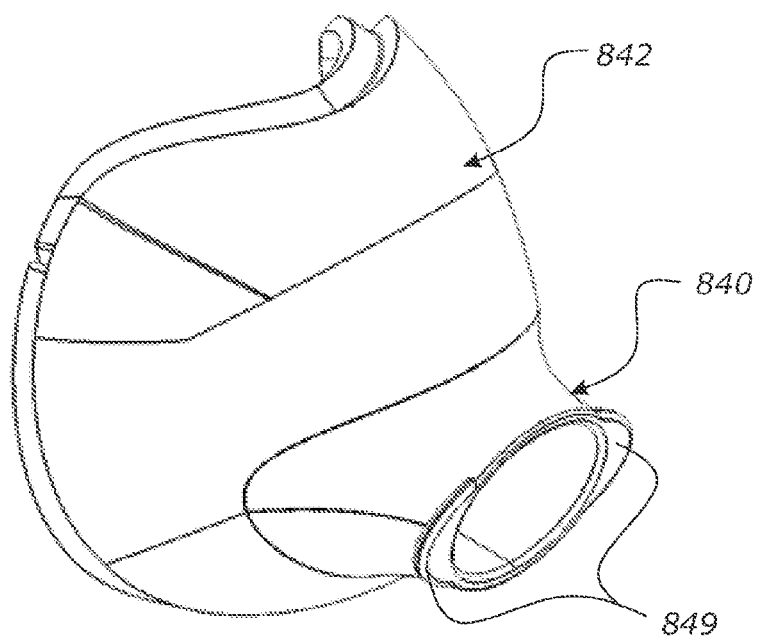
Figure 199:
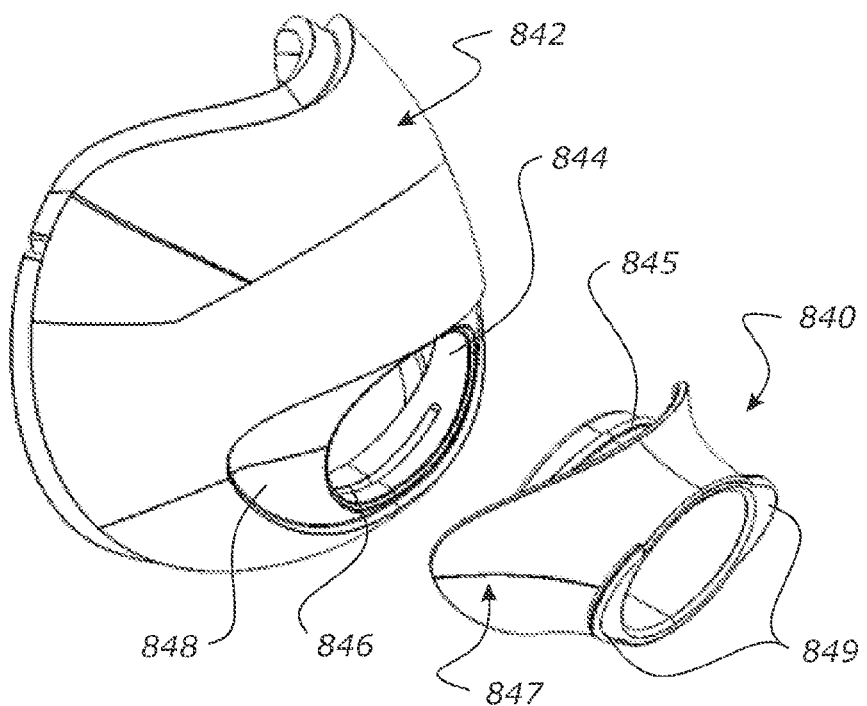
Figure 200:
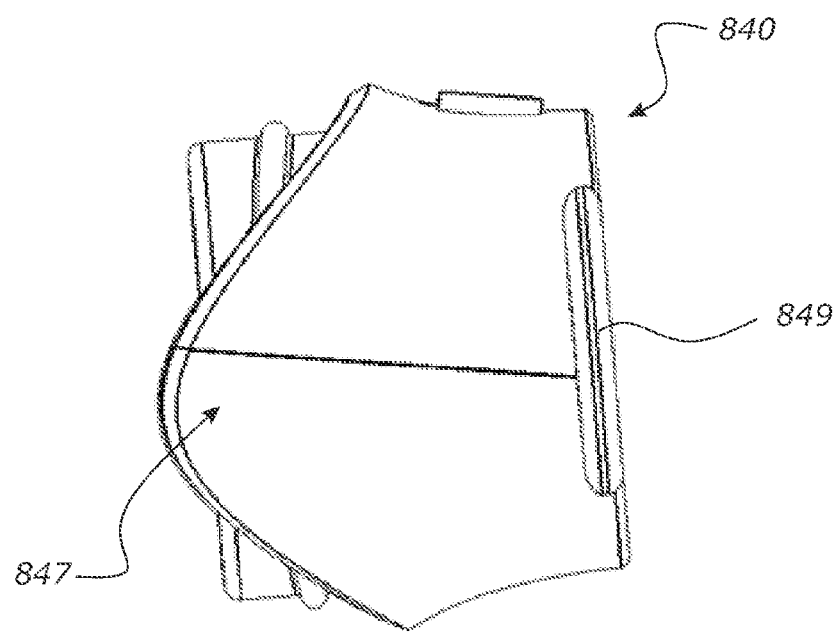
Figure 201:
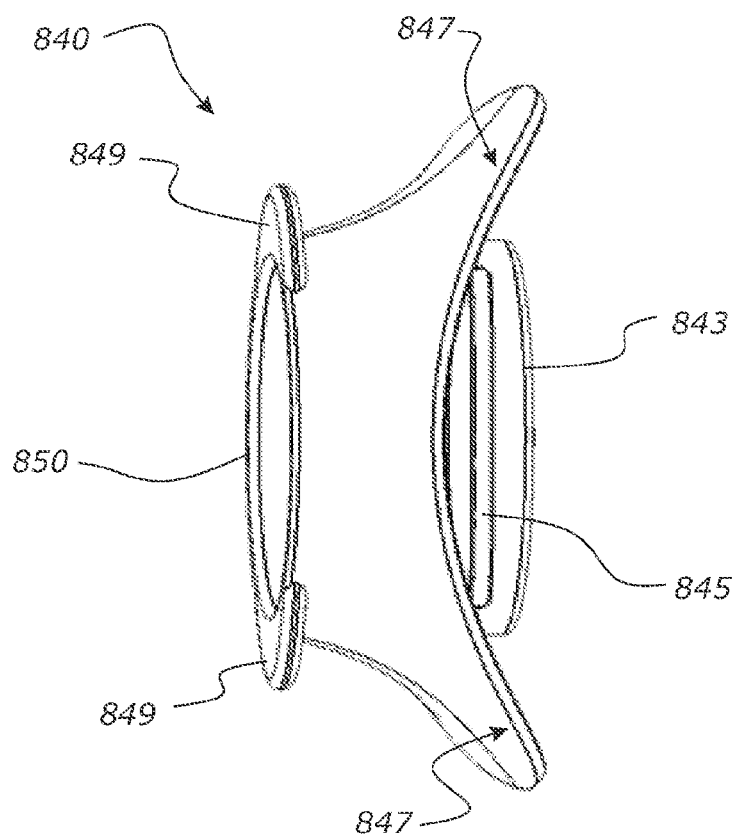
Figure 202:
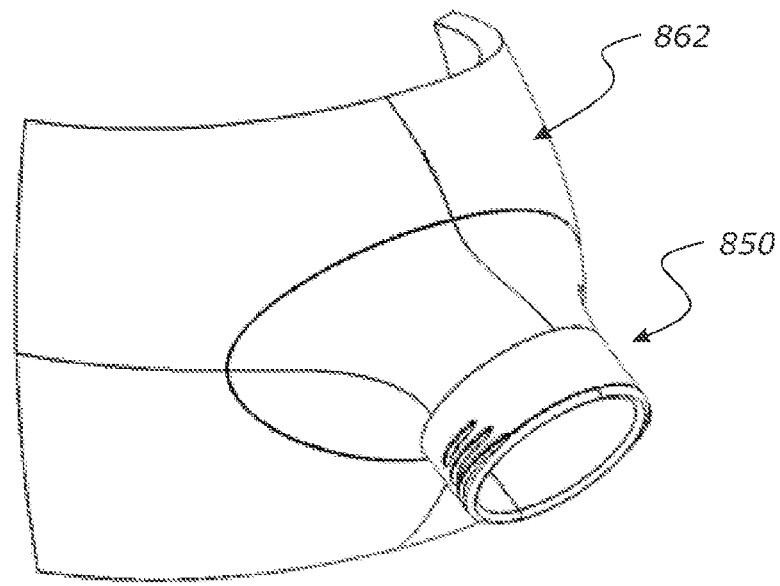
Figure 203:
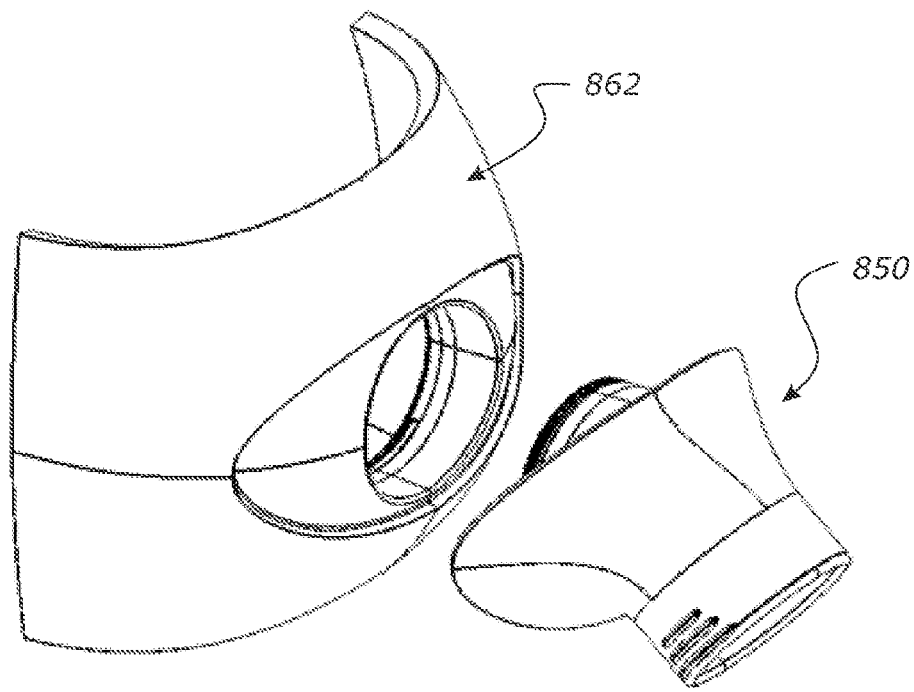
Figure 204:
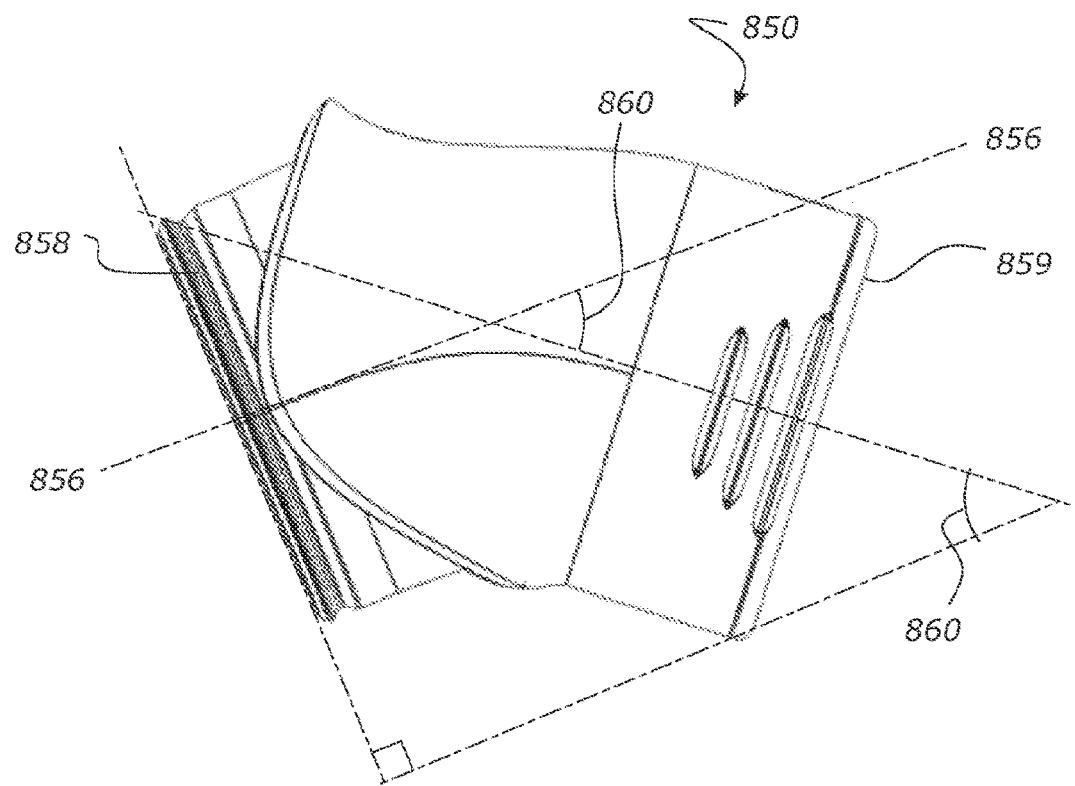
Figure 205:
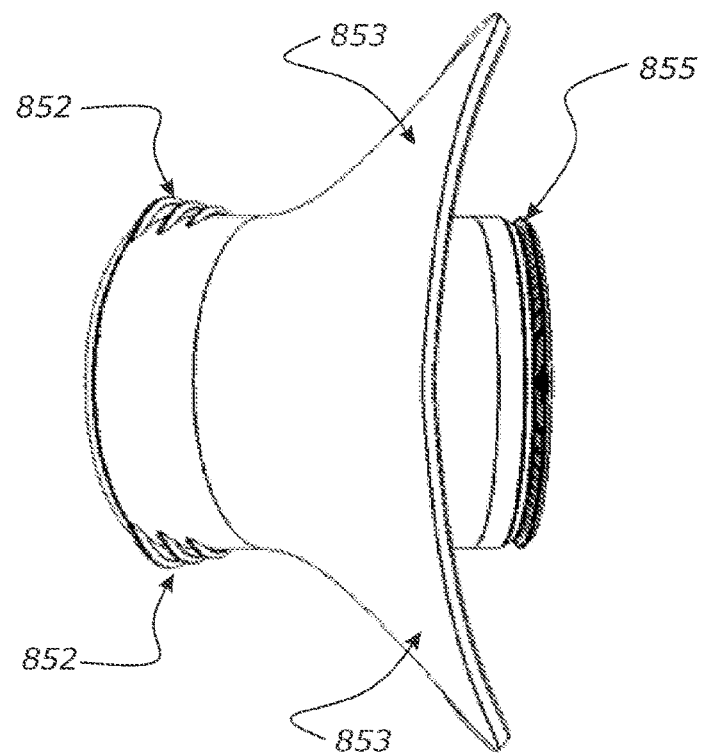
Figure 206:
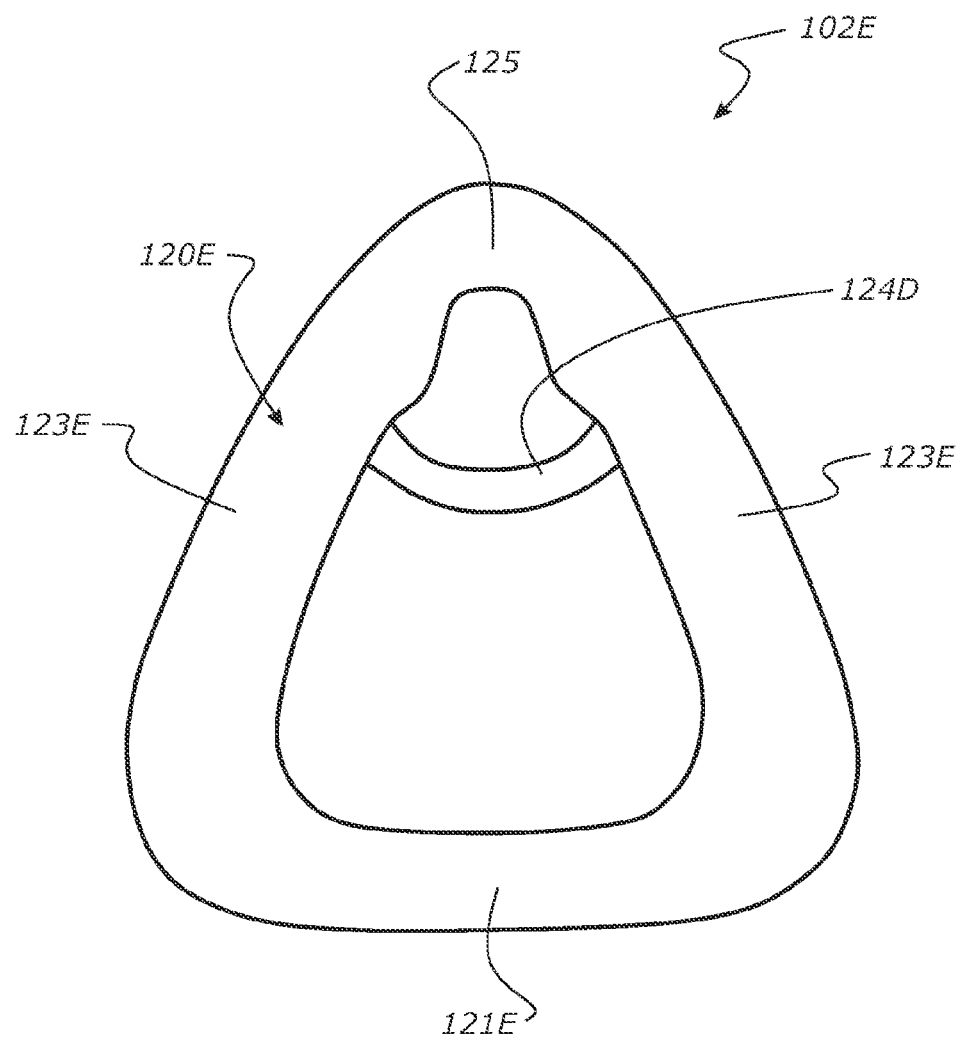

FIG. 135 is a face-contacting side view of the nasal seal of the third form nasal mask interface of FIG. 129;

FIG. 136 is an outer side view of the nasal seal of FIG. 135;

FIG. 137 is a perspective view of the face-contacting side of the nasal seal of FIG. 135;

FIG. 138 is a side elevation view of the nasal seal of FIG. 135;

FIG. 139 is a cross-sectional view of the nasal seal through line BE of FIG. 135;

FIG. 140 is an outer side perspective view of a fourth form of the fifth embodiment nasal mask interface;

FIG. 141 is a side elevation view of the fourth form nasal mask interface of FIG. 140;

FIG. 142 is an outer side view of the fourth form nasal mask interface of FIG. 140;

FIG. 143 is a face-contacting side view of the fourth form nasal mask interface of FIG. 140;

FIG. 144 is an outside view of the seal housing of the fourth form nasal mask interface of FIG. 140;

FIG. 145 is a side elevation view of the seal housing of FIG. 144;

FIG. 146 is a perspective view from the face-contacting side of the nasal seal of the fourth form nasal mask interface of FIG. 140;

FIG. 147 is a side elevation view of the nasal seal of FIG. 146;

FIG. 148 is a cross-sectional view of the nasal seal of FIG. 146 through the central line BF indicated in FIG. 146;

FIG. 149 is a cross-sectional view of the fourth form nasal mask interface through line BG of FIG. 142; and including an overlay of the nasal seal of the third form nasal mask interface of FIG. 135 for comparison as to shape and dimension;

FIG. 150 is a front or face-contacting side view of a sixth embodiment of the nasal mask interface, in particular showing the yoke being located below the conduit frame or inlet aperture of the seal housing;

FIG. 151 is an outer side view of the sixth embodiment nasal mask interface;

FIG. 152 is a side elevation view of the sixth embodiment nasal mask interface;

FIG. 153 is an outer side view of the seal housing and yoke of the sixth embodiment nasal mask interface;

FIG. 154 is a face-contacting side view of the seal housing and yoke of the nasal mask interface;

FIG. 155 is a face-contacting side view of a first form nasal seal of a seventh embodiment of the nasal mask interface, in which the nasal seal comprises wing portions extending from the sides of the nasal seal;

FIG. 156 is an outer side view of the first form nasal seal of FIG. 155;

FIG. 157 is a side elevation view of the first form nasal seal of FIG. 155;

FIG. 158 is an outer side perspective view of a second form nasal seal of the embodiment nasal mask interface, in particular showing longer wing portions (relative to the first form) extending from the sides of the nasal seal;

FIG. 159 is a face-contacting side view of the second form nasal seal of FIG. 158;

FIG. 160 is an outer side view of the second form nasal seal of FIG. 158;

FIG. 161 is a top view of the second form nasal seal of FIG. 158;

FIG. 162 is a perspective view of a seventh embodiment nasal mask interface comprising the second form nasal seal being worn by a user;

FIG. 163 is a side elevation view of a first form of an eighth embodiment of the nasal mask interface in which the interface comprises a forehead support extending from the nasal seal or seal housing;

FIG. 164 is a perspective view of a user wearing the first form of the nasal mask interface of FIG. 163;

FIG. 165 is a face-contacting side view of a second form of the eighth embodiment nasal mask interface in which the nasal seal comprises a nasal bridge support protrusion;

FIG. 166 shows an outer side view of the second form nasal seal of FIG. 165;

FIG. 167 shows a side elevation view of the second form nasal seal of FIG. 165;

FIG. 168 shows a cross-sectional view of the second form nasal seal of FIG. 165 through line EE of FIG. 166;

FIG. 169 is a perspective view of a user wearing the second form nasal seal of FIG. 165;

FIG. 170 is a side elevation view of the user wearing the second form nasal seal in FIG. 169 and showing a gap between the nasal bridge support protrusion and the user's nasal bridge;

FIG. 171 is an outer side view of a first form nasal seal of a ninth embodiment nasal mask interface, where the nasal seal includes additional support ribs within the nasal mask;

FIG. 172 is a face-contacting side view of the first form nasal seal of FIG. 171;

FIG. 173 is a cross-sectional view of the first form nasal seal through line FF of FIG. 171;

FIG. 174 is a perspective view of the cross-sectional view of FIG. 173 of the nasal seal;

FIG. 175 is a face-contacting side view of a second form nasal seal of the ninth embodiment nasal mask interface;

FIG. 176 is an outer side view of the second form nasal mask of FIG. 175;

FIG. 177 is a side elevation view of the second form nasal seal of FIG. 175;

FIG. 178 is a cross-sectional view of the second form nasal seal of through line FG of FIG. 175;

FIG. 179 is a perspective view of a user wearing the second form nasal seal of FIG. 175;

FIG. 180 is a side cross-sectional view of the user wearing the second form nasal seal in FIG. 179;

FIG. 181 is a cross-sectional view of the first form and second form nasal seals of FIGS. 171 and 175 overlaid onto each other to show a comparison of shape and dimension;

FIG. 182 is a face-contacting side view of the first and second form nasal seals of FIGS. 171 and 175 overlaid onto each other for comparison of shape and dimension;

FIG. 183 is an outer side perspective view of a third form nasal seal of the ninth embodiment nasal mask interface;

FIG. 184 is an outer side view of the third form nasal seal of FIG. 183;

FIG. 185 is a face-contacting side view of the third form nasal seal of FIG. 183;

FIG. 186 is an outer side perspective view of a first form of a seal housing and conduit frame assembly of a tenth embodiment nasal mask interface;

FIG. 187 is an exploded view of the first form seal housing and conduit frame assembly of FIG. 186;

FIG. 188 is a side elevation view of the conduit frame of the first form assembly of FIG. 186;

FIG. 189 is a top view of the conduit frame of the first form assembly of FIG. 186;

FIG. 190 is an outer side perspective view of a second form seal housing and conduit frame assembly of the tenth embodiment nasal mask interface;

FIG. 191 is an exploded view of the second form assembly of FIG. 190;

FIG. 192 is a side elevation view of the conduit frame of the second form assembly of FIG. 190;

FIG. 193 is a top view of the conduit frame of the second form assembly of FIG. 190;

FIG. 194 is an outer side perspective view of a third form seal housing and conduit frame assembly of the tenth embodiment nasal mask interface;

FIG. 195 is an exploded perspective view of the third form assembly of FIG. 194;

FIG. 196 is a side elevation view of the conduit frame of the third form assembly of FIG. 194;

FIG. 197 is a top view of the conduit frame of the third form assembly of FIG. 194;

FIG. 198 is an outer side perspective view of a fourth form seal housing and conduit frame assembly of the tenth embodiment nasal mask interface;

FIG. 199 is an exploded perspective view of the fourth form assembly of FIG. 198;

FIG. 200 is a side elevation view of the conduit frame of the fourth form assembly of FIG. 198;

FIG. 201 is a top view of the conduit frame of the fourth form assembly of FIG. 198;

FIG. 202 is an outer side perspective view of a fifth form seal housing and conduit frame assembly of the tenth embodiment nasal mask interface;

FIG. 203 is an exploded perspective view of the fifth form assembly of FIG. 202;

FIG. 204 a side elevation view of the conduit frame of the fifth form assembly of FIG. 202;

FIG. 205 is a top view of the conduit frame of the fifth form assembly of FIG. 202; and FIG. 206 is a front view of a full face seal with an under-nose support configuration in accordance with an eleventh embodiment.

DETAILED DESCRIPTION OF PREFERRED EMBODIMENTS

System Overview

Figure 1:
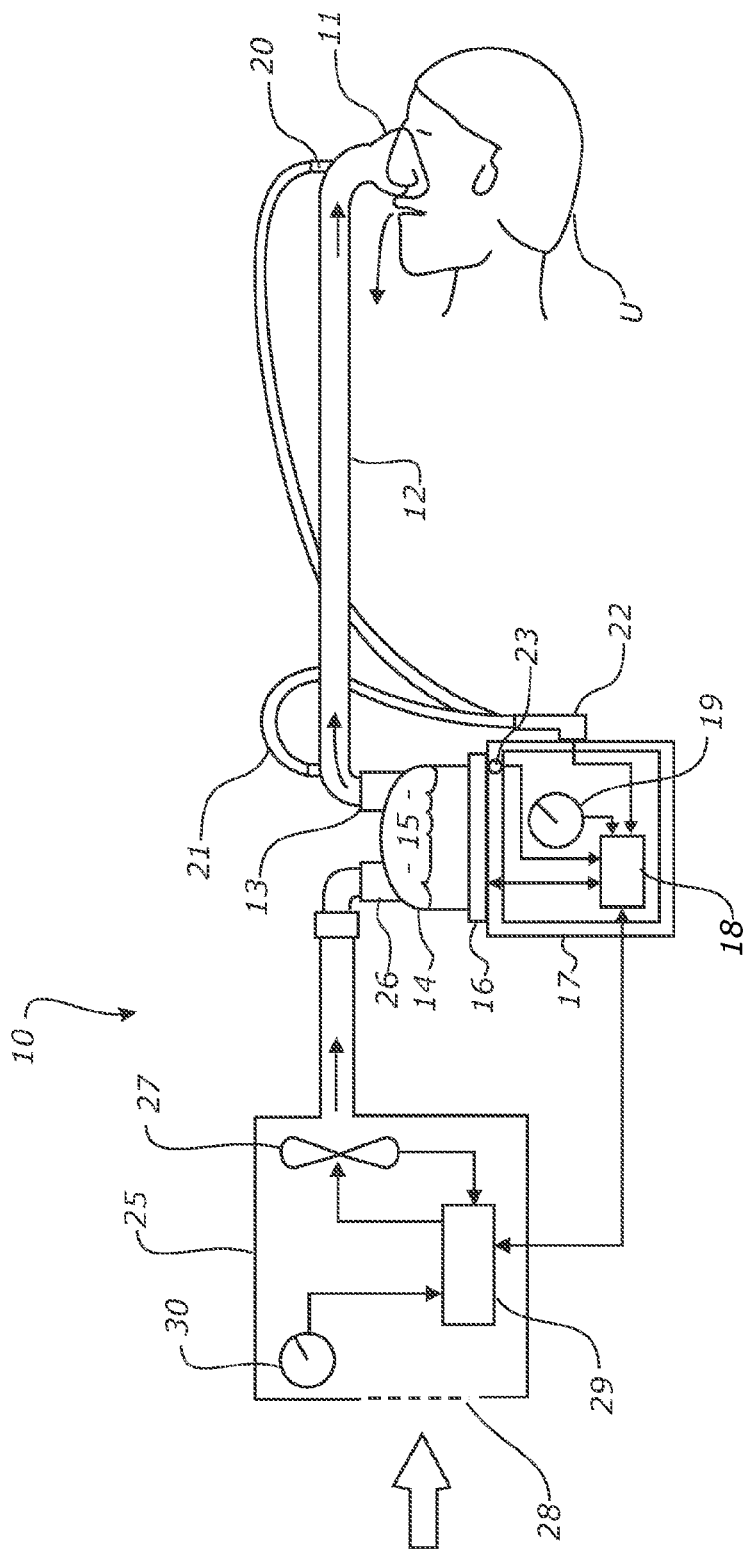
FIG. 1 is a schematic diagram of a system for providing a heated and humidified gases stream to a user, such as in a continuous positive airway pressure (CPAP) system.

FIG. 1 is a schematic diagram of a continuous positive airway pressure (CPAP) system 10 for providing a heated and humidified air stream to a user U through an interface 11 worn by the user, and which is connected to CPAP system 10 by a flexible conduit or tube 12.

A humidification chamber 14 has a heat conductive base in contact with a heater plate 16 of humidifier 17 to humidify the air stream. Conduit 12 is connected to an outlet 13 of humidification chamber 14 to convey humidified air to the user interface 11. The humidifier 17 comprises a controller 18, such as a microprocessor-based controller that executes computer software commands stored in an associated memory, for example but without limitation. The controller 18 receives input commands from multiple sources, including a user input interface 19 such as a dial or touch screen, which enables the setting of a predetermined value of humidity, temperature, or other characteristic of the humidified air supplied to the user U. The controller 18 also may receive input from one or more other sources, such as for example temperature and/or flow velocity sensors 20 and 21, which are connected through a connector 22 to communicate with controller 18, and/or a heater plate temperature sensor 23. In response to the user set humidity or temperature value the controller 19 determines when and/or to what level the heater plate 16 should be energized to suitably heat the water contained in the humidification chamber 14.

As the volume of water in the chamber is heated, water vapour begins to fill the volume of the chamber above a surface of the water. The water vapour passes out of the outlet 13 of the humidification chamber with a flow of air that is provided from a supply 25 such as a blower 27, which enters the humidification chamber 30 through an inlet 26. The blower 27 can be variable in speed fan, or can include a variable pressure regulator. The blower 27 draws air through an inlet 28. The blower can be controlled by controller 29 or controller 18 for example. The controller may control blower speed, regulated pressure, or the like according to any suitable criteria. For example, the controller may respond to inputs from controller 18 and a user set value (e.g., a preset value) of pressure and/or fan speed, which can be set with a user interface 30 (e.g., a dial).

The conduit 12 may comprise a heater such as a heater wire for example, to heat the walls of the conduit to reduce condensation of humidified gases within the conduit.

The seal and interfaces of this disclosure can be used in such a CPAP system as described whether humidified or not, or alternatively in other forms of respiratory systems, such as for example VPAP (Variable Positive Airway Pressure) systems, BiPAP (Bi level Positive Airway Pressure) systems, or with a ventilator, high-flow therapy system, and are described herein generally with reference to CPAP therapy by way of example only.

Nasal Mask Interface with Above-Ear Headgear

Figure 2A:
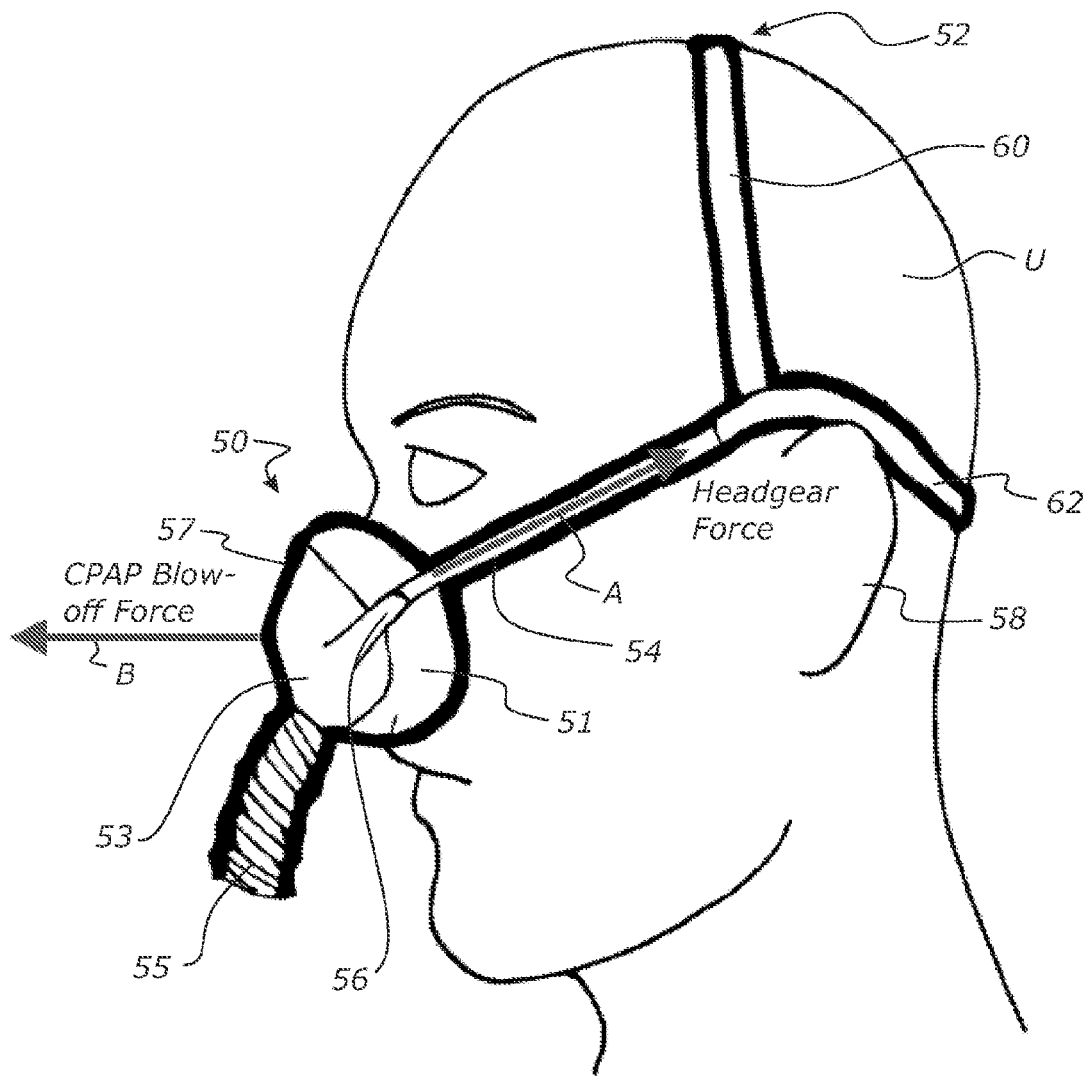
FIG. 2A is a schematic diagram of a nasal mask interface secured to the head of a user with an over-the-ear headgear configuration.
Figure 2B:
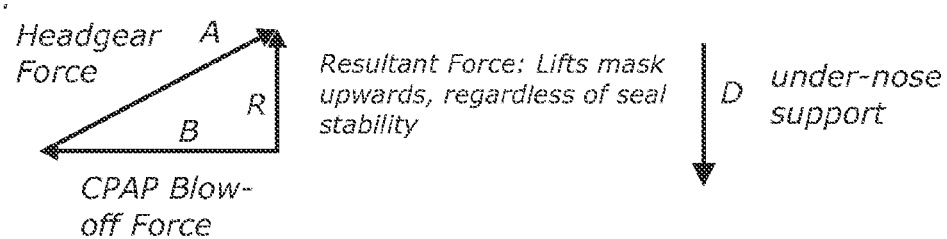
FIG. 2B shows a force diagram relating to the forces experienced by the nasal mask interface during use.

Referring to FIGS. 2A and 2B, a user U is depicted wearing a nasal mask interface 50 in accordance with an embodiment. The nasal mask interface 50 comprises a nasal mask including a seal 51 and a seal housing 53. The interface also includes headgear 52 for securing the mask to the wearer. Typically the interface also comprises a flexible supply conduit or tube 55 from the mask such as from a central connection at the front or underside of the mask, which is integral with or connects to the supply conduit 12 of the CPAP or other respiratory system. The conduit 55 may connect directly to the mask or indirectly via a connector or conduit frame such as, but not limited to, a straight connector or a swivel elbow 34, which may swivel relative to the mask or seal housing so that the path of the conduit relative to the positioning of the mask on the face of the patient can adapt to the sleeping position of the patient.

As will be explained later, the mask may include a limited flow outlet or vent (or bias flow outlet or vent) 57 for providing gas washout from the interface. The outlet 57 may be in the form of a collection of small apertures. The outlet may be provided on the seal housing 53 as shown, conduit connector or frame such as an elbow or straight connector, or elsewhere on the interface.

In this embodiment, the nasal mask is secured to the user U by headgear 52 that extends above the user's ears. By way of example, the headgear 52 comprises side straps 54 that connect to opposing sides of the nasal mask interface 50 at attachment points 56 (only one side visible) and which extend along the sides or cheeks of the user's face, and over the user's ears 58, and connect to one or more other straps or strap portions. The headgear 52 in this embodiment also comprises a top or crown strap 60 that extends over the user's head or crown and a back or rear strap 62. The side straps 54 are integrally formed or otherwise connected to the top 60 and back strap 62 as will be appreciated by a skilled person. In one embodiment the headgear straps are formed of or comprise a flexible breathable material such as Breath-o-Prene® breathable neoprene material, or neoprene material, or similar. In some embodiments, the headgear may be automatically adjusting headgear, examples of which will be explained later.

The depicted above-ear headgear 52 with single side straps 54 attaching to respective side attachment points or locations on the nasal mask interface 50 is a generally desirable configuration from a comfort viewpoint relative to a headgear configuration with a pair of upper and lower side straps that connects to a nasal mask interface having a T-piece frame. The above-ear single side strap headgear configuration 52 depicted in FIG. 2A does not require a T-piece frame extending up to the user's forehead and also eliminates the requirement for two pairs of upper and lower side straps, one pair extending over the user's ears from the top part of the T-piece frame at the user's forehead, and the other pair extending from the nasal mask interface below the user's ears, as previously explained.

Referring to FIGS. 2A and 2B, while the above-ear single side strap headgear configuration 52 is preferable from a comfort viewpoint relative to a headgear that is secured to a T-piece frame, it has been discovered that in use the forces acting on the nasal mask interface during flow therapy in which the mask is delivering gases at positive pressure to the user's nose, the nasal mask tends to ride, slide or slip up the user's face, which can impact on the robustness of the sealing about the user's nose and create leaks or leak paths. The riding up of the nasal seal can also be distracting and uncomfortable to the user. It has been discovered that the nasal mask interface experiences a substantially diagonal force represented by vector A along the general direction of the side straps between a user's nose and above the ear from each side strap, and a counteracting substantially horizontal blow-off force B forcing the nasal interface substantially horizontally away from the user's nose and face when a flow of positive pressure gases is being delivered to the wearer in use. The resultant force R of the headgear force A and blow-off force B acting on the nasal mask interface in a substantially vertical resultant force represented by vector R.

As will be explained with reference to the embodiments below, the nasal mask interface of this disclosure is provided with a nasal seal having an internal under-nose support that is configured contact or engage under the user's nose to generate an opposing downward force D that at least partially counteracts, resists or otherwise mitigates the resultant force R generated by the headgear force A and blow-off force B to thereby stabilize the nasal mask in place over the user's nose during use and prevent its tendency to slide or otherwise move up the user's face from its initially secured position prior to gas delivery being initiated.

Figure 3:
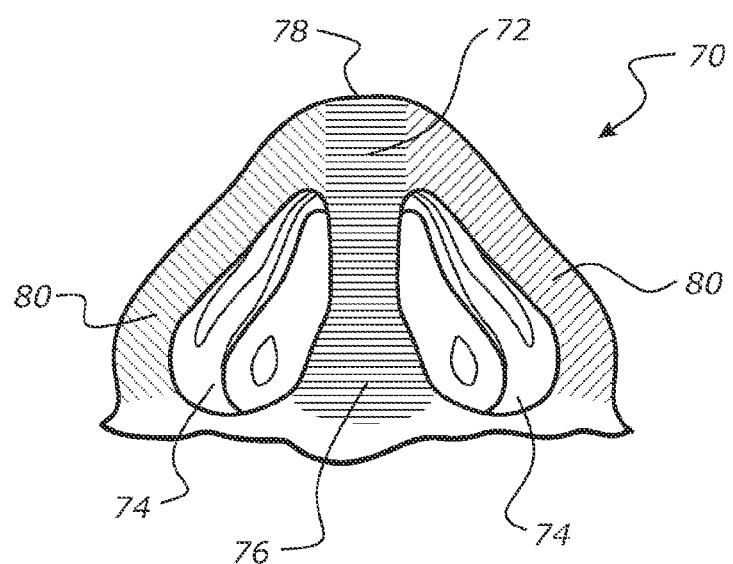
FIG. 3 is a schematic diagram of the nasal anatomy of the under-nose surface of a user's nose.
Figure 4:
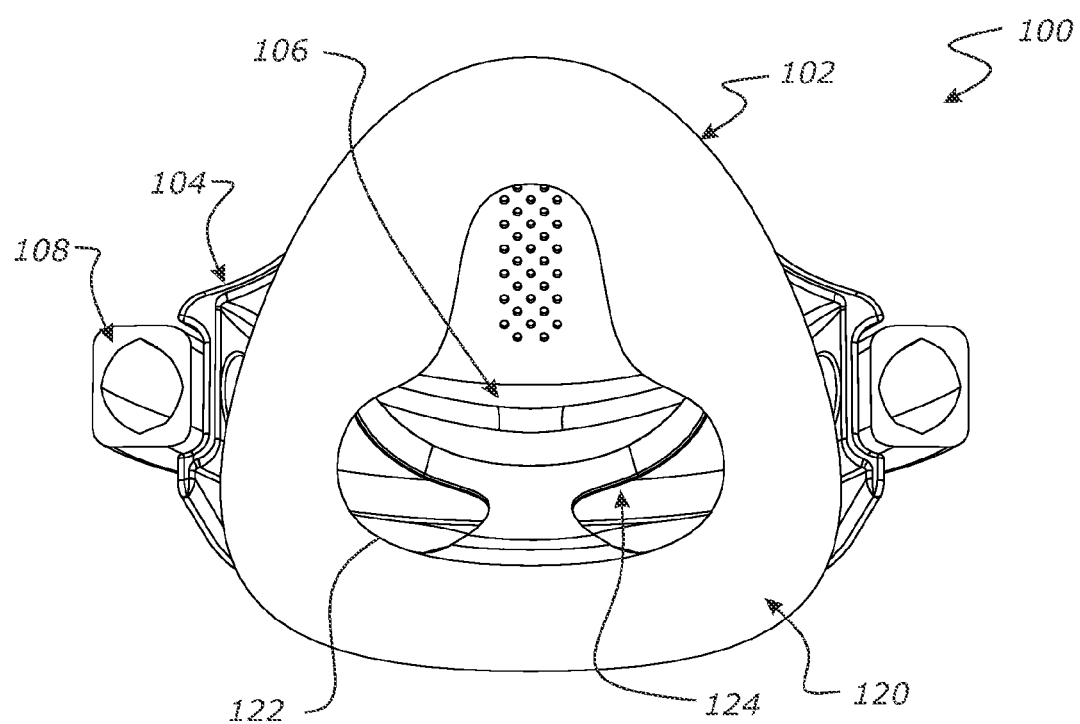
FIG. 4 is a front or face-contacting side (or wearer side) view of a nasal mask interface or assembly in accordance with a first form of a first embodiment, and showing a nasal seal with an under-nose support configuration with a central extension, seal housing and headgear frame of the assembly.
Figure 5:
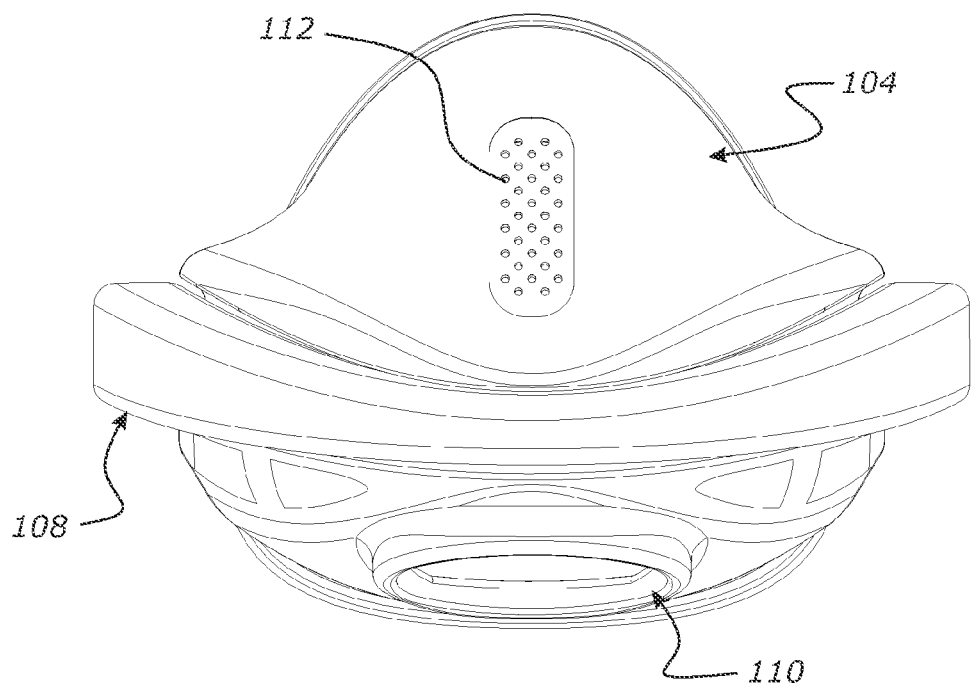
FIG. 5 is a rear or outer side view of the nasal mask interface of the first embodiment.
Figure 6:
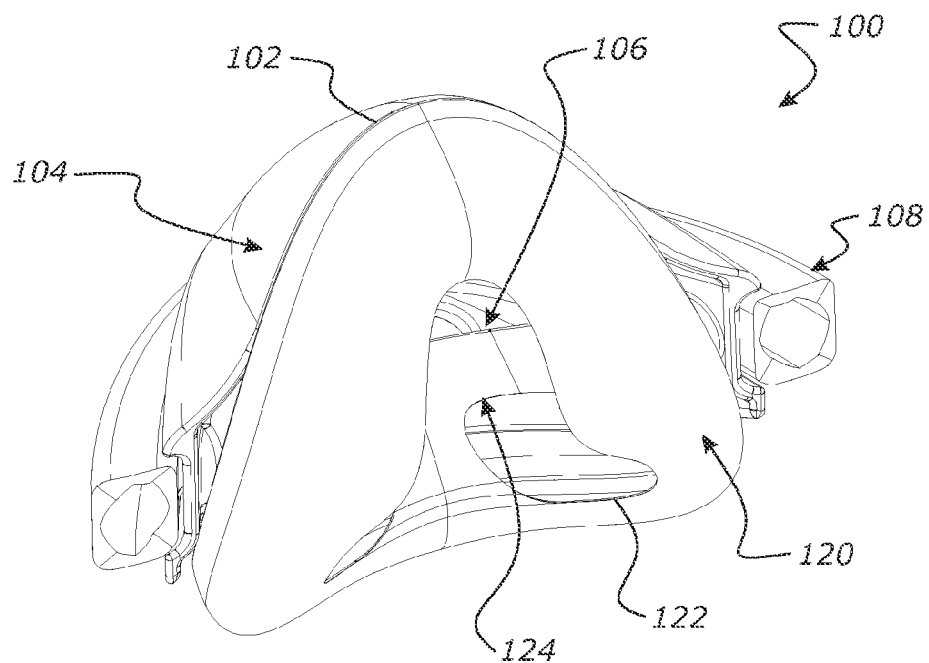
FIG. 6 is an upper front side perspective view of the nasal mask interface of the first embodiment.
Figure 7:
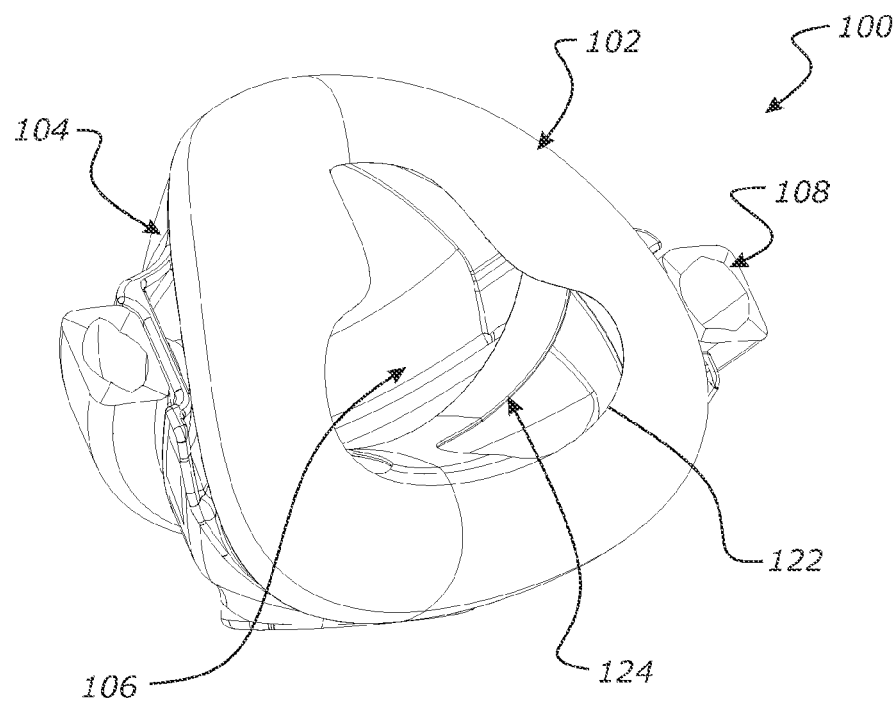
FIG. 7 is a lower front side perspective view of the nasal mask interface of the first embodiment.
Figure 8:
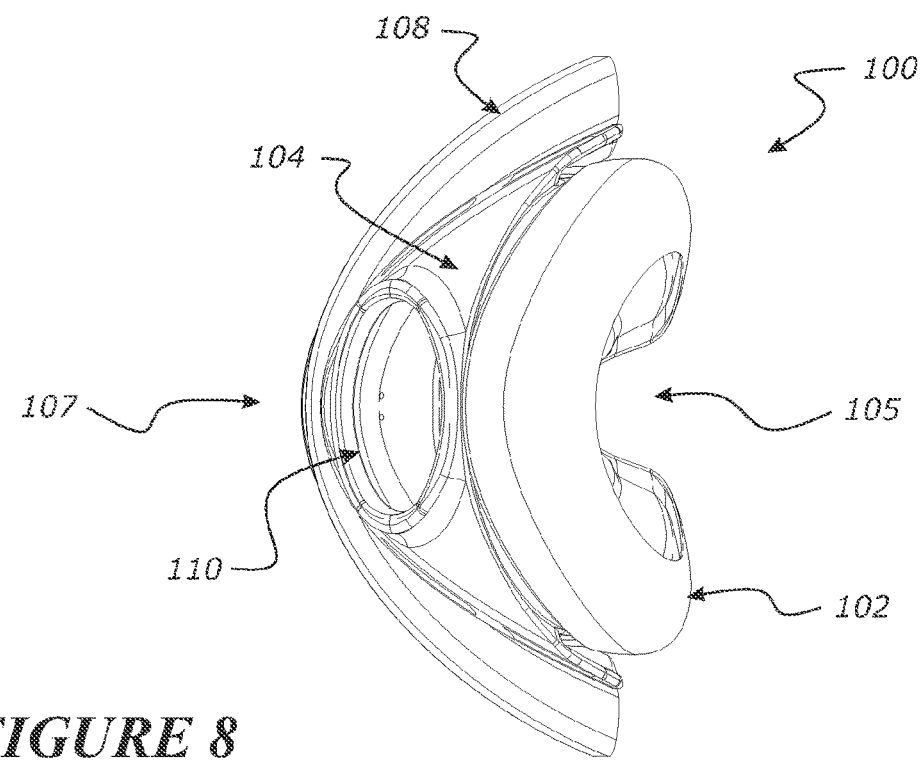
FIG. 8 is an underside view of the nasal mask interface of the first embodiment.
Figure 9:
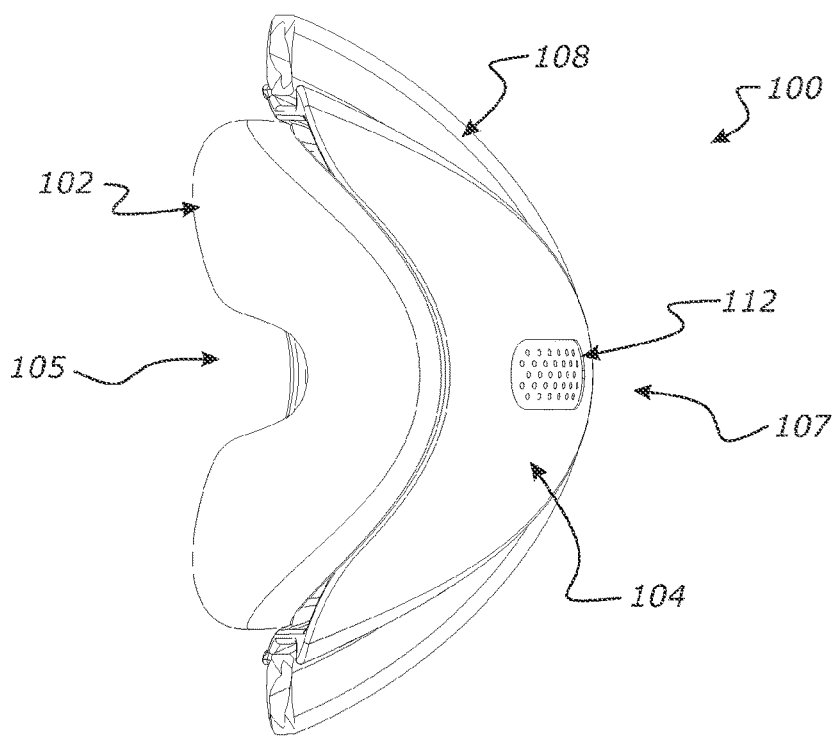
FIG. 9 is a top view of the nasal mask interface of the first embodiment.

Referring to FIG. 3, the under-nose support of the nasal mask assembly is configured to contact at least a portion or portions of the under-nose surface 70 of the user's nose when wearing the mask. The anatomy of the under-nose surface of a user's nose is generally defined by the central columella region 72 of the septum that extends between and divides the nostrils 74 from the base 76 to the tip 78 of the nose and the left and right alar rim regions 80. The columella 72 and alar regions 80 generally define the contactable skin surfaces of the underside of the user's nose about the nostrils or nare openings 74.

As will be explained in further detail with reference to the following example embodiments, the under-nose support of the nasal mask interface is configured to extend within the mask cavity that receives the user's nose in use and has a contact surface that is configured to contact at least a portion of the under-nose surface of the user's nose but without obstructing or completely obstructing the user's nostrils. Depending on the size of the user's nose, the under-nose support contacts a portion or portions of the under-nose surface without any obstruction of the user's nostrils as best case, or worst case only partially obstructs one or both nostrils.

Various embodiments of the nasal mask interface and nasal seals of the interface with the under-nose support will be described in the following. It will be appreciated that such nasal seals can be employed or used with varying different nasal interface assemblies and headgear configurations but are particularly suited to headgear configurations that generate a resultant upward lift force in use that causes the nasal mask to slide or ride up the user's face such as, but not limited to, the above-ear headgear described and shown with reference to FIG. 2A.

Various embodiments of a nasal seal will be described, and in some embodiments with reference to an overall nasal mask interface assembly including any one or more of a seal housing, conduit frame, headgear frame or yoke, and/or headgear. It will be appreciated that the various embodiments of the nasal seal described may also be interchangeably used in various suitable interface assemblies, and that the interface assembly examples and alternatives described in the context of one embodiment are also applicable to other embodiments of the nasal seals to be described. In general, it will be appreciated that the various components of the various embodiments may be interchanged and/or combined with each other to form alternative configurations, First Embodiment—Nasal Seal with Under-Nose Support Having a Central Extension or Connecting Portion Overview Referring to FIGS. 4-22, a first form of the first embodiment of the nasal seal and a nasal seal interface assembly comprising the nasal seal will be described in further detail. An alternative second form of the first embodiment nasal seal will also be described with reference to FIG. 23.

Referring to FIGS. 4-10, the first embodiment nasal mask interface assembly 100 comprises a flexible nasal seal 102 that is connected or connectable to a rigid (or at least more rigid relative to the nasal seal) seal housing 104 to define a mask cavity generally indicated at 106 that will receive the user's nose and a supply of gases for delivery to the user's airway via their nares or nostrils as will be appreciated by a skilled person. The rigid seal housing or shell 104 may either be directly connectable to headgear straps via one or more attachment or connection points or assemblies provided on the seal housing or alternatively indirectly connectible to headgear via a headgear frame component 108 mounted or provided on the seal housing. In this embodiment, the seal housing 104 is provided with an inlet opening or aperture 110 that is configured to connect to a flexible gases delivery conduit 55 of the type previously described to deliver a heated humidified gases stream from a respiratory apparatus such as a CPAP device or similar. The seal housing 104 in this embodiment is also provided with a collection of one or more apertures or holes in the form of an exhaust or bias-flow vent 112.

The flexible nasal seal 102 comprises a face-contacting surface 120 having an inner peripheral edge 122 that defines a nose-receiving opening into the mask cavity 106 for receiving the user's nose in use. In use, the nasal mask interface 100 is secured against the user's face using headgear such that the contacting surface 120 of the nasal seal 102 envelops or circumscribes the user's nose and sealingly engages about the user's nose such as against the cheek surfaces and/or lateral side surfaces of the user's nose, the upper lip region below the user's nose, and across the nasal bridge region of the user's nose. In this embodiment, the nasal seal 102 also comprises an under-nose support 124 that extends internally within the mask cavity 106 at a location or position substantially rearward of or relative to the face-contacting surface 120. The under-nose support 124 comprises a contacting surface that is configured or oriented to contact at least a portion of the under-nose surface of the nose of the user when in use to at least partially counteract the upward lift resultant force R generated by the blow-off force B and headgear force A as previously described.

Figure 10:
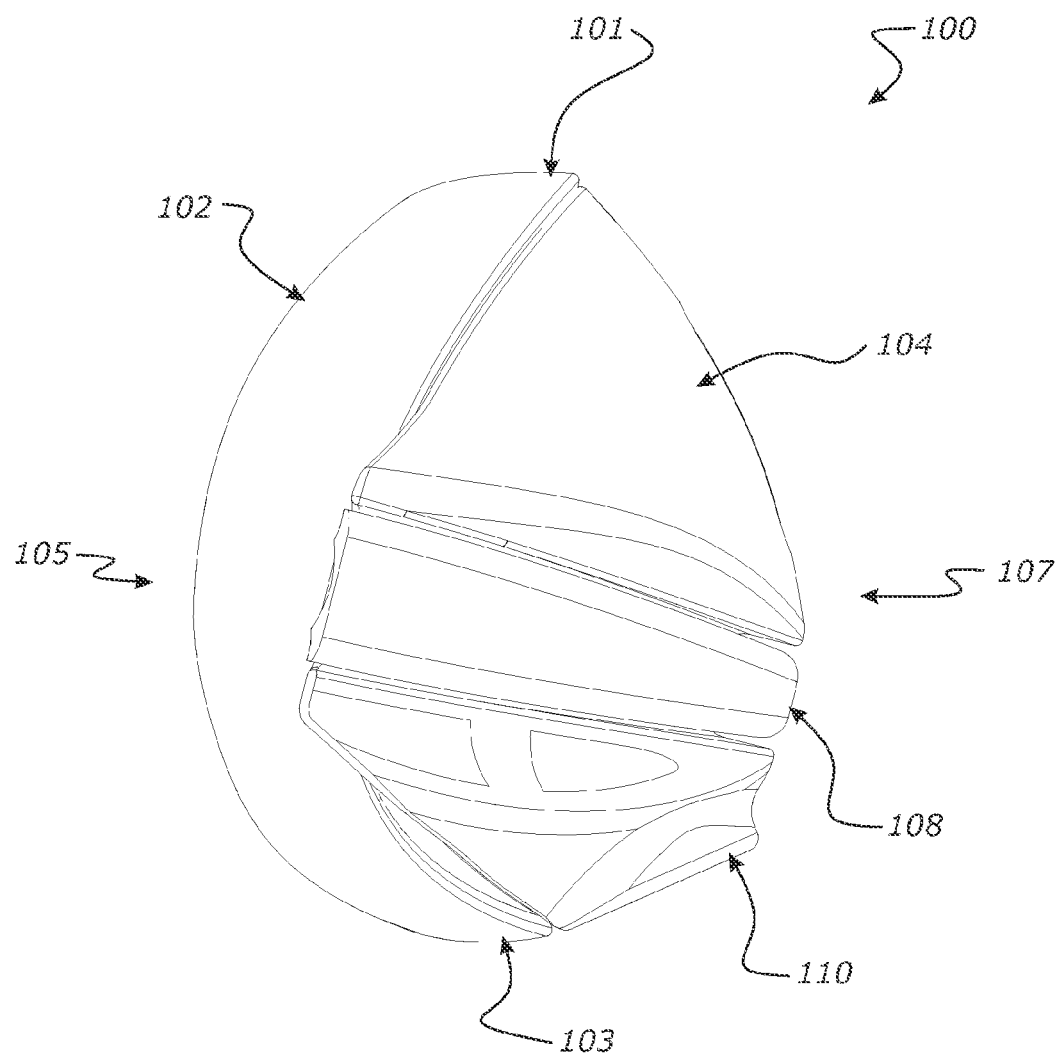
FIG. 10 is a side elevation view of the nasal mask interface of the first embodiment.

Referring to FIG. 10, the top of the nasal mask interface is indicated at 101 and the bottom at 103, the face-contacting side or wearer side of the nasal mask interface is indicated at 105 and the outer or exterior side of the nasal seal is indicated at 107, for future reference. The seal housing 104, headgear frame 108 and nasal seal 102 will each be described in further detail in the following.

Seal Housing and Frame

Figure 11:
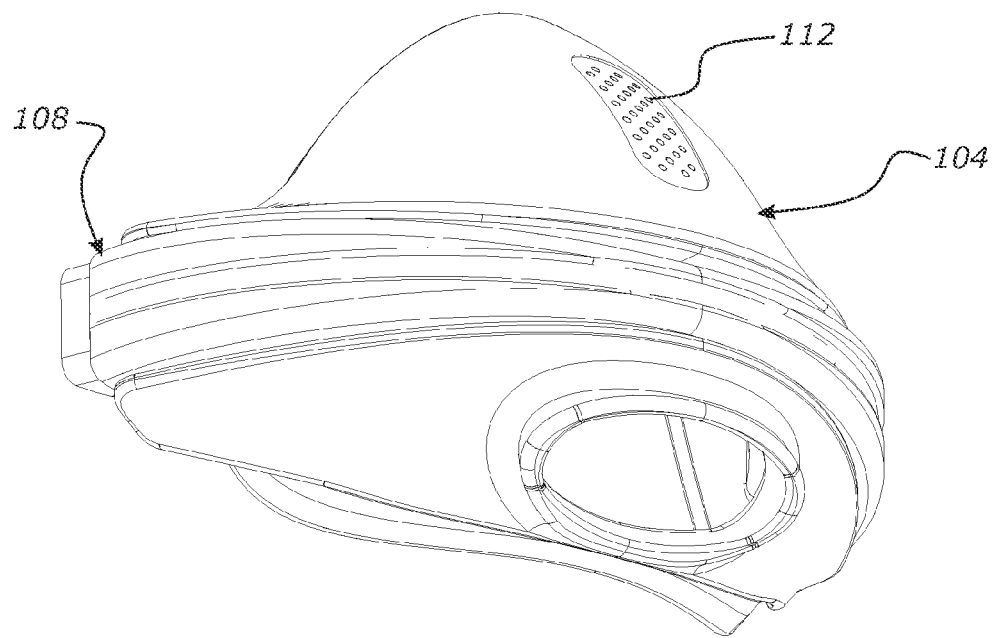
FIG. 11 is an outer side bottom perspective view of the seal housing and headgear frame of the nasal mask interface of the first embodiment.
Figure 12:
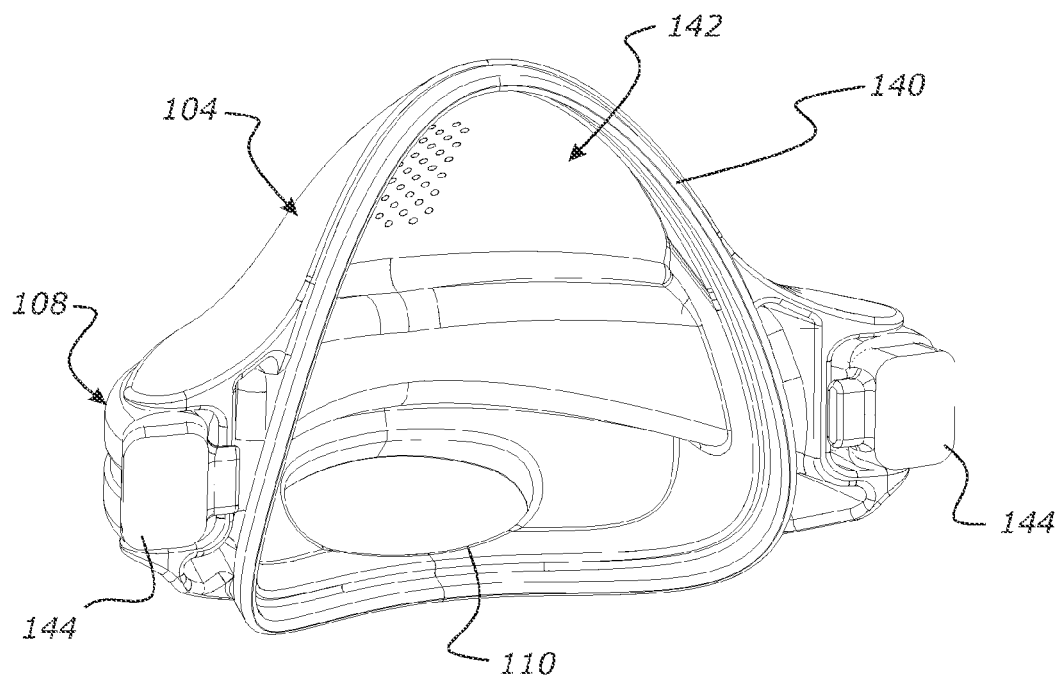
FIG. 12 is a wearer side upper perspective view of the seal housing and headgear frame of the nasal mask interface of the first embodiment.

Referring to FIGS. 11 and 12, the seal housing or shell 104 is defined by an opening generally indicated at 140 that connects or couples to the nasal seal 102 on the wearer side of the nasal mask interface 100 and extends to the exterior or outer side of the nasal interface comprising the inlet 110 and exhaust vent 112 shown in FIG. 11. The seal housing 104 is a substantially hollow component that is generally shaped to provide or define a cavity or volume indicated at 142 for receiving the gases stream from the inlet 110. The seal housing cavity 142 forms part of the overall mask cavity 106 when the seal housing 104 is assembled to the nasal seal 102. In this embodiment, the seal housing 104 generally tapers inwardly in shape as it extends rearwardly from the opening 140 to the exterior side.

In this embodiment, the exhaust vent 112 comprises collection or plurality of small holes or apertures that extend through the seal housing and which collectively define a vent 112 in the central middle to upper region of the seal housing 104. It will be appreciated that in other embodiments, the vent or exhaust holes 112 may be omitted from the seal housing and could be provided at another location in the respiratory circuit, such as in a connecting conduit or swivel elbow coupling the gases conduit to the inlet 110 of the nasal masking interface or elsewhere along the breathing circuit.

In this embodiment, the inlet aperture or port 110 is provided in the lower or bottom region of the seal housing 104 and is centrally located, although this location is not essential. It will be appreciated that the flexible gases conduit may be directly coupled via a connecting conduit to the inlet 110 or alternatively indirectly coupled via a straight connector or conduit frame, connecting elbow such as a swivel elbow, ball joint connection or similar.

In this embodiment, the nasal seal 102 is removably or releasably coupled or connectable to the seal housing 104 such that the nasal seal may be removed for cleaning or replacement if required. In this embodiment, the opening 140 of the seal housing 104 is provided with a peripheral ridge or extension that is configured to engage or receive a complimentary peripheral channel provided on the outer side of the nasal seal 102 as will be explained later to thereby releasably couple the components together. Once assembled, and secured to the user's nose, the nasal mask interface is substantially sealed and defines a substantially enclosed mask cavity 106.

In alternative embodiments, it will be appreciated that the nasal seal 102 may be permanently or semi-permanently connected or coupled to the seal housing 104. By way of example, the outer side of the nasal seal 102 distal to the face-contacting side may be over molded or otherwise secured or adhered to or at the opening 140 of the seal housing 104 in alternative embodiments.

Whether the nasal seal 102 is removable or permanently coupled to the seal housing 104, it will be appreciated that the edge or opening 140 of the seal housing is shaped and dimensioned to compliment or match the corresponding outer side edge or connecting portion at the outer side of the nasal seal 102 about the periphery of the nasal seal interface.

The seal housing 104 may be formed with any suitable material that provides a rigid housing or which is at least rigid relative to the flexible nasal seal. In this embodiment, the seal housing is typically formed of a plastic polymer such as polycarbonate or similar. In alternative embodiments, the seal housing may be semi-rigid. In one example, the seal housing may be formed from the same type of material as the nasal seal (e.g. silicone material) but may be substantially thicker so as to be generally less flexible or more rigid than the nasal seal.

With reference to FIG. 11 in particular, in this embodiment the nasal mask interface comprises a headgear frame component 108 in the form of a yoke that extends laterally about the exterior side of the seal housing 104 between the vent 112 and inlet 110 from one side of the seal housing to the other. In this embodiment, the frame component 108 is removably received within a complimentary channel formed into the surface of the seal housing 104 on the exterior side, although the frame may alternatively be permanently fixed or coupled into the receiving channel. As shown in FIG. 12, the frame component 108 provides single headgear attachment points 144 on the left and right sides of the seal housing 104. This provides a single connection point or location on each side of the seal housing for connecting or coupling to a respective single side strap of a headgear system, such as an above-ear headgear system as described with reference to FIG. 2A. In alternative embodiments, it will be appreciated that the frame 108 may be omitted, and that the seal housing may provide headgear attachment points on each side of the seal housing that are either integrally formed with the seal housing or otherwise provided on the sides of the seal housing for connecting to a headgear system such as the single side strap headgear system.

Nasal Seal

Referring to FIGS. 13-22, the nasal seal component 102 of the nasal mask interface 100 of a first embodiment will be described in further detail. The nasal seal 102 is flexible and soft, and may be formed of a silicone material or other suitable material.

Figure 13:
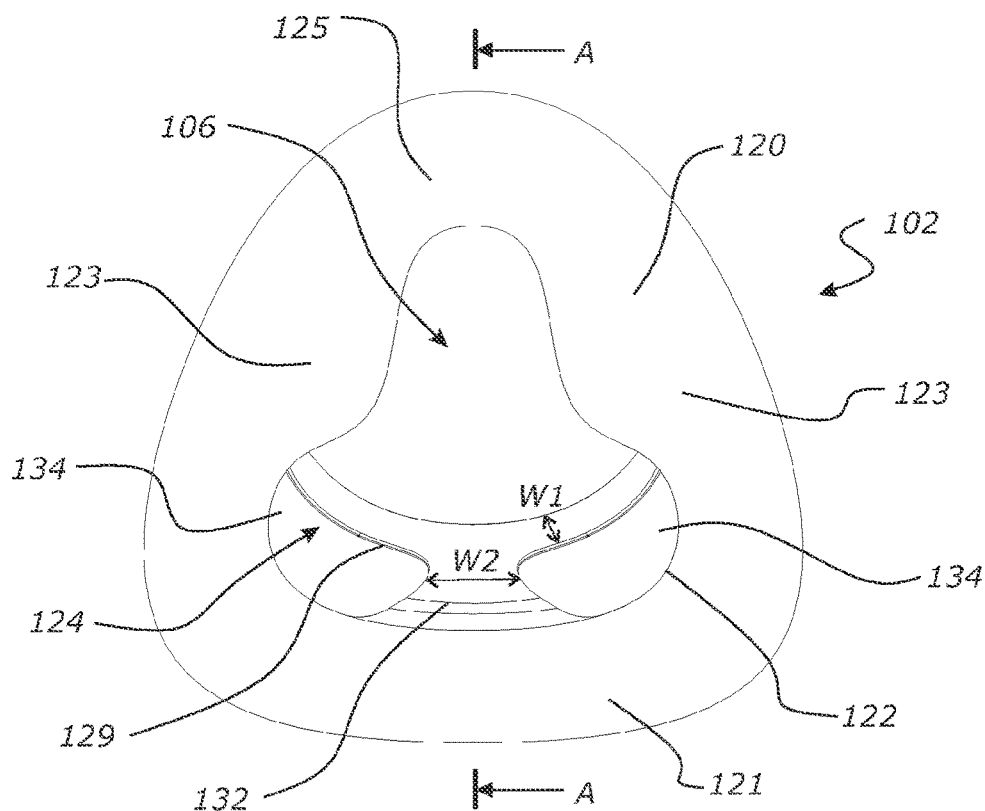
FIG. 13 is a front view from the face-contacting side (or wearer side) of the nasal seal of the nasal mask interface of the first embodiment.

Referring to the face-contacting or wearer side of the nasal seal 102 shown in FIG. 13, the contacting surface generally indicated at (120) is configured to seal about the user's nose, including across the bridge of the user's nose. In this embodiment, the contacting surface 120 circumscribes the nose and seals about the nose of the user. In this embodiment, the contacting surface portion of the nasal seal comprises an upper lip region generally indicated at 121 that is configured to contact the upper lip region of the face of the user such as at a location above the vermillion border and below the flares. The contacting surface 120 also comprises left and right cheek or side regions 123 that extend between the upper lip region 121 at the bottom of the seal 102 and a region 125 corresponding to or proximal to the nasal bridge region at the top of the seal 102. The cheek regions 123 of the contacting surface 120 are configured to contact the medial cheek surface of the user and/or lateral nose surface of the user on either side of the nose. The nasal bridge region 125 of the contacting surface 120 is configured to extend over nose and contacts the nasal bridge region of the user's nose and connects the two cheek regions 123. The overall shape and configuration of the contacting surface 120 is configured to sealingly conform to the contour of the user's face about the nose and to sealingly engage about the user's nose when secured to the user's head via headgear and when the nasal mask interface receives flow of gases. The nasal seal 102 can be considered to be of the inflating type as under pressure the seal urges the face-contacting surface 120 against the face of the user and deforms to substantially seal against the facial contours of the user, including one or more of the upper lip, the medial cheek, the lateral nose and the bridge of the nose.

As previously discussed, the contacting surface 120 of the nasal seal 102 terminates in an inner peripheral edge 122 that defines a nose-receiving opening into the mask cavity when the seal 102 is assembled to the seal housing 104.

Figure 21:
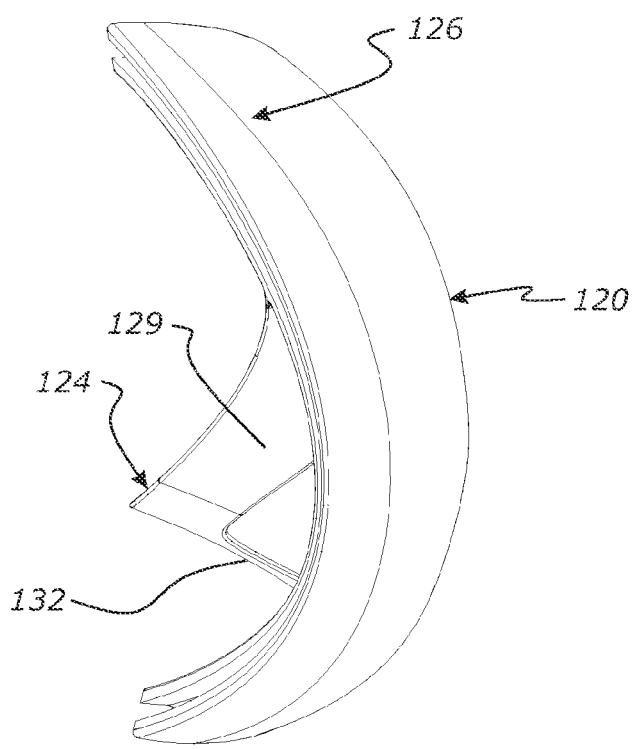
FIG. 21 is a side elevation view of the first embodiment nasal seal.
Figure 22:
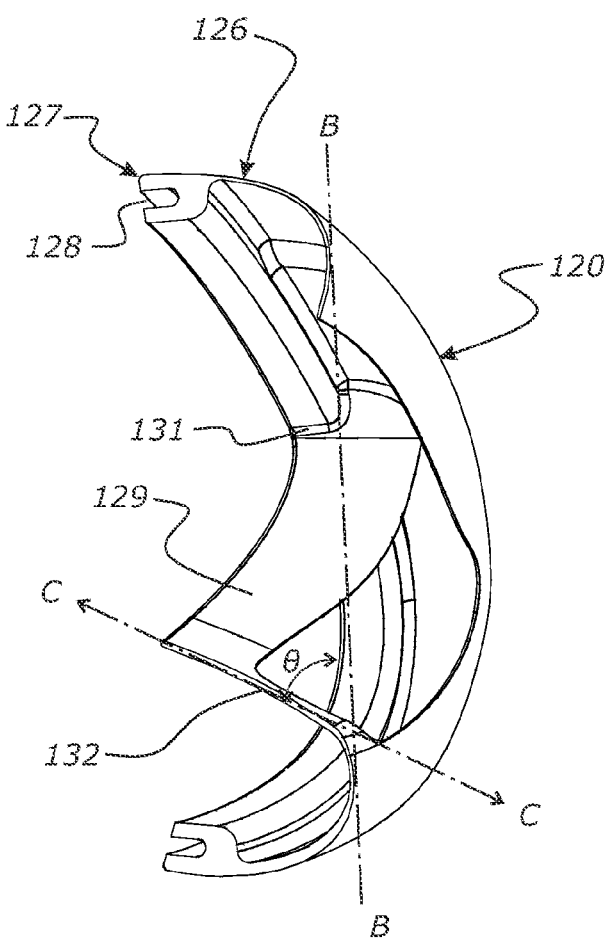
FIG. 22 is a cross-sectional view of the first embodiment nasal seal through a central line A-A of FIG. 13.

Referring to FIGS. 21 and 22, the nasal seal 102 is substantially defined by the face-contacting surface portion 120 and a sidewall portion 126 that extends rearwardly from the contacting surface 120 about the periphery of the seal and which terminates at a connecting edge generally indicated at 127 at the exterior or outer side of the seal that couples or is connectable to the opening 140 seal housing 104. As previously described, in this embodiment the nasal seal 102 is releasably connectable to the seal housing and the terminating edge of the sidewall 126 comprises a peripheral channel 128 that is configured to engage with a complimentary peripheral ridge or extension provided at the opening 140 of the seal housing 104. As previously discussed, in alternative embodiments, the flexible nasal seal 102 may be permanently or semi-permanently connected or coupled to the seal housing 104 such as via over molding, welding or other connecting methods. In further alternative embodiments, interface may be provided with a semi-rigid or rigid clip component that is shaped to correspond to the connecting edge 127 on the exterior or outer side of the nasal seal. In such embodiments, the connecting edge 127 of the seal may be overmolded or otherwise permanently connected to the rigid clip component, so as to provide a rigid edge or portion at the outer side of the seal. The rigid clip component may be configured to engage or otherwise connect with a complementary base or housing component to thereby couple the nasal seal to the base or housing.

As shown in FIG. 22, the face-contacting surface 120 of the nasal seal forms a flange that curls or extends inward from the sidewall 126 portion of the nasal seal. In this embodiment, the region at or toward the terminating edge 127 of the sidewall 126 may be a thickened region relative to the remainder of the sidewall and contacting surface portions of the nasal seal, so as to accommodate the connecting channel 128 or to otherwise provide some stability at the outerside to the overall shape of the nasal seal.

As discussed, the nasal seal 102 is formed of a flexible and soft material such that nasal seal 102 is flexible relative to the rigid housing 104. By way of example, the seal 102 may be formed of silicone material or similar.

Under-Nose Support of Nasal Seal

In this embodiment, the nasal seal 102 comprises an under-nose support 124 (or nasal sling) that at least extends or is suspended laterally across the nasal seal between the sides of the seal and within the mask cavity 106 when the nasal seal 102 is assembled to the seal housing 104. The under-nose support 124 is configured to contact at least a portion of the under-nose surface of the user's nose so as to counteract any resultant lift force created when the nasal mask is worn and in use as previously discussed.

In this embodiment, the under-nose support at least extends laterally across the nasal seal between the opposing left and right sides of the nasal seal. As shown, the under-nose support is disposed or located behind or rearward of the nasal seal opening 106. The under-nose support 124 is fixedly connected to the nasal seal in that it is not removable. In one form, the under-nose support 124 is integrally molded within the nasal seal. In alternative forms, it will be appreciated that the under-nose support part or portion of the nasal seal 102 may be formed separately and then fixedly coupled within the nasal seal such as via an adhesive or welding, or the like, or it could be connected to the seal housing.

Figure 14:
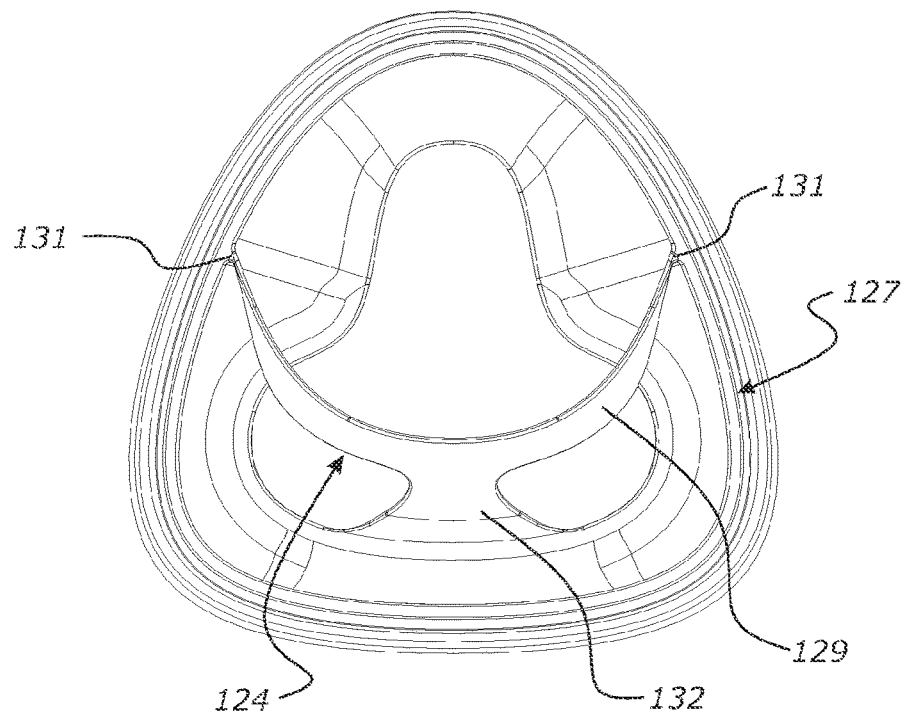
FIG. 14 is a rear view from the outer side of the first embodiment nasal seal.
Figure 15:
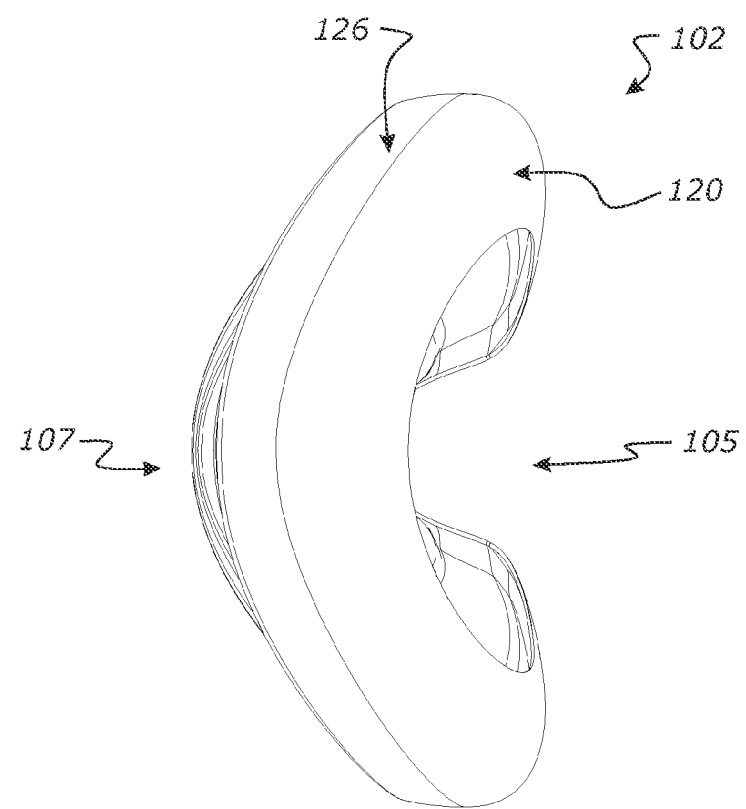
FIG. 15 is a top view of the first embodiment nasal seal.
Figure 16:
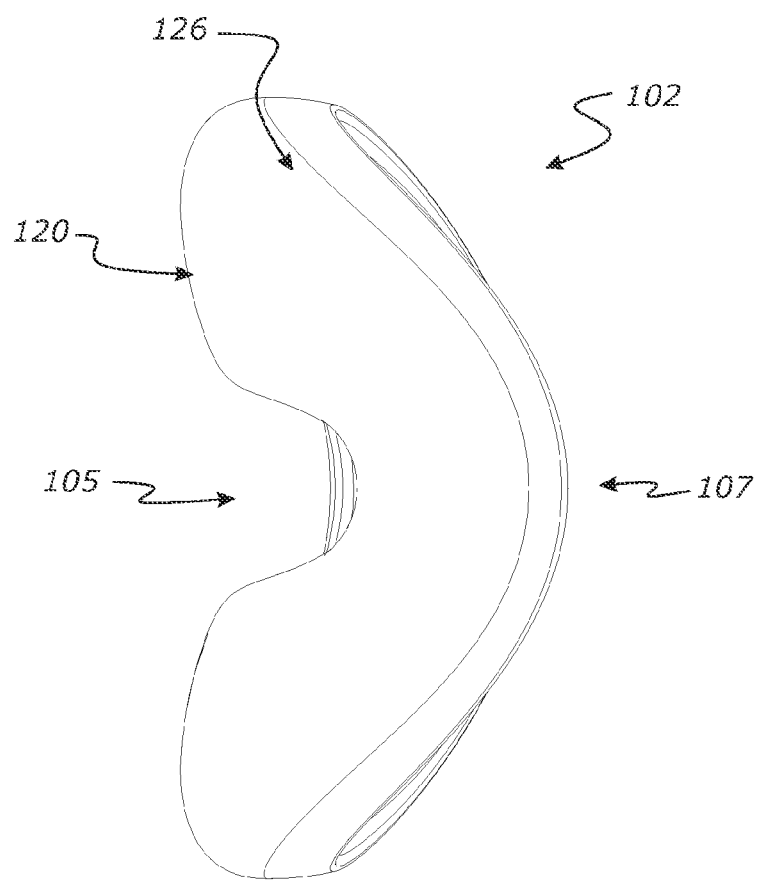
FIG. 16 is an underside view of the first embodiment nasal seal.
Figure 17:
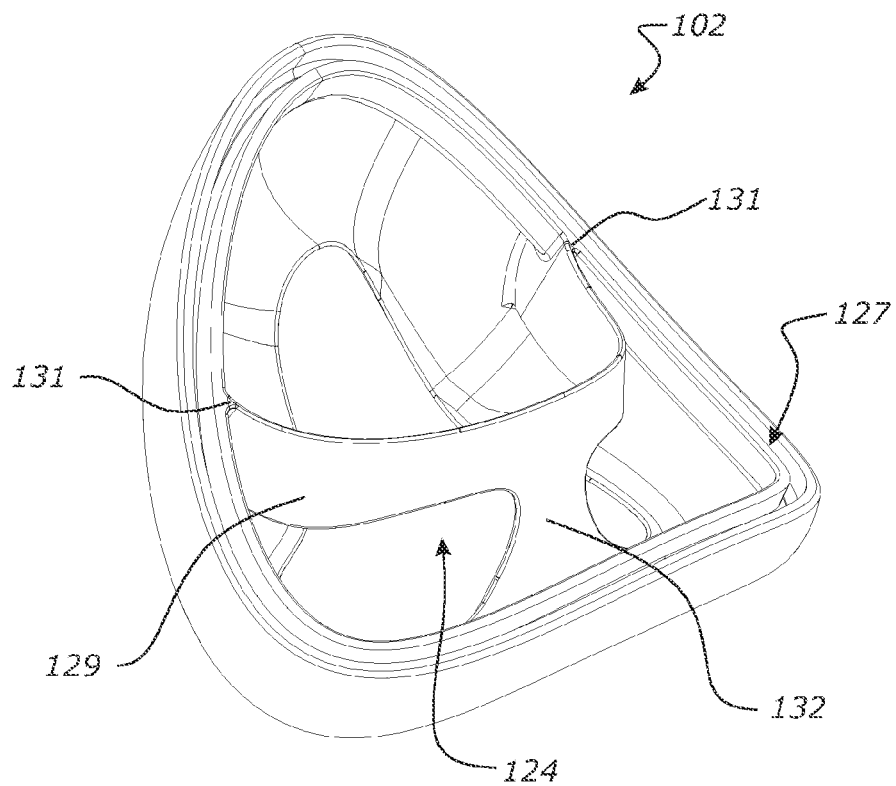
FIG. 17 is a first rear underside perspective view from the outer side of the first embodiment nasal seal.
Figure 18:
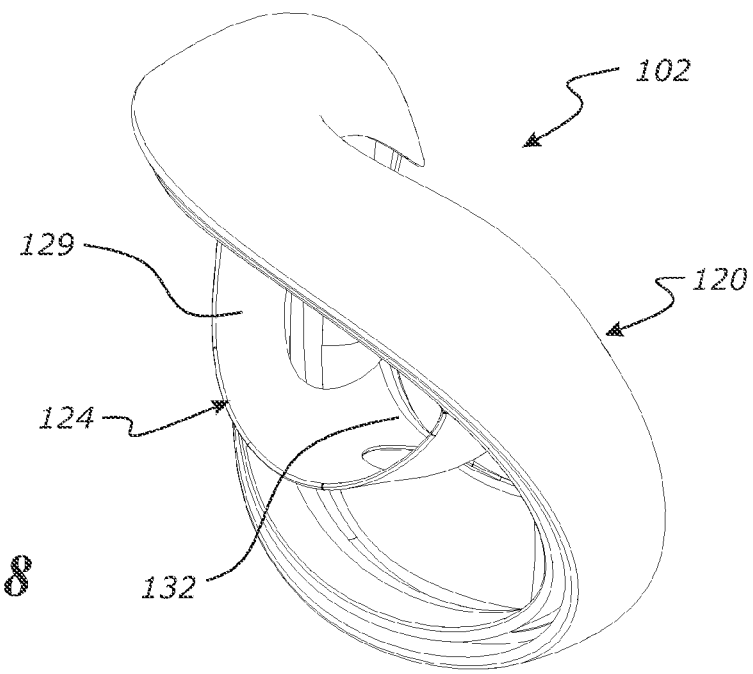
FIG. 18 is a second rear upper perspective view from the outer side of the first embodiment nasal seal.
Figure 19:
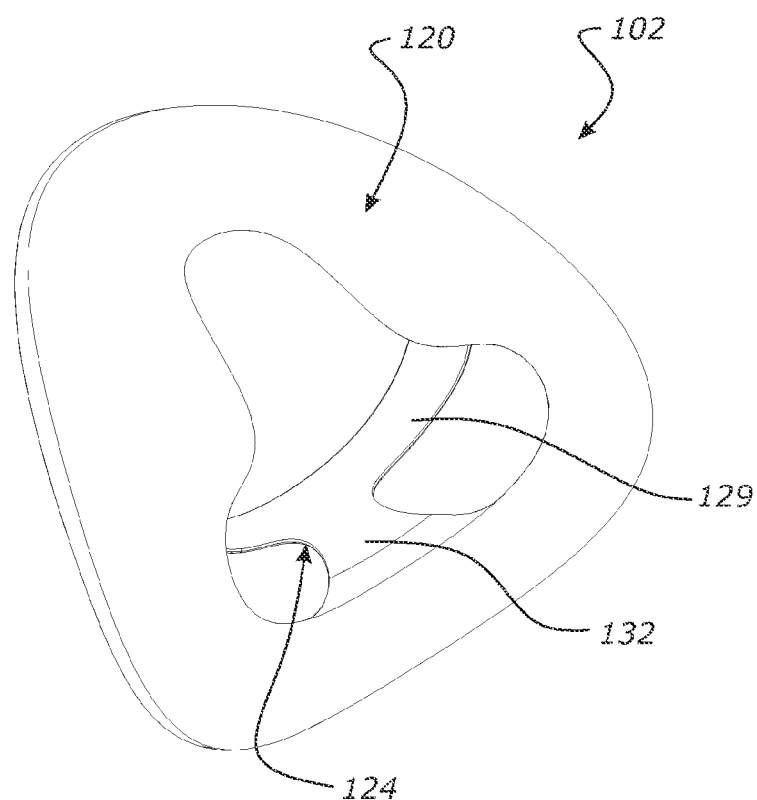
FIG. 19 is a first upper perspective view from the face-contacting side of the first embodiment nasal seal.
Figure 20:
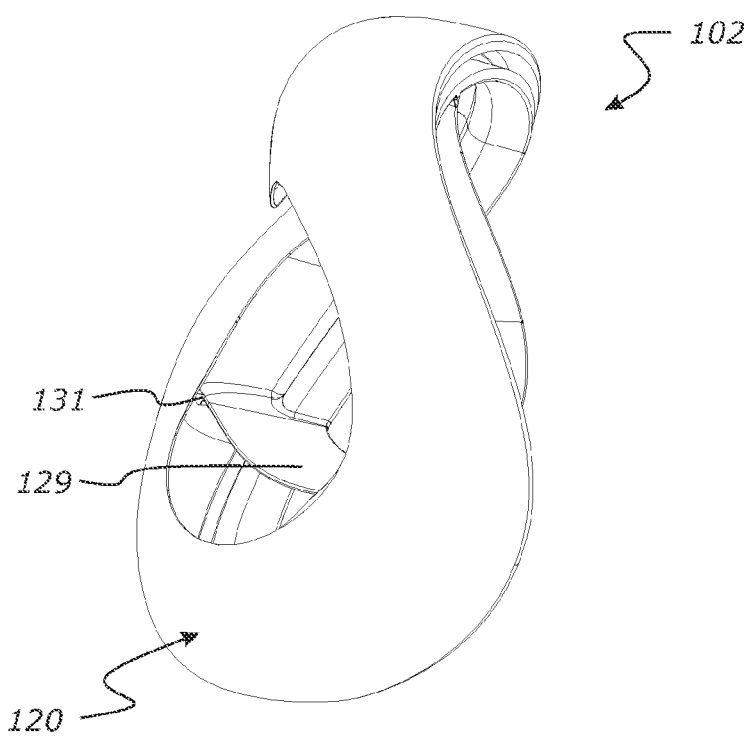
FIG. 20 is a second underside perspective view from the face-contacting side of the first embodiment nasal seal.

In this embodiment, the under-nose support configuration 124 comprises an elongate main lateral portion or band 129 that extends across and within the nasal seal, such as suspended between opposing sides of the seal. With reference to FIGS. 14, 17 and 22, the main lateral portion 129 of the under-nose support is connected or extends from the nasal seal at locations isolated or displaced from at least the peripheral opening edge 122 of the contacting surface 120, but also in this embodiment is entirely decoupled or displaced from the contacting surface 120 such that the lateral portion 129 does not inhibit or reduce the sealing engagement or deformability of the contacting surface 120 with the user's face in the cheek and/or lateral nose regions 123. In this embodiment, the main lateral portion 129 extends from or is connected at locations 131 on the inner surfaces of opposing sidewall 126 portions of the nasal seal rearwardly of the contacting surface 120. In this embodiment, the connecting locations 131 correspond with or include the terminating edge 127 of the sidewall 126, although this is not essential.

In this embodiment, the under-nose support 124 further comprises a central extension portion 132 that extends centrally from the main lateral portion 129 and is coupled or connected to or at the opening edge 122 of the contacting surface 120 in the upper lip region 121. In alternative embodiments, as will be explained later with reference to FIG. 23, the central extension portion 132 may alternatively be connected to a lower part of the upper lip region 121 of the contacting surface 120 below the opening edge 122 of the seal, or alternatively may be connected at a location at least partially or entirely displaced or isolated from the contacting surface 121, such as connected to a lower part of the sidewall 126 of the nasal seal that is rearward of the contacting surface 120.

The under-nose support 124 comprising main lateral portion 129 and central extension portion 132 provides a contact surface that is configured and/or orientated to contact at least a part of the under-nose surface of the user's nose in use. In this configuration, the main contact surface of the main lateral portion 129 is configured to engage with at least a portion of the tip of the under-nose surface of the user's nose, which may for example include the tip end of the columella 72 and portions of the alar rim 80 toward the tip of the nose (as shown in FIG. 3). The central extension portion 132 is configured to contact the columella 72 region of the under-nose surface of the user's nose, or at least a portion of the columella between the tip and base of the nose, but preferably the majority of the columella extending from the base. The ultimate contact surface area of the under-nose support depends on the shape and size of the user's nose. The configuration of the under-nose support is designed to contact the maximum portion or portions of the under-nose surface without substantially obstructing the user's nostrils 74 which tend to be aligned with the open spaces 134 on either side of the central extension portion 132 as shown in FIG. 13. Depending on the size and shape of the user's nose, the under-nose support 124 is generally configured to at best completely avoid obstruction of the user's nostrils, but at worst only partially obstruct one or both nostrils.

As shown, the contact surface of the under-nose support 124 is generally oriented and configured relative to the nasal seal so as to engage the under-nose surface of the user's nose. In this embodiment, the portions of the under-nose support 124 are integral thin webs or strips of the nasal seal formed during molding of the seal. For example, the thickness of the under-nose support transverse to its contact surface is significantly smaller than the corresponding width of the contacting surface at any location on the under-nose support. In one configuration, the thickness of the under-nose support portions may be substantially similar to the thickness of the seal in the region of the contacting surface 120 of the nasal seal.

In this embodiment, the width of the main lateral portion 129 of the under-nose support 124 may vary along its length between the opposing sides of the nasal seal. In this example, the width W1 of the main lateral portion 129 may progressively increase from the centre of the nasal seal toward each side. In this embodiment, the width W2 of the central extension portion 132 of the under-nose support 124 progressively increases in width W2 as it extends from the main lateral portion 129 to the contacting surface 120. In alternative embodiments, it will be appreciated that the width of either or both of the main lateral portions or central extension portions may be uniform along their length, or have alternative width profiles along their length.

Referring to FIG. 22, a central seal axis BB is defined as extending tangentially between the outer uppermost and lowermost contact points at the center of the contacting surface 120 when in a relaxed condition (e.g. not in use). As shown in FIG. 22, at least a portion (e.g indicated by axis CC extending coincident with the contact surface of the under-nose support portion(s) in the central region) of the contact surface of the under-nose support 124 in a central region of the under-nose support extends at an angle $\theta$ relative to seal axis BB such that the contact surface of the under-nose support is not parallel or aligned with the seal axis BB. In this embodiment, the contact surface in the central region of the under-nose support 124 is oriented at an angle offset from the seal axis BB in the range of approximately 30 to approximately 90 degrees, more preferably approximately 45 to approximately 75 degrees, and more preferably approximately 60 degrees. This angular orientation of at least the main nose contacting portion or surface of the under-nose support in the central region is configured to substantially align with the general or typical angular orientation of the under-nose surface of the user's nose when their nose is within the nasal seal.

As explained above, the under-nose support 124 in this embodiment is fixedly connected or is otherwise an integral component of the nasal seal 102. The accompanying drawings depict the nasal seal and its under-nose support 124 in a rest state, i.e. un-used. Like the contacting surface 120 of the nasal seal, the under-nose support 124 is also configured to be soft and flexible or pliable such that its shape and position may conform with a sling-like effect to the under-nose surface of the user's nose when the nasal mask interface is secured to a user's face in use or is otherwise worn.

Typically, the under-nose support is non-stretchable in any direction, although may have a degree of stretch in alternative embodiments.

Figure 23:
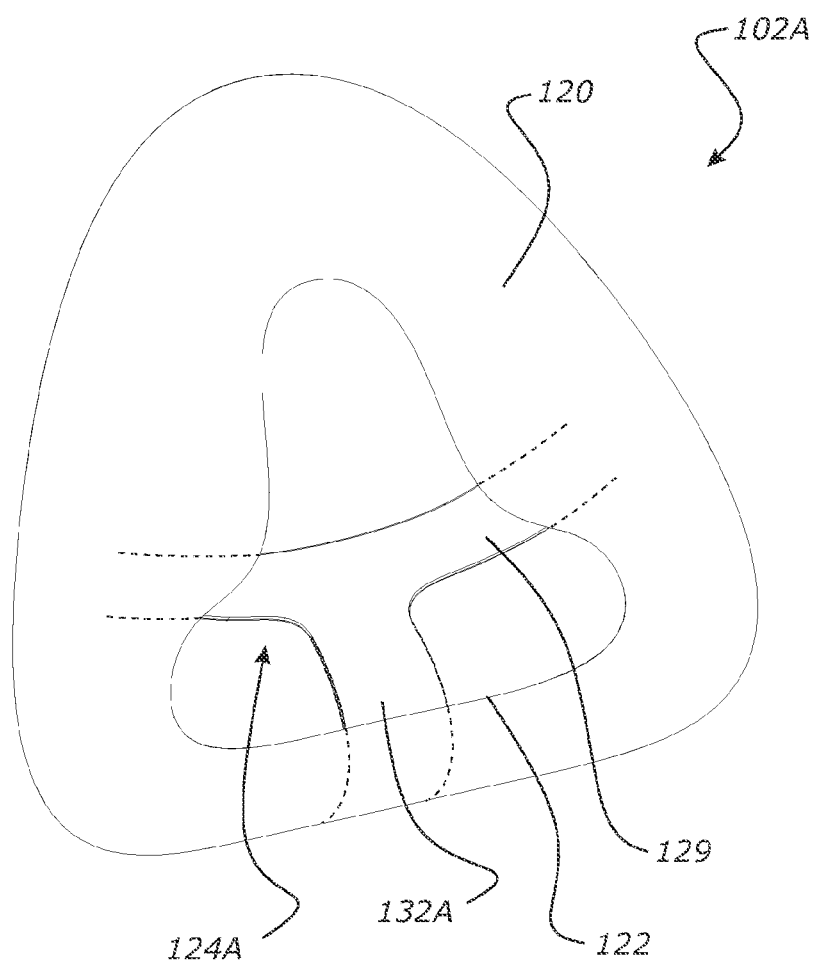
FIG. 23 is a front perspective view from the face-contacting side of a second form of the first embodiment nasal seal in which the under-nose support configuration is fully de-coupled or isolated from the edge of the face-contacting surface of the nasal seal.
Figure 24:
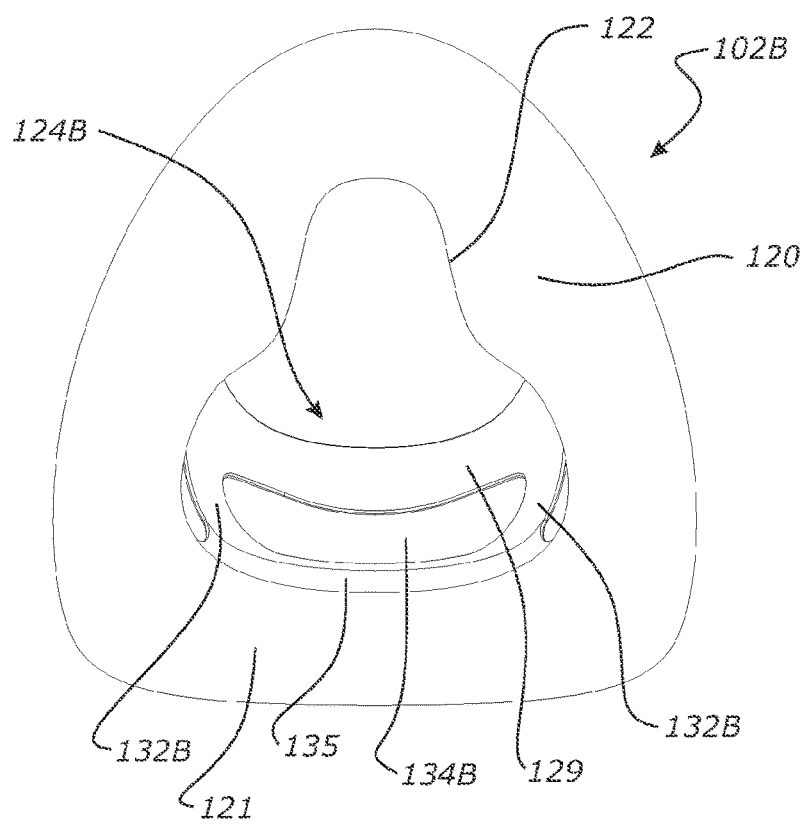
FIG. 24 is a front view from the face-contacting side of a first form of a second embodiment nasal seal having an under-nose support configuration with left and right side extension portions.
Figure 25:
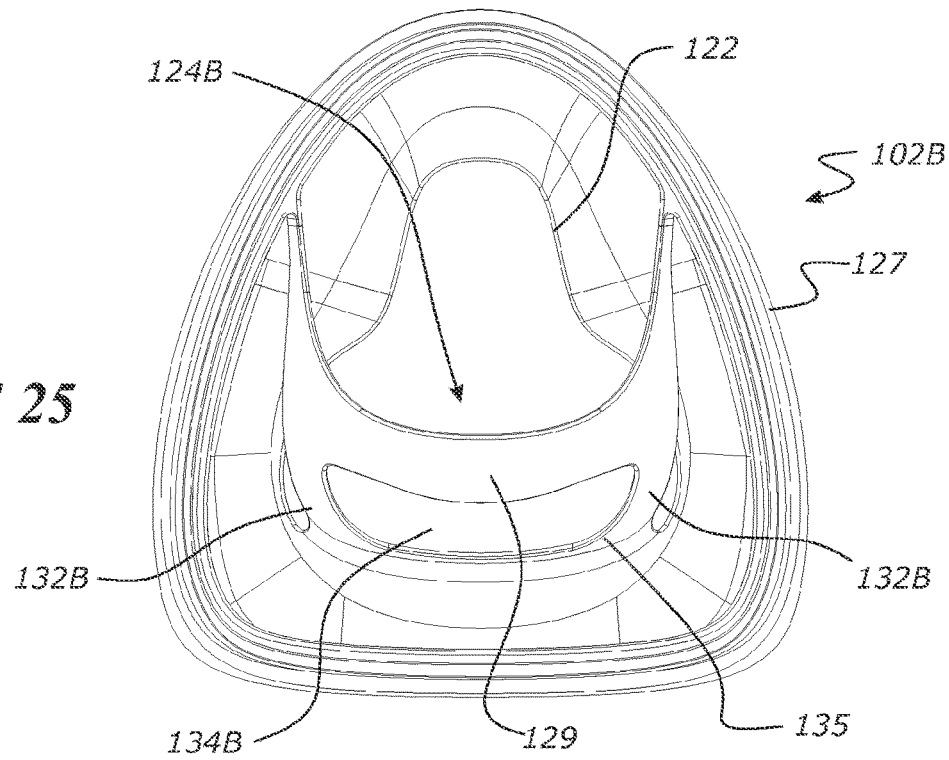
FIG. 25 is a rear view from the outer side of the second embodiment nasal seal.
Figure 26:
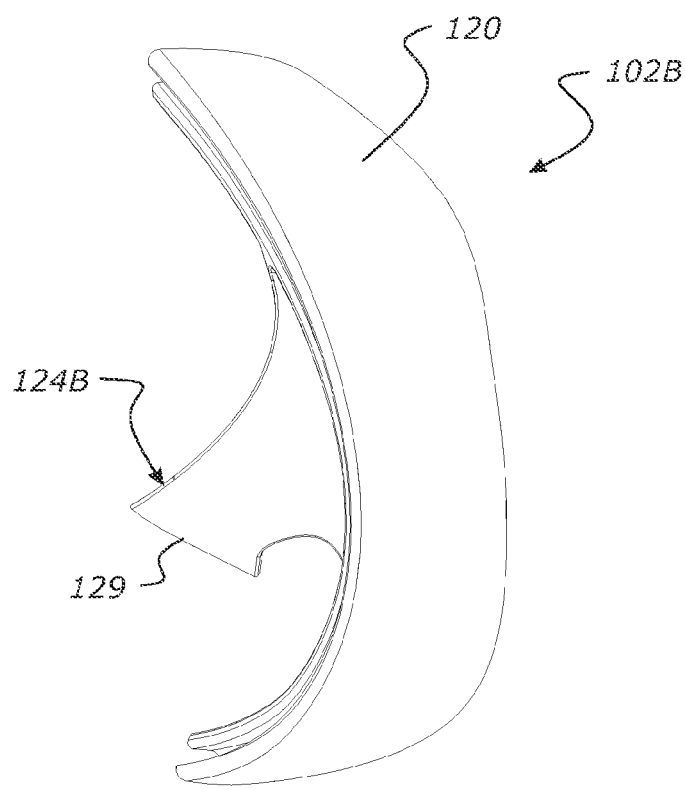
FIG. 26 is a side elevation view of the second embodiment nasal seal.
Figure 27:
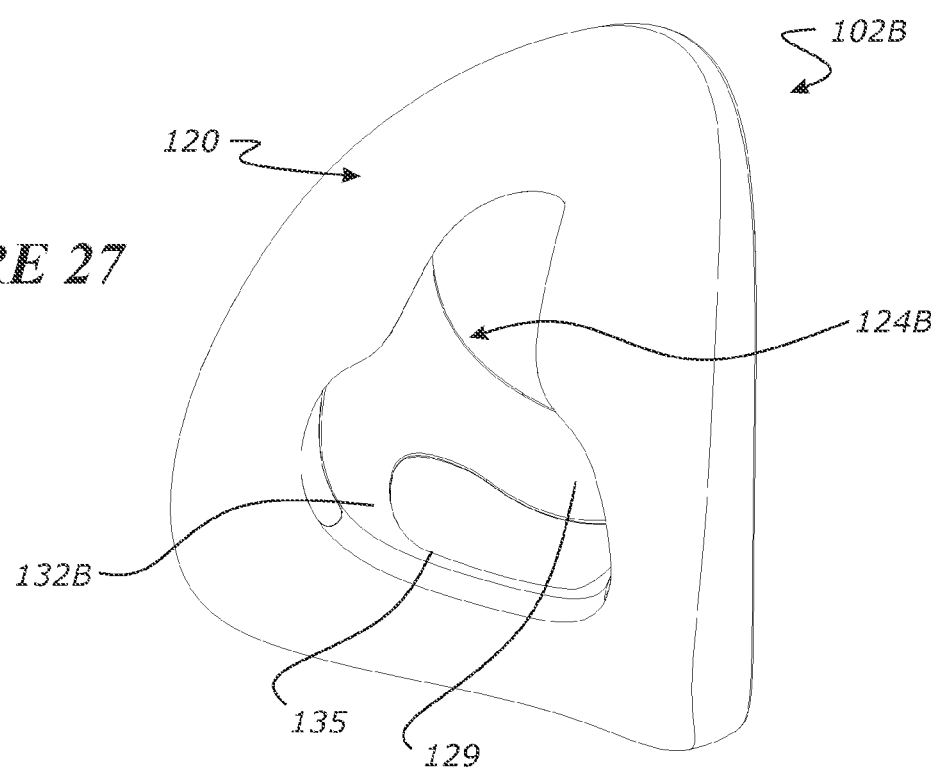
FIG. 27 is a perspective view from the outer side of the second embodiment nasal seal.
Figure 28:
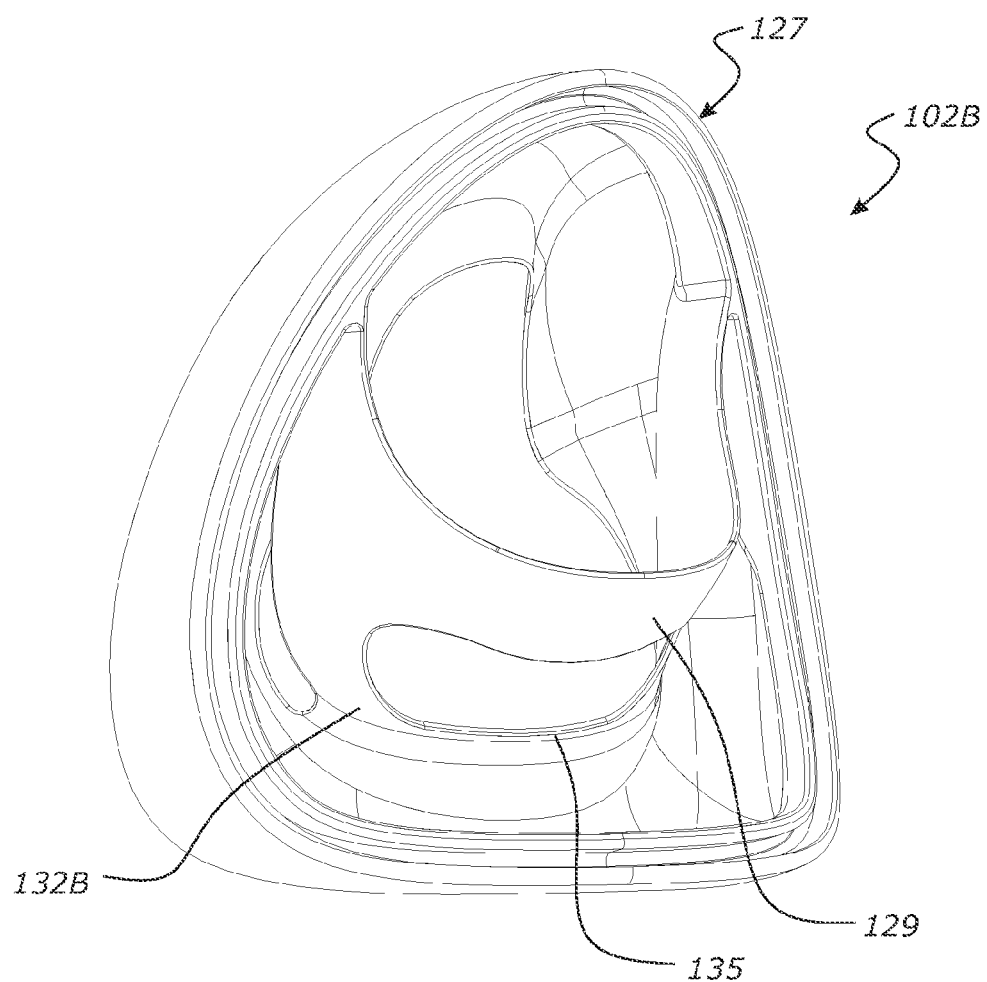
FIG. 28 is a rear perspective view from the outer side of the second embodiment nasal seal.

Alternative Second Form—Central Extension Portion that is Fully Decoupled or Isolated from Opening Edge of the Nasal Seal Referring to FIG. 23, an alternative form of the nasal seal 102A of the first embodiment is shown. The nasal seal 102A is similar to the first embodiment nasal seal 102 except it has a different under-nose support configuration 124A that is fully decoupled or isolated from the edge of the face-contacting surface 120 of the nasal seal. Like numerals represent like components. The alternative under-nose support configuration 124A comprises a main lateral proportion 129 and a central extension portion 132A. The difference relative to nasal seal 102 is that the central extension portion 132A does not couple or connect to the edge 122 of the contacting surface 120 but rather to a lower part of the contacting surface in the upper lip region or alternatively to a part of the lower region of the seal that is not part of the contacting surface 120, such as a part of the lower sidewall 126 of the nasal seal. In this configuration, the under-nose support 124A is fully decoupled from the edge 122 of the contacting surface 120, and in some configuration is completely decoupled from the contacting surface 120 altogether such that the main lateral portion 129 and central extension portion 132A connect to respective sidewall portions of the nasal seal at locations displaced from or adjacent to the contact contacting surface 120 that engages the user's face. The alternative embodiment of the nasal seal 102A is otherwise similar in function and configuration as nasal seal 102 and may be coupled to the seal housing 104 to form the nasal seal interface assembly as with the first embodiment nasal seal 102.

Second Embodiment—Nasal Seal with Under-Nose Support Having Side Extension Portions Referring to FIGS. 24-29, various forms of a second embodiment of the nasal mask interface will be described. The nasal mask interface of the second embodiment is substantially similar to the first embodiment, except in a first form comprises a nasal seal 102B that has an alternative under-nose support configuration 124B. The nasal seal 102 is otherwise similar to the first embodiment nasal seal 102 and can be coupled to a seal housing 104 to form the nasal seal interface assembly as previously described. Like reference numerals represent like features.

In this first form of the second embodiment, the alternative under-nose support configuration 124B still comprises a main lateral portion 129 extending across within the nasal seal between opposing sides of the nasal seal and rearwardly of the contacting surface 120. A central extension portion is not provided as in the first embodiment configuration. Rather, the under-nose support 124B comprises left and right side extension portions 132B that extend from opposing sides of the main lateral portion 129 and each connecting to the lower opening edge 122 of the contacting surface 120 at respective locations toward the sides of the seal in the upper lip region 121 of the contacting surface 120. In this embodiment, the under-nose support 124B may also comprise a lateral extension 135 that extends along or adjacent the lower opening edge 122 of the contacting surface 120 between the side extension portions 132B. Alternatively, lateral extension 135 may be considered as an extension of contact surface 120 in the upper lip region to which the side extension portions 132B connect to. It will be appreciated that the lateral extension portion 135 could omitted in alternative embodiments such that the side extension portions 132B may extend down to connect directly to the edge 122 of the contacting surface 120 without a lateral extension portion 135.

In this alternative configuration 124B, the main lateral portion 129 is again configured to substantially contact a portion of the columella 72 of the user's under-nose surface such as at or toward the tip of the user's nose and end portions of the alar rim 80 at the tip of the nose. The side extension portions 132B are each configured for substantial alignment and contact with respective portions of the alar rims 80 of the under-nose surface, such as including portions of the alar rim extending from the base of the nose. This configuration therefore leaves a main opening 134B in the under-nose support between the main lateral portion 129, side extension portions 132B, and contacting surface 120 in the upper lip region, for the user's nostrils 74.

Figure 29:
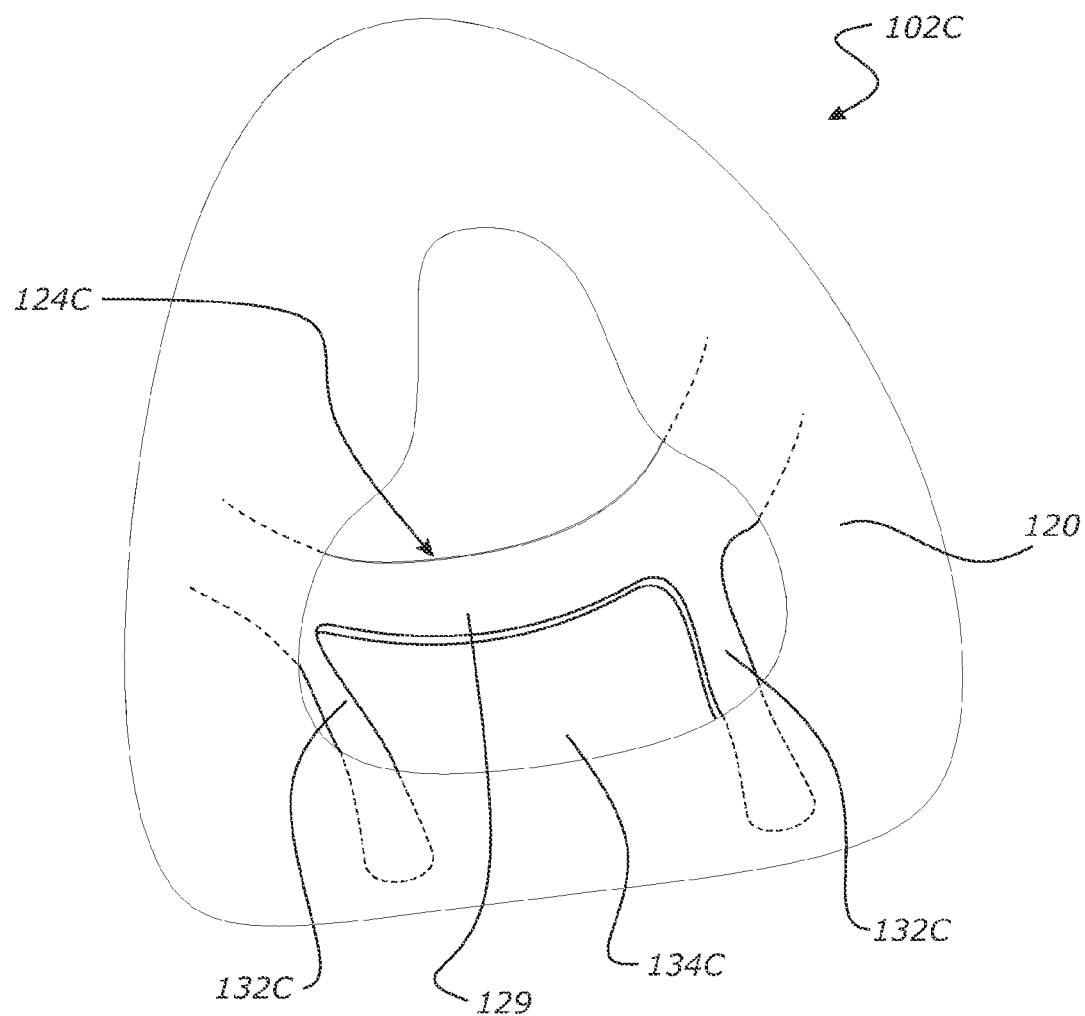
FIG. 29 is a front perspective view of a second form of the second embodiment nasal seal in which the under-nose support configuration that is fully de-coupled or isolated from the edge of the face-contacting surface of the nasal seal.
Figure 30:
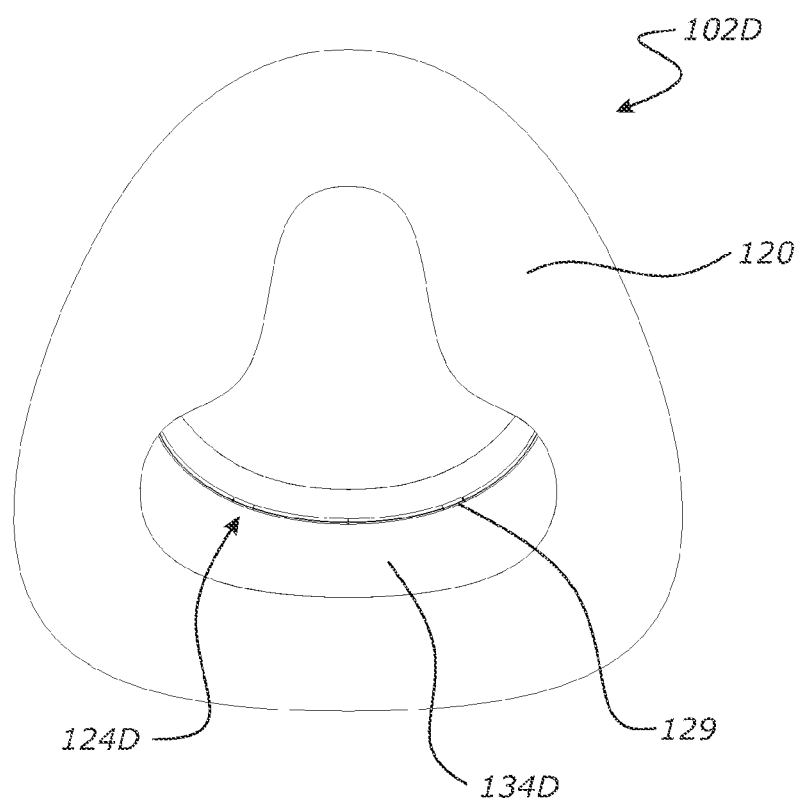
FIG. 30 is a front view of a third embodiment nasal seal having a 'floating' under-nose support configuration.
Figure 31:
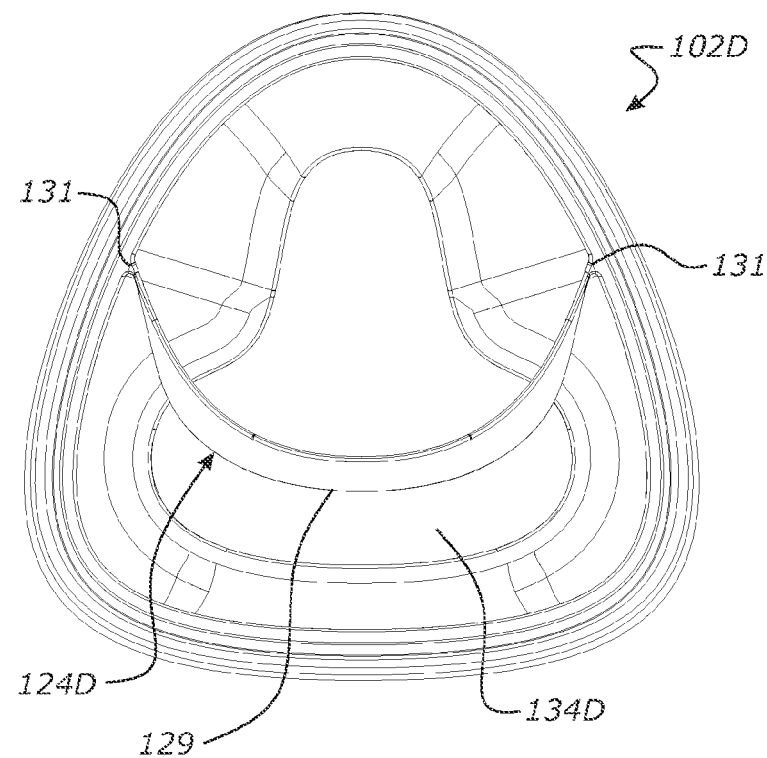
FIG. 31 is a rear view from the outer side of the third embodiment nasal seal.
Figure 32:
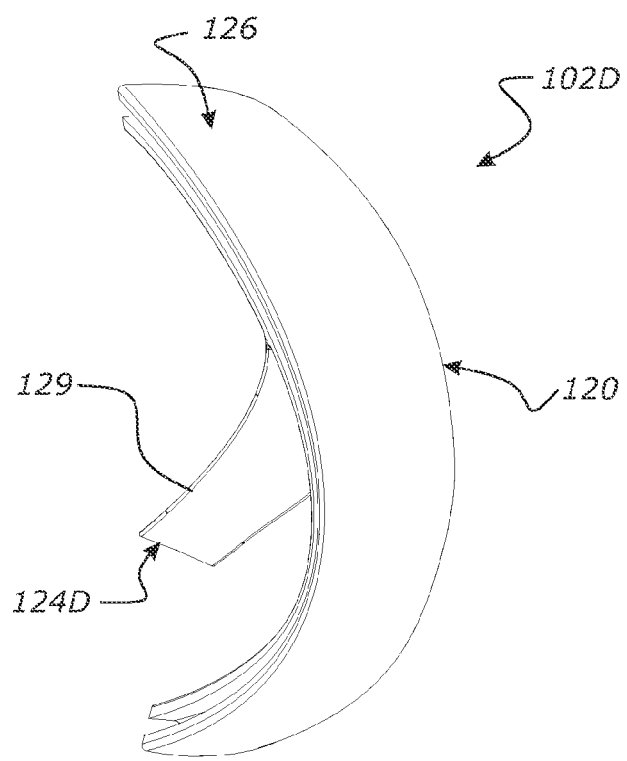
FIG. 32 is a side elevation view of the third embodiment nasal seal.
Figure 33:
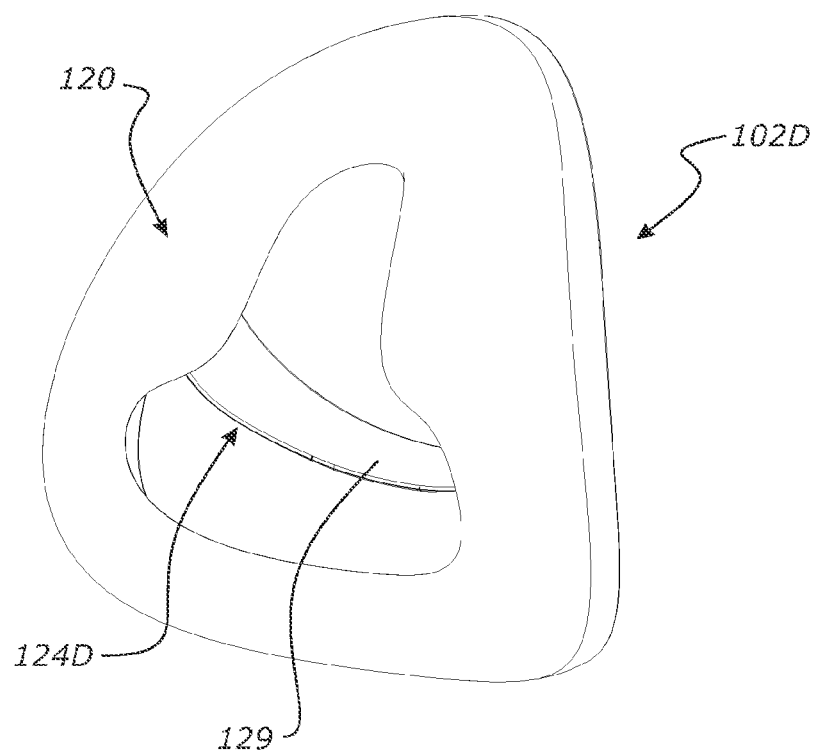
FIG. 33 is a front perspective view from the face-contacting side of the third embodiment nasal seal.
Figure 34:
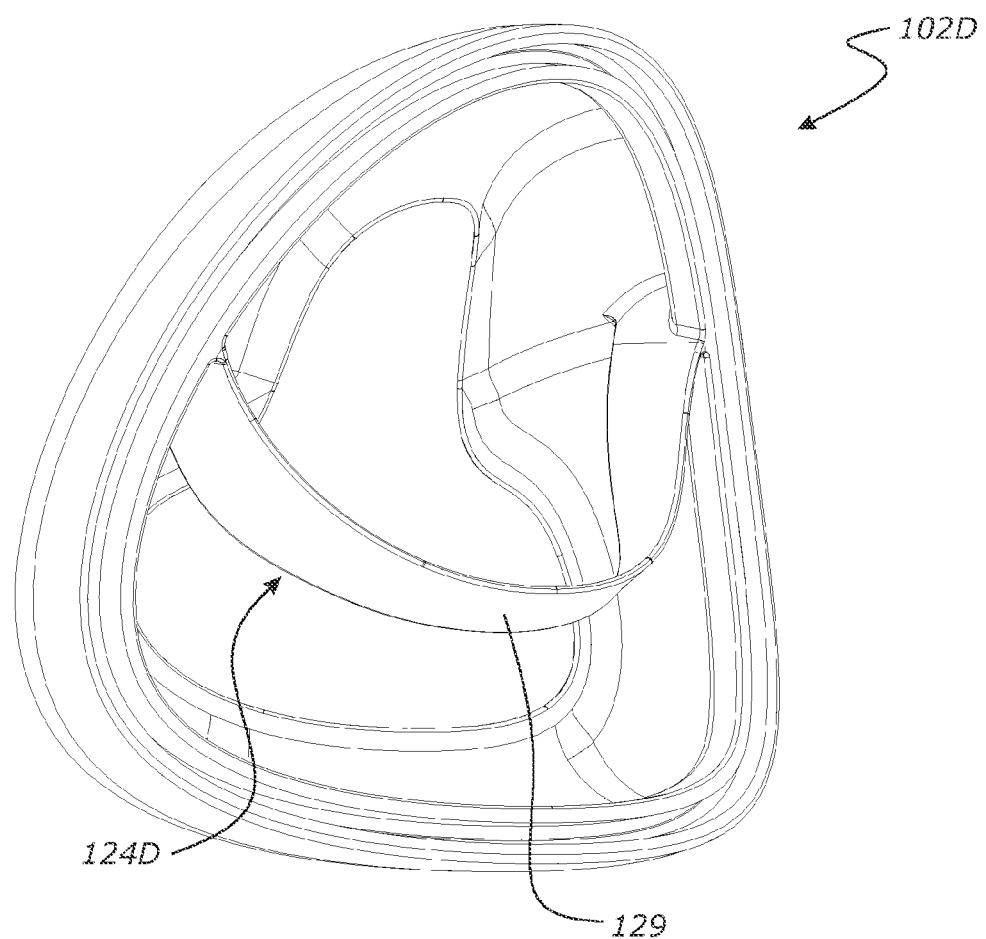
FIG. 34 is a rear perspective view from the outer side of the third embodiment nasal seal.

Alternative Second Form—Side Extension Portions that are Fully Decoupled or Isolated from Opening Edge of the Nasal Seal Referring to FIG. 29, an alternative second form of the nasal seal 102C of the second embodiment is shown. Like numerals representing like features. Again, this nasal seal 102C is otherwise similar to the second embodiment nasal seal but with an alternative under-nose support configuration 124C in which the side extension portions 132C extend from the main lateral portion 129 and connect to a portion of the nasal seal in the upper lip region that is displaced or isolated from edge 122 of the nasal seal such that the side extension portions 132C are decoupled from the edge 122 of the nasal seal. In one configuration, the side extension portions 132C connect or extend to a portion of the contact surface 120 below the edge in the upper lip region, or in an alternative configuration connect to the nasal seal at locations displaced from the contact surface 120 entirely, such as connecting to the respective locations on the sidewall of the seal in the upper lip region below the lower edge 122 of the opening. This configuration provides an under-nose support 124C that is decoupled from the edge 122 of the contacting surface 120 of the nasal seal.

Third Embodiment—Nasal Seal with a 'Floating' Under-Nose Support

Referring to FIGS. 30-34, a third embodiment of the nasal seal 102D will be explained. As with the previous embodiments, the nasal seal 102D is similar to the first embodiment nasal seal 102 in that it may be used in a nasal mask interface assembly as previously described, for example, by being coupled or connected to a seal housing 104. Like reference numerals represent like features.

The third embodiment nasal seal 102D comprises an alternative under-nose support 124D that consists only of the main lateral portion or band 129 without any central or side extension portions. In particular, the under-nose support 124D comprises an elongated strip or band of material that extends laterally across the nasal seal between opposing sides of the seal and which extends or is located rearwardly of the face contact surface 120, as in the previous embodiments. As with the previous embodiments, the lateral band 129 may be coupled or connected at each end to a respective portion of the sidewall 126 or other portion of the seal such that the under-nose support is decoupled or isolated from the contacting surface 120, or at least the edge of the contacting surface. Without the central or side extension portions of the previous embodiments, the under-nose support 124D can be considered as a 'floating' support that has a greater degree of movability within the seal.

In this configuration, the under-nose seal 124D has less contact surface area and therefore contacts less of the under-nose surface of the nose of the user. In particular, without any of the central or side extension portions, less of the under-nose surface tends to be contacted by the floating under-nose support configuration 124D. The floating under-nose support tends to engage or contact the columella and portions of the adjacent alar rims 80 at or toward the tip of the nose, depending on the size of the user's nose. For those with larger noses, the under-nose support may contact in the middle region of the under-nose surface or further toward the under-nose surface at the base of the nose.

Fourth Embodiment—Low-Profile Nasal Mask Interface

Overview

Figure 102:
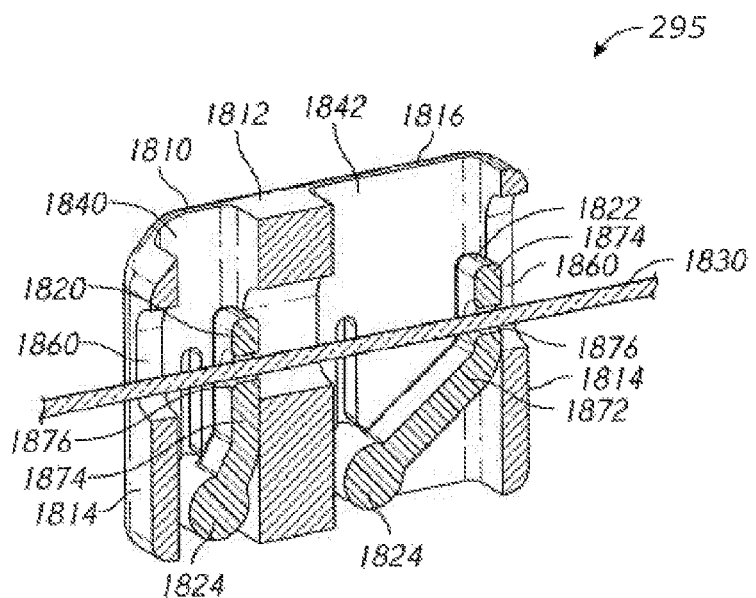
FIG. 102 is a perspective cross-sectional view of the directional lock in FIG. 99 in the unlocked position.
Figure 103:
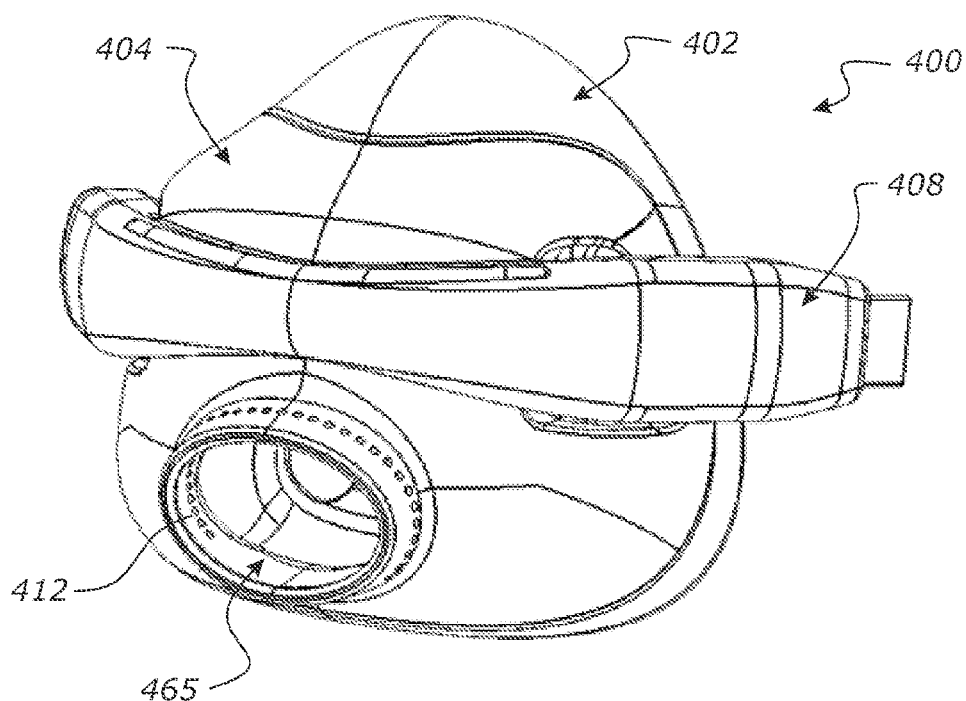
FIG. 103 is a perspective view of an outer side of a first form of a fifth embodiment nasal mask interface, including a nasal seal, nasal seal housing with integrated conduit connector, and yoke.
Figure 104:
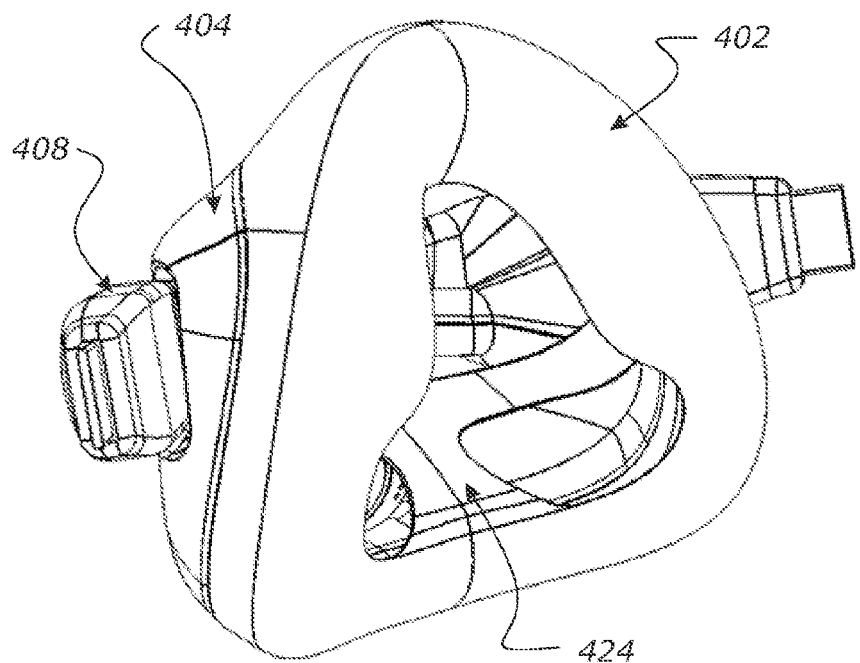
FIG. 104 is an upper perspective view of the first form nasal mask interface of FIG. 103 from the front or face-contacting side.
Figure 105:
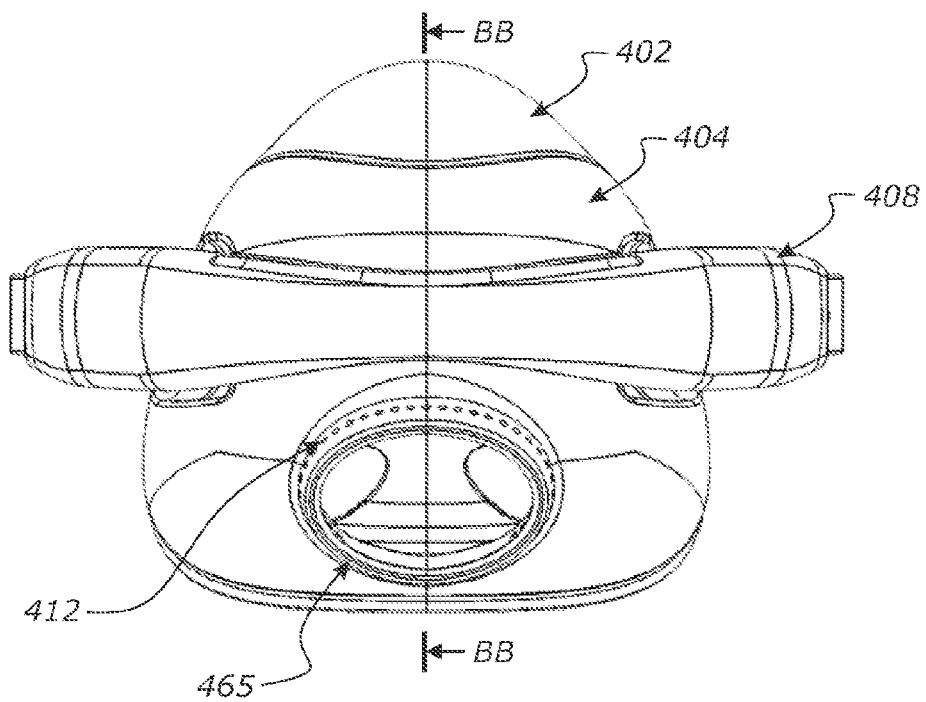
FIG. 105 is an outer side view of the first form nasal mask interface of FIG. 103.
Figure 106:
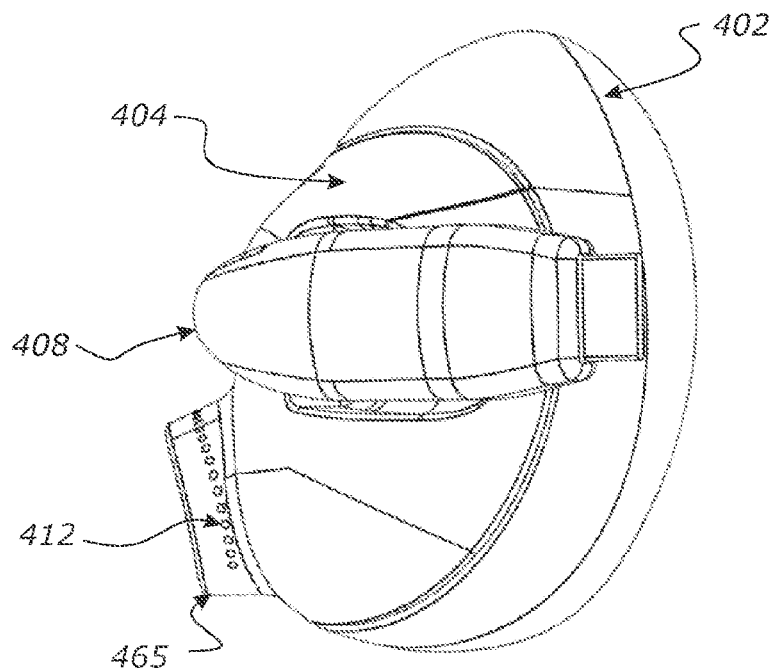
FIG. 106 is a side elevation view of the first form nasal mask interface of FIG. 103.
Figure 107:
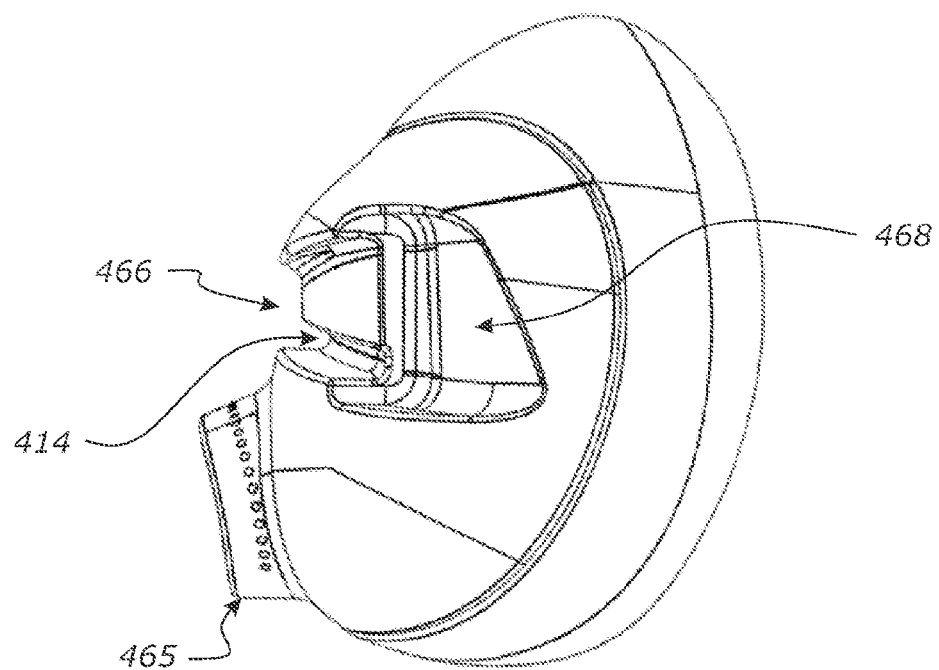
FIG. 107 is a side elevation view of the first form nasal mask interface of FIG. 106 without the yoke.
Figure 108:
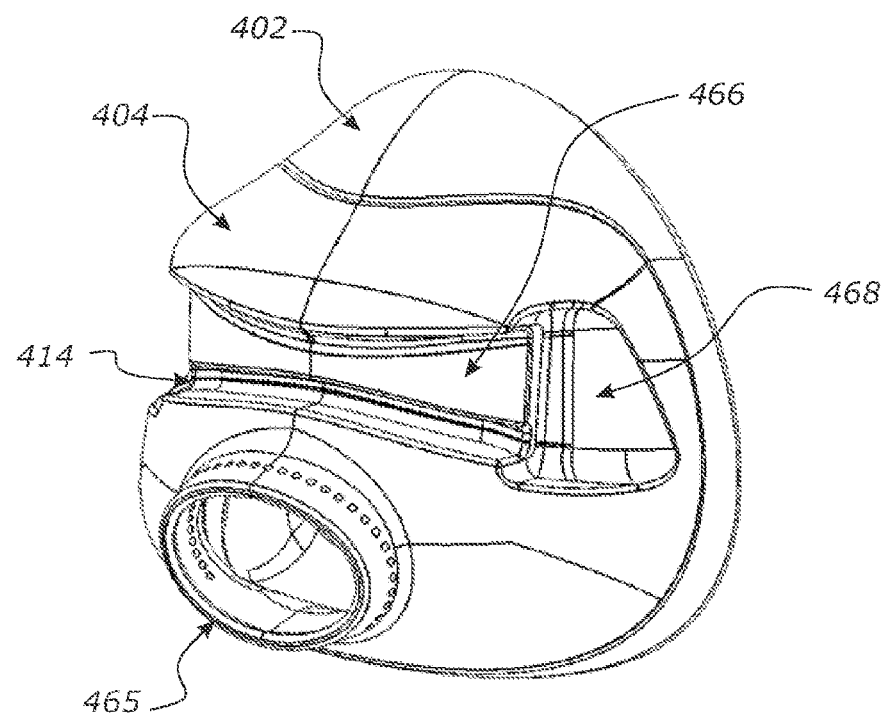
FIG. 108 is an outer side perspective view of the first form nasal mask interface shown in FIG. 107.
Figure 109:
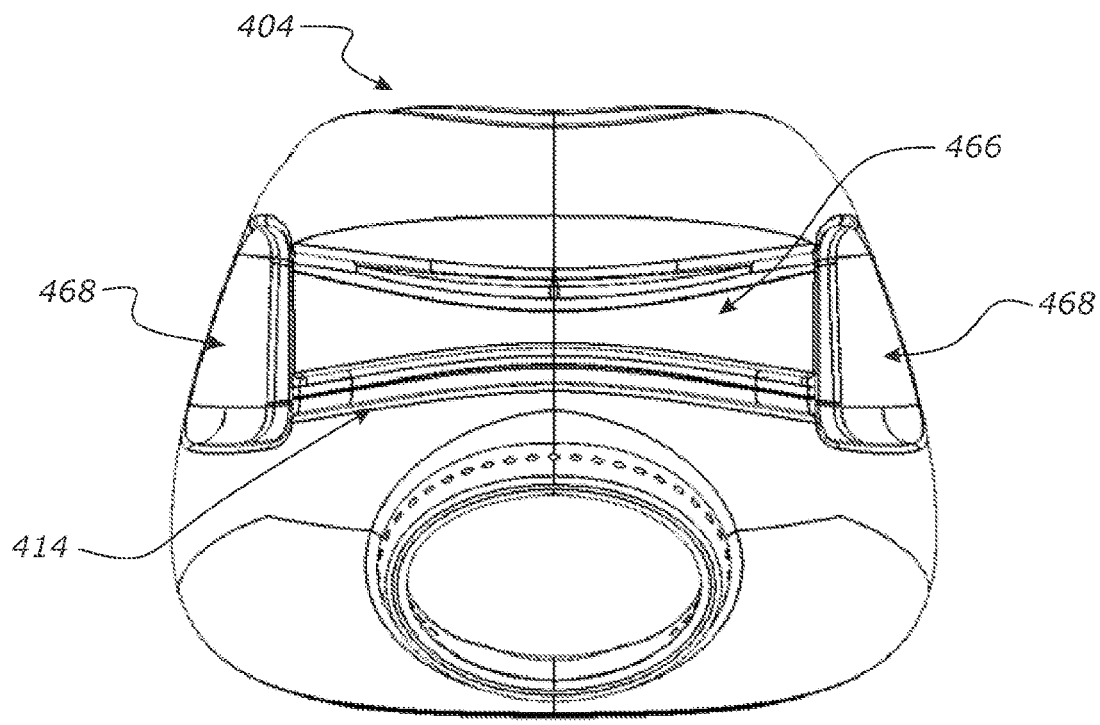
FIG. 109 is an outer side view of the seal housing of the first form nasal mask interface of FIG. 103.
Figure 110:
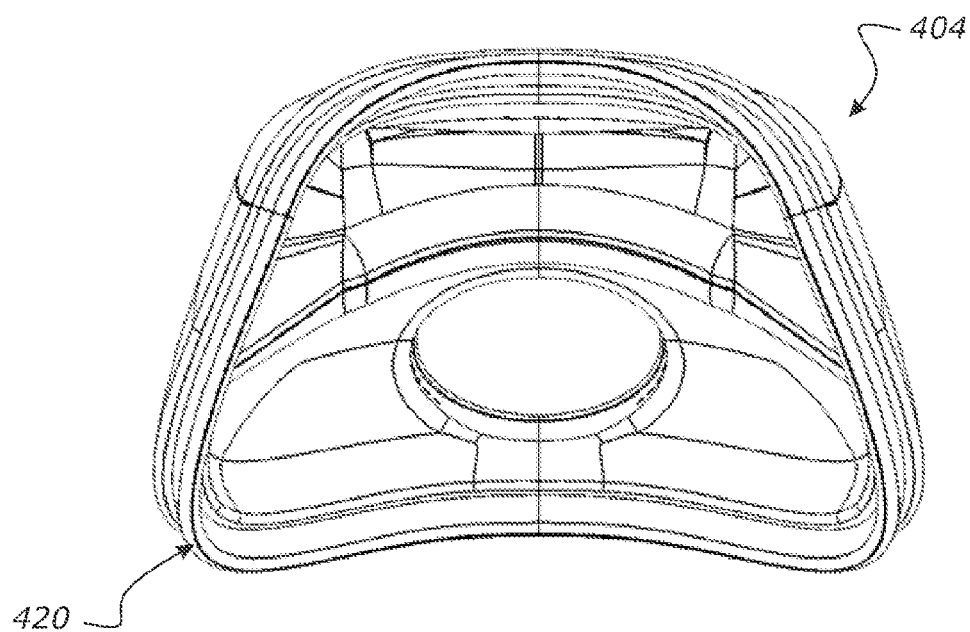
FIG. 110 is a wearer side view of the seal housing of FIG. 109.

A fourth embodiment nasal mask assembly will now be described with reference to FIGS. 35-102.

Figure 35:
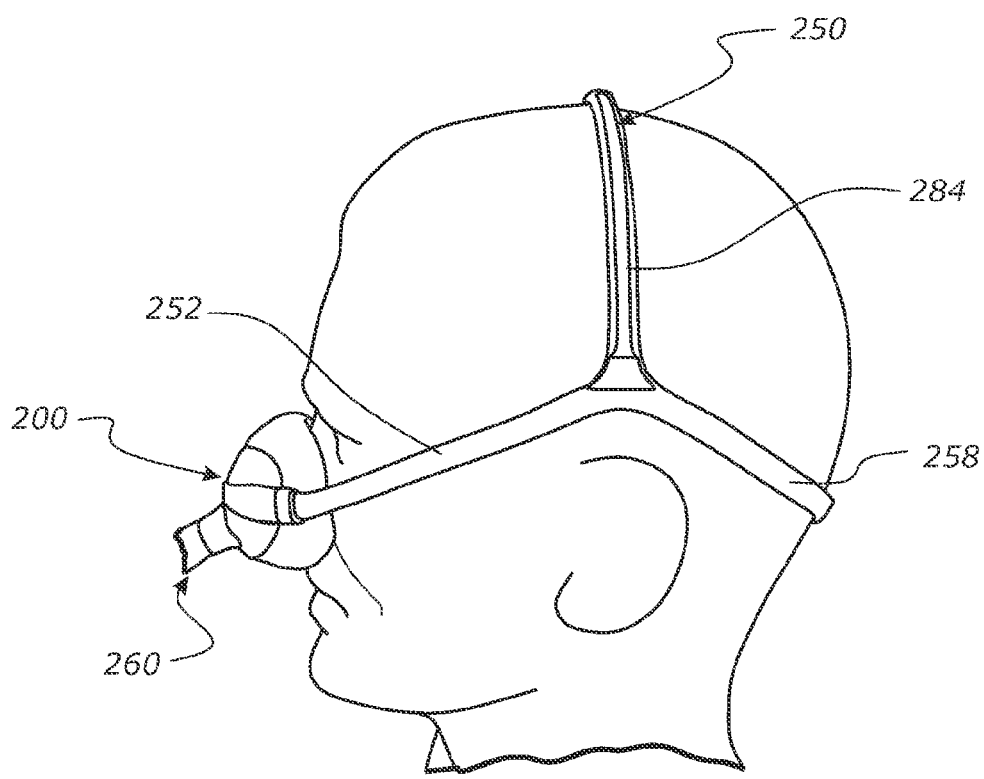
FIG. 35 is a side elevation view of a nasal mask assembly in accordance with a fourth embodiment, shown in use on a wearer.
Figure 36:
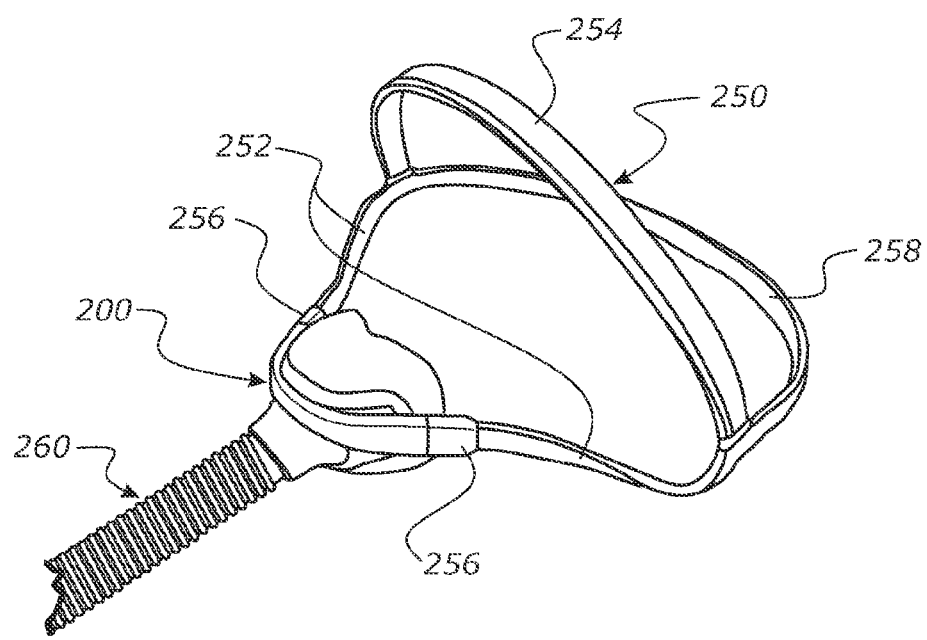
FIG. 36 is a perspective view of the fourth embodiment nasal mask assembly, and in particular showing the nasal mask interface comprising a nasal seal, seal housing, yoke, and conduit frame, and the nasal mask interface connected to a headgear and flexible gases supply conduit.
Figure 37:
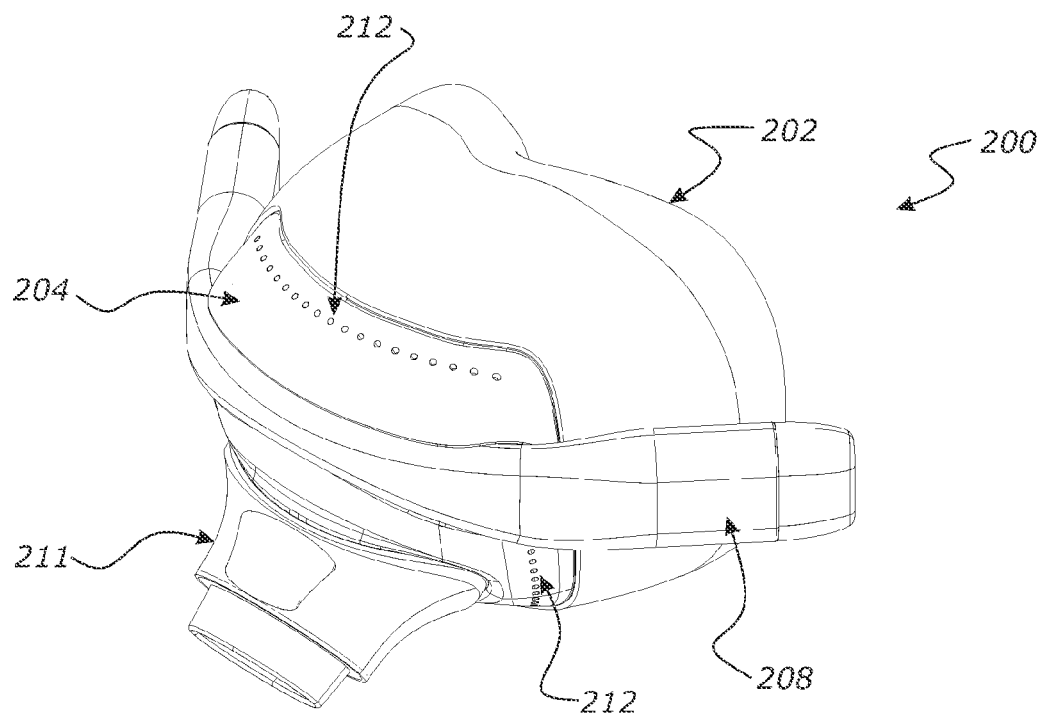
FIG. 37 is an upper perspective view from the outer side of the fourth embodiment nasal mask interface showing the nasal seal, seal housing, yoke, and conduit frame.
Figure 38:
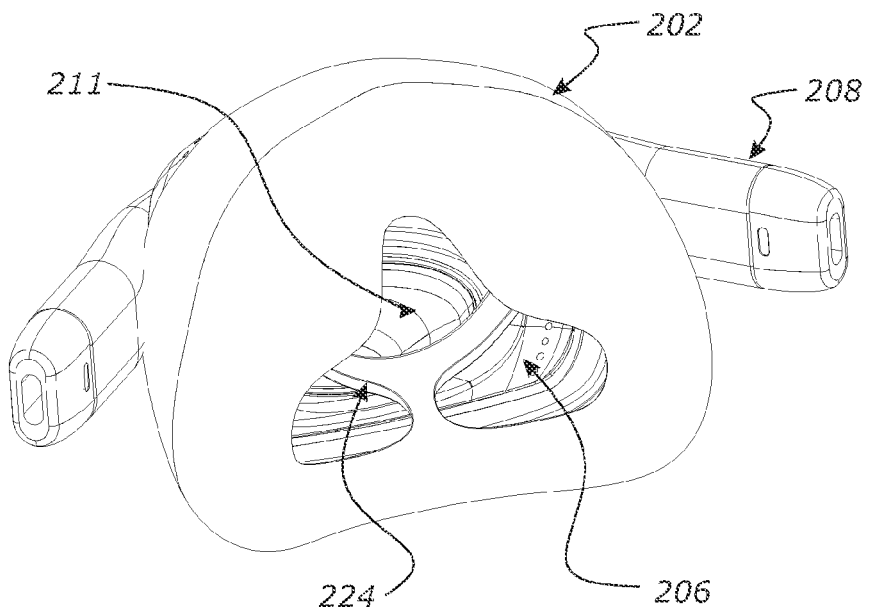
FIG. 38 is an upper perspective view from the front or face-contacting side of the fourth embodiment nasal mask interface.
Figure 39:
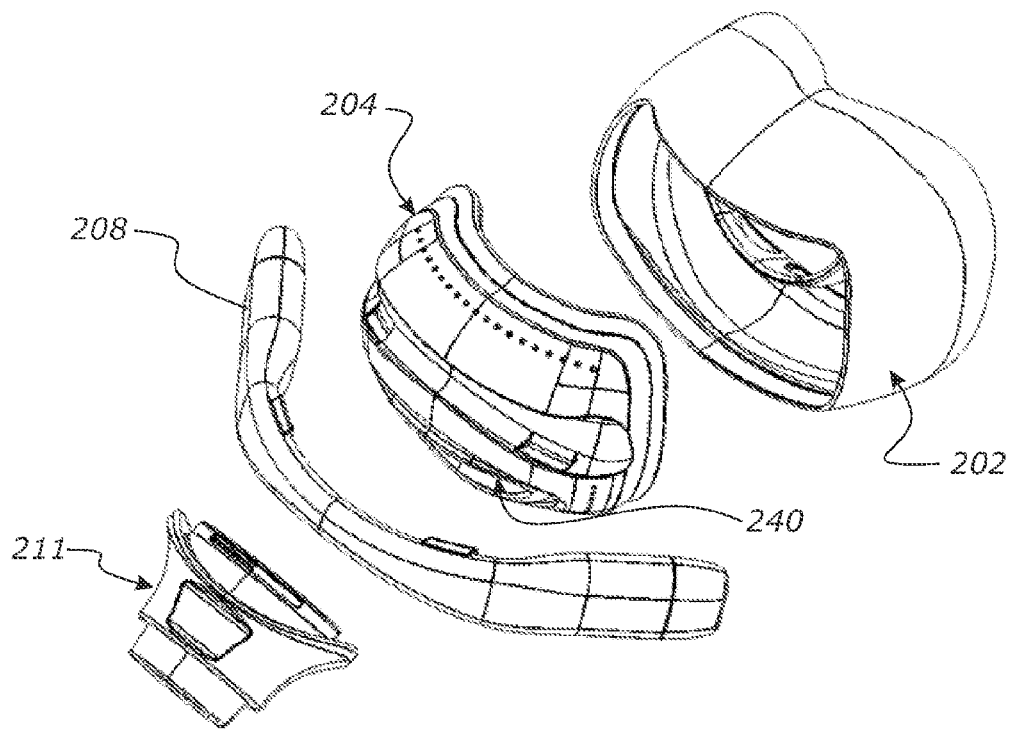
FIGS. 39 and 40 show upper and lower perspective exploded views respectively of the fourth embodiment nasal mask interface.
Figure 40:
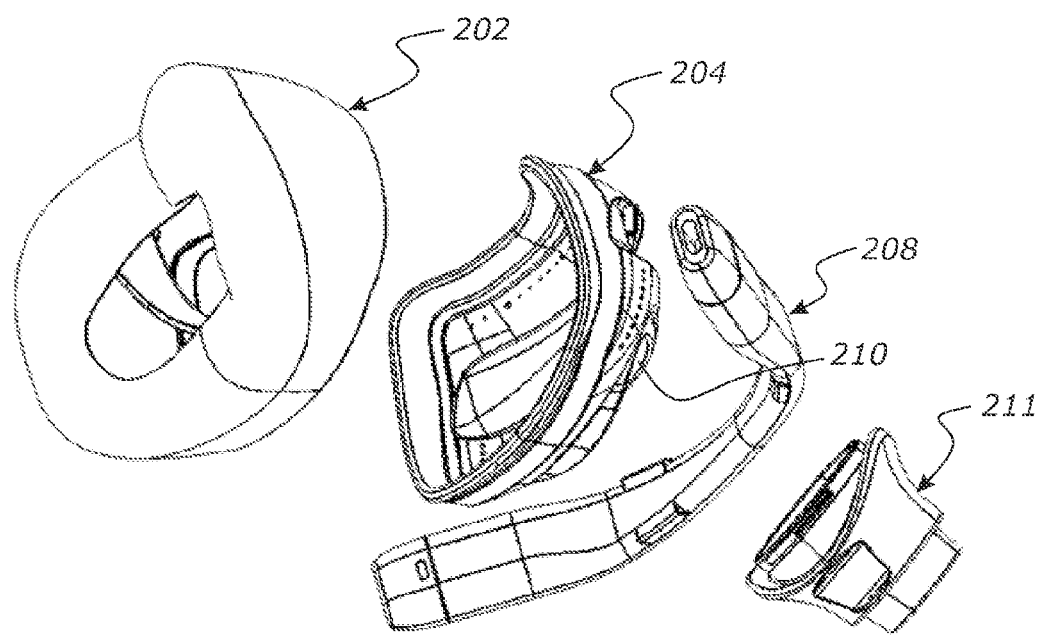
Figure 41:
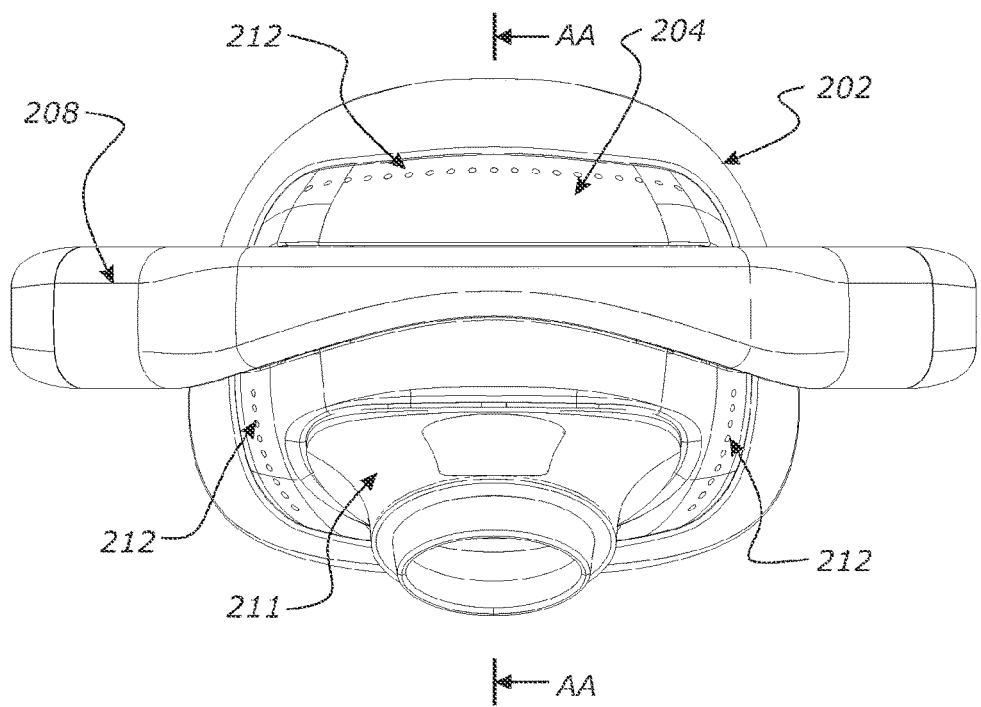
FIG. 41 shows a rear or outer side view of the fourth embodiment nasal mask interface.

With reference to FIGS. 35 and 36, the fourth embodiment nasal mask assembly comprises a nasal mask interface 200 that is secured to a user's head via headgear 250 and the nasal mask interface 200 is connected to a flexible gases supply conduit 260, which in use delivers a supply of breathable gas to the nasal mask interface 200 for delivery to the user's airways via their nose. In this embodiment, the headgear 250 comprises side or front straps 252 that connect to opposing sides of the nasal mask interface 200 at attachment points 256 and which extend along the sides or cheeks of the user's face and over the user's ears. The pair of front or side straps 252 connect to or integrally extend into one or more other straps or strap portions. In this embodiment, the headgear 250 comprises a top or crown strap 254 that extends over the user's head or crown, and a back or rear strap 258 that extends around the back of the user's head. The side straps 252 are integrally formed or otherwise connected to the top 254 and back 258 straps as will be appreciated by a skilled person. As with the previous embodiments, the headgear straps are typically formed of or comprise a flexible breathable material such as Breath-o-Prene®, a breathable neoprene material, or neoprene material or similar. Further aspects of the headgear configuration and its attachment and interaction with the nasal mask interface 200 will be explained later. In this embodiment, the headgear may have automatic adjustment capability or mechanisms, as will be further described, although these are not essential to all embodiments.

Referring to FIGS. 37-46 in particular, the nasal mask interface 200 comprises a flexible nasal seal 202 that is either permanently or releasably connected or mounted to a complementary seal housing 204. The seal housing 204 is typically formed of a rigid material or is at least more rigid than the flexible nasal seal 202. As with the previous embodiments, the nasal seal 202 and seal housing 204 together collectively define or form a mask cavity or volume that is configured to receive at least a portion of the user's nose in use and which receives a supply of a breathable gas from the gases supply conduit 260. In this embodiment, the gases supply conduit 260 is releasably connected to the seal housing 204 although it will be appreciated that in alternative embodiments the conduit may be permanently or integrally connected into the seal housing 204. In this embodiment, the nasal mask interface 200 comprises a conduit frame 211 that is either permanently or releasably connected to an end of a gases supply conduit. The conduit frame 211 in this embodiment is releasably connectable to a complementary central air aperture or inlet 210 provided in the seal housing to thereby connect the supply conduit 260 to the nasal mask interface 200.

In this embodiment, a headgear frame in the form of a yoke 208 is releasably connected to the outer side surface of the seal housing 204. The yoke 208 is generally curved (outer front surface being convex, and inner surface engaging with seal housing being concave) in shape an extends laterally across the seal housing 204 and at each end extends in a direction toward the face-contacting side of the nasal mask interface but outwardly away from the lateral sides of the nasal seal 202. Each distal end of the yoke 208 connects to a respective end of one of the side straps 252 of the headgear 250 such that the headgear 250 has a single attachment point on each side of the nasal mask interface 200. In this embodiment, the headgear may be permanently or non-releasably connected to the yoke 208. The yoke may be releasably connected to the seal housing 204 such that the yoke 208 and headgear 250 may be removed or released from the seal housing if desired.

In this embodiment, the nasal mask interface 200 is provided with one or more bias flow outlet or vents 212 for providing gas washout from the nasal mask interface 200. In this embodiment, the bias flow vent comprises an arrangement of small apertures or holes extending through the seal housing 204. The vent arrangement comprises one or more arrays of apertures at particular locations on the seal housing as will be explained in further detail. As with the previous embodiments, the nasal seal 202 is provided with an under nose support 224 that extends or is suspended laterally across the nasal seal within the mask cavity and which is configured to contact at least a portion of the under-nose surface of the user's nose so as to counteract any result in lift force created with the nasal mask is worn and in use as previously discussed.

Further details and aspects of the various components of the nasal mask interface 200 will now be described.

General Shape and Configurations Aspects

Figure 42:
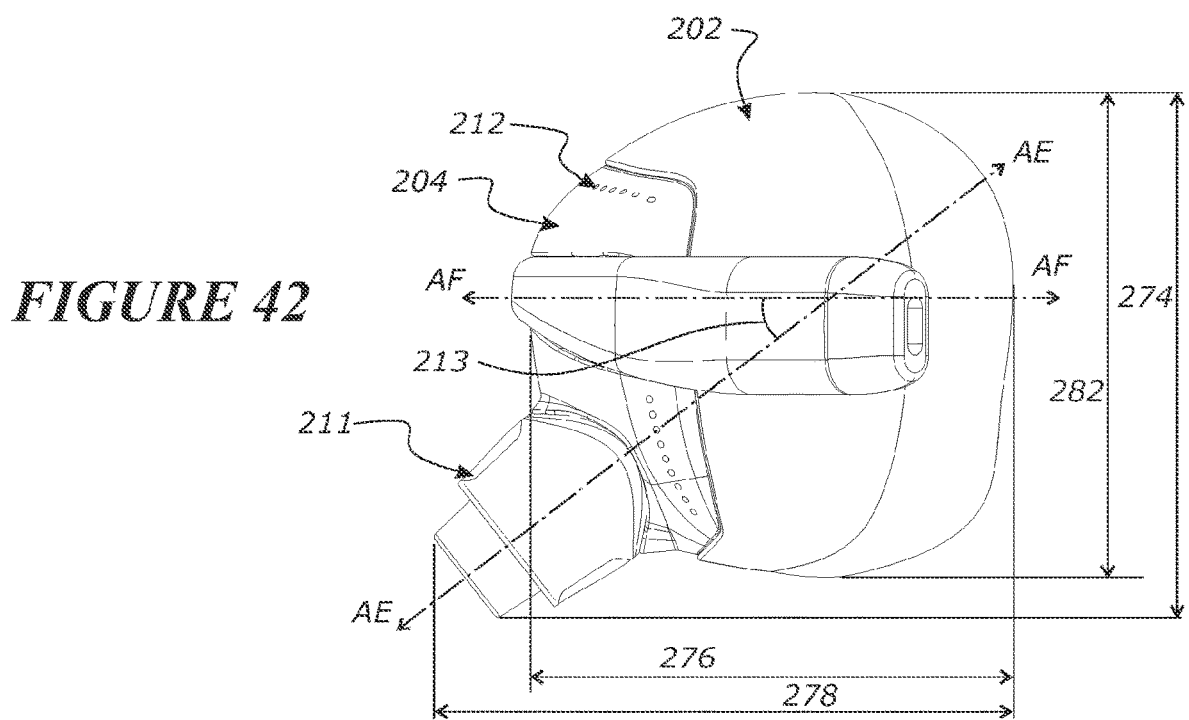
FIG. 42 is a side elevation view of the fourth embodiment nasal mask interface.

Referring to FIG. 42, in this embodiment the orientation or angle of the yoke 208 and conduit frame 211 are offset relative to each other. For example, the longitudinal axis of the conduit frame 211 represented by line AE is angled with respect to the longitudinal axis or plane extending through or defining the yoke 208 represented by line AF. In this embodiment, the angle between the longitudinal axis AE of the conduit frame 211 and longitudinal axis AF of the yoke 208 when viewed from the side of the nasal mask interface 200 is preferably in the range of approximately 20° to approximately 60°, more preferably approximately 30° to approximately 50°, even more preferably approximately 35° to approximately 45°, and even more preferably approximately 38°. In this example, the longitudinal axis AE of the conduit frame 211 and longitudinal axis AF of the yoke 208 are defined relative to a side elevation view of the nasal mask interface 200 by way of explanation only. In some embodiments, this angular offset between the conduit frame and yoke may assist in directing the gases supply conduit away from the user, and also may assist in reducing hose drag.

Figure 44:
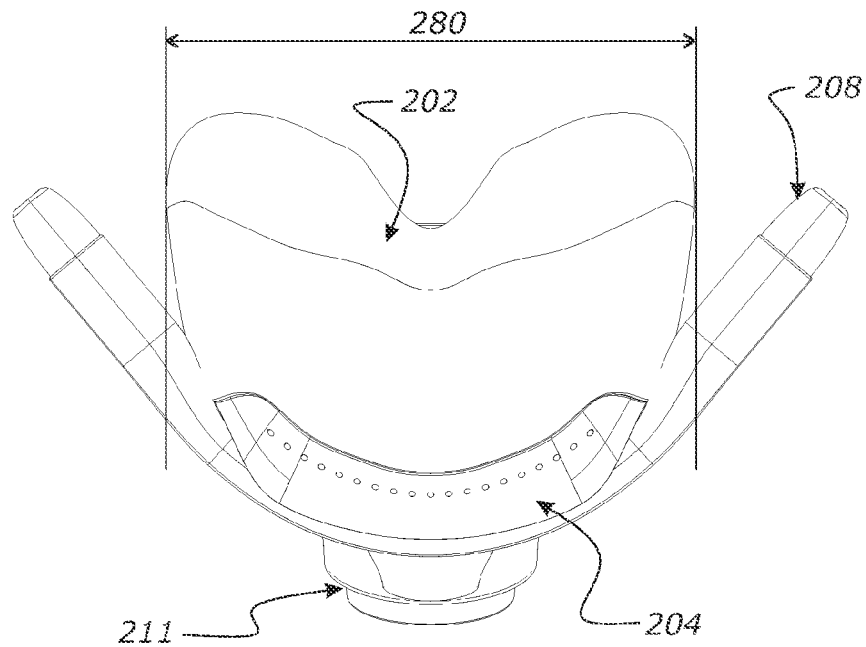
FIG. 44 is a top view of the fourth embodiment nasal mask interface.
Figure 45:
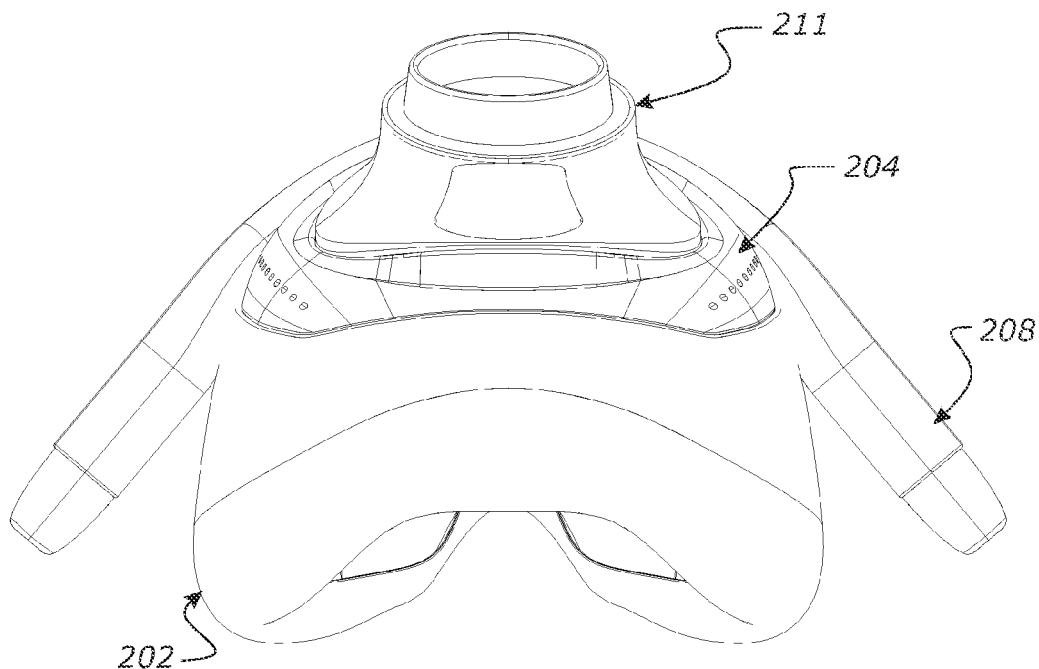
FIG. 45 is an underside view of the fourth embodiment nasal mask interface.

Referring to FIG. 44, the conduit frame 211, seal housing 204, nasal seal 202, and yoke 208 all generally exhibit a substantially concave curvature (on their face facing surfaces) that generally follows the curvature of a user's face and assists in the nasal mask interface conforming to the user's face about their nose. In this embodiment, as can be seen from the top view in FIG. 44, the radius of curvature of the yoke 208 (at least in the lateral side portions) is generally larger than that of the conduit frame 211 and/or seal housing 204 as the yoke is not intended to contact the user's face and is configured to extend at an angle away from the outer wall of the nasal seal 202 that extends between the face-contacting surface of the nasal seal and the outer side of the nasal seal that connects to the seal housing 204.

Figure 43:
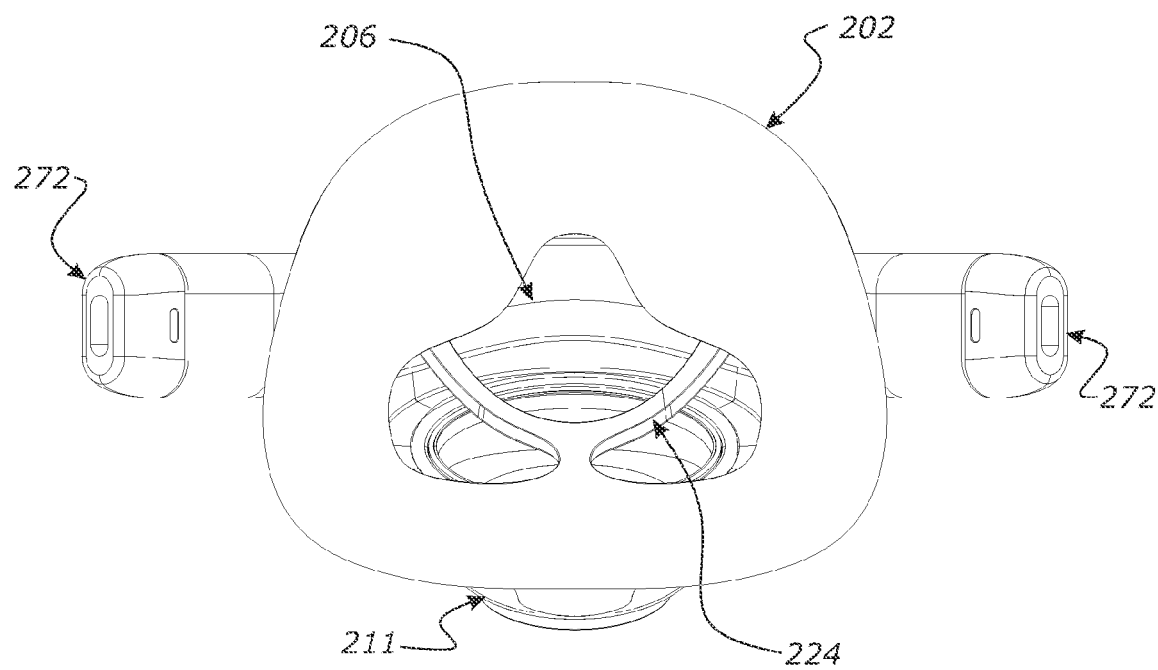
FIG. 43 is a front or face-contacting side view of the fourth embodiment nasal mask interface.

Referring to FIG. 43, the nasal aperture or nose-receiving opening 206 on the face-contacting side of the nasal seal 202 is shown. The pair of single headgear attachment or connection points 272 on each side of the nasal mask interface are shown at 272 at each distal end of the yoke 208. In this embodiment the headgear connection points 272 are located on each lateral side of the nasal mask interface 200 at locations on the yoke 208 that are most distal from the centre of the nasal mask interface. The under-nose support 224 can be seen through the nasal aperture 206 and extends within the mask cavity provided by the nasal seal 202 and seal housing 204. In this embodiment, the under-nose support 224 has three connection points to the nasal seal 202. As will be explained in detail later, the under-nose support 224 comprises a connection point toward each upper inner lateral side or surface of the nasal seal, and a third connection point at or toward the centre bottom of the nasal seal. In this embodiment, the third connection is to the center bottom edge of the nasal aperture 206.

Referring to FIGS. 42 and 44, some main outer dimensions of the overall profile of the nasal mask interface 200 in this embodiment will be described by way of example only to provide a sense of scale. In this embodiment, the ratio of the overall height to the overall depth of the seal housing 204 and nasal seal 202 assembly is in the range of approximately 1:0.8 to approximately 1:1.2, and in this example embodiment the overall height is substantially equal to the overall depth of the seal housing and nasal seal assembly, i.e. a ratio of approximately 1:1. In this embodiment, the overall lateral width of the seal housing and nasal seal assembly is greater than the overall height and depth of the assembly. In this embodiment, the ratio of the overall height to overall depth to overall lateral width of the seal housing and nasal seal assembly is in the range of approximately 1:0.8:1 to approximately 1:1.2:1.4, and approximately 1:1:1.2 in this example embodiment By way of example only, example dimensions of one example configuration of the nasal mask interface will be set out with reference to FIGS. 42 and 44. In this example, the overall height of the seal housing 204 and nasal seal 202 assembly from the top to the bottom as indicated at 282 is in the range of approximately 27 mm to approximately 67 mm, and preferably approximately 47 mm. The overall height of the seal housing 204, nasal seal and installed conduit frame 211 as indicated at 274 is in the range of approximately 30 mm to approximately 70 mm, and preferably approximately 50 mm. The overall depth of the seal housing 204 and nasal seal 202 assembly as indicated at 276 is in the range of approximately 41 mm to approximately 66 mm, and preferably approximately 46 mm, and the overall depth of the seal housing 204, nasal seal 202 and installed conduit frame 211 as indicated at 278 is in the range of approximately 51 mm to approximately 76 mm, and preferably approximately 56 mm. The lateral width of the seal housing 204 and nasal seal 202 assembly (see FIG. 44) as indicated at 280 is in the range of approximately 52 mm to approximately 77 mm, and preferably approximately 57 mm.

Nasal Seal

Referring to FIGS. 47-67, the nasal seal 202 of the nasal mask interface 200 will be described in further detail. The nasal seal 202 is flexible and soft, and may be formed of a silicone material or other suitable material as will be appreciated by a skilled person.

Figure 47:
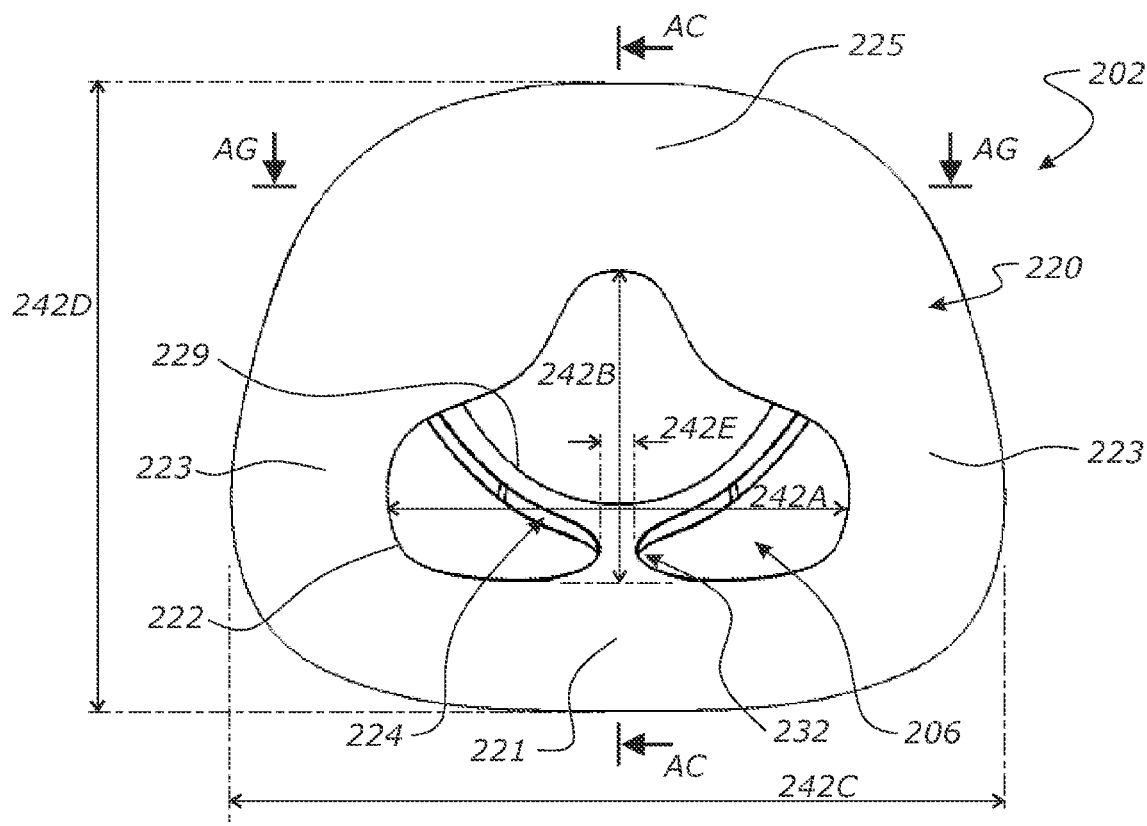
FIG. 47 is a front or face-contacting side view of the nasal seal of the fourth embodiment nasal mask interface.

Referring to the face-contacting or wearer side of the nasal seal 202 shown in FIG. 47, the contacting surface is generally indicated at 220 and is configured to seal about the user's nose, including across the bridge of the user's nose. In this embodiment, the contacting surface 220 circumscribes at least a portion of the nose and seals about that portion of the nose of the user. The contacting surface 220 of the nasal seal comprises an upper lip region generally indicated at 221 that is configured to contact the upper lip region of the face of the user such as at a location above the vermillion border and below the nares. The contacting surface 220 also comprises left and right cheek or side regions 223 that extend between the upper lip region 221 at the bottom of the seal and an upper region 225 corresponding to or proximal to the nasal bridge region at the top of the nasal seal 202. The cheek regions 223 of the contacting surface 220 are configured to contact the medial cheek surface of the user and/or lateral nose surface of the user on either side of the nose. The nasal bridge region 225 of the contacting surface 220 is configured to extend over the nose and contacts the nasal bridge region of the user's nose, and connects to the two cheek regions 223. As will be explained in further detail later, in this embodiment the nasal seal 202 comprises a lower profile height dimension than conventional nasal masks such that the nasal bridge region 225 of the contacting surface is configured to contact the user's nasal bridge in a middle region of the nasal bridge at a location on the nasal bridge between the lower tip of the user's nose and the upper extremity of the nasal bridge between the user's eyes. In this embodiment, the nasal bridge region 225 of the contacting surface 220 is configured to contact the user's nasal bridge in a region of the nasal bridge that is below the user's eyes. In an embodiment, the nasal bridge region 225 of the nasal seal is configured to contact the user's nasal bridge in the region defined between the nares of the nose and the center of the nasal bridge. In an embodiment, the nasal bridge region 225 of the nasal seal is configured to contact the bottom half of the user's nose.

Figure 52:
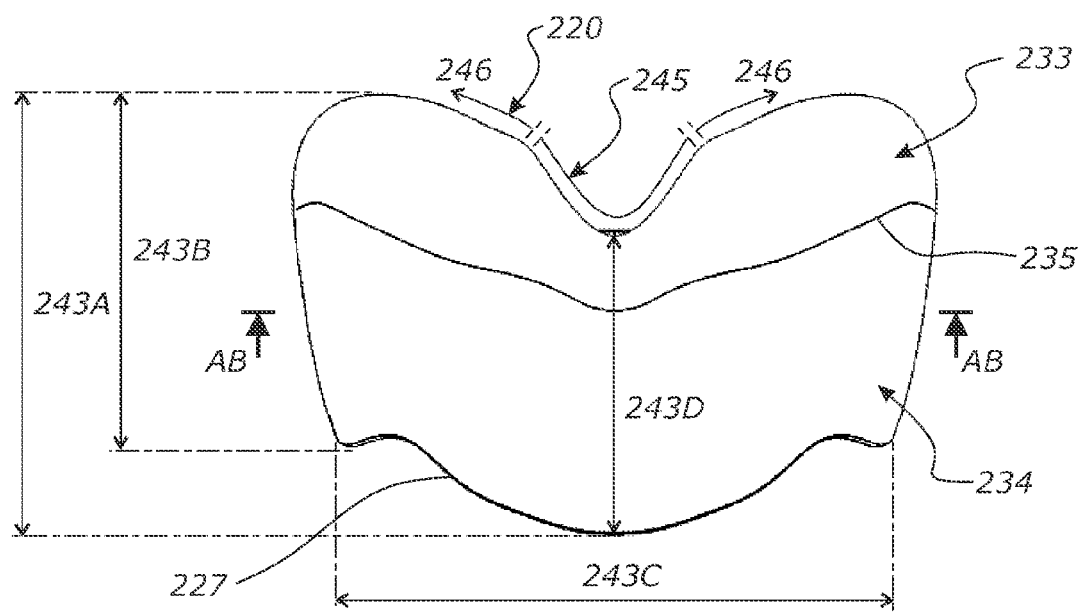
FIG. 52 is a top view of the nasal seal of the fourth embodiment nasal mask interface.

Referring to FIG. 52, in this embodiment the nasal bridge region 225 of the contacting surface 220 comprises a central valley region or portion indicated at 245 that is recessed relative to the remainder of the contacting surface. The valley region 245 is configured to engage with the user's nasal bridge and is shaped to conform substantially to the nasal bridge of a user.

The overall shape and configuration of the contacting surface 220 is arranged to sealingly conform to the contour of the user's face about the nose and to sealingly engage about the user's nose when secured to the user's head via headgear and when the nasal mask interface receives a flow of gases. In this embodiment, the nasal seal can be considered to be of the inflating type as under pressure the seal urges the face-contacting surface 220 against the face of the user and deforms to substantially seal against the facial contours of the user, including one or more of the upper lip, the medial cheek, the lateral nose and the bridge of the nose.

Figure 48:
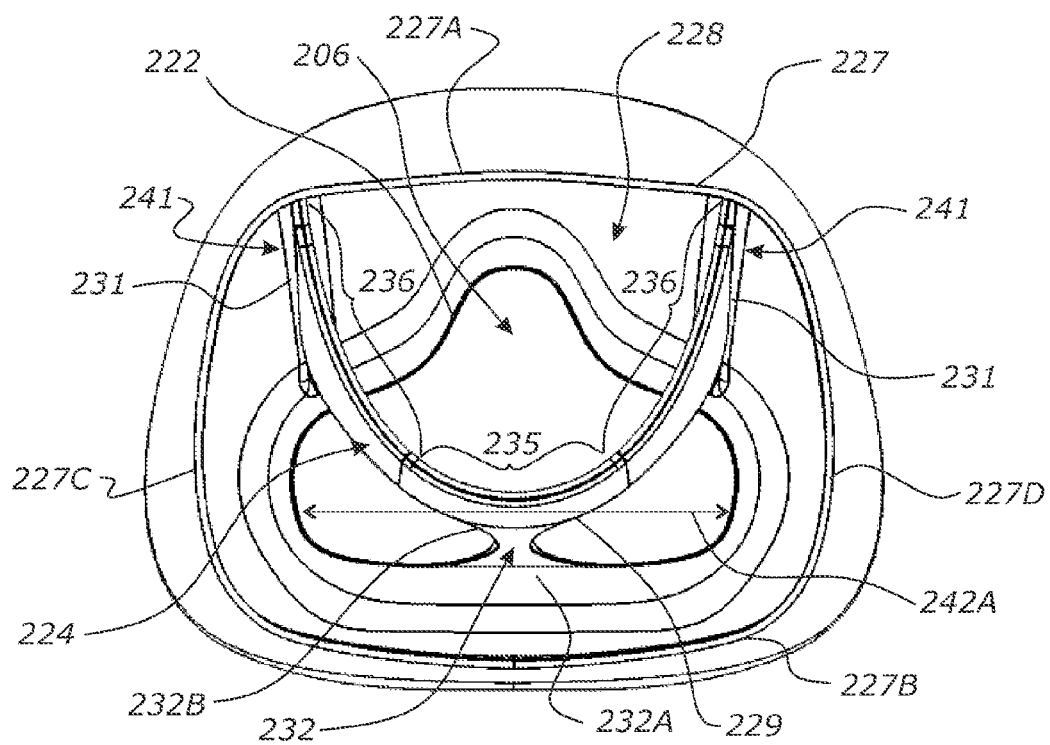
FIG. 48 is a rear view of the nasal seal of the fourth embodiment nasal mask interface.
Figure 49:
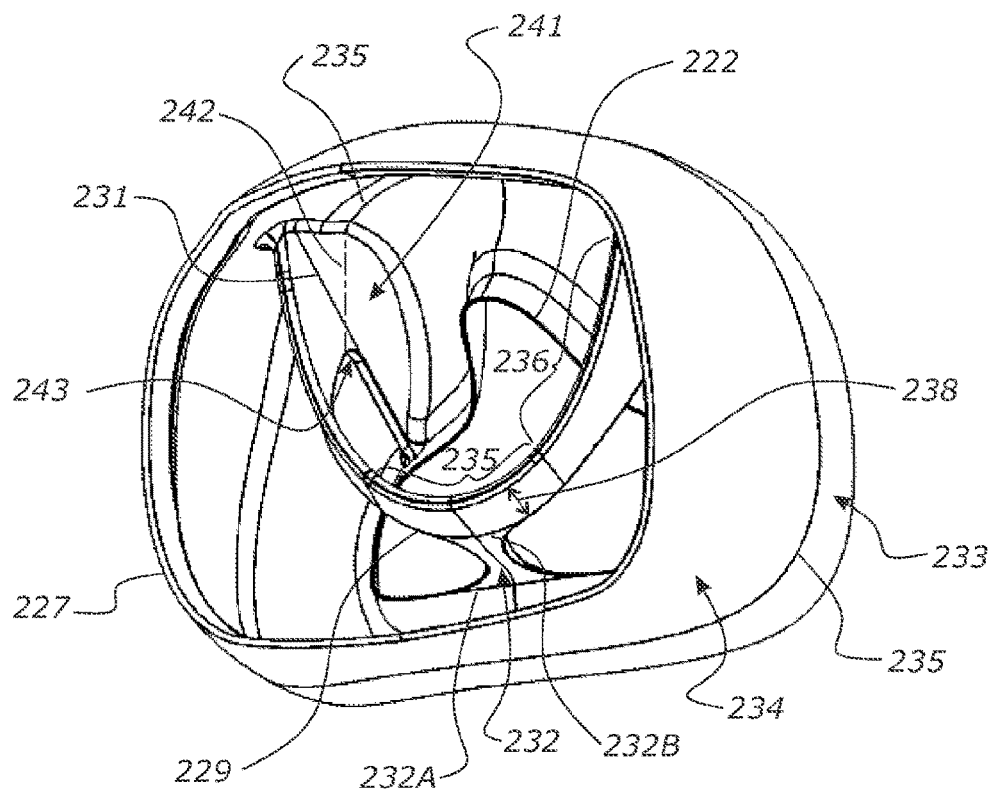
FIG. 49 is a underside perspective view from the outer side of the nasal seal of the fourth embodiment nasal mask interface.
Figure 50:
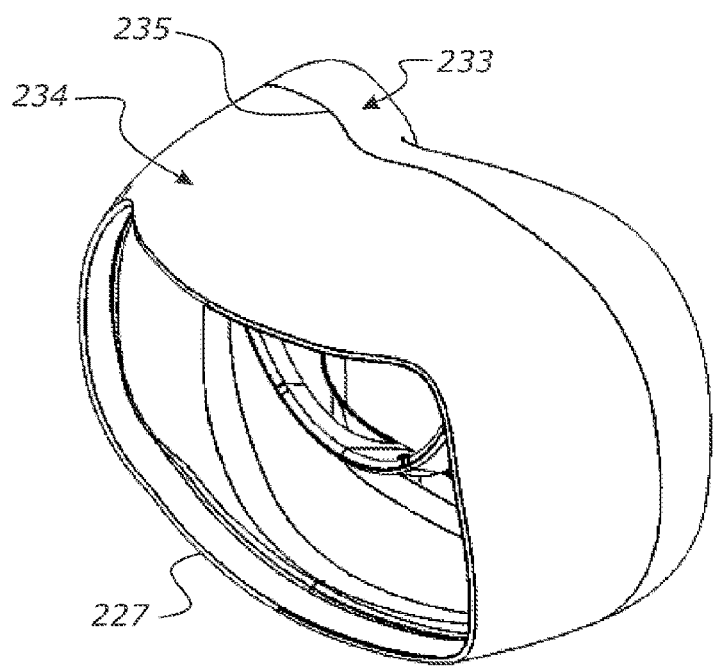
FIG. 50 is an upper perspective view from the outer side of the nasal seal of the fourth embodiment nasal mask interface.

The contacting surface 220 of the nasal seal 202 terminates at an inner peripheral edge 222 that defines the nose-receiving opening or nasal aperture 206 into the mask cavity. The mask cavity is defined or formed when the nasal seal 202 is assembled or connected to the seal housing 204. Referring to FIG. 48, the outer side of the nasal seal opposite to the face-contacting side of FIG. 47 is shown. The outer side of the nasal seal 202 connects to the seal housing 204. In this embodiment, the outer side of the nasal seal 202 terminates at a connecting edge 227 that defines an outer side or housing aperture 228 for receiving or connecting with the seal housing 204.

Figure 51:
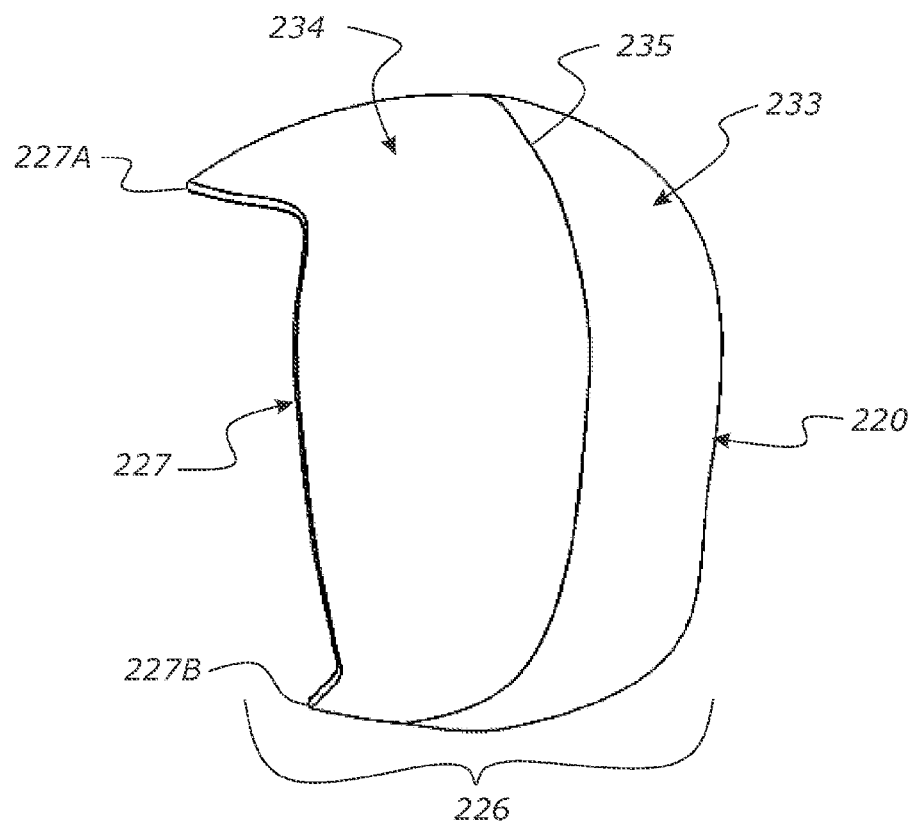
FIG. 51 is a side elevation view of the nasal seal of the fourth embodiment nasal mask interface.
Figure 53:
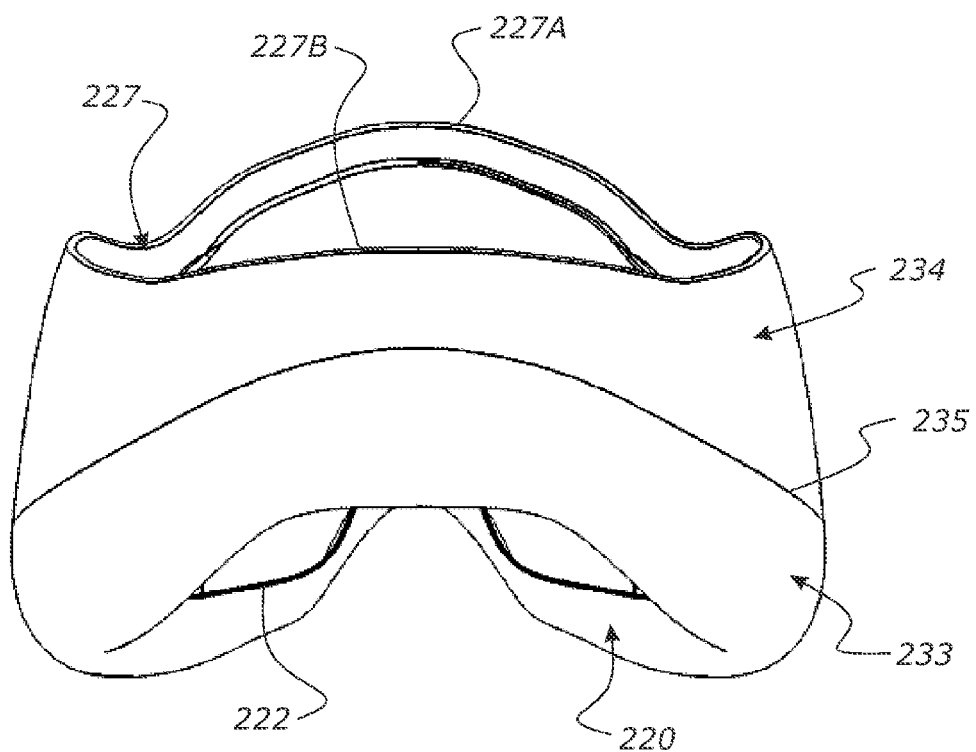
FIG. 53 is an underside view of the nasal seal of the fourth embodiment nasal mask interface.

Referring to FIG. 51, the connecting edge 227 at the outer side of the nasal seal 202 is not coincident with a single plane or extends in a single plane. Referring to FIGS. 48 and 51, in this embodiment the connecting edge 227 at the outer side of the nasal seal comprises an upper edge 227A, a lower edge 227B and lateral side edges 227C, 227D that extend between the upper 227A and lower 227B edges. In this embodiment, the upper edge 227A protrudes rearwardly of the side lateral edges 227C and 227D. At least a central portion of the lower edge 227B may also protrude rearwardly of the lateral edges 227. In this embodiment, at least a central portion of the upper connecting edge 227A protrudes rearwardly beyond both the lateral edges 227C, 227D and the lower edge 227B. As shown in FIG. 53, the upper edge 227A protrudes or bulges outwardly to an apex at a centre of the nasal seal.

In this embodiment, the nasal aperture 206 formed on the face-contacting side of the nasal seal 202 is generally or semi triangular in shape to match the natural geometry of a human nose. The housing aperture 228 on the outer side of the nasal seal 202 is generally or semi rectangular in shape.

Referring to FIGS. 47 and 48, the under-nose support 224 can be seen and is generally concave or U-shaped with three connection or attachment points to or within the nasal seal 202. As shown, the under-nose support 224 is suspended like a sling or hammock between two upper connection points 231 located at opposing upper lateral positions or surfaces within the nasal seal 202. In particular, the upper lateral connections 231 are located on the inside surface of the nasal seal 202, one on each side of the central apex region of the nasal aperture 206. In this embodiment, the lateral connections 231 of the under-nose support 224 are configured or arranged in a vertical orientation such that the inner or contact surfaces of the under-nose support 224 substantially face or oppose each other at or toward the lateral connection points 231. In particular, the lateral contact surfaces of the under-nose support 224 may be substantially parallel to each other at or toward the lateral connection points 231. The under-nose support 224 in this embodiment further comprises a third connection at or toward the centre bottom of the nasal seal. In this embodiment, the bottom centre connection point 232 couples to or at the centre bottom region of the edge 222 of the contacting surface 220 of the nasal seal that defines the nasal aperture 206. The under-nose support 224 and its connections will be explained further in detail later.

Referring to FIGS. 51-53, the nasal seal to 202 is substantially defined by the face-contacting surface portion 220 (shown in FIG. 47) and a sidewall portion 226 (shown in FIG. 51) that extends rearwardly from the contacting surface about the periphery of the seal and which terminates at the connecting edge 227 at the exterior or outer side of the seal that couples or is connected to the seal housing 204. In this embodiment, the nasal seal 202 may comprise varying thickness profiles or regions extending from the nasal aperture edge 222 on the face-contacting side of the nasal seal to the connecting edge 227 at the outer side of the nasal seal.

In this embodiment, the nasal seal 202 comprises at least a first front region generally indicated at 233 that extends from the nasal aperture edge 222 to an intermediate peripheral boundary 235 located on the side wall portion 226 and a second rear region 234 that extends from the intermediate peripheral transition boundary 235 to the connecting edge 227 on the outer side of the seal.

In this embodiment, the front region 233 includes the contacting surface 220 and at least a portion of the side wall portion 226 of the nasal seal adjacently contact surface 220. The rear region 234 comprises the remainder of the side wall portion 226 extending back from the transition boundary 235 to the connecting edge 227.

Figure 56:
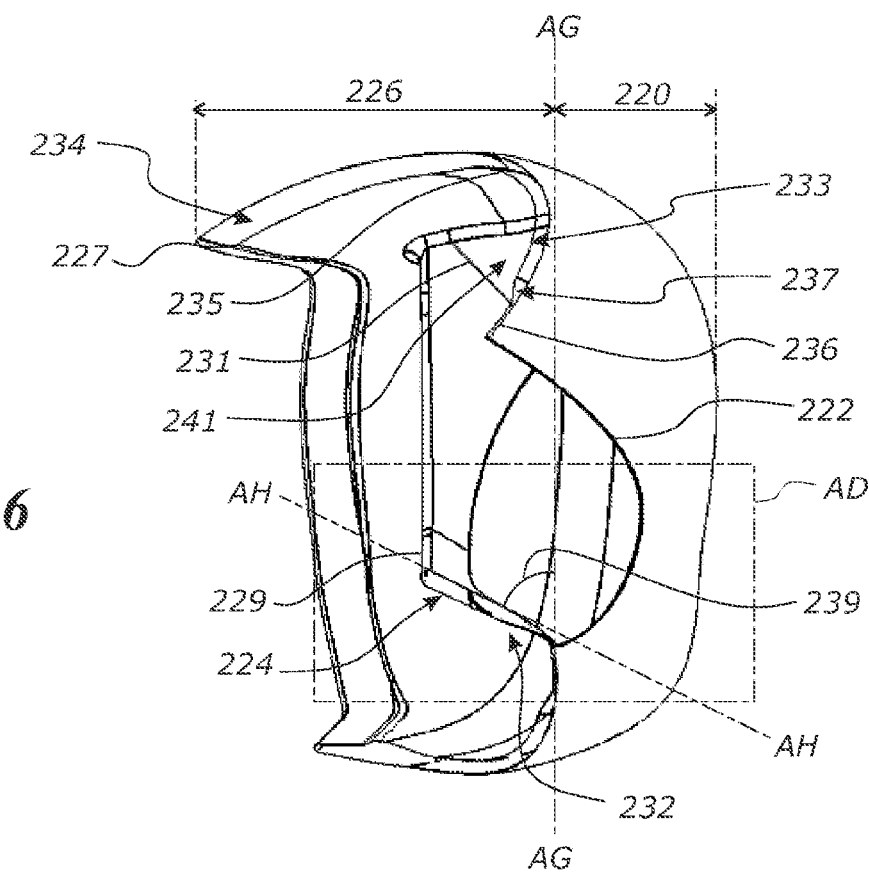
FIG. 56 is a cross-sectional view of the nasal seal of the fourth embodiment nasal mask interface through line AC of FIG. 47.

Referring to FIG. 56, in this embodiment the front region 233 of the nasal seal comprising the contact surface is thinner or of reduced thickness on average relative to the rear region 234 of the nasal seal. In this embodiment, the nasal seal further comprises an additional third thickness region 236 within the front region 233. In particular, the front region 233 transitions into a thinner edge region 236 adjacent the nasal aperture edge 222. The edge region 236 is thinner than the remaining portion of the front region 233. In this embodiment, the edge region 236 is a minor portion of the front region 233.

The described thickness profile provides the nasal seal 202 with stability and enhances the sealing engagement with the user's nose. In particular, the thicker rear region 234 provides stability to the overall nasal seal shape, while the reduced thickness of the front region 233 comprising the contacting surface 220 encourages conformity of the nasal seal with the user's nose. Furthermore, the edge region 236 about the periphery of the nasal aperture edge 222 is the thinnest part of the contacting surface 220 and provides increased user comfort and sealing conformity. It will be appreciated that the thicknesses of the rear region 234, front region 233 and edge region 236 may be uniform within the respective regions or may have varying thicknesses within the regions. For example, in this embodiment, the rear region 234 gradually reduces in thickness from the contacting edge 227 to the intermediate transition boundary 235. The front region 233 is of substantially uniform thickness in the majority portion and the minor thinned edge portion 236, with the edge portion 236 having a uniform thicknesses reduced relative to the majority of the front region. In this embodiment, the majority portion of the front region 233 transitions gradually to the thinner edge region 236 as shown at the body transition zone 237 in FIG. 56. As shown in FIG. 56, the face-contacting surface 220 of the nasal seal forms a flange that curls or extends inward from the side wall portion 226 of the nasal seal, the flange including the thinned edge portion 236.

Under-Nose Support of Nasal Seal

In this embodiment, the under-nose support 224 of the nasal seal 202 is in the form of a nasal sling or hammock that at least extends or is suspended laterally across a central portion of the nasal seal within the mask cavity. The under-nose support 224 is configured to contact at least a portion of the under-nose surface of the user's nose so is to counteract any resultant lift force created when the nasal mask is worn and in use with pressurised gases flowing as previously discussed.

In this embodiment, the under-nose support 224 is entirely defined or enclosed within the outer envelope of the nasal seal, i.e. it does not protrude or extend beyond the connecting edge 227 on the outer side of the nasal seal that connects to the seal housing or the contacting surface edge 222 of the nasal aperture 206. However, it will be appreciated that at least a portion of the under-nose support 224 may protrude beyond the housing aperture defined by the connecting edge 227 in alternative embodiments.

In this embodiment, the under-nose support 224 is suspended laterally across a central region of the nasal seal 202 between left and right sides of the nasal seal. As shown, the under-nose support is disposed or located behind or rearward of the nasal aperture or opening 206 on the face-contacting side of the nasal seal. The under-nose support 224 is fixedly connected to the nasal seal in that it is not removable in this embodiment. In one form, the under-nose support is integrally moulded within the nasal seal. In alternative forms, the under-nose support part or portion of the nasal seal may be formed separately and then fixedly coupled within the nasal seal via adhesive or welding or the like, or it could be connected to the seal housing.

In this embodiment, the under-nose support configuration 224 comprises an elongate main lateral portion or band 229 that extends laterally across at least a portion of the nasal seal and within the nasal seal. With reference to FIGS. 47-49, and 54-56, and 57, in this embodiment the main lateral portion 229 of the under-nose support 224 is suspended or connected at each opposite end to a respective upper connection point 231 located on the upper internal surface of the nasal seal on opposite sides of the seal relative to the apex region of the nasal aperture 206. In this embodiment, the distal ends of the main lateral portion 229 of the under-nose support 224 are connected to the inner surface of the nasal seal via respective reinforcing portions or regions, for example in the form of ribs 241. In this embodiment, the ribs 241 extend in a substantially vertical orientation from the upper lateral positions within the nasal seal inner surface and extend into or connect to a respective distal end of the main lateral portion 229 at connection locations 231. In this embodiment, the ribs 241 are integrally moulded with the main lateral portion 229 of the under-nose support 224. It will also be appreciated that the ribs 241 at the ends of the main lateral portion 229 can be considered to be part of the under-nose support and main lateral portion 229. In other words, the reinforcing portions or regions 241 may be considered as extension portions of the main lateral portion, or simply end portions of the main lateral portions. Alternatively, the reinforcing portions or regions may be considered to be separate components or formations that are connected or integrally formed with the ends of the main lateral portions. The functionality and effect of the reinforcing portions or ribs 241 remains substantially the same under either interpretation.

Figure 55:
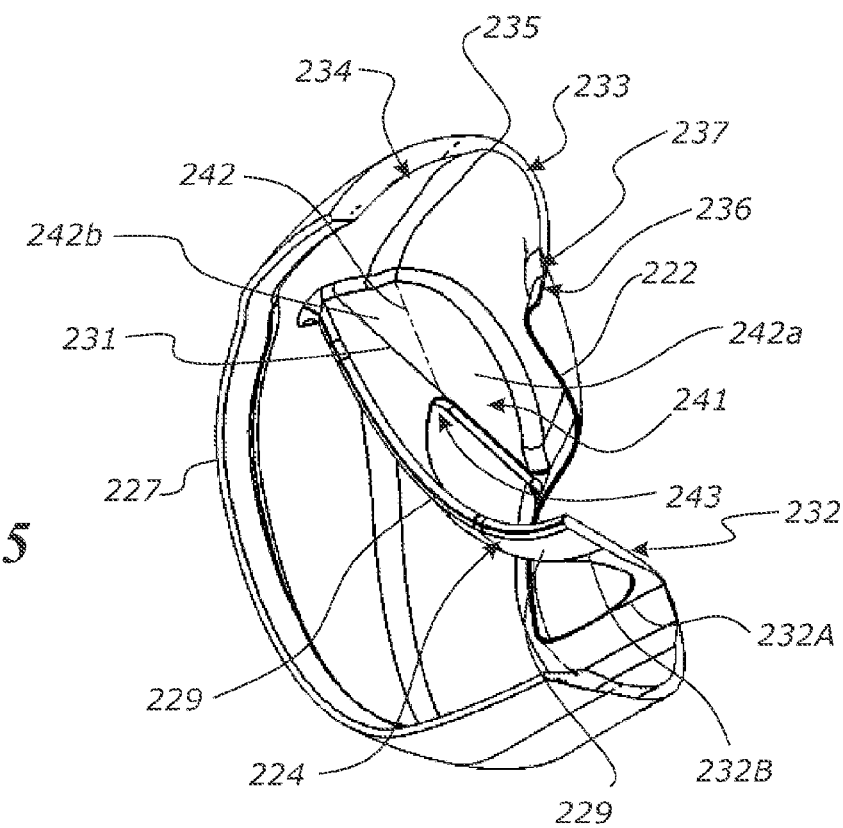
FIG. 55 is a perspective cross-sectional view of the nasal seal of the fourth embodiment nasal mask interface through line AC of FIG. 47.

Referring to FIG. 55, the rib 241 is at a portion of its peripheral edge coupled to or extends from a region of the inner surface of the nasal seal comprising a portion of the rear region 234 and front region 233. In this embodiment, the ribs extend across a portion of the rear region 234 and the majority of the front region 233 comprising the contact surface, but excluding the thinned edge region 236 adjacent the nasal aperture. However, it will be appreciated that in alternative embodiments the ribs 241 may also extend from or contact or extend into at least a portion of the thinned edge region 236. In this embodiment, the main lateral portion 229 of the under-nose support connects to each respective rib 241 at a portion of the rib that extends or is coincident with the thicker rear region 234 of the nasal seal wall. The ribs 241 provide the main lateral portion 229 of the under-nose support 224 with a solid connection within the nasal seal and also provide the dual function of structural support to the nasal seal by increasing the rigidity in that area or region of the nasal seal that contacts the patient on either side of the nose. In particular, the ribs 241 flank or are located either side of the upper valley region 245 of the contacting surface 220 (see FIG. 52) associated with the nasal bridge region of the contacting surface 220. In particular the ribs or panels 241 preventing the nasal seal from collapsing under excessive compression force while also allowing for a secure connection between the under-nose support and the inside surface of the nasal seal.

In some embodiments, the ribs may also function, either directly or indirectly, to give feedback to the user when the mask is overtightened. As described further below, the buckling of the ribs may be configured to deform or change the shape of the under-nose support to squeeze upon the user's nose, and/or to cause portions of the contacting surface adjacent or associated with the ribs to progressively press tighter into the side of the nose under increased compression of the nasal seal, e.g. due to tightening of the headgear.

Referring to FIG. 55, in this embodiment, a recessed region or zone 243 is provided or formed between the front portion 242a of the rib 241 and the rear portion 242b that connects to the main lateral portion 229 of the under-nose support 224. This recessed region 243 creates a buckling zone or axis 242 in each rib 241. In this embodiment, the buckling axis 242 extends from between toward the thickness region transition boundary 235 and the apex of the recessed region 243.

In some configurations, the buckling axis 242 enables the rib 241 to buckle outwardly toward its adjacent inner surface of its associated lateral wall of the nasal seal in use when the nasal seal is compressed in its depth dimension when worn by a user. This buckling of the ribs allows the front regions 242a of the ribs 241 to bend or compress inwardly toward the user's nose to enhance the seal created in use, and may also lift the under-nose support into the under-nose surface of the user.

In other configurations, the buckling axis 242 enables the ribs 241 to buckle inwardly toward each other in use when the nasal seal is compressed in its depth dimension when worn by a user. This inwards buckling of the ribs causes the under-nose support 224 to tighten or close-up at least in a lateral width direction and this acts to cause the under-nose support squeeze on or tighten onto the surface of the user's nose. In other words, the inwards buckling of the ribs causes the contact surfaces of the lateral regions of the main lateral portion of the under-nose support to move toward each other to effectively narrow or tighten the U-shape of the under-nose support so as to squeeze upon the user's nose.

The recessed region 243 can also be a region or zone of the rib 241 that has reduced depth (i.e. distance of the free peripheral edge of the rib from the edge of the rib connected to the inner surface of the seal) or surface area relative to other portions of the rib.

Referring to FIG. 48, in this embodiment the upper connecting locations 231 of the under-nose support are located in bound of the lateral extremities or sides of the nasal seal. In particular, the vertical connecting ribs 241 and connection points 231 are offset relative to the outer lateral width of the nasal seal on their respective sides. In this embodiment, the distance between the connection locations 231 is generally equal to or less than the outermost width of the nasal aperture indicated at 242A in FIGS. 47 and 48. In particular, the connection points 231 of the main lateral portion 229 of the under-nose support are located within the same width zone as the nasal aperture 206 in the context of the nasal seal. In this embodiment, the connecting ribs 241 extend from the contacting surface 220 in the upper lateral cheek regions 223 of the contacting surface at a location that engages with the cheek and/or outer nose or lateral nose surface of a user relative to their nasal bridge.

Figure 57:
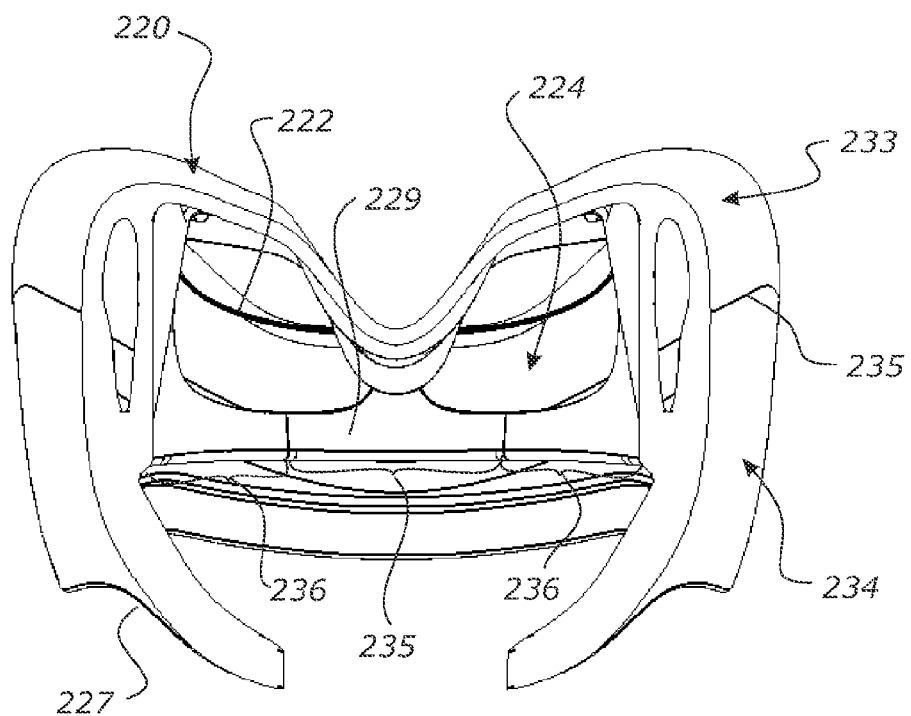
FIG. 57 is a cross-sectional view of the nasal seal of the fourth embodiment nasal mask interface through line AG of FIG. 47.

In some embodiment, referring to FIG. 57, the main lateral portion 229 of the under-nose support 224 is arranged to extend laterally across the nasal seal 202 at a depth that is approximately midway or in the centre of the overall depth profile of the nasal seal in the dimension extending from the contacting surface 220 to the outermost portion of the connecting edge 227 on the outer side of the nasal seal. However, in alternative embodiments the main lateral portion may be arranged to extend laterally across the nasal seal at other depths, whether closer or further from the contacting surface, and may also have portions that extend or protrude beyond the outer side connecting edge 227 or main envelope of the nasal seal.

In this embodiment, the under-nose support 224 also comprises a third connection to nasal seal in addition to the two upper lateral connections 231. In this embodiment, the under-nose support is connected to a central lower or bottom portion of the nasal seal as indicated at 232. In this embodiment, the lower central connection of the under-nose support 224 is in the form of a central extension or connecting portion 232 that extends centrally from the main lateral portion 229 and is coupled or connected to or at the nasal aperture edge 222 of the contacting surface 220 in the upper lip region 221 of the nasal seal. In this embodiment, the central connecting portion 232 has an approximately hour glass width profile. In particular, the width dimension of the central connecting portion 232 at both the nasal aperture edge 222 and the interface with the main lateral band 229 is larger than a width dimension of the central connecting portion 232 in a middle or intermediate region. For example, the central connecting portion 232 is an elongate portion that extends from a first end 232A that is coupled or integrally formed with the nasal aperture edge 222 of the contacting surface 220 to a second end 232B that is coupled or integrally formed to the main lateral band 229 of the under-nose support 224 (see FIGS. 48, 49 and 54). In this embodiment, the width dimension of the central connecting portion 232 progressively reduces from each of its ends 232A, 232B toward a central or middle region of reduced width to provide an approximately hourglass width dimension profile.

Referring to FIGS. 55 and 56, the central connecting portion 232 of the under-nose support comprises a varying thickness profile in the direction transverse to the contacting surface of the connection portion 232. In this embodiment, the thickness of the central connecting portion 232 tapes or reduces in width from its second end 232B at the main lateral portion 229 to its first end 232A at the nasal aperture edge 222. For example, the thickness of the central connecting portion 232 at the second end 232B is substantially equal or uniform with the thickness of the main lateral portion or band 229 in that region, and the thickness tapers or reduces either from the second end 232B or at a point in the middle region of the connecting portion 232 to a reduced thickness at the first end 232A at the nasal aperture edge 222. In this embodiment, the reduced thickness at the first end 232A is substantially equal to or uniform with the thickness of the nasal aperture edge 222 of the contacting surface. For example, the thickness of the central connecting portion 232 at its first end 232A may be substantially equal to the thickness of the thinned edge region 236 of the contacting surface 220 of the nasal seal.

Referring to FIGS. 47-49 and 54 in particular, in this embodiment the under-nose support 224 is configured with a curved profile across the lateral width of the under-nose support between the upper lateral connections 231. The curvature profile may vary across the lateral width of the under-nose support in some embodiments, but alternatively it may have a uniform curvature in other embodiments. In the embodiment shown, the curvature profile varies. In this embodiment, the contacting surface of the main lateral portion 229 of the under-nose support 224 has a steeper curved profile in a middle or central region 235 relative to a flatter curved profile in the remaining lateral or outer regions 236 that extend to the upper lateral connections 231. For example, in the central region indicated at 235 the main lateral portion 229 is provided with a first radius of curvature that is substantially uniform in the central region 235. The radius of curvature of the remaining lateral regions 236 on either side of the central region 235 may be constant or varying, but generally has a radius of curvature that is larger than the first radius of curvature of the central region 235 such that it is generally of flatter curvature. In this embodiment, the main lateral portion 229 is or comprises a curved contact surface profile across its entire lateral width without any flat regions.

In this embodiment, the width of the contacting surface of the main lateral portion 229 of the under-nose support 224 may vary along its length between the opposing sides of the nasal seal. In this embodiment, the main lateral portion 229 comprises a substantially uniform width indicated at 238 (see Figure A15) in the central region 235, with the width then progressively increasing in the outer lateral regions 236 toward the connection points 231.

Referring to FIG. 56, a central seal axis AG is defined as extending tangentially between the outermost upper and lower contact points of the central region of the contacting surface 220 when the nasal seal is in a relaxed condition (e.g not in use). As shown in FIG. 56, at least a portion of the contact surface of the under-nose support in a central region is indicated by axis AH extends at an angle defined or indicated at 239 relative to the seal axis AG such that the contact surface of the under-nose support is not parallel or aligned with the seal axis AG. In this embodiment, the contact surface in the central region of the under-nose support 224 is oriented at an angle offset from the seal axis AG in a range of approximately 40° to approximately 80°, more preferably approximately 45° to approximately 75°, even more preferably approximately 50° to approximately 70°, even more preferably approximately 55° to approximately 65°. As shown, at least a portion of the central connecting portion 232 also has a corresponding or aligned angular offset.

As explained above, the under-nose support 224 in this embodiment is fixedly connected or otherwise an integral component of the nasal seal 202. The drawings depict the nasal seal 202 and its under-nose support 224 in a rest state, i.e. un-used. Like the contacting surface 220 of the nasal seal, the under-nose support 224 is also configured to be soft and flexible or pliable such that its shape and position may conform in a sling or hammock like manner to the under-nose surface of the user's nose when the nasal mask interface is secured to the user's face or is otherwise worn. In this embodiment, the under-nose support is non-stretchable in any direction, although it may have a degree of stretching in same directions in alternative embodiments.

Alternative Under-Nose Support

The main lateral portion 229 or band of the under-nose support 224 is generally U-shaped with some curvature across the lateral width of the under-nose support. In alternative embodiments, the under-nose support may have flat sections or portions, or generally more rectangular or squarish in shape. For example, referring to FIG. 61, in alternative embodiments, the under-nose support indicated at 224A may have a substantially flat central horizontal portion 229A, and two substantially vertical or upright portions 229B extending upwardly from a respective end of the central horizontal portion 229A and each connecting at connecting points 229C to an inner surface on each upper later side of the nasal seal either directly or via a rib as with the previous embodiment.

Example of Nasal Seal Dimensions

In this embodiment, the ratio of the overall height to overall lateral width of the nasal seal 202 is in the range of approximately 1:1 to approximately 1:1.4, and in this example embodiment approximately 1:1.2. In this embodiment, the ratio of the overall height to overall lateral width to overall depth of the nasal seal is in the range of approximately 1:1:0.6 to approximately 1:1.4:1, and in this example embodiment approximately 1:1.2:0.8.

Figure 54:
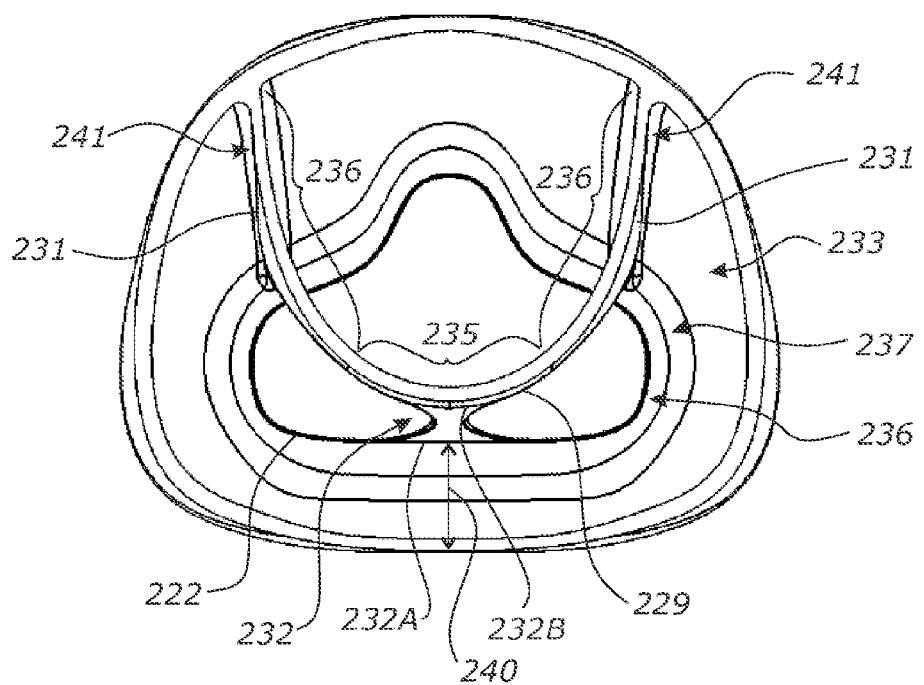
FIG. 54 is a cross-sectional view of the nasal seal of the fourth embodiment nasal mask interface through line AB of FIG. 52.

By way of example, the main dimensions of aspects of one nasal seal configuration will be described to provide a sense of scale. Referring to FIG. 47, the height of the nasal aperture defined by contacting surface edge 222 indicated in the central region at 242B is in the range of approximately 8 mm to approximately 43 mm, preferably approximately 23 mm and the outermost width of the nasal aperture indicated at 242A is in the range of approximately 24 mm to approximately 49 mm, preferably approximately 34 mm. The overall height of the nasal seal as indicated at 242D is in the range of approximately 22 mm to approximately 72 mm, preferably approximately 47 mm, and the overall width as indicated at 242C is in the range of approximately 47 mm to approximately 87 mm, preferably approximately 57 mm. In this embodiment, the width of the central connecting portion 232 in the reduced width middle region is in the range of approximately 2 mm to approximately 15 mm, preferably approximately 3 mm as indicated at 242E. Referring to FIG. 52, the overall depth of the nasal seal indicated at 243A is in the range of approximately 29 mm to approximately 49 mm, preferably approximately 39 mm. The depth of the nasal seal between the lateral contacting surface and lateral edge of the housing aperture as indicated at 243B is in the range of approximately 21 mm to approximately 36 mm, preferably approximately 31 mm. The depth of the nasal seal between the central nasal bridge valley 245 of the contacting surface 220 and the corresponding central housing aperture edge 227 is in the range of approximately 18 mm to approximately 33 mm, preferably approximately 28 mm. The lateral width of the nasal seal between the outer lateral points of the connecting edge 227 at the outer side of the nasal seal is in the range of approximately 40 mm to approximately 50 mm, preferably approximately 49 mm. Referring to FIG. 54, the height of the nasal seal between the bottom edge 222 of the nasal aperture 206 and the bottom surface of the nasal seal 202 is in the range of approximately 5 mm to approximately 20 mm.

Figure 58:
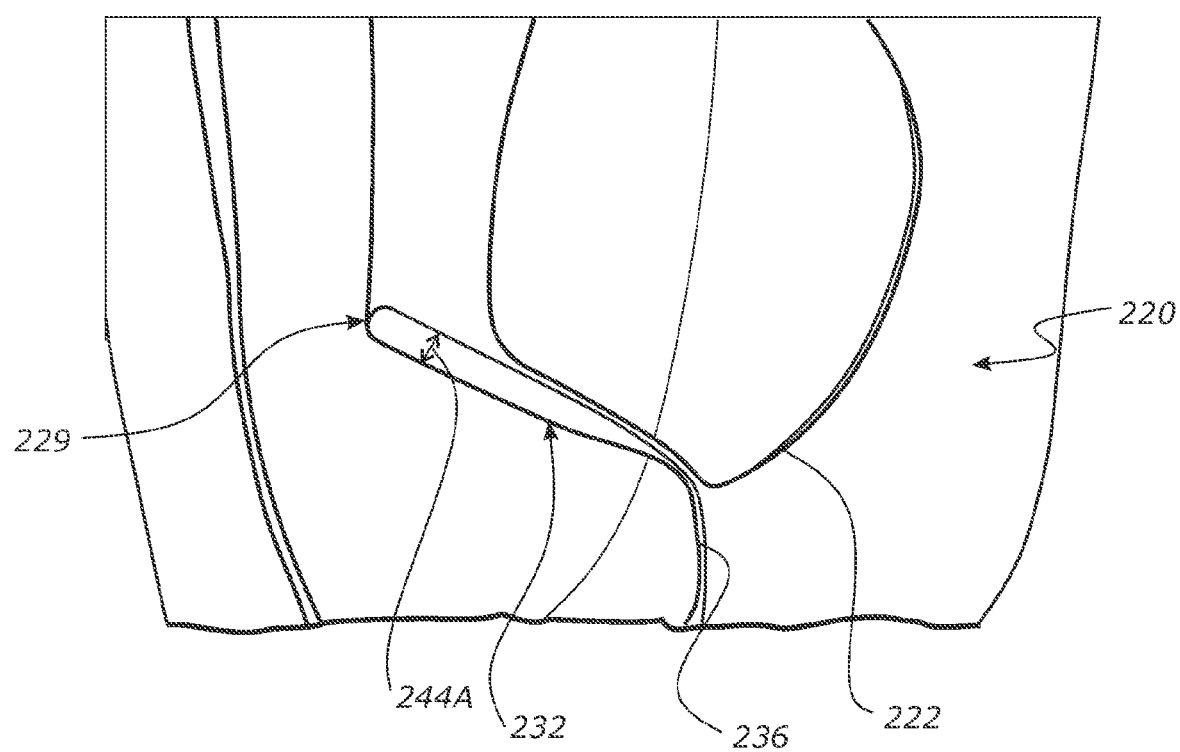
FIG. 58 is a close-up view of area AD of FIG. 56, and in particular showing the angular dimensional profile of a portion of the under-nose support of the nasal seal of the fourth embodiment nasal mask interface.

Referring to FIG. 58, the thickness of the main lateral portion 229 of the under-nose support 224 in a direction transverse to the contacting surface of the main lateral portion as indicated at 244A is in the range of approximately 0.2 mm to approximately 3 mm, preferably approximately 1.1 mm. The central connecting portion 232 extending from the centre of the main lateral portion 229 starts with a similar thickness and then transitions to a thinner thickness as shown as it connects to the nasal aperture edge 222 of the contacting surface 220. In this example embodiment, the thickness in the edge region 236 of the contacting surface is approximately 0.2 mm.

Figure 59:
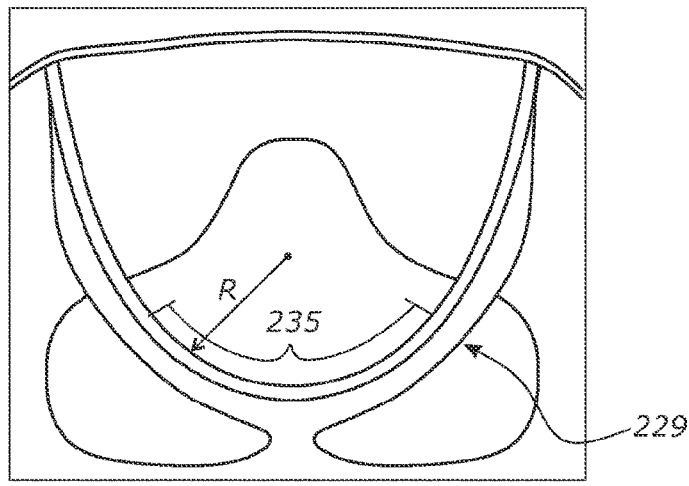
FIG. 59 is a rear close-up view of the under-nose support of the fourth embodiment nasal mask interface configured for a small-medium sized seal configuration, and in particular showing the radius of curvature of a central portion of the under-nose support.
Figure 60:
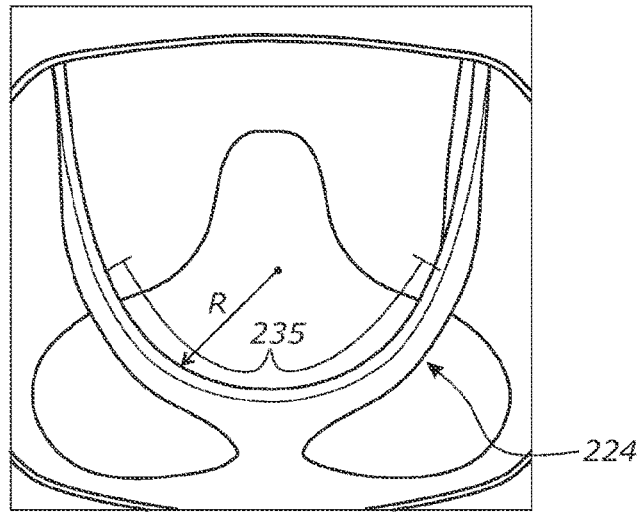
FIG. 60 is a rear close-up view of the under-nose support of the fourth embodiment nasal mask interface configured for a medium-large sized seal configuration, and in particular showing the radius of curvature of a central portion of the under-nose support.
Figure 61:
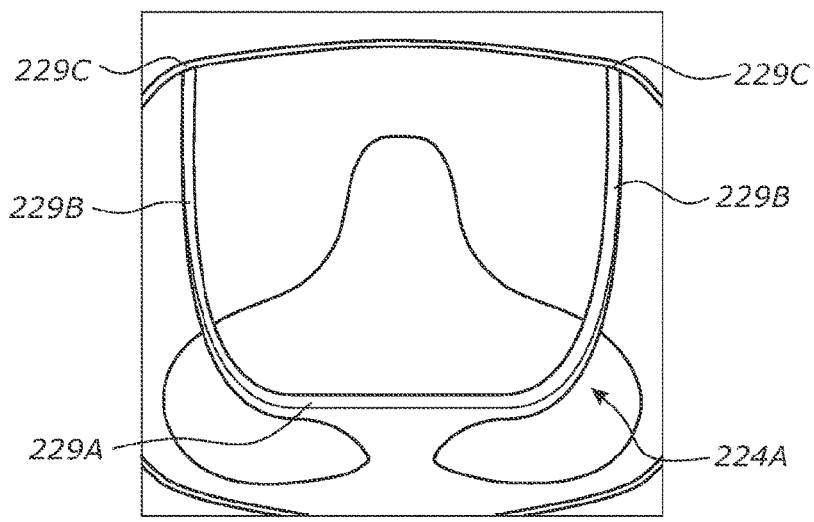
FIG. 61 shows a rear close-up view of another form of under-nose support of the fourth embodiment nasal mask interface, the under-nose support having a modified alternative squarish-shape.
Figure 62:
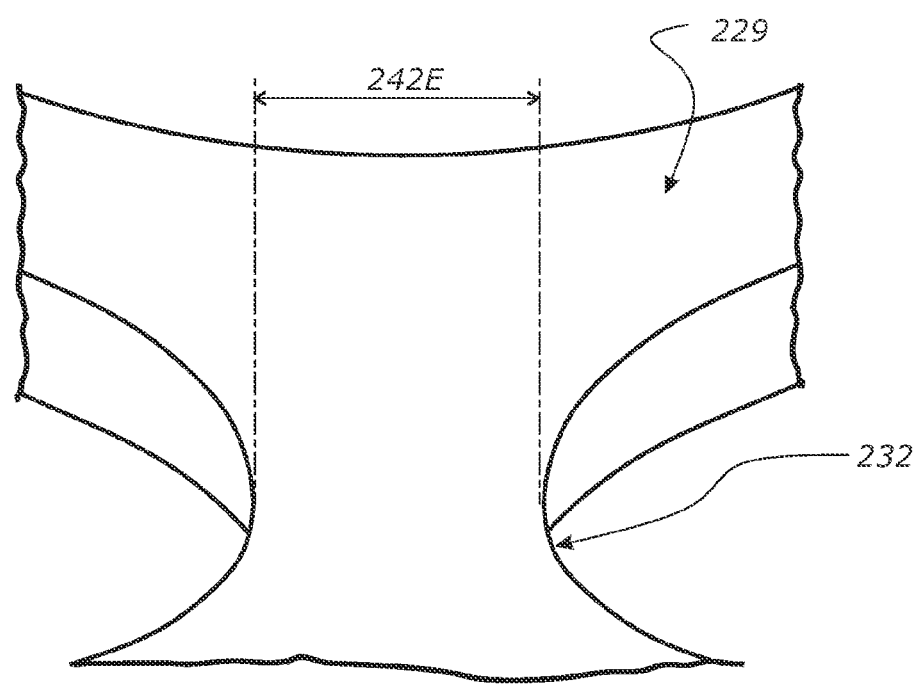
FIG. 62 shows a close-up upper perspective view of a central region of the under-nose support of the nasal seal of the fourth embodiment nasal mask interface, and in particular identifies a width dimension of a portion of the under-nose support for a small-medium sized seal configuration.
Figure 63:
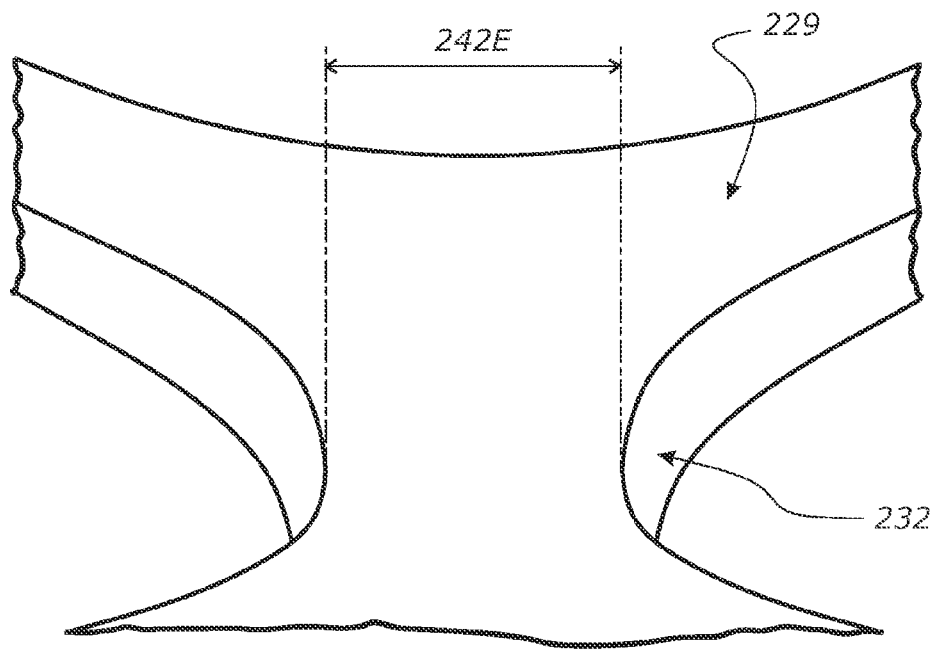
FIG. 63 shows a close-up upper perspective view of a central region of the under-nose support of the nasal seal of the fourth embodiment nasal mask interface, and in particular identifies a width dimension of a portion of the under-nose support for a medium-large sized seal configuration.
Figure 64:
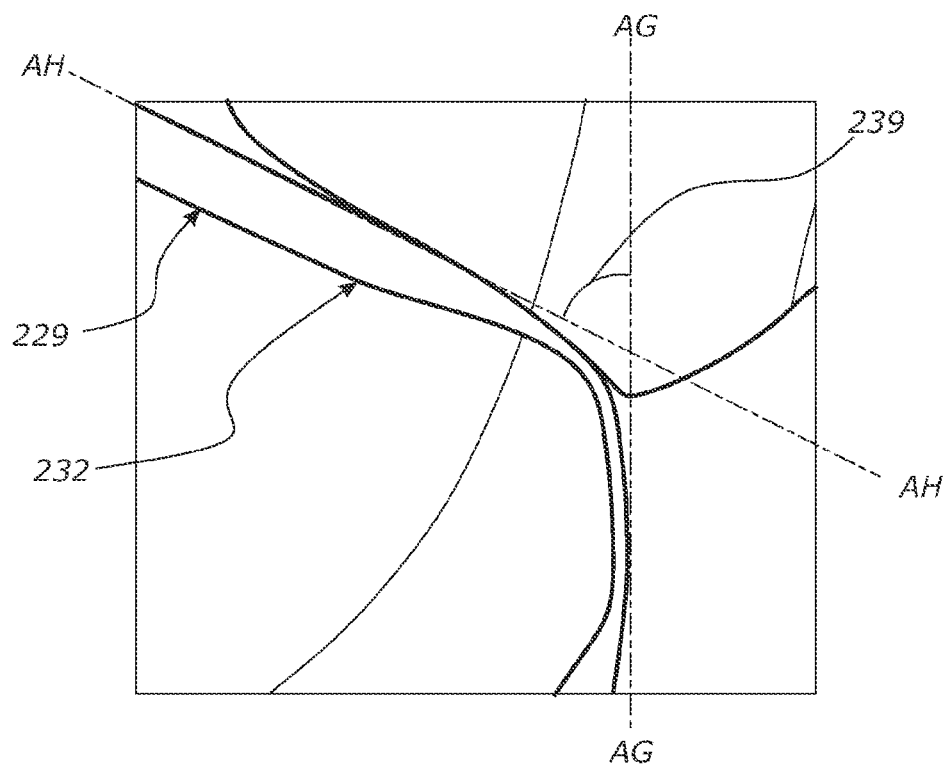
FIG. 64 shows a close-up cross-sectional view of a portion of the central connecting portion of the under-nose support of the nasal seal of the fourth embodiment nasal mask interface, and in particular an angular dimension of the central connecting portion for a small-medium sized seal configuration.
Figure 65:
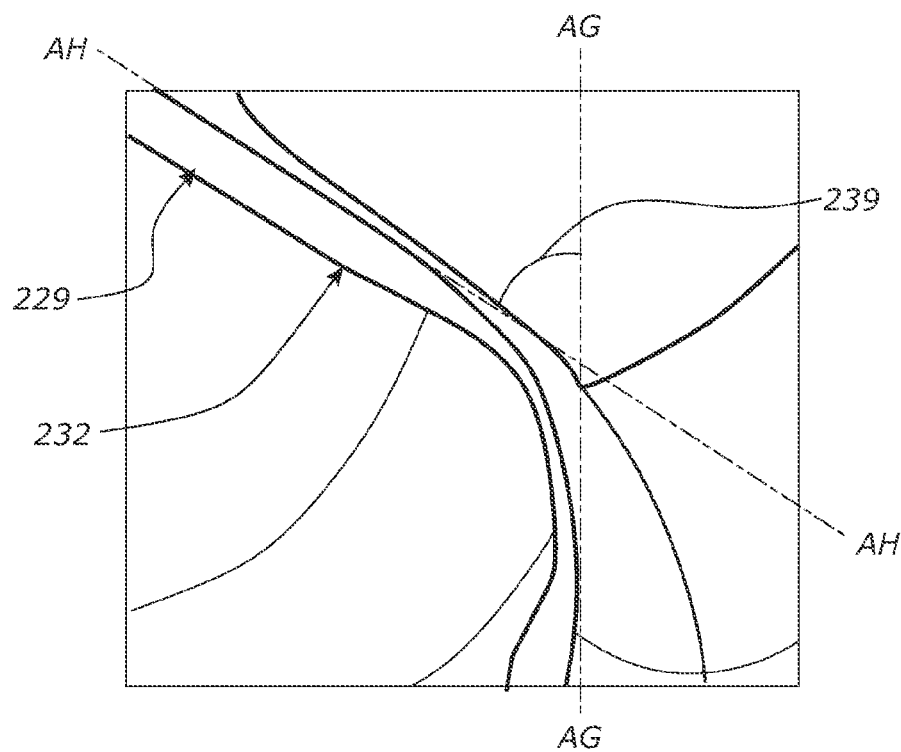
FIG. 65 shows a close-up cross-sectional view of a portion of a central connecting portion of the under-nose support of the nasal seal of the fourth embodiment nasal mask interface, and in particular an angular dimension of the central connecting portion for a medium-large sized seal configuration.
Figure 66:
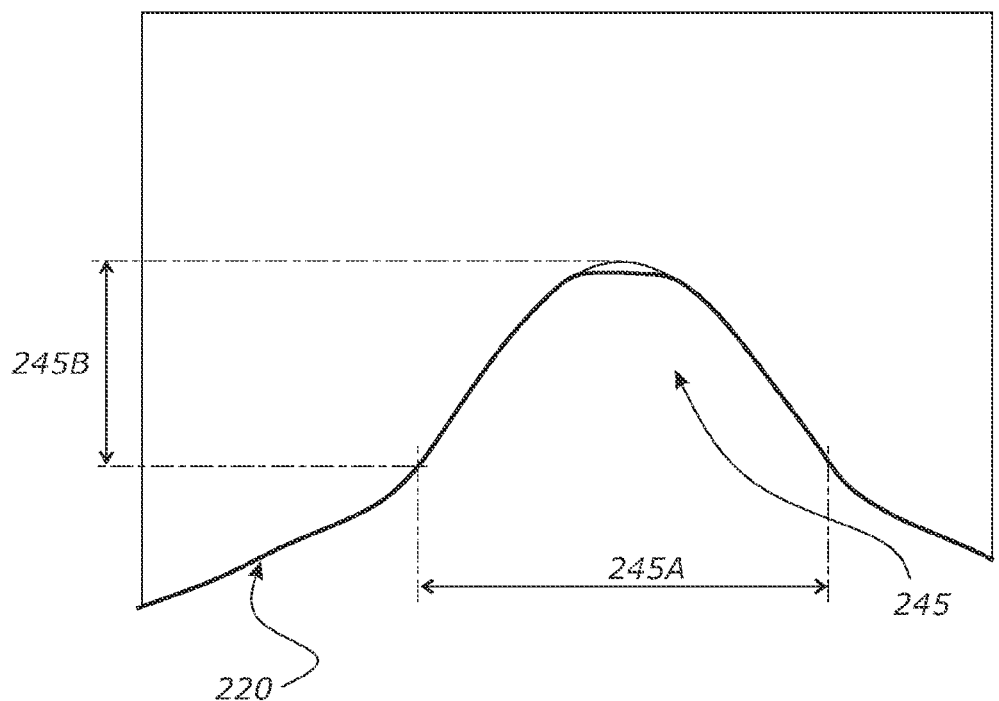
FIG. 66 shows a close-up upper view of a nasal bridge region of the nasal seal of the fourth embodiment nasal mask interface, and in particular a valley region of the contacting surface for a small-medium sized seal configuration.
Figure 67:
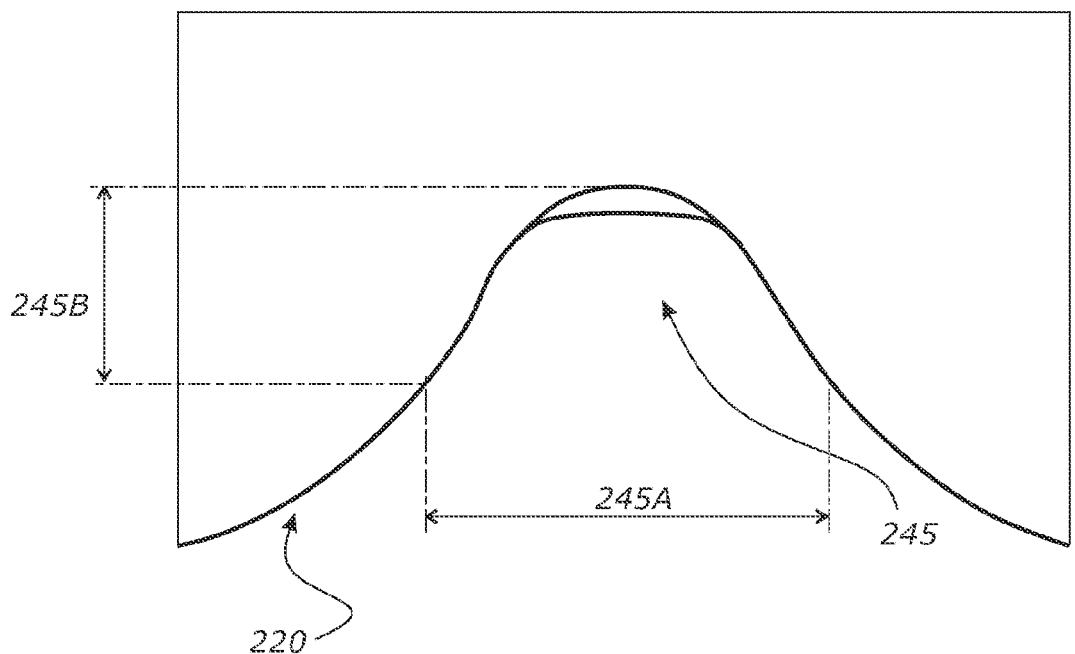
FIG. 67 shows a close-up upper view of a nasal bridge region of the nasal seal of the fourth embodiment nasal mask interface, and in particular a valley region of the contacting surface for a medium-large sized seal configuration.

The dimensions of various aspects of the nasal seal may be varied to provide for different sized patients. In one embodiment, the nasal seal and interface may be provided in a number of different sizes such as small, medium and large, or a larger number of size categories. In another embodiment, the nasal seal may be provided in two sizes, such as a small-medium size and a medium-large size. By way of example, dimensional aspects of a small-medium nasal seal compared to a medium-large nasal seal will be provided by way of example, with reference to FIGS. 59-67. Referring to FIGS. 59 and 60, the radius of curvature R of a central region 235 of the main lateral band 229 of the under-nose support is in the range of approximately 8 mm to approximately 18 mm, preferably for a small-medium nasal seal is approximately 12.5 mm, and for a medium-large size nasal seal the central region 235 is longer and comprises a substantially constant larger radius of curvature of approximately 14 mm. Referring to FIGS. 62 and 63, the width of the central connecting portion 232 in the middle thin region is approximately 2.9 mm for a small-medium size configuration and approximately 4.12 mm for a medium-large size configuration. Referring to FIGS. 64 and 65, the angular offset indicated at 239 between the axis AH of the central region of the main lateral portion 229 and the seal tangential axis AG is approximately 64° for a small-medium size configuration and approximately 58° for a medium-large size configuration. Referring to FIGS. 66 and 67, the nasal bridge region of the contacting surface of the nasal seal comprises a recessed valley portion 245 as previously described. In this embodiment, the depth of the valley region 245 as indicated at 245B is approximately 7 mm for both the small-medium and medium-large size configurations. The width of the valley region as indicated at 245A is in the range of approximately 7 mm to approximately 17 mm, preferably approximately 13.8 mm for the small-medium size configuration, and approximately 14.1 mm for the medium-large configuration.

As described, the nasal seal is generally dimensionally and/or configured so as to have a generally rectangular shape when viewed from the outer side as shown in FIG. 48 and from the front or face-contacting side as shown in FIG. 47.

Seal Housing

Referring to FIGS. 68-74, the seal housing 204 of this embodiment of the nasal mask interface 200 will be described in further detail. In this embodiment, the seal housing 204 is formed of a rigid material or is more rigid that the flexible nasal seal. For example, the seal housing may be formed from a plastic polymer such as polycarbonate or similar.

Figure 72:
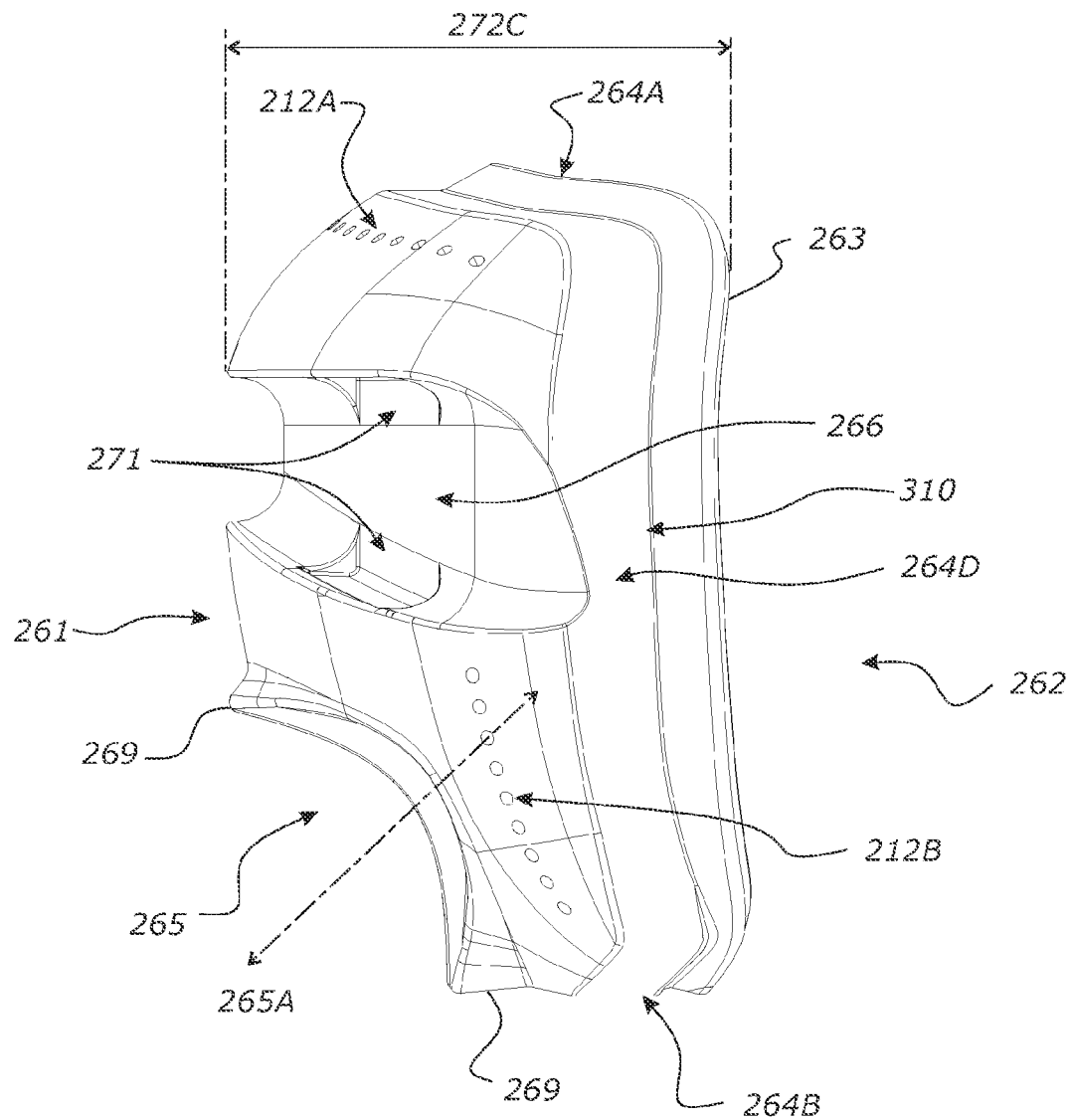
FIG. 72 is a side elevation view of the seal housing of the fourth embodiment nasal mask interface.
Figure 73:
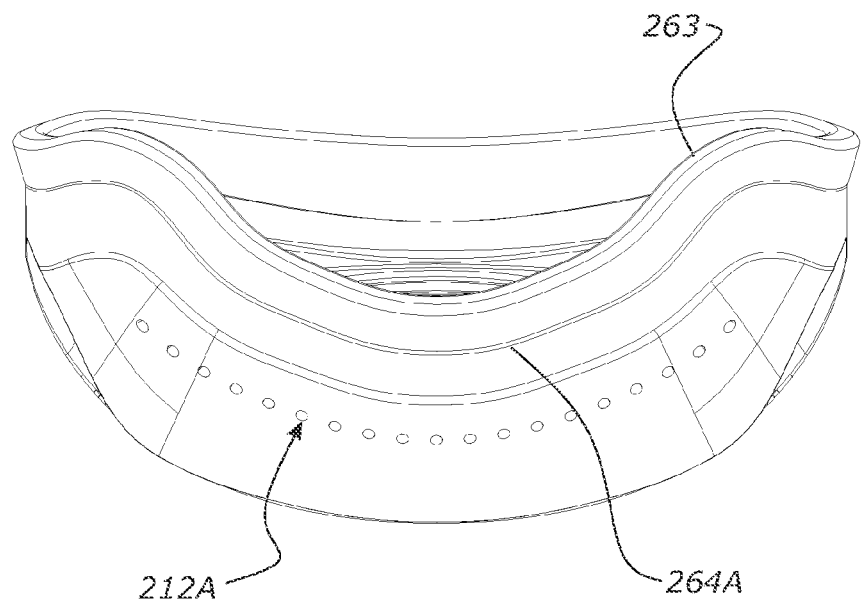
FIG. 73 is a top view of the seal housing of the fourth embodiment nasal mask interface.

The seal housing or shell 204 is a generally hollow component that extends from a main opening on the seal connecting side indicated at 262 to an outer side indicated at 261 (see FIG. 72). The opening on the seal contacting side 262 of the seal housing 204 is defined by a perimeter edge 263 of the seal housing 204. The seal housing 204 is generally defined by a concave shaped exterior surface that extends from the perimeter edge 263 of the opening to the outer side 261 of the seal housing between top 264A, bottom 264B and lateral sides 264C, 264D of the seal housing to thereby provide a substantially hollow component with depth that cooperates with the nasal seal 202 to collectively define a mask cavity or volume for receiving a gases stream from an inlet opening 265 provided on the exterior surface at the outer side 261 of the seal housing.

The perimeter edge 263 of the main opening of seal housing 204 is configured to connect or couple to the connecting edge 222 of the nasal seal 202 to couple the nasal seal to the seal housing to form the mask cavity. It will be appreciated that the nasal seal 202 and seal housing 204 may be permanently or semi-permanently connected or coupled via various methods, including overmoulding, welding, adhesive, mechanical coupling configuration, or a combination of these.

Figure 46:
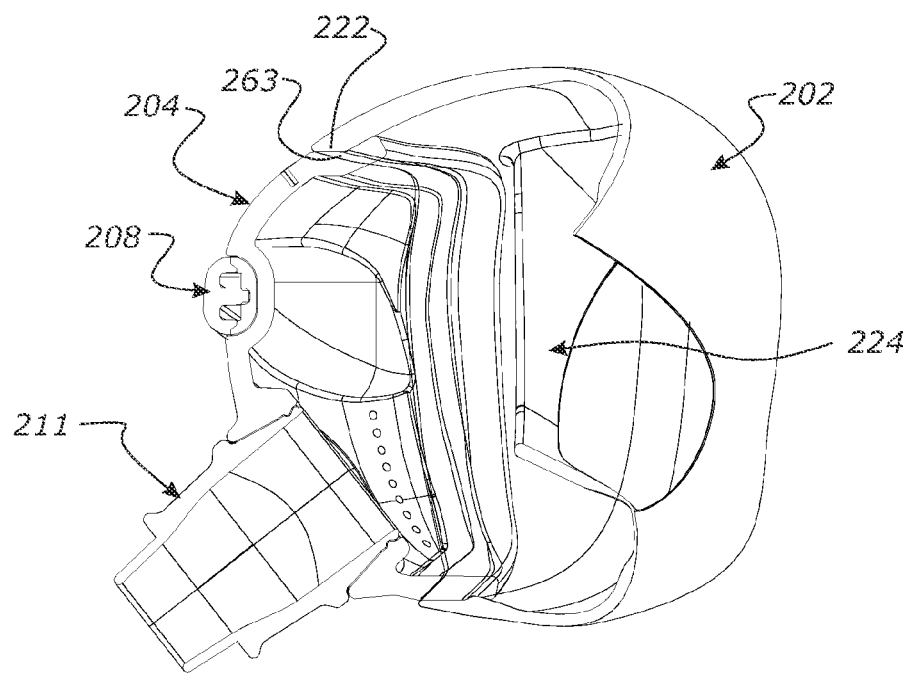
FIG. 46 is a cross-sectional view of the fourth embodiment nasal mask interface through a central line AA shown in FIG. 41.

Referring to FIG. 46, in this embodiment the connecting edge 222 of the nasal seal 202 is permanently connected or coupled to the perimeter edge 263 of the seal housing 204 via adhesive, overmoulding or welding of complementary surfaces at the interface between the edges 222, 263 of the components. However, it will be appreciated that in alternative embodiments that either of the connecting edge 222 or perimeter edge 263 may be provided with a channel or a complementary ridge or vice versa that engage with each other to form a mechanical connection, and that in addition to this mechanical coupling, overmoulding, adhesive, or welding may be applied to secure the connection. For example, the ridge and channel configuration may be similar to that described with reference to the first embodiment nasal mask interace.

In this embodiment, the shape and dimension of the peripheral edge 263 of the seal housing 204 and connecting edge 222 of the nasal seal 202 complement each other to enable a secure connection between the components as will be appreciated. In alternative embodiments, it will be appreciated by a skilled person that the nasal seal 202 may be releasably connectable to the seal housing 204 via a rigid clip or other releasable coupling mechanism if desired.

In this embodiment, the exterior surface of the seal housing 204 is provided with a channel or recess generally indicated at 266 that forms a yoke channel for releasably receiving and retaining the yoke 208 associated with the headgear 250. In this embodiment, the yoke channel 266 extends laterally across the exterior surface of the seal housing 204 in a middle or upper region of the seal housing. Below the yoke channel 266 at or toward the bottom of the seal housing is a central inlet opening 265 that is configured to receive a supply of gases into the nasal mask interface when in use. In this embodiment, the inlet opening 265 of the seal housing 204 is configured to releasably couple to a conduit frame 211 that is in turn releasably or permanently connected to an end of a gases supply conduit 260 as previously described.

Figure 70:
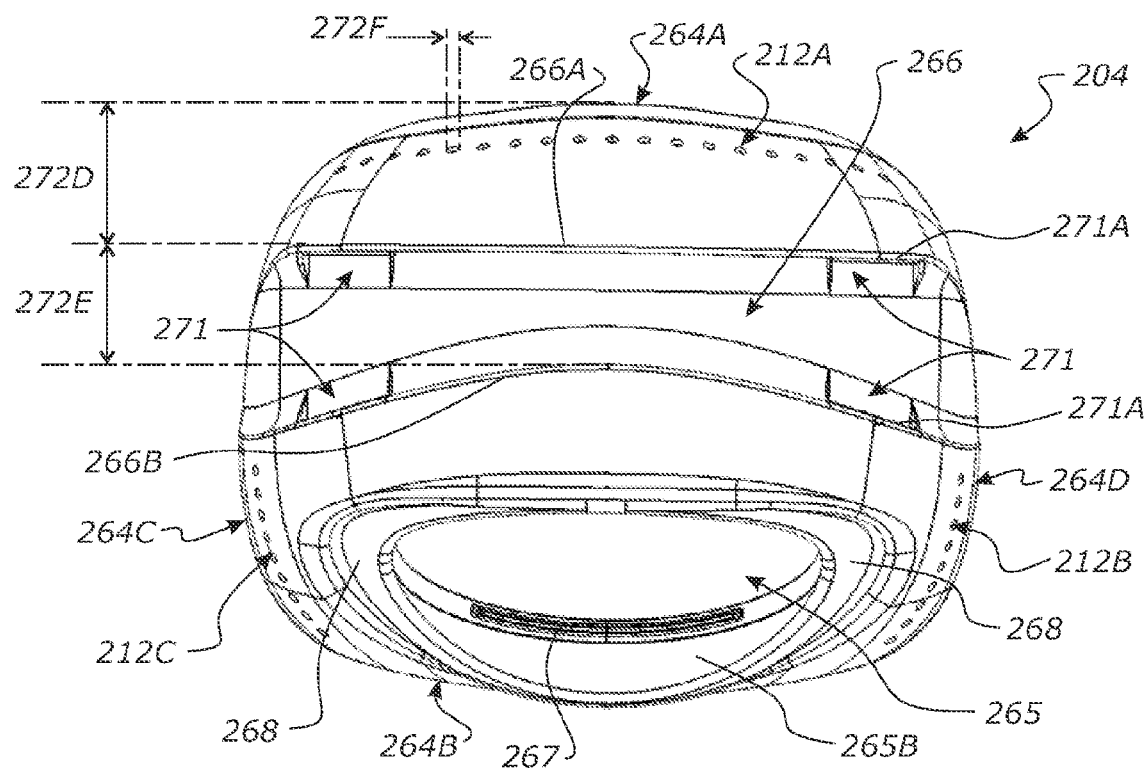
FIG. 70 is a rear view of the outer side of the seal housing of the fourth embodiment nasal mask interface.
Figure 74:
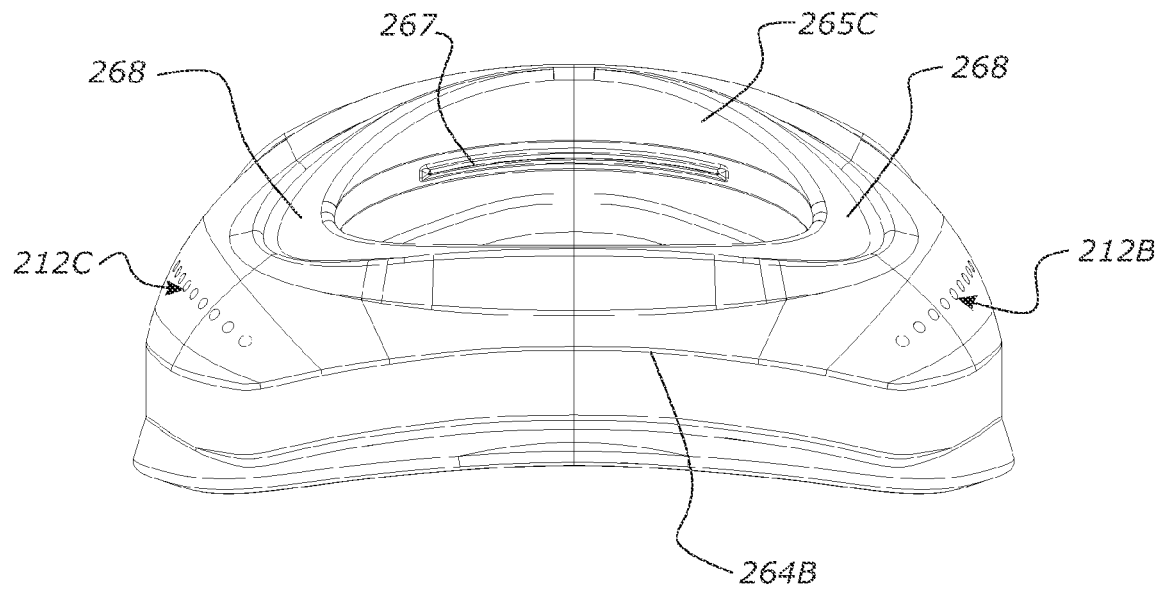
FIG. 74 is a bottom or underside view of the seal housing of the fourth embodiment nasal mask interface.

In this embodiment, the inlet opening 265 of the seal housing 204 is substantially oval in shape with the major axis extending laterally across the seal housing. As such, when viewed from the outside as shown in FIG. 70, the inlet opening 265 is wider in the lateral direction than it is high. As shown in FIG. 72, the inlet opening 265 is substantially symmetrical relative to a plane 265A extending through the major axis of the oval aperture, such as indicated by line AE in FIG. 42. With reference to FIGS. 70 and 74, the inlet opening 265 forms a conduit portion through the front wall surface of the seal housing 204 in that is has depth around at least portions of the perimeter. For example, the inlet aperture 265 comprises upper 265C and lower 265B surfaces extending into the seal housing from the outer surface to the inner surface of the seal housing. In this embodiment, protrusions of formations 267 are provided across the upper and lower surfaces 265B, 265C of the inlet aperture 265. In this embodiment, the protrusions 267 are elongate protrusions extending along a central portion of the perimeter of the oval aperture 265 in the upper and lower regions at or toward the inner surface of the seal housing. In operation, the protrusions 267 engage with complementary recesses or channels 287 of the conduit frame 211 to provide a snap-fit releasable engagement of the conduit frame into the inlet aperture 265.

In this embodiment, as shown in FIG. 72, at least a portion of the upper and lower regions of the inlet aperture 265 protrude beyond the majority of the front surface of the seal housing 204. Referring to FIGS. 70 and 74, in this embodiment the inlet aperture configuration is also provided with recessed regional regions about at least a portion of the periphery of the inlet aperture as indicated at 268. In this embodiment, the inlet aperture 265 is provided with two discrete recessed regions or surfaces indicated at 268 at or toward each of the lateral sides of the inlet aperture. In this embodiment, the recessed regions 268 terminate prior to meeting each other, although in alternative embodiments it will be appreciated that a recessed region may extend around the entire perimeter of the oval inlet aperture 265. In operation, the recessed regions 268 are shaped and dimensioned to receive complementary engagement surfaces of the conduit frame 211 such that the interface region between the conduit frame and outer peripheral surface of the seal housing surrounding the inlet aperture is substantially smooth or flush to provide a continuous or blended outer surface when the conduit frame 211 is assembled into the inlet aperture 265 of the seal housing 204.

In this embodiment, the yoke channel 266 is provided with locating features 271 that engage with complementary locking features provided on the yoke 208. In this embodiment, the locating features 271 of the yoke channel 266 are recessed formations into which complementary locating protrusions or formations provided on the yoke 208 engage to lock the yoke 208 to the seal housing 204. In this embodiment, the recesses 271 of the yoke channel 266 and complementary protrusions on the yoke 208 are aligned such that when the components are engaged together with the yoke protrusions engaged within their complementary recesses 271 of the yoke channel, the yoke is slightly deformed such that a residual tensile or compressive force exists that locks or secures the two components together. The yoke channel 266, yoke 208, and headgear assembly generally will be described in further detail later.

The seal housing 204 comprises a bias flow vent 212 in the form of an arrangement of inlet apertures. In this embodiment, the seal housing 204 comprises an arrangement of one or more arrays of bias vent holes. In this embodiment, the seal housing 204 comprises three separate line arrays of spaced bias vent holes. Firstly, an upper array 212 of bias vent holes extends across the upper surface of the seal housing above the yoke channel 266 as indicated at 212A. In this embodiment, the upper horizontal row or array of bias vent holes extends substantially across the entire width of the upper region of the seal housing between the lateral sides. A vertical line array of bias vent holes 212B, 212C is also provided on each of the lateral sides of the seal housing on either side of the inlet aperture 265. As shown, the vertical arrays of bias vent holes 212B, 212C extend from below the yoke channel 266 and terminate at or toward the lower surface of the seal housing 204. In this embodiment, the holes or apertures of the arrays 212A, 212B, 212C are laser drilled, but could be formed by alternative means. Additionally, it will be appreciated that each of the upper 212A and lower lateral 212B and 212C vent arrays may comprise multiple line arrays or rows in that the configurations are not limited to singular line arrays. Additionally, the arrays of apertures need not be uniformly spaced in alternative configurations. The configuration shown with upper 212A and lower lateral 212B, 212C vent arrays is configured to prevent noise and draft when the nasal mask interface is used. Alternatively, or additionally, the bias vent holes may be provided on the conduit frame 211.

Figure 68:
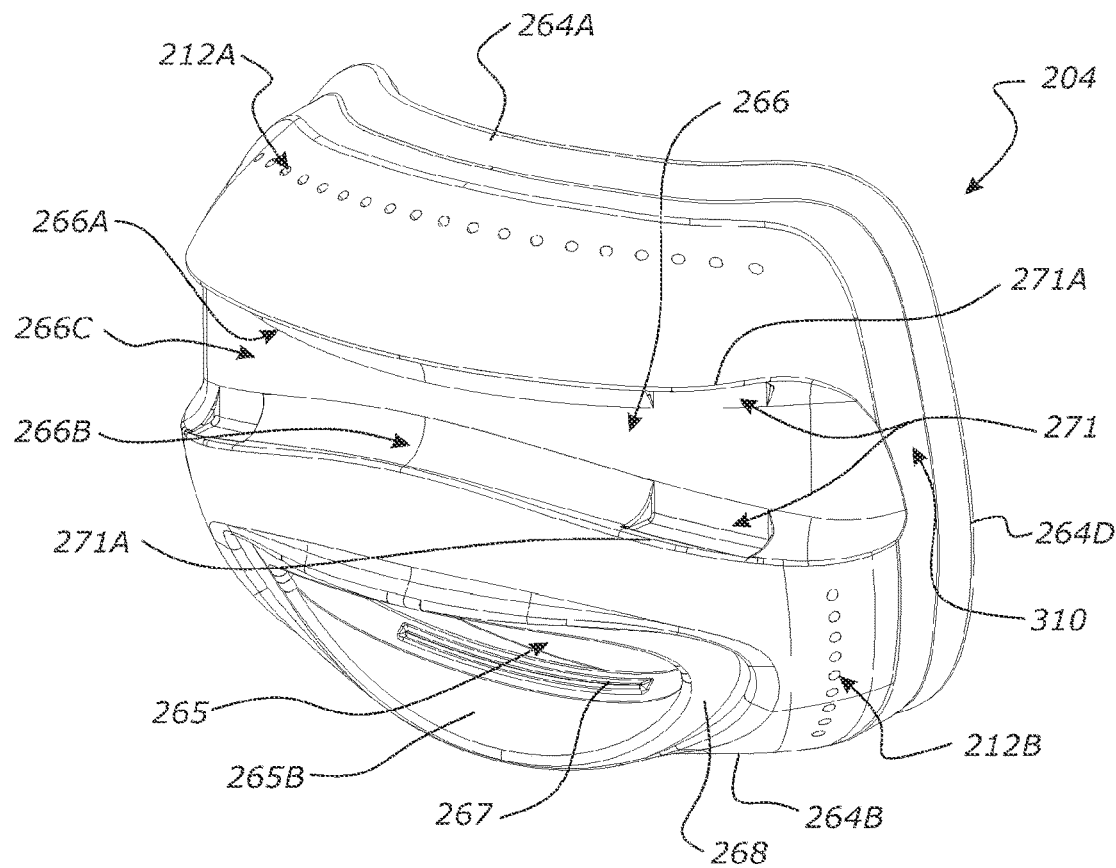
FIG. 68 is an upper perspective view from the outer side of the seal housing of the fourth embodiment nasal mask interface.
Figure 69:
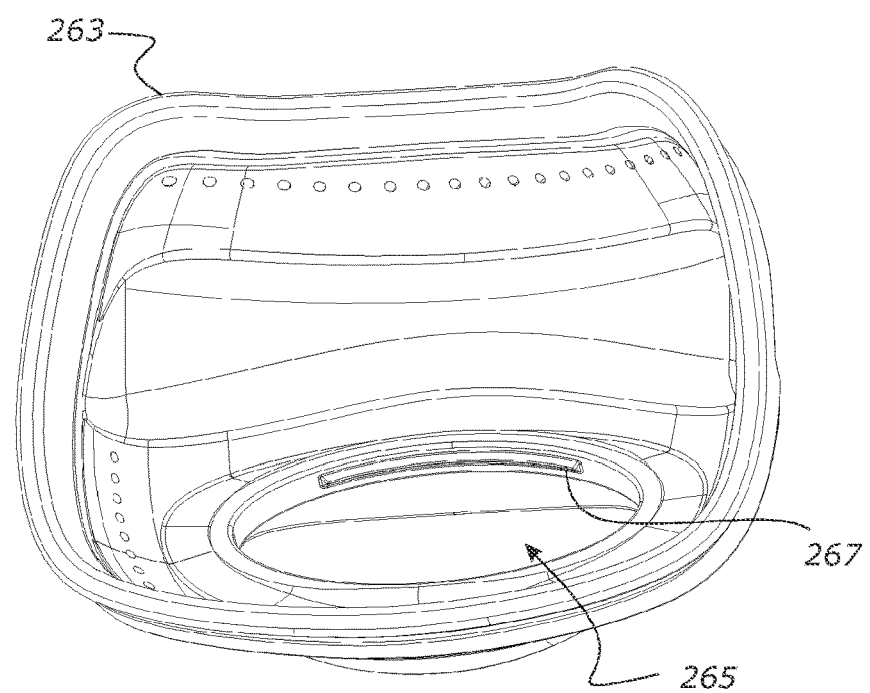
FIG. 69 is a lower perspective view from the wearer side of the seal housing of the fourth embodiment nasal mask interface.
Figure 71:
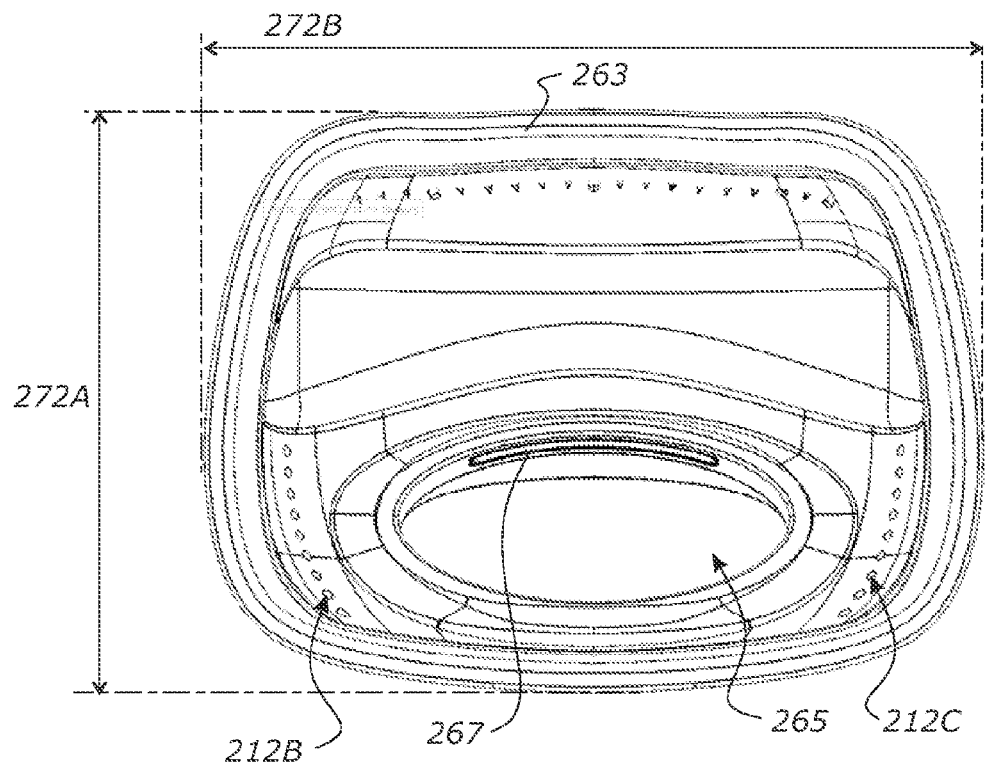
FIG. 71 is a front view of the wearer side of the seal housing of the fourth embodiment nasal mask interface.

Referring to FIGS. 70, 71 and 72, example dimensions of a configuration of the seal housing 204 will be provided by way of example only to provide a sense of scale. Referring to FIG. 71, the overall height of the seal housing 204 between the top 264A and bottom 264B surfaces as indicated at 272A is in the range of approximately 19 mm to approximately 59 mm, preferably approximately 39 mm, and the overall width of the seal housing between the lateral sides 264C and 264D as indicated at 272B is in the range of approximately 45 mm to approximately 75 mm, preferably approximately 50 mm. Referring to FIG. 72, the overall depth of the seal housing between the seal contacting side 262 and outer side 261 as indicated at 272C is in the range of approximately 19 mm to approximately 49 mm, preferably approximately 24 mm. Referring to FIGS. 68 and 70, in this example the distance or height between the top surface 264A and upper inner surface 266A of the yoke channel 266 in the centre of the seal housing as indicated at 272D is in the range of approximately 5 mm to approximately 20 mm, preferably approximately 10 mm. In this embodiment, the diameter 272F of the apertures in the bias flow vent arrays 212A, 212B, 212C is in the range of approximately 0.6 mm to approximately 0.8 mm, preferably approximately 0.7 mm.

Conduit Frame

Referring to FIGS. 75-81, the conduit frame 211 that releasably engages into the inlet aperture 265 of the seal housing 204 will be described in further detail.

In this embodiment, the conduit frame 211 is configured to releasably engage or connect into the inlet aperture 265 of the seal housing via a snap-fit engagement, although it will be appreciated that any other operable mechanism or mechanical coupling arrangement for releasably connecting these components may alternatively be used.

Figure 79:
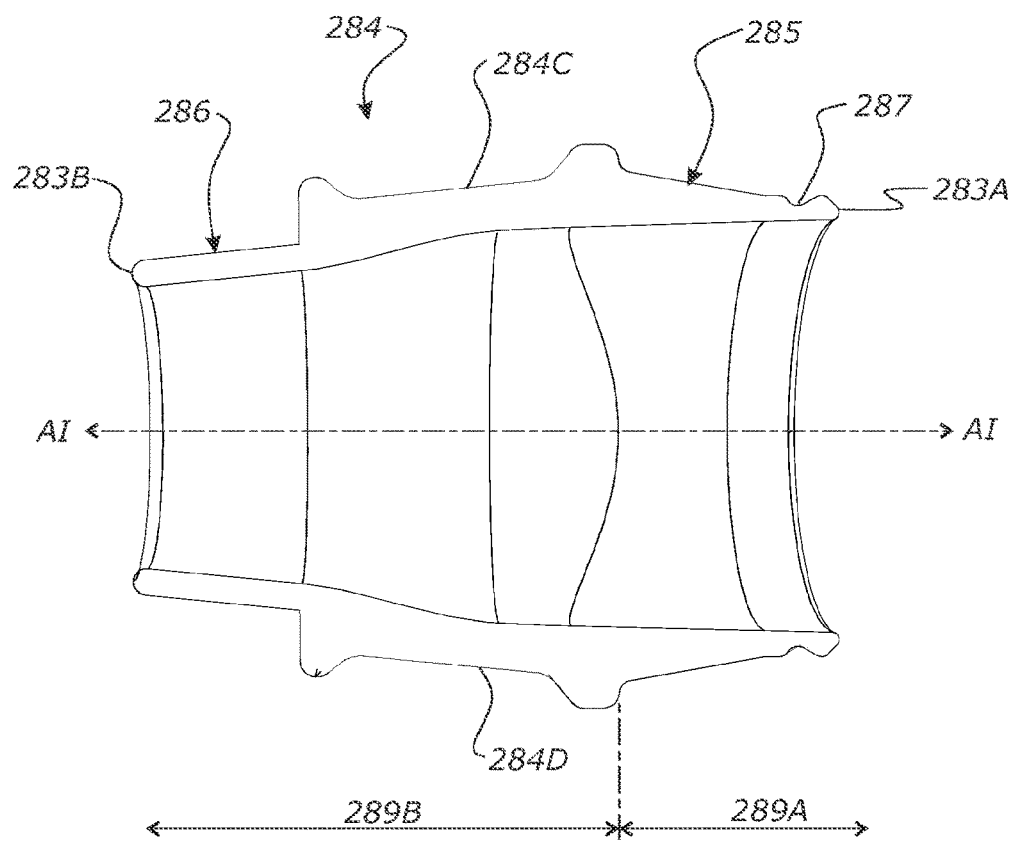
FIG. 79 is a cross-sectional view of the conduit frame of the fourth embodiment nasal mask interface through line AL of FIG. 77.
Figure 81:
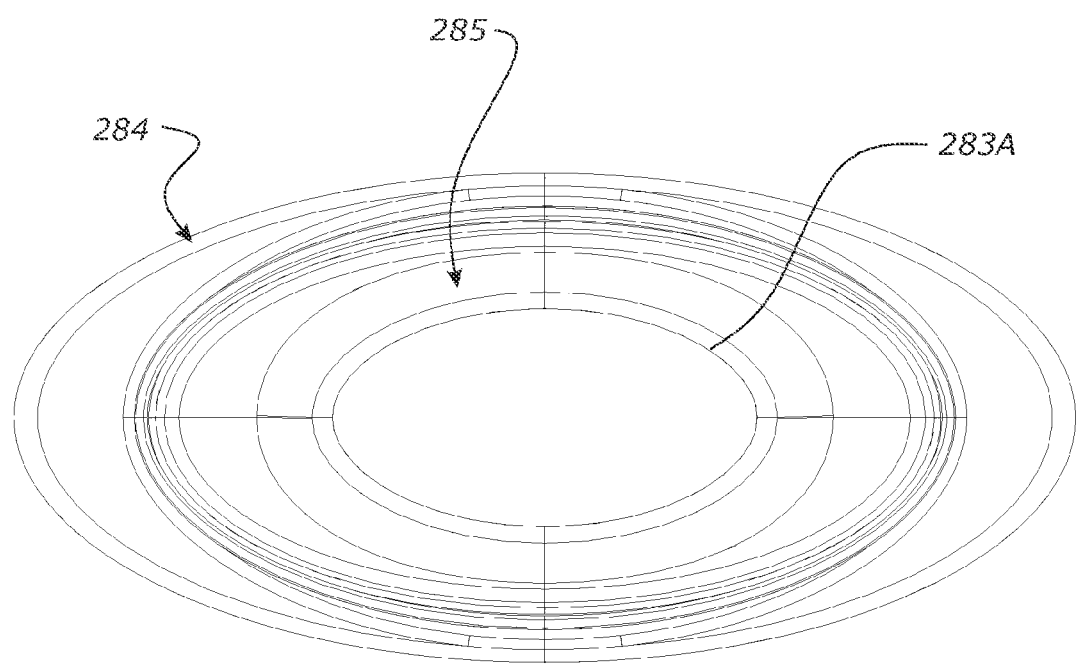
FIG. 81 is an end view of the conduit frame of the fourth embodiment nasal mask interface from the seal housing connecting end of the conduit frame.
Figure 82:
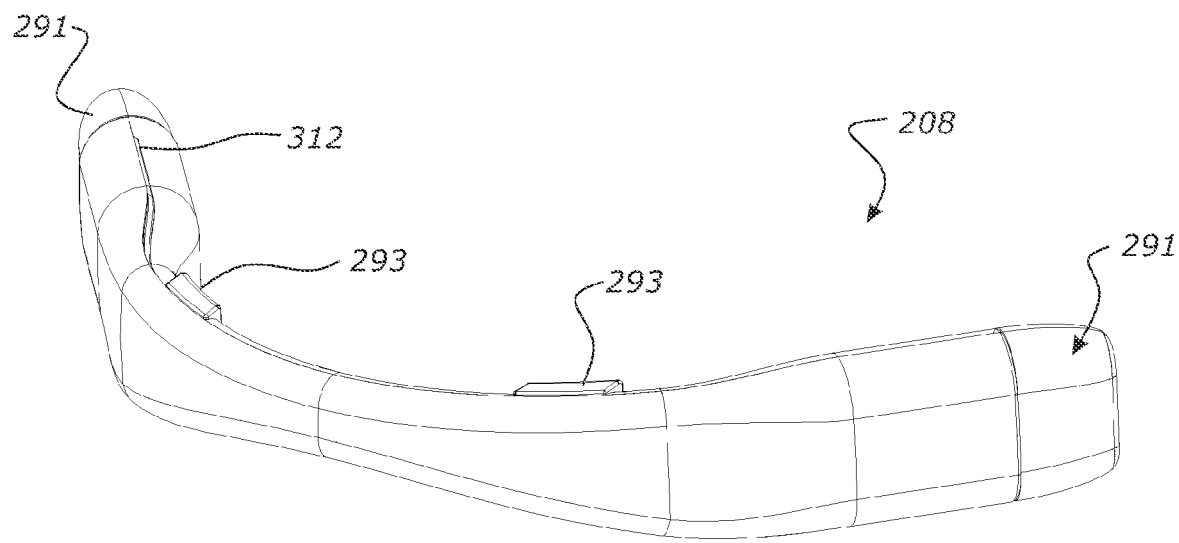
FIG. 82 is an upper perspective view of the yoke of the fourth embodiment nasal mask interface from the outer side.

In this embodiment, the conduit frame 211 comprises a main hollow body that extends from a first end 283A that is configured to engage into the air inlet aperture 265 of the seal housing 204 to a second end 283B that is configured to connect or couple with an end of a gases supply conduit either directly or indirectly via a connector. The conduit frame 211, as shown in FIGS. 81 and 82, forms a hollow conduit along the longitudinal axis of its main body between its first 283A and second 283B ends. The conduit is open at each end of the main body and in this embodiment is substantially oval in cross-sectional shape along the length of the main body of the conduit frame 211. Referring to FIG. 79, in this embodiment the internal circumference of the oval conduit extending through the main body varies along the length of the main body from the first end 283A to the second end 283B. In this embodiment, the circumference of the conduit at the first end 283A (connecting to the seal housing) is larger relative to the circumference of the oval conduit at the second end 283B (connecting to the gasses supply conduit) to create a funnel-like profile.

Figure 80:
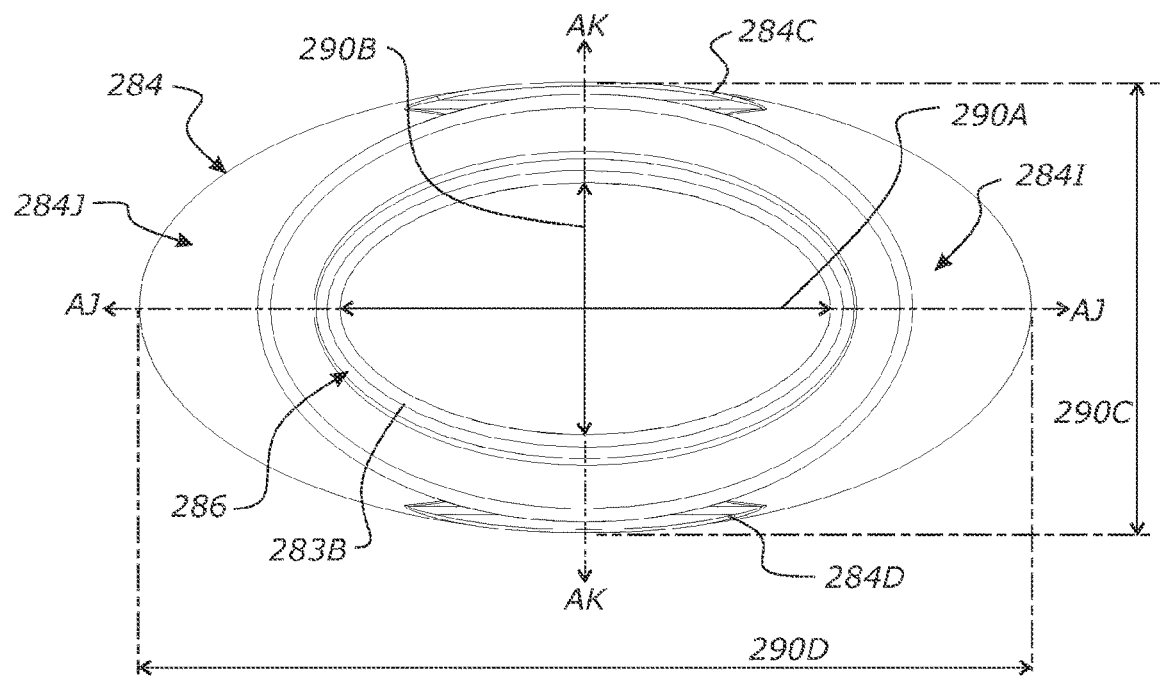
FIG. 80 is an end view of the conduit frame of the fourth embodiment nasal mask interface from the conduit connecting end of the conduit frame.

Referring to FIGS. 79 and 80, in this embodiment the conduit frame 211 is symmetrical about at least a horizontal plane extending through the longitudinal axis AI (see FIG. 79) as indicated at AJ (see FIG. 80). In this embodiment, the axis of symmetry AJ corresponds to the major axis extending through the oval conduit. This symmetry corresponds to the symmetry of the inlet aperture 265 of the seal housing 204 and enables the conduit frame 211 to be connected to the seal housing 204 in either of two orientations. In other words, the conduit frame 211 may be removably coupled into the inlet aperture 265 of the seal housing in either of two orientations that are rotated 180 relative to each other. In this embodiment, the conduit frame 211 is also symmetrical relative to a vertical plane indicated at AK that extends along the longitudinal axis AI of the conduit frame. The vertical plane corresponds to the minor axis of the oval-shaped conduit, and is orthogonal or transverse to the horizontal plane AJ. In particular, the conduit frame is symmetrical relative to two transverse planes extending through the longitudinal axis of the conduit frame.

Figure 75:
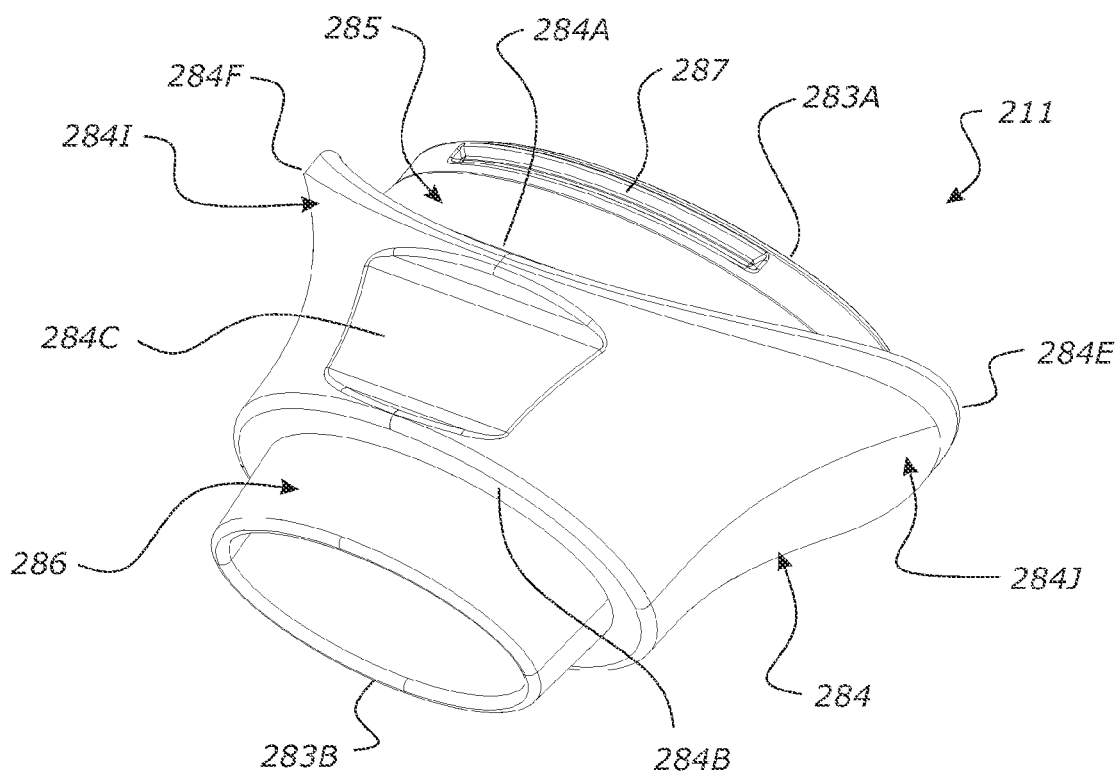
FIG. 75 is an upper perspective view from the conduit connecting end of the conduit frame of the fourth embodiment nasal mask interface.
Figure 76:
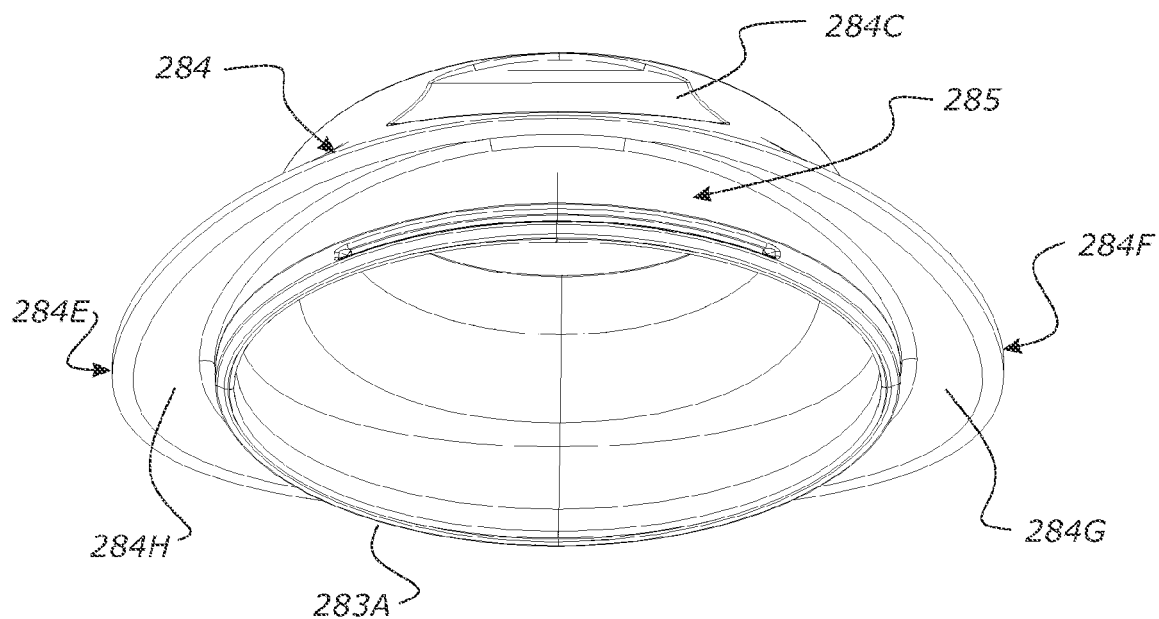
FIG. 76 is an upper perspective view from the seal housing connecting end of the conduit frame of the fourth embodiment nasal mask interface.

Referring to FIG. 75, in this embodiment the main body of the conduit frame 211 comprises a central gripping portion 284, a first connecting portion 285 at the first end 283A for connecting to the inlet aperture 265 of the seal housing, and a second connecting portion 286 at the second end 283B for connecting to a gases supply conduit.

The seal housing connecting portion 285 extends from a first end 284A of the central gripping portion 284 and terminates at the first end 283A of the conduit frame. The conduit connecting portion 286 extends from a second end 284B of the central gripping portion 284 and terminates at the second end 283B of the conduit frame 211. As shown in the Figures, both the seal housing connecting portion 285 and conduit connecting portion 286 are oval in cross-section relative to the longitudinal axis of the conduit frame. In this embodiment, with reference to FIG. 79, both the exterior circumference of the connecting portions 285, 286 reduce or taper from their respective ends of the central gripping portion 284 to their respective ends 283A, 283B of the conduit frame 211. It will be appreciated that the conduit frame may have alternative shape profiles to oval in alternative embodiments. For example, the conduit frame may have an internal conduit having a circular cross-section in alternative forms.

In this embodiment, the gripping portion 284 comprises upper and lower recessed grip portions 284C, 284D on the upper and lower surfaces of the conduit frame. The recessed grip regions 284C, 284D on the upper and lower surfaces enable a user to use a pinch grip between a thumb and forefinger to insert or release the conduit frame 211 from the seal housing in use when desired.

Figure 77:
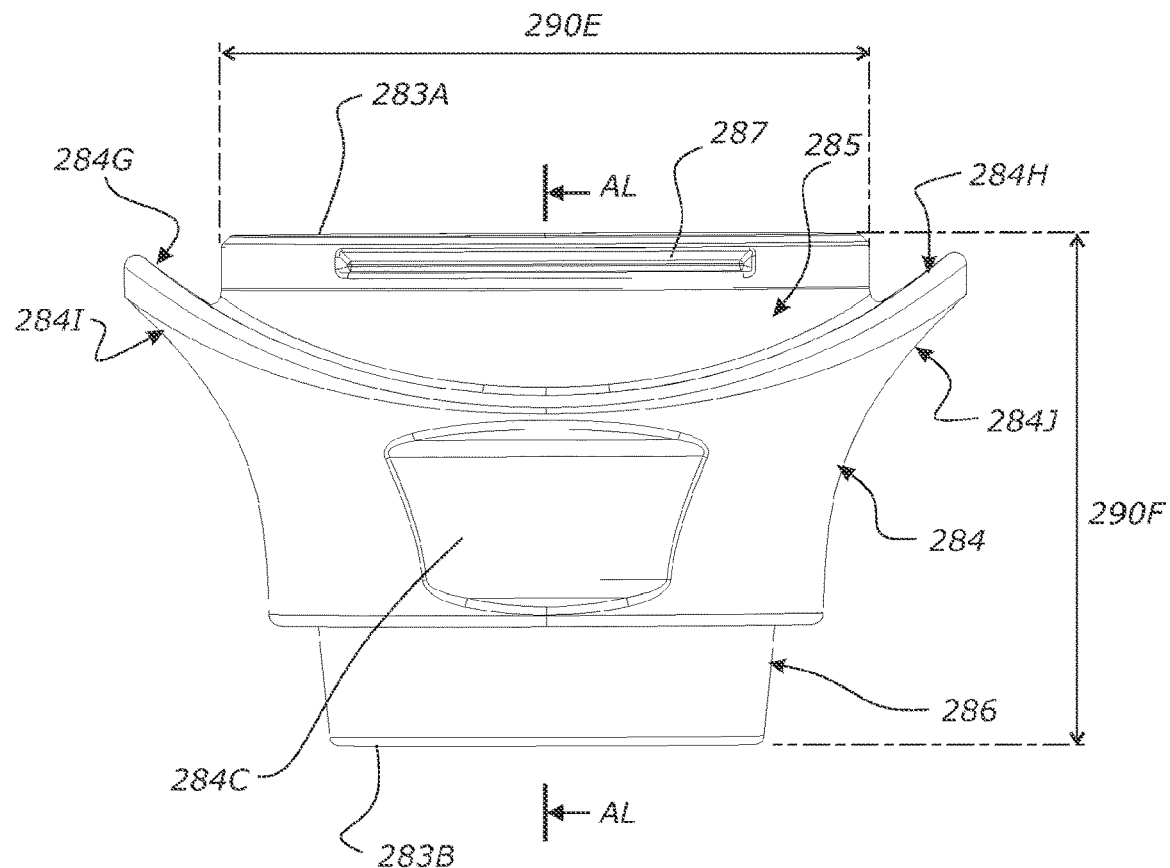
FIG. 77 is a top view of the conduit frame of the fourth embodiment nasal mask interface.
Figure 78:
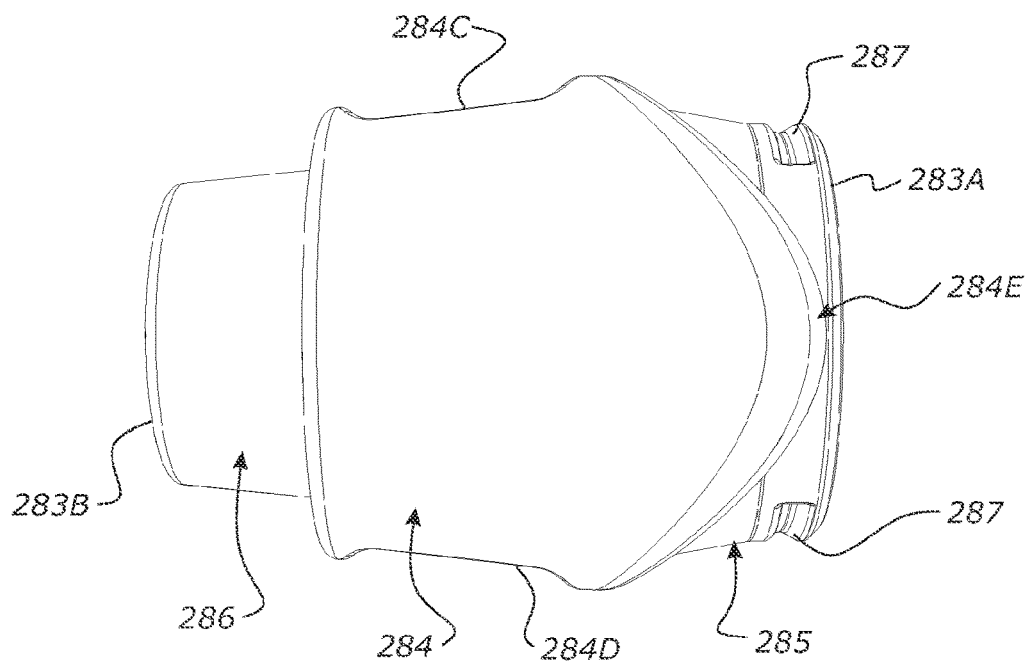
FIG. 78 is a side elevation view of the conduit frame of the fourth embodiment nasal mask interface.

In this embodiment, the central gripping portion 284 increases in width at the lateral sides toward the first end 284A to form winged regions 284E, 284F of a lip protruding from the lateral sides of the conduit frame. In this embodiment, the first end 284A of the central gripping portion is substantially concave in shape as shown in FIG. 77. In this embodiment, the inner surfaces 284G, 284H of the winged regions 284E, 284F adjacent the seal housing connecting portion 285 are complementary in shape and size to the recessed lateral regions 268 of the inlet aperture 265 of the seal housing. In particular, the inner surfaces 284H, 284G of the winged regions of the conduit frame 211 abut or engage with the complementary recessed regions 268 associated with the inlet aperture 265. In this embodiment, the exterior or outer surface profile of the gripping portion 284 in the regions indicated at 284I and 284J associated with the winged regions have a curvature or a shape that complements the curvature or shape of the seal housing on the lateral sides of the inlet aperture 265. This complementary shape of the winged regions 284I, 284J provides a flush and continuous surface profile at the external mating or interface region of the conduit frame 211 and seal housing 204 when they are assembled together. The concave profile of the first end 284A of the gripping portion or region 284 is configured or arranged to complement the concave surface profile adjacent or surrounding the periphery of the inlet aperture 265 of the seal housing 204 to provide a continuous and flush or blended external surface at the interface between the conduit frame and seal housing when assembled together.

Referring to FIGS. 75 and 77, the upper and lower portions of the seal housing connecting portion 285 at the first end 283A of the conduit frame are provided with undercut or recessed grooves 287. These grooves 287 are shaped and dimensioned to complement the upper and lower protrusions 267 of the inlet aperture 265 of the seal housing to enable the conduit frame 211 to engage securely into the inlet aperture 265 of the seal housing via a snap-fit engagement.

In this embodiment, as shown, the main body of the conduit frame 211 is a substantially ovular body along its length between the first 283A and second 283B ends. However, it will be appreciated that alternative cross-sectional shapes may be used for the internal conduit and/or general shape of the body in alternative embodiments if desired such as circular or other suitable shape. In this embodiment, the ovular main body is slightly deformable with respect to at least the vertical plane axis AK extending through the longitudinal axis of the body. This enables the grip regions 284C, 284D to be compressed toward each other by a user to slightly deform the conduit frame 211 and thereby enable disengagement of the snap-fit connection between the conduit frame 211 in the seal housing 204 to enable the conduit frame (and its associated gasses supply conduit) to be removed or disconnected from the seal housing.

Referring to FIGS. 77 and 80, example dimensions of one configuration of the conduit frame of this embodiment will be described to provide a sense of scale. Referring to FIG. 80, the dimension of the oval aperture at the conduit connecting end 283B for the major axis 290A is in the range of approximately 9 mm to approximately 29 mm, preferably approximately 19 mm, and for the minor axis 290B is in the range of approximately 5 mm to approximately 21 mm, preferably approximately 11 mm. The oval extrusion of the conduit connecting portion 286 progressively increases in dimension to a major axis in the range of approximately 14 mm to approximately 34 mm, preferably approximately 24 mm, and to a minor axis in the range of approximately 6 mm to approximately 26 mm, preferably approximately 16 mm, at or toward the gripping portion 284 of the main body. The overall height 290C of the conduit frame 211 between the outermost upper and lower surfaces in the dimension aligned or parallel with the minor axis 290B is in the range of approximately 12 mm to approximately 22 mm, preferably approximately 17 mm. The overall width 290D of the conduit frame 211 between the outermost wing regions of the central gripping portion 284 in the dimension aligned or parallel with the major axis 290A is in the range of approximately 25 mm to approximately 45 mm, preferably approximately 35 mm. Referring to FIG. 77, the overall length of the conduit frame between its first and second ends 283A,283B as indicated at 290F is in the range of approximately 10 mm to approximately 30 mm, and the width of the seal housing connecting portion 285 as indicated at 290E is in the range of approximately 14 mm to approximately 34 mm, preferably approximately 24 mm. It will be appreciated that the dimensions may be varied in an alternative embodiments if desired.

Referring to FIG. 79, the first region indicated 289A of the conduit frame 211 identifies the connection portion 285 that protrudes or extends into engagement into the complimentary inlet aperture 265 of the seal housing 204. The second remaining portion of the conduit frame indicated at 289B toward the second end 283B extends or protrudes from the seal housing. It will be appreciated that the first end 283A of the conduit frame 211 may define a housing aperture opening that engages or compliments the inlet aperture 265 of the seal housing, and the end 283B the conduit frame represents a conduit aperture that engages or couples to an end of a gases supply conduit either directly or via a connector.

Yoke Assembly, Yoke Connection to Seal Housing, and Headgear

With particular reference to FIGS. 82-102, the yoke 208 and its connection to the seal housing 204 and headgear 250 will be explained in further detail. As previously described, in this embodiment the headgear assembly comprises a yoke or collector 208, which is configured to releasably attach or couple to the nasal mask assembly, and in particular the seal housing 204 of the nasal mask assembly.

The yoke 208 is configured to attach to straps of the headgear 250. In the embodiment, as shown in FIGS. 35 and 36, the headgear 200 comprises an assembly of straps, including a rear strap 258 configured to wrap behind a patient's head, an upper strap 254 configured to wrap over the top of a patient's head, and a pair of front or side straps 252 configured to extend along the patient's cheeks during use. Each of the various straps may be either formed as integral components with some being extension portions of the other, and/or otherwise separately formed strap portions that are then either permanently connected together or configured for releasable connection to each other. For example, in one form shown, the rear strap 258 comprises side extensions that form the front or side straps 252 to extend along the patient's cheeks during use, and the upper strap 254 is connected at each end to a respective portion of either the rear 258 or side 252 straps on each respective side of the headgear. In another form, each side strap 252 is attached or releasably connected to the rear strap 258 of the headgear assembly, e.g., to a free end of the rear strap 258 or a connector coupled to the free end, by a rear connector component, and with the upper strap 254 integrally formed or releasably connected to the rear strap 258. In yet another form, the upper strap 254 comprises side extensions that form the front or side straps 252 to extend along patient's cheeks during use, and the rear strap 258 is connected (permanently or releasably) at each end to a respective portion of either the upper 254 or side 252 straps on each respective side of the headgear.

In one form, the headgear can be automatically adjustable and/or can incorporate one or more directional locks that allow the headgear to reduce in length with a relatively low amount of resistance and resist an increase in length of the headgear. In some configurations, a locking force of the directional locks can be overcome to allow lengthening of the headgear for donning of the interface assembly. In some forms the yoke 208 may form a collector for filaments used in an automatically adjustable headgear system. In this form, the yoke 208 may incorporate one or more directional locks, each of which can comprise a washer mechanism, which may be configured to frictionally engage with the filament during elongation of the headgear, but allows relatively friction-free movement during retraction of the headgear. The washer mechanism may be incorporated into the ends of the yoke 208 and the body of the yoke may be substantially hollow to receive the filaments within the body. The headgear or any portion thereof can be configured in accordance with any of the embodiments disclosed in Applicant's U.S. Patent Application Publication No. 2016/0082217, U.S. Patent Application Publication No. 2016/0144146, and PCT Patent Application Publication No. WO2016/043603, the entireties of which are incorporated by reference herein.

Each side strap 256 may comprise a free end to which may be attached a connector. Each connector may engage with a complementary strap connector located on the yoke 208. In this embodiment, the yoke 208 is substantially elongate and comprises a strap connector located at or near each end of the yoke 202.

The connection between the side straps 256 and yoke 208 may be any suitable form of connection, such as a snap-fit connection, a screw and thread type connection, or a hooked connection. In one form, each strap connector of the yoke 208 comprises an end cap 291 (see FIG. 83) located at each end of the yoke 208. Each end cap 291 may comprise an opening, such as an aperture or recess, configured to receive the connector of a respective side strap 256 to secure an end cap 291 to each end of a respective side strap 256. The end caps 291 are then either releasably (e.g. via a snap-fit arrangement) or permanently connected to a respective end of the yoke 208 to thereby connect yoke 208 to the side straps 256 of the headgear assembly. In another form, the free ends of the side straps 256 may be directly coupled or permanently fixed into a respective end cap 291, which is then either releasably or permanently connected to a respective end of the yoke 208 to thereby connect the yoke to the side straps 256 of the headgear assembly.

Referring to FIGS. 68, 70, and FIGS. 82-87, as mentioned above, the yoke 208 is also configured to attach to the seal housing 204 of the nasal mask interface. In one form, as discussed, the seal housing 204 may comprise a recessed region or yoke channel 266 configured to receive at least a portion of the yoke 208 therein when the yoke 208 and seal housing 204 are attached together. The yoke channel 266 is formed or defined by an upper wall 266A, rear wall 266C, and lower wall 266B. In this embodiment, the yoke 266 has asymmetry between upper 292A and lower 292B edges of the yoke 208. In the illustrated embodiment, the upper edge 292A of the yoke 208 is straighter than the lower edge 292B (see FIG. 86). The asymmetry advantageously provides improved visual cues as to the correct orientation for assembly of the yoke 208 into the yoke channel 266 of the seal housing 204 and helps inhibit incorrect assembly.

As shown in FIGS. 68 and 70, the yoke channel 266 of the seal housing 204 includes locating features or connector recesses 271 in the upper 266A and lower 266B walls. In the illustrated embodiment, a connector recess 271 is positioned at, adjacent, or proximate each lateral end of the yoke channel 266. The connector recesses 271 at least partially define or form retention lips 271A at or along front edges of the yoke channel 266 (e.g., at or along front edges of internally facing surfaces of the upper wall 266A and lower wall 266B). The yoke 208 includes connector protrusions 293 protruding rearwardly from upper, lower, and/or rear surfaces of the yoke 208. In the illustrated embodiment, the yoke 208 includes a connector protrusion 293 on each side of a center of the yoke 208. In the illustrated embodiment, the yoke 208 includes a yoke front 294A and yoke back 294B that are coupled together, as described in greater detail herein, and the connector protrusions 293 are formed in the yoke back 294B. The connector recesses 271 of the yoke channel 266 are configured to receive the complementary connector protrusions 293 when the seal housing 204 and yoke 208 are coupled together to form a snap-fit connection between the seal housing 204 and yoke 208. When the seal housing 204 and yoke 208 are coupled together, the retention lips 271A engage the yoke 208 forward of the connector protrusions 293 to contribute to the snap-fit connection and retain the yoke 208 in the yoke channel 516. In the illustrated embodiment, the connector protrusions 293 and connector recesses 271 have a square or rectangular profile, which inhibits the yoke 208 from rotating out of the yoke channel 266.

Figure 88:
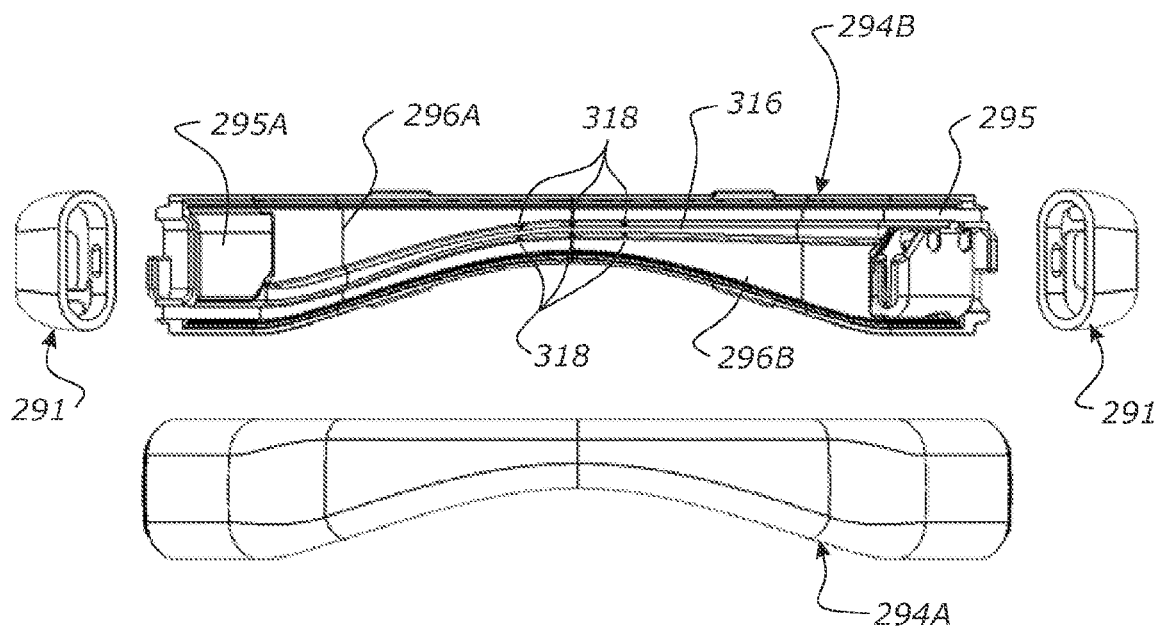
FIG. 88 is a partially exploded front view of the yoke of the fourth embodiment nasal mask interface, and in particular showing the end caps of the yoke detached.
Figure 89:
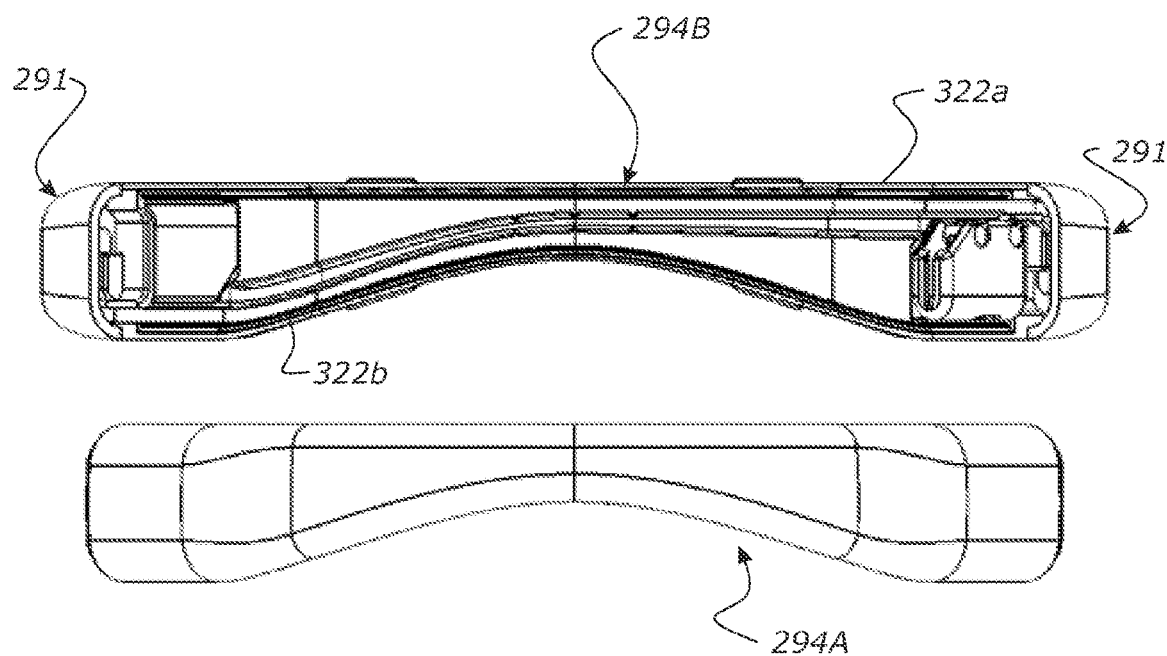
FIG. 89 is another partially exploded front view of the yoke of the fourth embodiment nasal mask interface, and in particular showing the end caps of the yoke connected to the yoke back.
Figure 90:
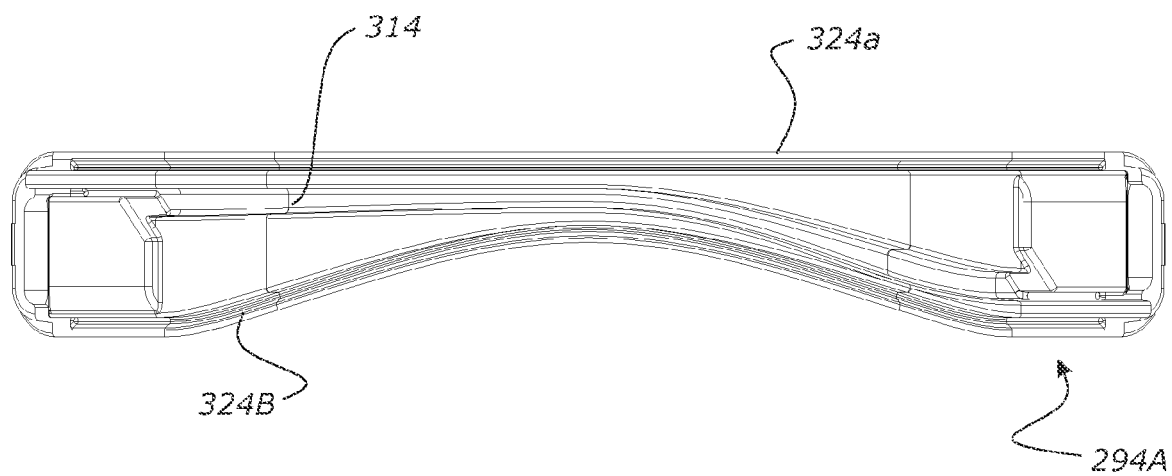
FIG. 90 is a rear or inner-side view of the yoke front of the yoke assembly of the fourth embodiment nasal mask interface.

In some embodiments, the yoke 266 has an oval or substantially oval cross-section along its length, for example. This shape advantageously reduces the size or bulk of the yoke 266 and/or provides an improved aesthetic appearance. The washer housings 295 of the directional locks, discussed in greater detail herein, can have a D-shaped, substantially D-shaped, U-shaped, or substantially U-shaped cross-section, for example as shown in FIGS. 88-89, to allow for and/or contribute to the overall oval or substantially oval cross-section of the yoke 266. A washer housing 295 is located at or toward each end of the yoke 266 within the body. Only the right washer housing 295 is shown in one end of the yoke in FIGS. 88-89 for clarity, with the mounting space 295A of the other omitted left washer housing shown at the other end. The pair of washer housings 295 can be oriented opposite each other (see FIG. 91). In other words one of the washer housings 295, e.g., the right washer housing 295 as shown in FIG. 136C, can be oriented as an upward-facing U-shape, and the other washer housing, e.g., the left washer housing (omitted from view), can be oriented as a downward-facing U-shape. This arrangement and orientation can advantageously help allow the line or filament tracks 296A, 296B to extend above and below the left and right washer housings 295, respectively, as discussed in greater detail herein.

In some embodiments, the yoke 208, or a central portion of the yoke 208, has a depth (when viewer from the top, e.g. FIG. 84) that is the same as or similar to or corresponds to a depth of the yoke channel 266 such that the yoke 208 does not protrude, or does not substantially protrude, from the yoke channel 266. In other embodiments, as shown in FIG. 46, at least a portion of the yoke 208 may protrude beyond the yoke channel 266.

Figure 84:
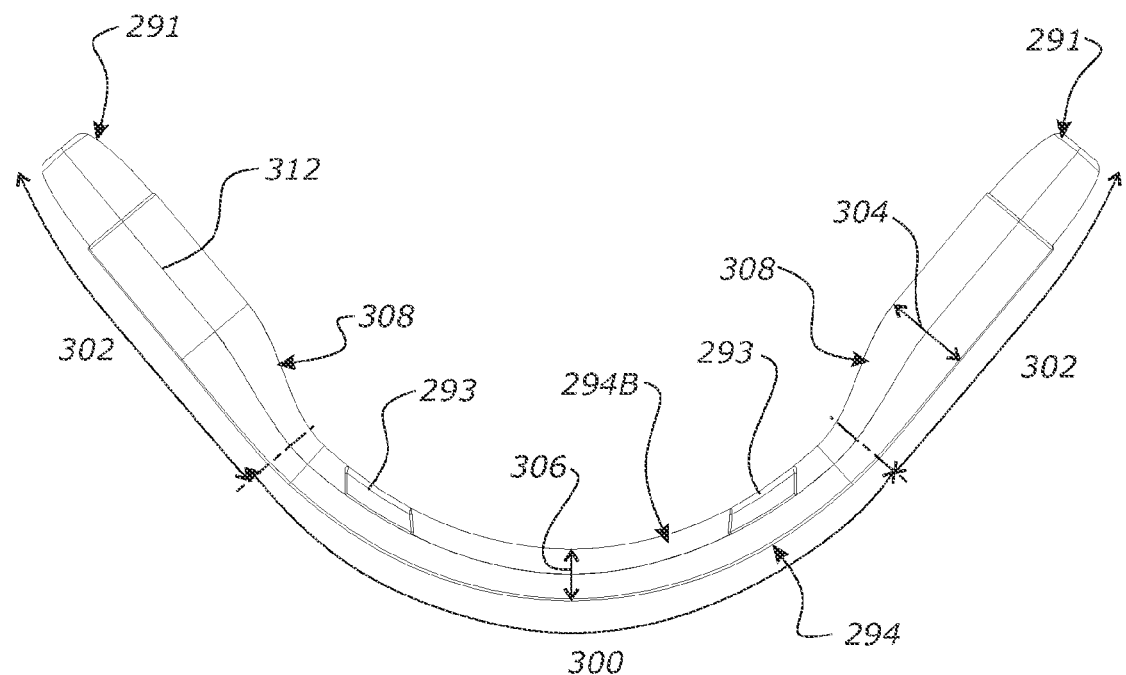
FIG. 84 is a top view of the yoke of the fourth embodiment nasal mask interface.
Figure 85:
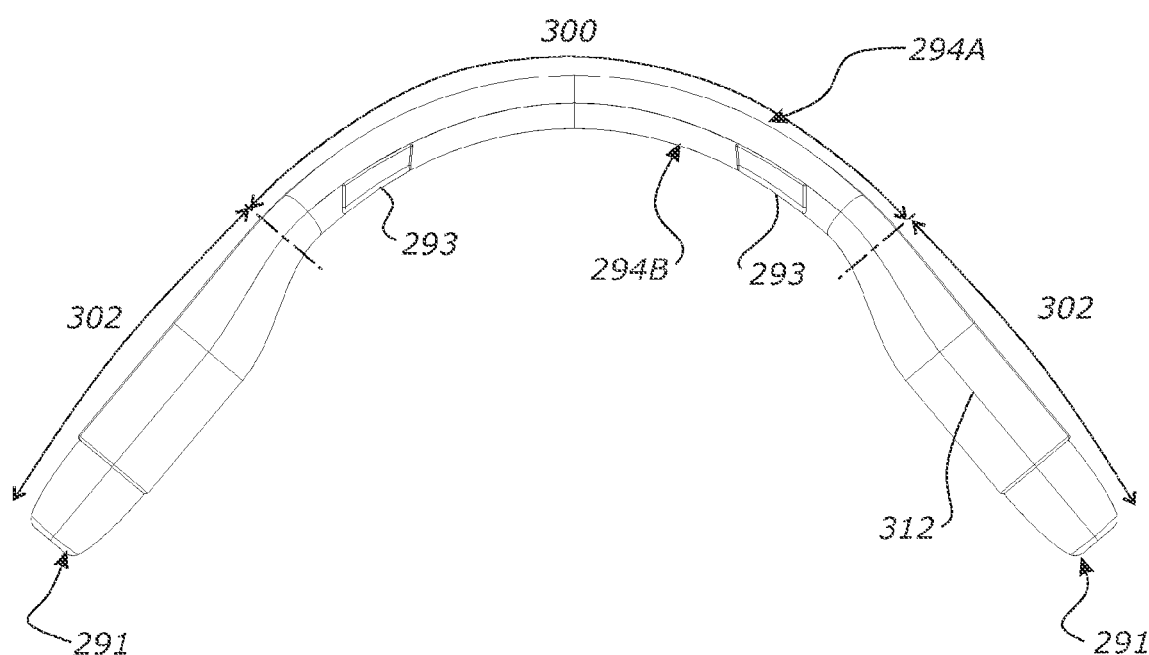
FIG. 85 is an underside view of the yoke of the fourth embodiment nasal mask interface.

As shown in FIGS. 84 and 85, in the illustrated embodiment, a rear or back surface of the yoke 208 includes a rearward step or transition on each side or lateral end 302 of the central portion 300 of the yoke 208 such that the yoke 208 has a stepped or varying depth (when viewed from the top). In other words, lateral portions 302 of the yoke 208, which are positioned laterally outside of the yoke channel 266 when the yoke 208 is coupled to the seal housing 204, have a greater depth 304 (in at least the front to back surface direction) or thickness than the depth or thickness 306 of the central portion 300 of the yoke 208, which is positioned in the yoke channel 266 when the yoke 208 is coupled to the seal housing 204. The steps or transitions form or define abutment surfaces 308 at the transitions between the central portion 300 and lateral portions 302 of the yoke 208. When the yoke 208 is coupled to the seal housing 204, each of the abutment surfaces 308 abuts or is positioned adjacent or proximate one of the lateral edges or surfaces 310 (see FIGS. 68 and 72) of the seal housing 204. The abutment surfaces 308 and lateral edges 310 help properly align the yoke 208 with the seal housing 204 during assembly. The abutment surfaces 308 and lateral edges 310 also or alternatively provide a more secure connection between the yoke 208 and seal housing 204. The reduced depth or thickness of the central portion of the yoke 208 advantageously reduces the overall size of the seal housing 204 and yoke 208 assembly.

Figure 86:
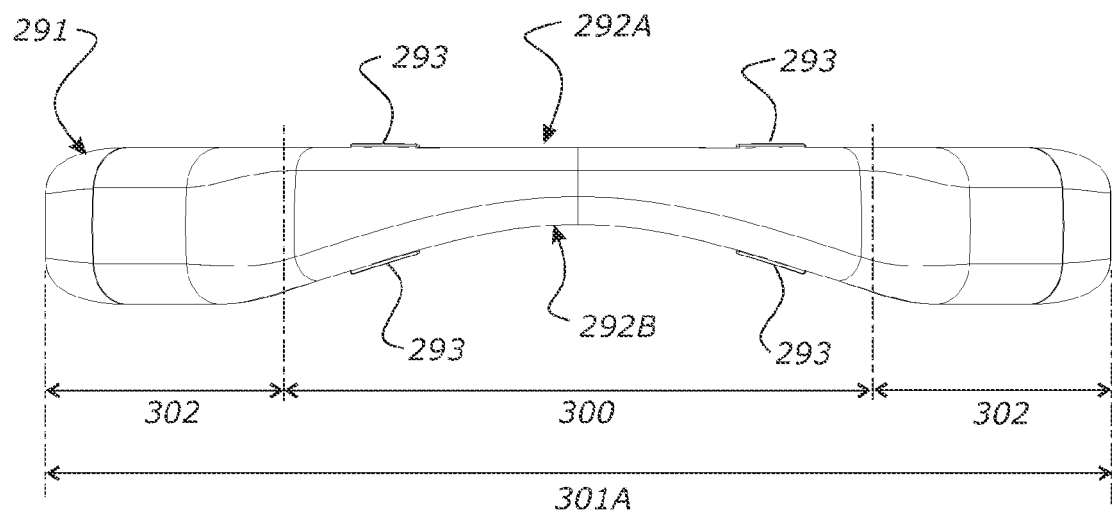
FIG. 86 is a front view of the yoke of the fourth embodiment nasal mask interface from an outer side.
Figure 87:
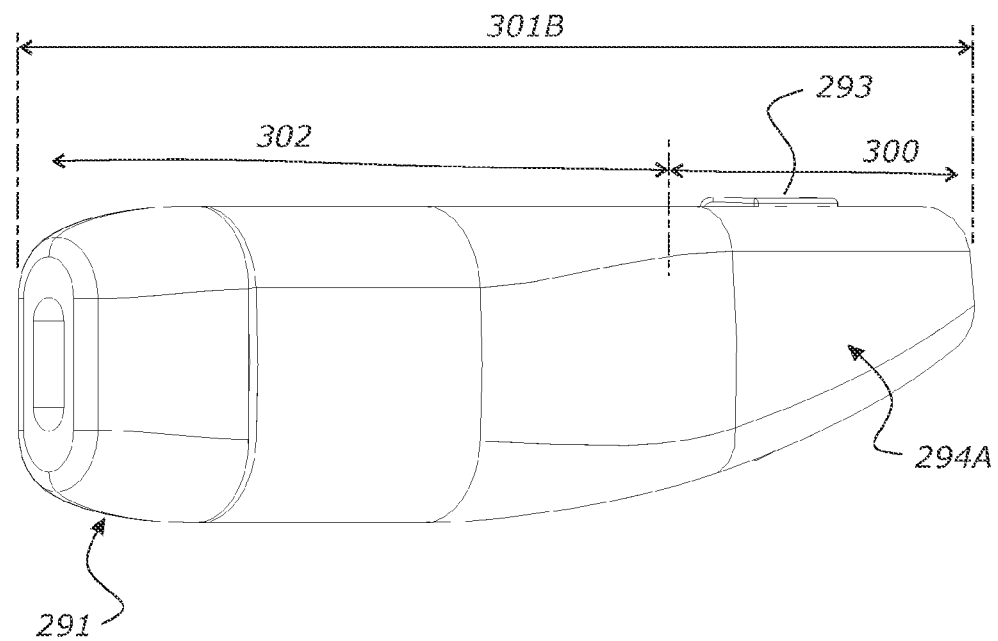
FIG. 87 is a side elevation view of the yoke of the fourth embodiment nasal mask interface.

As previously described, in this embodiment the yoke 208 has asymmetry between its upper edge or surface 292A and lower edge or surface 292B. Referring to FIG. 86, in this embodiment, the upper edge 292A is straighter than the lower edge 292B. In this embodiment, the height profile of the yoke 208 (when viewed from the front, e.g. FIG. 86) varies across the lateral width of the yoke between the end caps 291. In the illustrated embodiment, as shown in FIGS. 86 and 87, the height of the yoke 208 in a central region 300 that is generally received in the yoke channel 266 of the seal housing is reduced relative to the height of the yoke in the lateral side regions 302. In this embodiment, the height of the yoke in the central region 300 gradually reduces via a curved (e.g. concave) surface profile of the lower edge 292B of the yoke in the central region to an apex at the center of the yoke at which it is of most reduced height.

Referring to FIGS. 84-87, in this embodiment the varying depth (viewed from top) and height (viewed from front) profiles of the yoke 208 along is length provide a varying overall thickness profile along the yokes length. For example, the overall thickness (in depth and height) of the yoke in the central region 300 is smaller or thinner than the overall thickness (in depth and height) of the lateral regions 302. In particular, the yoke can be considered as having a thin central region 300, and thicker lateral regions 302 either side of the central region. The thinner region 300 is generally received in the yoke channel 266 of the seal housing 204, while the thicker lateral regions do not contact the seal housing 204 and extend outwardly away from the sides of the seal housing. The length, thickness, and convex curvature profile of the yoke are configured to blend in with the seal housing, and also configured such that the lateral sides of the yoke do not contact the user's face in use.

Referring to FIGS. 84 and 85, in this embodiment, the radius of curvature of the yoke 208 (when viewed from the top) is substantially constant in majority of the thinner central region 300 of the yoke, and then the radius of curvature increases or is larger at the thicker lateral sides 302 of the yoke. In some embodiments, the thicker lateral regions 302 may extend at a substantially constant angle along their length, without any curvature.

Referring to FIG. 86, the overall width 301A of the yoke 208 between each lateral edge (e.g. when viewed from the front like in FIG. 86) will be in the range of approximately 60 mm to approximately 120 mm. Referring to FIG. 87, the overall depth 301B of the yoke 208 front to the rear end caps 291 (e.g. when viewed from the side like in FIG. 87) will be in the range of approximately 30 mm to approximately 55 mm.

Figure 83:
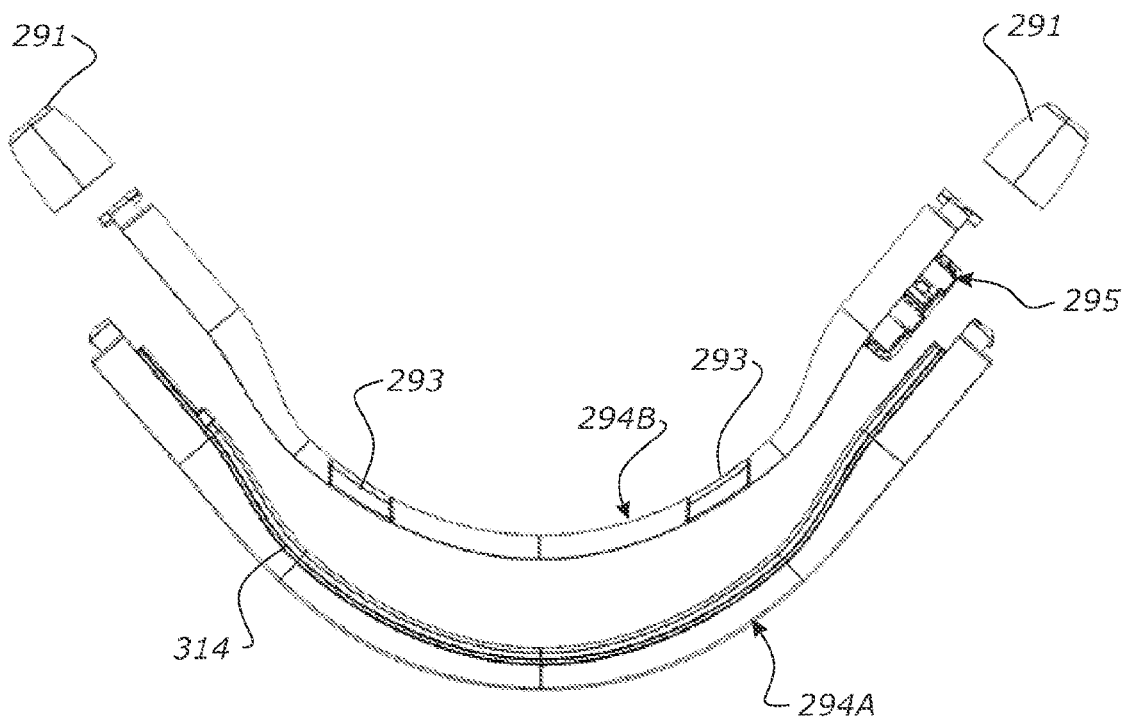
FIG. 83 is a top exploded view of the yoke of the fourth embodiment nasal mask interface.

As shown in FIG. 83, in the illustrated embodiment, the yoke 208 includes a yoke front 294A and a yoke back 294B. The yoke 208 can also include two end caps 291, one at each lateral end of the yoke 208. In the illustrated embodiment, the yoke front 294A and yoke back 294B are formed as separate components that are coupled together. In this embodiment, a split line 312 (shown in FIG. 82, 84, 85) between the yoke front 294A and yoke back 294B is centered or generally centered. This can improve ease of manufacturing.

The yoke front 294A and yoke back 294B can be coupled together via a snap fit. In the illustrated embodiment, the yoke front 294A includes a yoke fastener 314 projecting rearwardly from a rear surface of the yoke front 294A. In the illustrated embodiment, the yoke fastener 314 is positioned centrally or generally centrally with respect to the yoke front 294A. The yoke back 294B includes a fastener aperture or recess 316 that is sized, shaped, and positioned to receive the yoke fastener 314 to form a snap-fit connection when the yoke front 294A and yoke back 294B are coupled together. The central connection between the yoke front 294A and yoke back 294B via the yoke fastener 314 and fastener aperture or recess 316 provides more rigidity to the connection between the yoke front 294A and yoke back 294B and/or provides support against or inhibits twisting between the yoke front 294A and yoke back 294B. In some embodiments, the yoke front 294A instead includes the fastener aperture or recess 316 and the yoke back 294B includes the yoke fastener 314. In some embodiments, the fastener aperture or recess 316 includes one or more fastener or interference bumps 318 (see FIG. 88) extending along (e.g., laterally along) upper and/or lower edges of the fastener aperture or recess 316 and protruding into the fastener aperture or recess 316 from the upper and/or lower edges. In some embodiments, the yoke fastener 314 includes one or more corresponding notches extending along (e.g., laterally along) upper and/or lower surfaces of the yoke fastener 314 that are sized, shaped, and positioned to receive the fastener bump(s) 318 to form a snap-fit connection. In some embodiments, the fastener aperture or recess 316 includes one or more notches 320 and the yoke fastener 314 includes one or more fastener bumps 318. In some embodiments, the interference bumps 318 may simply assist in form an interference fit by engaging with the surface of the yoke fastener 314.

The illustrated embodiment shows a fastener recess 316 that does not extend all the way through the thickness of the yoke back 294B. In a variation, a fastener aperture 316 may be provided alternatively, which does extend through the entire thickness of the yoke back 294B. However, the fastener recess 316 configuration can advantageously allow for easier manufacturing, provide a neater finish (without an aperture in the yoke back 294B), and/or inhibit the ingress of dirt or other debris into the line tracks 296A, 296B (due to the lack of aperture, which allows the yoke 208 to be fully enclosed along its length), which can help maintain the function of the automatic headgear adjustment mechanism. Either form of fastener aperture or fastener recess functions to receive the complementary yoke fastener 314 in a snap-fit and/or friction fit engagement as described above when the yoke front 294A and yoke back 294B are coupled together.

In this embodiment, the yoke back 294B includes an upper alignment bead 322a protruding forward from the yoke back 294B and extending along a length of the yoke back 294B adjacent or proximate the upper surface of the yoke back 294B, and/or a lower alignment bead 322b protruding forward from the yoke back 294B and extending a length of the yoke back 294B adjacent or proximate the lower surface of the yoke back 294B. The yoke front 294A (see FIG. 90) includes an upper alignment groove 324a in a rear surface of the yoke front 294A extending along a length of the yoke front 294A adjacent or proximate the upper surface of the yoke front 294A, and/or a lower alignment groove 324b in the rear surface of the yoke front 294A extending a length of the yoke front 294A adjacent or proximate the lower surface of the yoke front 294A. The upper and/or lower alignment grooves 324a, 324b receive the upper and/or lower alignment beads 322a, 322b, respectively, when the yoke front 294A and yoke back 294B are coupled together. The alignment beads 322a, 322b and alignment grooves 324a, 324b help correctly align the yoke front 294A and yoke back 294B. The alignment beads 322a, 322b and alignment grooves 324a, 324b can also or alternatively resist or support against torsion, e.g., between the yoke front 294A and yoke back 294B. In some embodiments, the alignment beads 322a, 322b and alignment grooves 324a, 324b can be positively engaged with each other, for example, in the form of a friction fit or snap fit connection.

The end caps 291 can help secure the yoke front 294A and yoke back 294B together by clipping over or snap fitting over or onto the lateral ends of the yoke front 294A and yoke back 294B. The end caps 291 can also allow for connection of a front strap of a headgear to the yoke 208. In some embodiments, each end cap 291 is over-molded onto a braided portion of the front strap.

Figure 93:
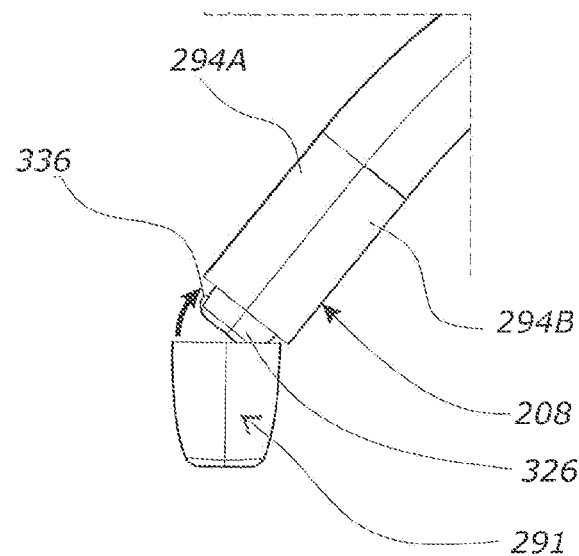
FIG. 93 shows a method of coupling an end cap onto an end of the yoke of the fourth embodiment nasal mask interface.

As shown in FIGS. 93-98, the lateral ends of the yoke front 294A and yoke back 294B include or are formed by end cap inserts 326. The end cap inserts 326 can be integrally formed with or attached to the lateral ends of the yoke front 294A and yoke back 294B. The end cap inserts 326 have a reduced dimension or profile compared to the lateral portions of the yoke 208. The end caps 291 have internal cavities 328 that receive the end cap inserts 326. During assembly, the end caps 291 are connected over or snapped onto the end cap inserts 326 in a hinged manner, as shown in FIG. 93.

Figure 94:
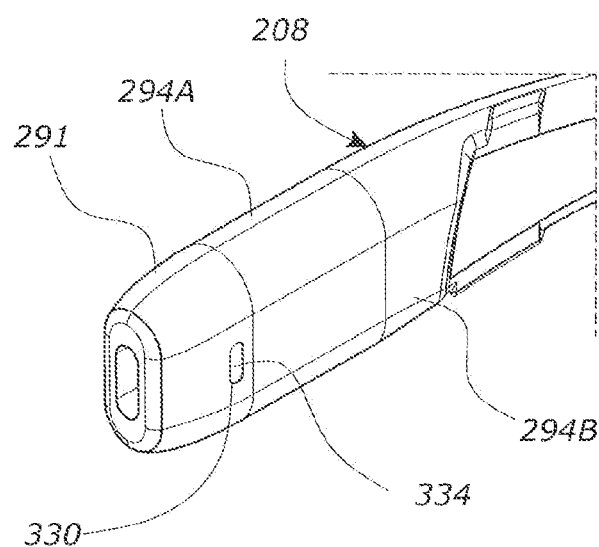
FIG. 94 is a partial rear perspective view of the assembled end cap and yoke of FIG. 93.
Figure 95:
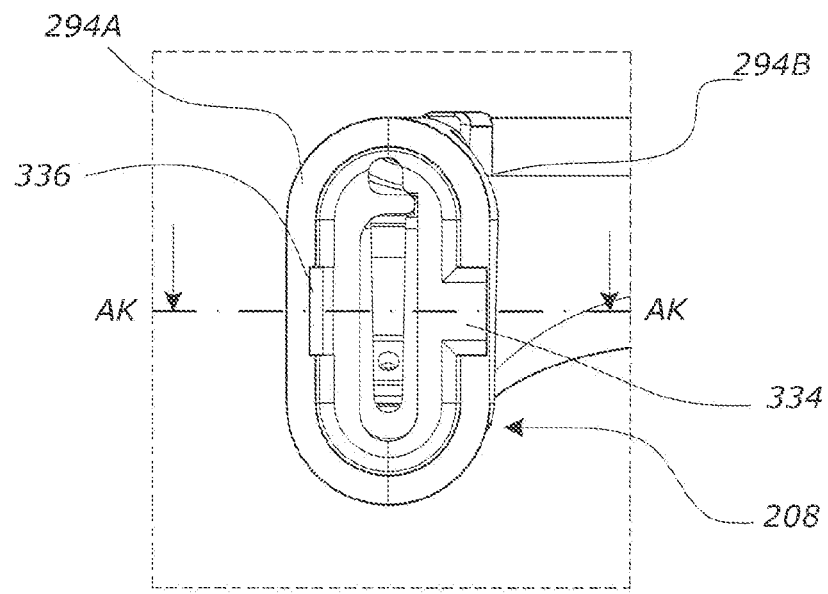
FIG. 95 is an end view of a yoke end of the yoke of the fourth embodiment nasal mask interface.
Figure 96:
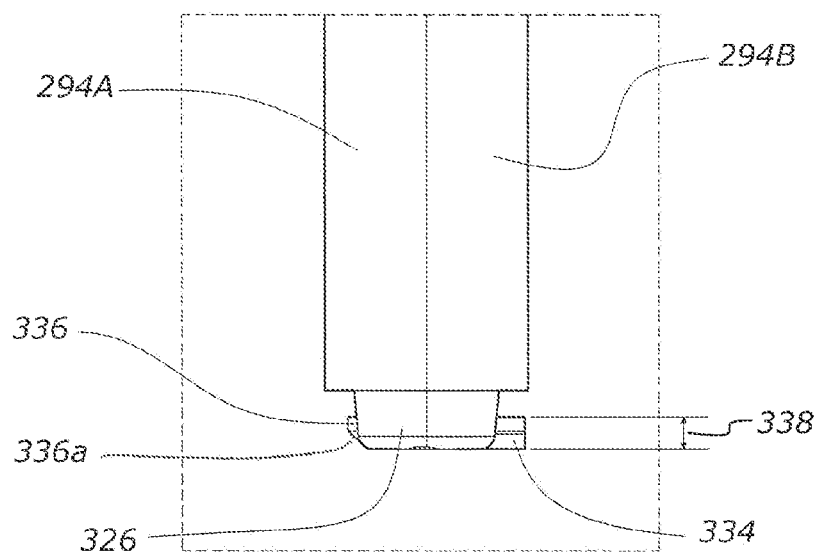
FIG. 96 is a top view of the yoke end of FIG. 95.
Figure 97:
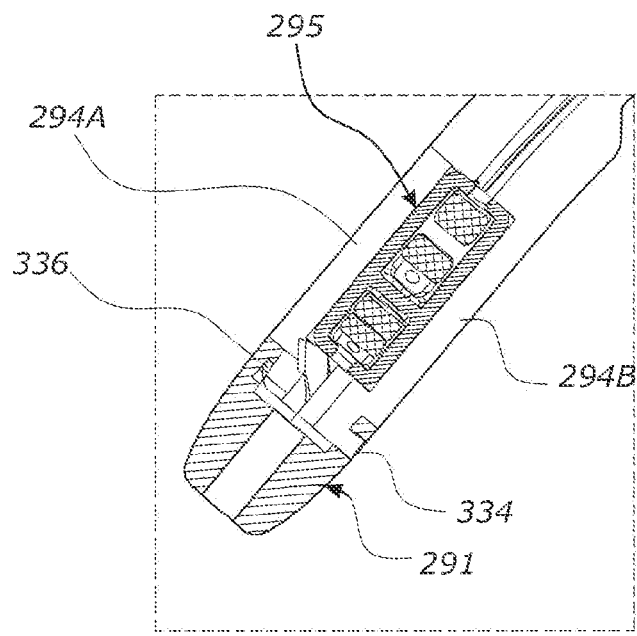
FIG. 97 is a section view of the end cap coupled to the yoke end taken along line AK in FIG. 95.
Figure 98:
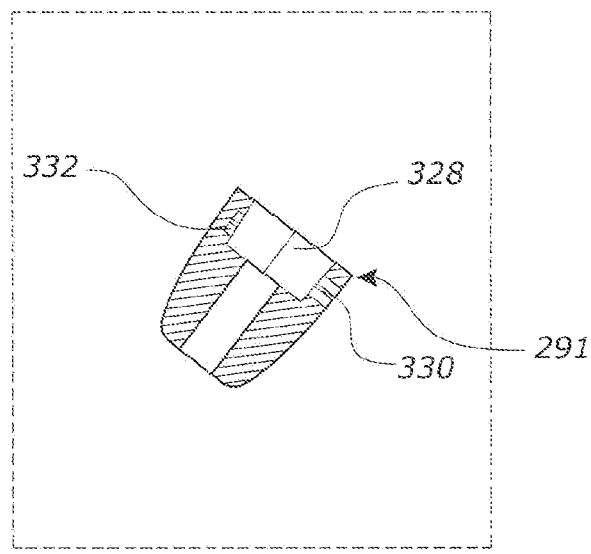
FIG. 98 is a section view of the end cap of FIG. 97.

As shown in FIG. 98, each end cap 291 includes a retention hole 330 on one side (e.g., in a rear side in the illustrated embodiment) and a retention notch 332 on an opposite side (e.g., a front side in the illustrated embodiment). In other embodiments, the position of the retention hole 330 and retention notch 332 can be reversed. The positioning of the retention hole 330 in the rear of the end cap 291 in the illustrated embodiment, advantageously hides the retention hole 330 in use, which provides an improved aesthetic appearance. The retention notch 332 extends from the end cap cavity 328 forward into the end cap 291. The end cap inserts 326 include a first retention feature 334 on one of the front and back surfaces (e.g., extending rearwardly from the yoke back 294B portion of the end cap insert 326 in the illustrated embodiment) and a second retention feature 336 on an opposite surface (e.g., extending forward from the yoke front 294A portion of the end cap insert 326 in the illustrated embodiment). To attach the end cap 291 to the yoke 208, e.g., to the end cap insert 326, the retention hole 330 is engaged with the first retention feature 334 as shown in FIG. 94. The first retention feature 334 then acts as a hinge or pivot point, and the end cap 291 is pivoted over the end cap insert 326 in the direction indicated by the arrow in FIG. 93 until the second retention feature 336 and retention notch 332 engage, e.g., in a bump or snap fit connection. The hinged connection can provide a strong connection between the yoke 208 and end caps 291 with a reduced end cap insert 326 length 338 (indicated in FIG. 144). The end caps 291 can therefore taper more steeply. The reduced length of the end cap inserts 326, end caps 291, and/or overall yoke 208 can advantageously reduce or minimize the yoke 208 digging into the patient's face.

In the illustrated embodiment, the first retention feature 334 is or includes an oval or stadium shaped post extending rearward from the yoke back 294B. The first retention feature 334 has a length or depth selected such that an outer or rearmost surface of the first retention feature 334 is flush or substantially flush with the rear surface of the yoke back 294B. This increases the contact area and interaction between the end caps 291 and end cap inserts 326 and increases the retention forces. The connection between the end caps 291 and end cap inserts 326 can therefore resist greater torsional forces along the length of the yoke 208 and/or rotational forces about the joint.

In the illustrated embodiment, the second retention feature 336 is or includes a raised tab extending forward from the yoke front 294A. The second retention feature 336 has a reduced length or depth compared to the first retention feature 334, which allows the end cap 291 to pass over the second retention feature 336 during assembly. In the illustrated embodiment, the second retention feature 336 has a chamfered lead-in 336a on one edge, e.g., on the lateral (relative to the yoke 208) edge in the illustrated embodiment, which allows the end cap 291 to be hinged or pivoted over and/or onto the second retention feature 336 more easily.

In some embodiments, the end caps 291 can be over-molded onto an end of a braided element (e.g. side strap 252) of an automatic headgear adjustment mechanism, for example, braided elements as shown and described in U.S. Provisional Patent Application No. 62/343,711, entitled "Directional Lock for Interface Headgear Arrangement" and filed May 31, 2016, PCT Application No. PCT/IB2017/051522, and PCT Application Publication No. WO2014/175752, the entireties of which are hereby incorporated by reference herein. The core elements or filaments 340 can extend within the braided elements (e.g. side straps 252). The end caps 291 can connect the braided element, and therefore the headgear, to the yoke 208 and create a closed loop headgear system.

Figure 91:
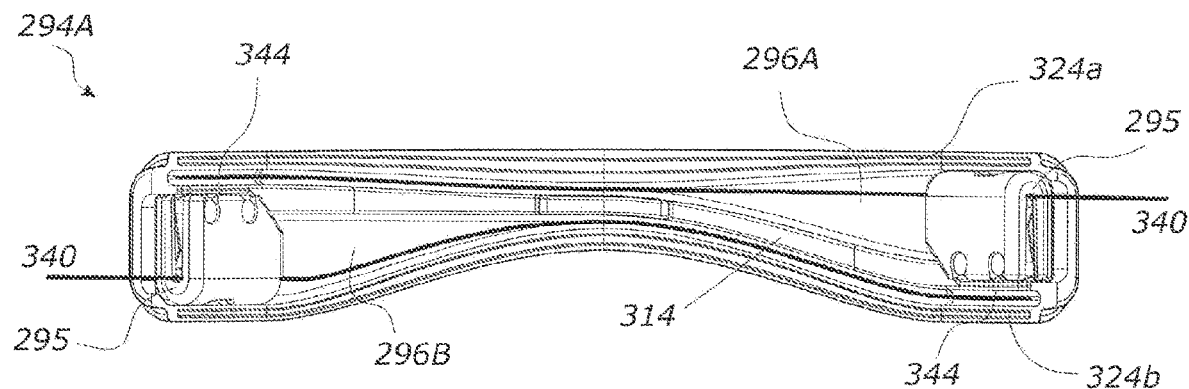
FIG. 91 is a rear or inner-side view of the yoke front of the yoke assembly of the fourth embodiment nasal mask interface, and shows the directional locks and filaments of an automatically adjustable headgear assembly.

As described herein, in some embodiments, the yoke 208 may form a collector for core elements, such as filaments 340, used in an automatically adjustable or self-adjusting headgear system. As shown in FIG. 91, the yoke front 294A includes an upper line track 296A and a lower line track 296B. In this embodiment, a line track divider protrudes rearwardly from a rear or internal surface of the yoke front 294A. In some embodiments, the yoke fastener 314 forms or functions as the line track divider extends generally at a diagonal across a portion of the length of the yoke front 294A. In the illustrated embodiment, a divider wall 344 extends between each of the washer housings 295 and the opposing line track. The divider wall 644 separates the opposing line track from the washer housing 295 so that a free end of the filament 340 is inhibited from being caught in the opposing washer housing 295 during retraction. In the illustrated embodiment, the line tracks 296A, 296B are not symmetrically mirrored due to the asymmetry of the upper and lower edges of the yoke 208.

Figure 92:
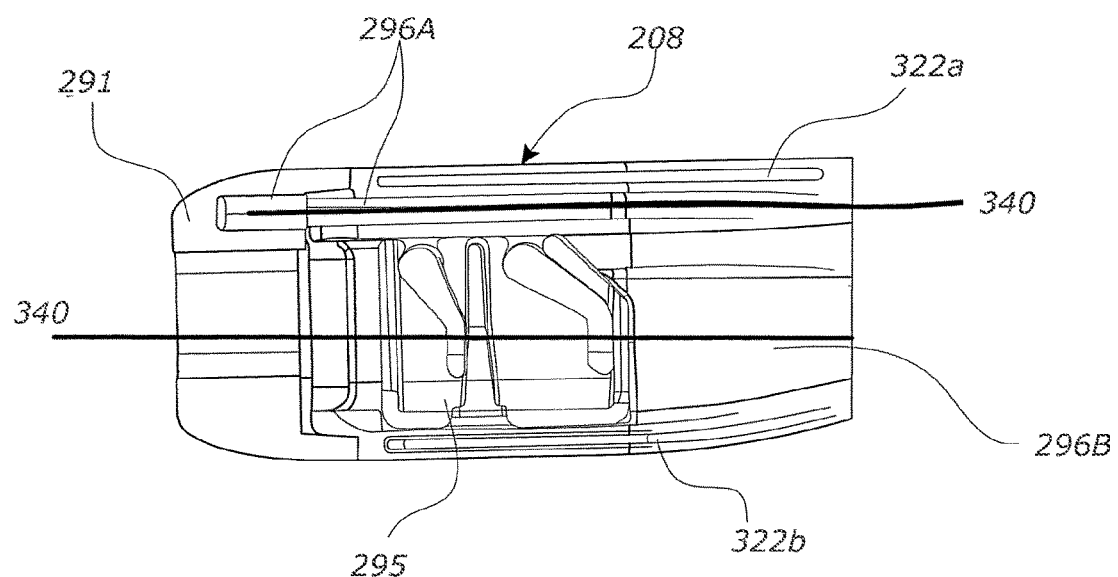
FIG. 92 is a partial section view of an alternative configuration of the yoke assembly showing components of a headgear adjustment mechanism in accordance with the fourth embodiment nasal mask interface.

FIG. 92 illustrates a variation of the yoke 208 in which the line tracks 296A, 296B extend into and terminate within the end caps 291. The lengths of the line tracks 296A, 296B are therefore extended beyond the ends of the yoke front 294A and yoke back 294B. This increases the length of filament 340 that can be stored within the yoke 208, which increases the range of adjustment or variability in the size of the headgear. The headgear assembly defines a headgear loop that extends around a user's head in use. The filament 340 forms part of the automatic headgear adjustment mechanism that allows a total length of the headgear loop to be extended during donning and doffing of the mask system. In some such embodiments, the length of each of the line tracks 296A, 296B can be increased or extended by about 5 mm. In such embodiments, the total length of the headgear loop, in an extended state, can therefore increase by about 10 mm.

Referring to FIGS. 99-102, show an embodiment of a directional lock of the automatically adjusting headgear that will be explained in further detail. The directional lock comprises a washer housing 295, a first and a second lock element (e.g., washer 1820, 1822) and a filament or core member 340. The housing comprises a first and a second chamber 1840, 1842 wherein the first and second chambers 1840, 1842 are configured to house the first and second lock washers 1820, 1822, respectively. In the illustrated arrangement, the first and second chambers 1840, 1842 are separated by an internal wall 1812 of the housing 295. However, in other arrangements, the first and second chambers 1840, 1842 are not necessarily physically separate spaces, but can be portions of a chamber. The housing 295 has two end walls 1814, which along with the internal wall 1812, have an elongate core opening 1860 for the core member 340 pass through. The core openings 1860 are substantially aligned with each other. The core opening 1860 of the end wall 1814 shown on the right side of the figures is larger than the core opening of the internal wall 1812 and the end wall 1814 shown on the left of the figures. This allows for manipulation of the path of the core member 340 through the housing 295. The first and second chambers 1840, 1842 are each delimited by the internal wall 1812, one of the end walls 1814 and a pair of side walls 1816; wherein the side walls 1816 extend between the end walls 1814 of the housing 295. The first and second chambers 1840, 1842 are configured to be open at one or both of a top and a bottom of the housing 295.

Each of the first and second chambers 1840, 1842 has a pair of washer retainers 1850 that are aligned on opposing side walls 1816 of the housing 295. Each pair of washer retainers 1850 is configured to pivotally retain one of the first or second lock washers 1820, 1822 within the respective first or second chamber 1840, 1842. The washer retainers comprise a circular bush 1852 and an elongate slot 1854, wherein circular bushes 1852 intersect with the bottom of the housing such that an entrance is formed. The entrance is configured to allow the first and/or second lock washers 1820, 1822 to be received into the washer retainers 1850. The slot 1854 extends radially from the circular bush 1852 towards the top of the housing 295.

The first and second washers 1820, 1822 comprise a cylindrical shaft 1824 and an arm 1826 that extends from the shaft 1824. The cylindrical shaft 1824 is substantially the same width W, as the housing 295 and the arm 1826 is narrower to fit within the first and second chambers 1840, 1842. In the illustrated arrangement, the arm 1826 comprises a first section 1872 and a second section 1874, wherein the first section 1872 extends radially or perpendicularly from the cylindrical shaft 1824 and the second section 1874 extends at an obtuse angle from the end of the first section 1872. The first section 1872 of the arm 1826 of the first washer 1820 is shorter than the first section 1872 of the arm 1826 of the second washer 1822. The angle between the first and second sections 1872, 1874 of the arm 1826 of the first washer 1820 is greater than the corresponding angle of the second washer 1822. The angles can be selected such that the second section 1874 of one or both of the first and second washers 1820, 1822 lies substantially flat against the corresponding wall (e.g., internal wall 1812 and end wall 1814, respectively) of the housing 295 in one position of the washers 1820, 1822. The second section 1874 of the arm 1826 comprises a centrally located circular aperture 1876 configured to receive the core member 340. The first and second chambers 1840, 1842 differ in size according to the size of the washer that is to be housed within it, i.e. the first chamber 1840 is smaller than the second chamber 1842 because the first washer 1820 is smaller than the second washer 1822.

The cylindrical shafts 1824 of the first and second lock washers 1820, 1822 have a diameter substantially the same as that of the circular bushes 1852 of the washer retainer 1850, and are configured to be received and retained by the circular bush 1852 in a snap-fit configuration. The snap-fit configuration is provided by the entrance of the circular bush 1852 being narrower than the diameter of the cylindrical shaft 1824. The slots 1854 of the washer retainers 1850 are configured to allow the entrance to be flexed open to increase the ease with which the first and second lock washers 1820, 1822 can be pushed through the entrances and assembled to the housing 295. Once assembled within the first and second chambers 1840, 1842 of the housing 295, the first and second washers 1820, 1822 can pivot back and forward around a central axis that runs through the cylindrical shaft 1824.

Figure 99:
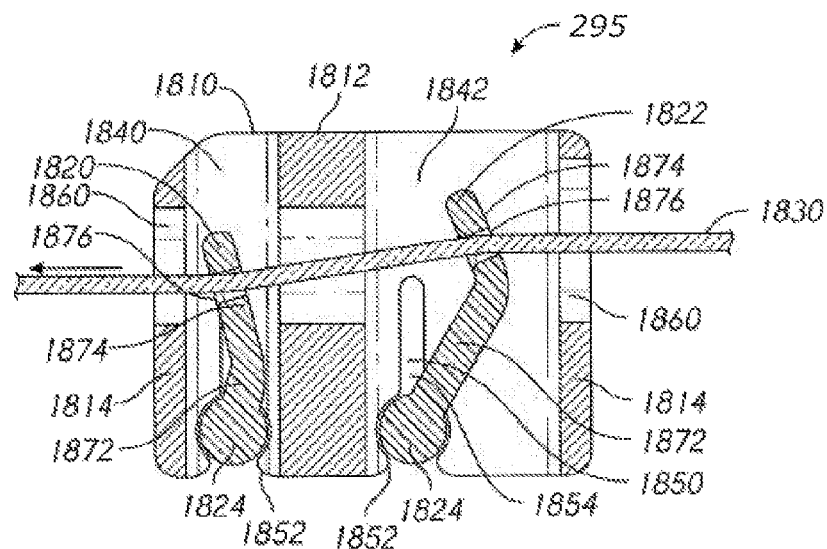
FIG. 99 is a cross-sectional view of a directional lock of the yoke of the fourth embodiment nasal mask interface, the lock shown in a locked position.
Figure 100:
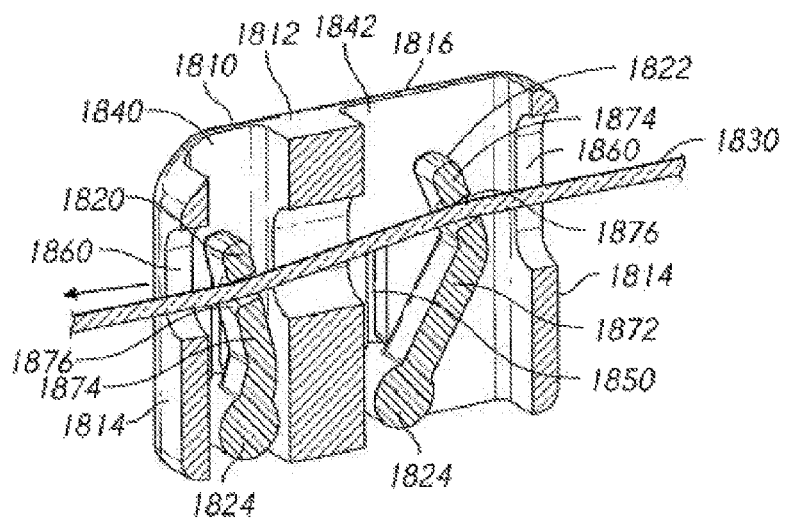
FIG. 100 is a perspective cross-sectional view of the directional lock of FIG. 99 in the locked position.
Figure 101:
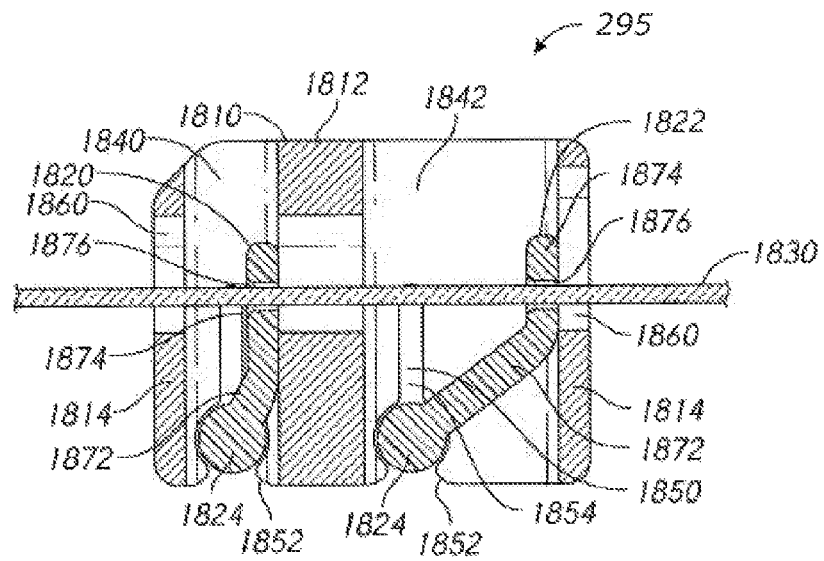
FIG. 101 is a cross-sectional view of the directional lock in FIG. 99 in the unlocked position.

The core member 340 is configured to pass through the core openings 1860 of the housing 295 and the apertures 1876 of the first and second washers 1820, 1822. Application of a tension force to the core member 340 causes the first and second lock washers 1820, 1822 to pivot back and/or forward between a locked position and/or open position. FIGS. 99 and 100 show the directional lock in a locked configuration in which a force is applied to the core member 340 in a direction towards the left side of the figure (as indicated by the arrow). The force applied to the core member 340 in this configuration causes the first and second lock washers 1820, 1822 to pivot in an anti-clockwise direction, such that the path of the core member 340 through the directional lock 1800 is non-linear or tortuous and movement of the core member 340 is restricted. FIGS. 101 and 102 show the directional lock in an open configuration in which a force is applied to the core member 340 in a direction towards the right side of the figure (as indicated by the arrow). In this configuration, the first and second lock washers 1820, 1822 are pivoted in a clockwise direction such that the circular apertures 1876 and core openings 1860 are aligned in a substantially straight line. This provides a smooth path for the core member 340 to be pulled substantially freely through the directional lock 1800. Additional particulars of the operation of the directional locks 1800 are described above and in Applicant's PCT Application Publication No. WO2014/175752.

Summary of Features of Fourth Embodiment

Aspects of the fourth embodiment nasal mask interface, in some embodiments, may provide the following advantages or features:
- A nasal mask interface that can be used with automatically adjusting headgear (or any single side strap type headgear) without the need for a forehead T-piece component,
- Yoke 208 enables the headgear 250 to be removably connectable to the seal housing 204 and nasal seal 202,
- Under-nose support 224 in combination with a lower-profile or shorter nasal seal and ribs 241 contribute to increases mask stability on the user's face during use,
- The low-profile or shorter height of the nasal seal means that the seal contacts the user's nasal bridge at a lower position that conventional nasal seals and this is generally less intrusive,
- Removably connectable conduit frame 211 is symmetrical and allows the conduit frame to be connected in either of two orientations,
- The secondary seal lip (e.g. including 284e, 284F) at the end 284A of the central gripping portion 284 of the conduit frame 211 assists in creating a back-up seal at the connection of the conduit frame into the seal housing.

Fifth Embodiment—Various Alternative Nasal Mask Interface Configurations

Various forms of a fifth embodiment nasal mask interface assembly will now be described with reference to FIGS. 103-149. The various forms of the fifth embodiment nasal mask interface are similar in configuration and construction to the fourth embodiment generally, although there are differences. The following description will focus on the differences between the embodiments. It would be appreciated that the various alternatives and configurations described with reference to the fourth embodiment or other embodiments disclosed may also apply to the fifth embodiment forms.

First Form Nasal Mask Interface of the Fifth Embodiment

Referring to FIGS. 103-117, the first form 400 of the fifth embodiment nasal mask assembly will be described. As with the fourth embodiment, the nasal mask interface 400 comprises a nasal seal 402 coupled to a seal housing 404 and a yoke 408 received within a yoke channel 466 of the seal housing 404. As shown in Figure in 104, the nasal seal 402 comprises an under-nose support 424 that extends within the mask cavity. As with the fourth embodiment, the first form nasal mask interface 400 may connect to a headgear assembly of the type previously described via the yoke 408 attachment.

In this embodiment, the central lower part or portion of the outer side of the seal housing 404 comprises an integral inlet aperture 465. In this embodiment, the inlet aperture 465 is an oval protrusion or extrusion from the seal housing and is configured to connect or couple directly or indirectly to a gases supply conduit to supply a flow of gasses into the mask cavity when in use. In this embodiment, an arrangement of bias vent holes 412 are provided in an array about the periphery of the inlet aperture protrusion 465. The array of bias flow apertures 412 may extend around the entire periphery of the inlet aperture protrusion 465 or a portion or portions of the periphery depending on the embodiment.

Referring to FIGS. 107-110, the connection of the yoke 408 to the seal housing 404 will be described in further detail. In this embodiment, the yoke channel 466 is modified (relative to the fourth embodiment) in that it provides larger singular locating features 468 on each lateral side of the yoke channel 466 which are shaped and dimensioned to receive complementary portions of the thicker lateral regions 410 of the yoke 408.

In this embodiment, a lower portion of the rear surface of the yoke channel 466 is provided with a recessed elongate channel 414 that is shaped and dimensioned to receive a complementary shaped elongate protrusion or rib 416 located along the bottom of the rear surface of a thinner central region 412 of the yoke 408. In particular, the protrusion 416 of the yoke is configured to engage with an interference or friction fit into the complementary recess channel 414 of the yoke channel 466 to thereby couple the yoke 408 to the seal housing 404.

Figure 112:
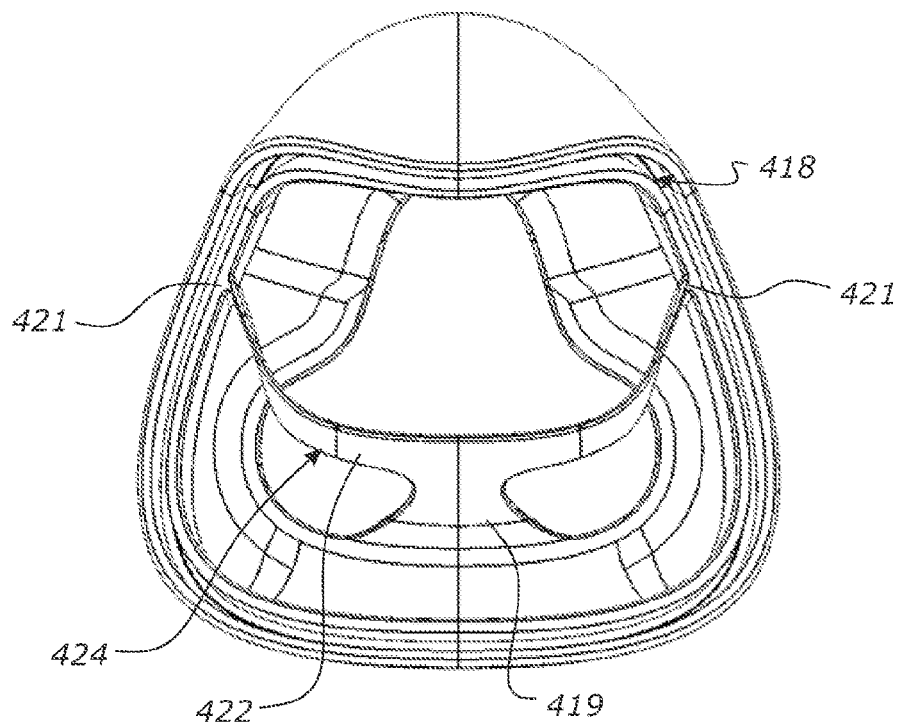
FIG. 112 is a rear or outer side view of the nasal seal of FIG. 111.
Figure 113:
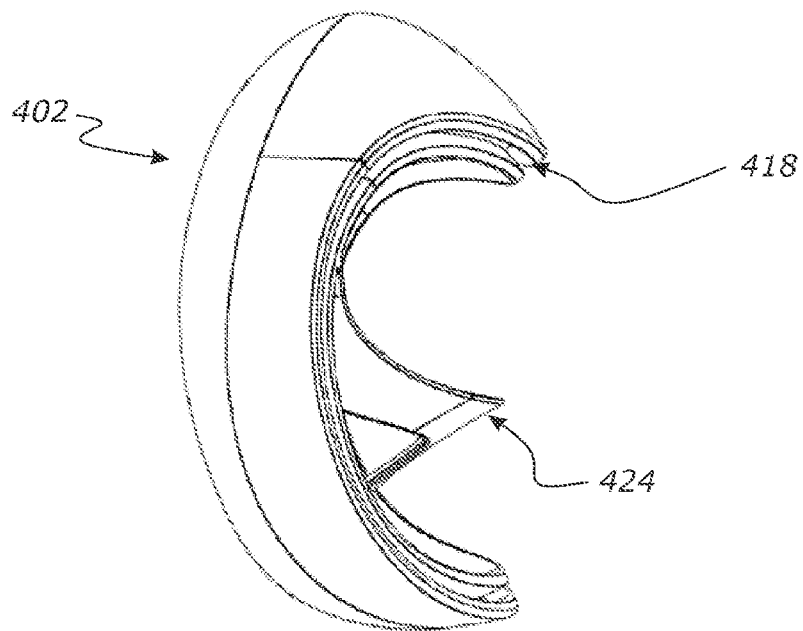
FIG. 113 is a side elevation view of the nasal seal of FIG. 111.
Figure 114:
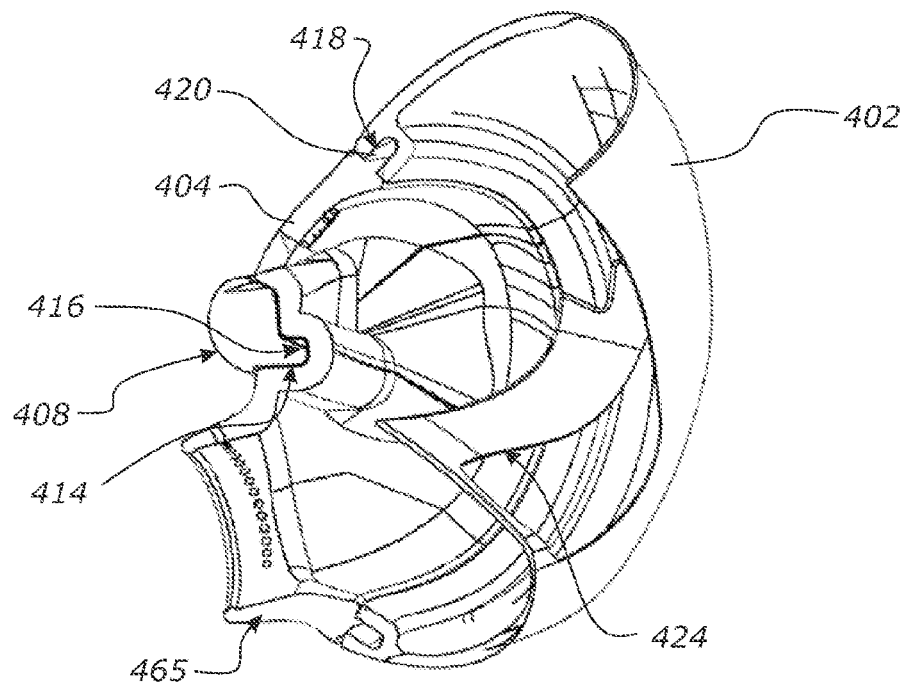
FIG. 114 is a cross-sectional view of the first form nasal mask interface of FIG. 103 through line BB of FIG. 105.
Figure 115:
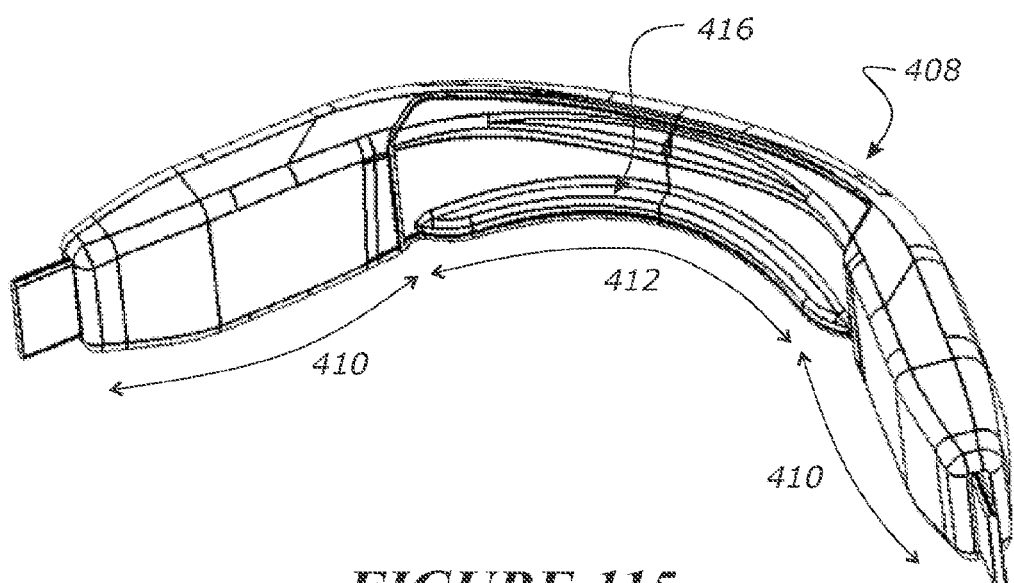
FIGS. 115, 116 and 117 show a wearer side perspective view, front outer side view, and top view respectively of the yoke of the first form nasal mask interface of FIG. 103.
Figure 116:
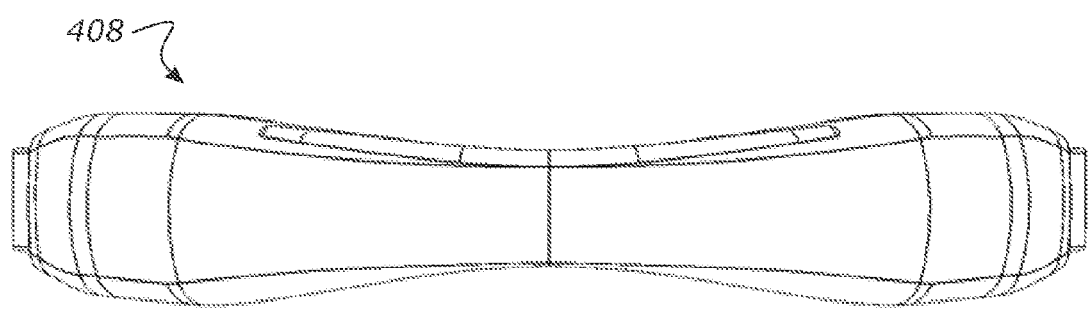
Figure 117:
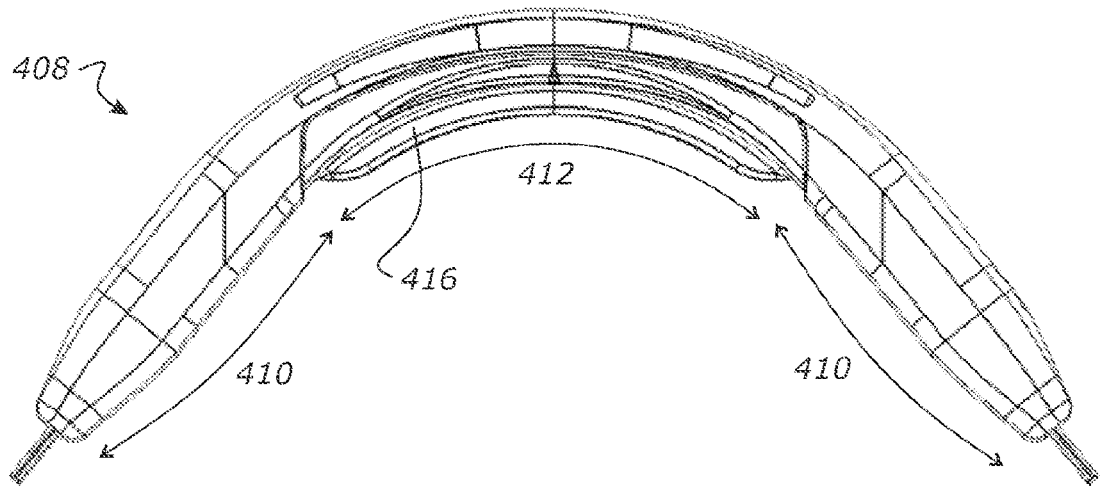
Figure 118:
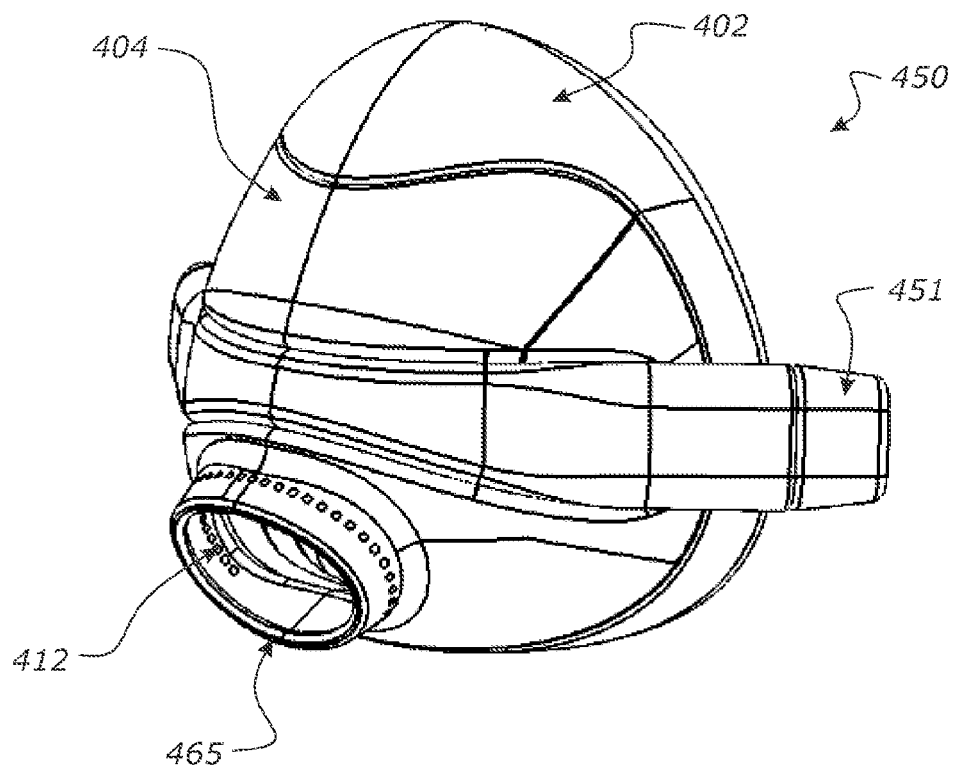
FIG. 118 is a perspective view of an outer side of a second form of the fifth embodiment nasal mask interface.
Figure 119:
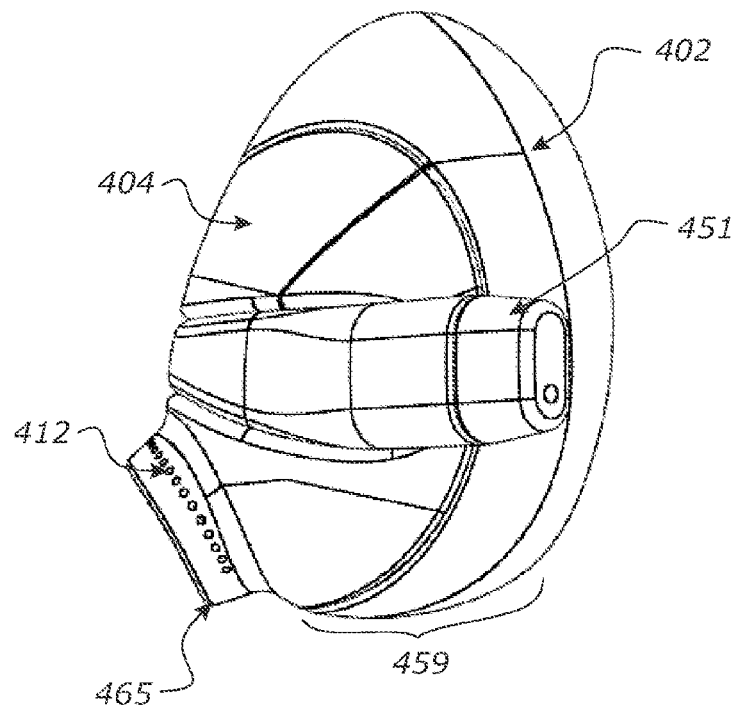
FIG. 119 is a side elevation view of the second form nasal mask interface of FIG. 118.
Figure 120:
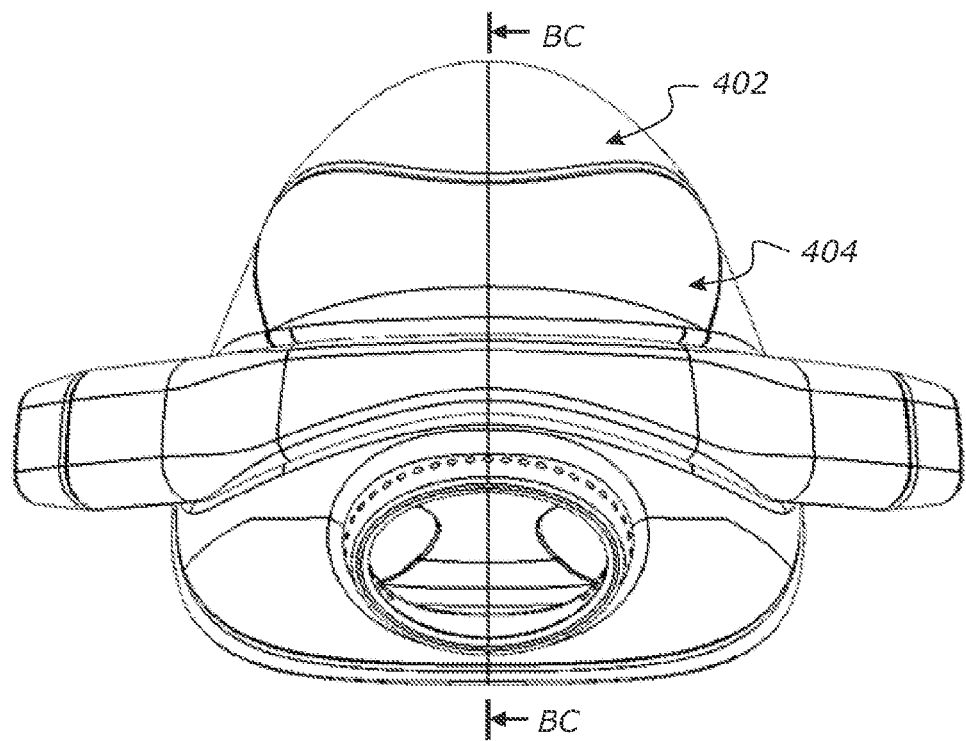
FIG. 120 is an outer side view of the second form nasal mask interface of FIG. 118.

Referring to FIGS. 112 and 113, in this first form of the fifth embodiment, the nasal seal 402 is provided with a channel 418 on its outer seal housing connecting edge. This channel 418 is configured to engage with a complementary shaped and dimensioned ridge 420 extending about the opening of the seal housing 404 (see FIG. 110). The coupling of the nasal seal 402 to the seal housing 404 can be seen in the cross-sectional view of FIG. 114, in particular, the coupling of the seal housing ridge 420 into the complementary channel 418 of the nasal seal. It will be appreciated that this configuration may be inverted with the channel being provided on the seal housing 404 and the protruding ridge being provided on the nasal seal 402, in alternative embodiments.

Figure 111:
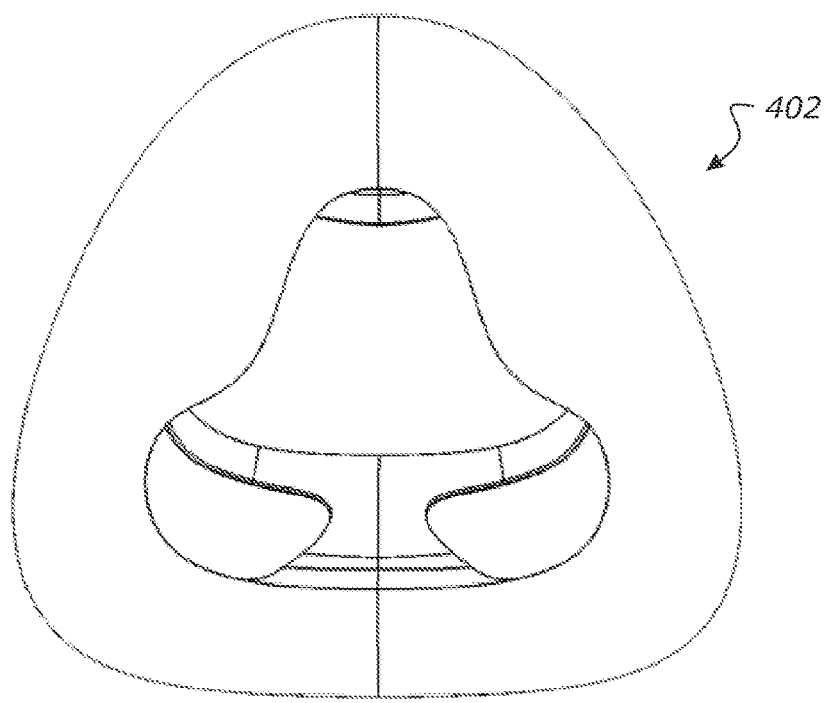
FIG. 111 is a front or face-contacting side view of the nasal seal of the first form nasal mask interface of FIG. 103.

Referring to FIGS. 111 and 112, the lower central connecting portion 419 of the under nose support 424 is similar to that of the fourth embodiment. The lateral connections 421 of the main lateral portion or band 422 of the under-nose support 424 connects directly to the lateral outer side wall portion of the nasal seal in the region of the channel 418. In this embodiment, the lateral connections of the main lateral band 422 are lower within the nasal seal relative to the fourth embodiment and this provides a generally flatter curvature to the main lateral band 422 in the central region of the mask cavity relative to the fourth embodiment.

Second Form Nasal Mask Interface of Fifth Embodiment

With reference to FIGS. 118-128, a second form nasal mask interface 450 of the fifth embodiment will be described. The second form nasal mask interface 450 is similar to first form, and like reference numerals correspond to like components.

The main difference in the second form nasal mask interface relates to the configuration of the yoke 451 and yoke channel 452. In this second form, the yoke channel 452 does not provide any specific locating features. Rather, the yoke channel 452 is configured to securely receive and retain the yoke 451 via an interference fit between the surfaces of the channel 452 and the abutting outer surfaces of the yoke 451. In particular, with reference to FIG. 128, the maximum height of the yoke as indicated at 453 is larger than the corresponding width of the yoke channel opening. A force is required to deform the yoke sufficiently to press it into the yoke channel 451 to create a semi-permanent interference fit connection.

Third Form Nasal Mask Interface of Fifth Embodiment

With reference to FIGS. 129-139, a third form of the fifth embodiment nasal mask interface will be described.

Figure 130:
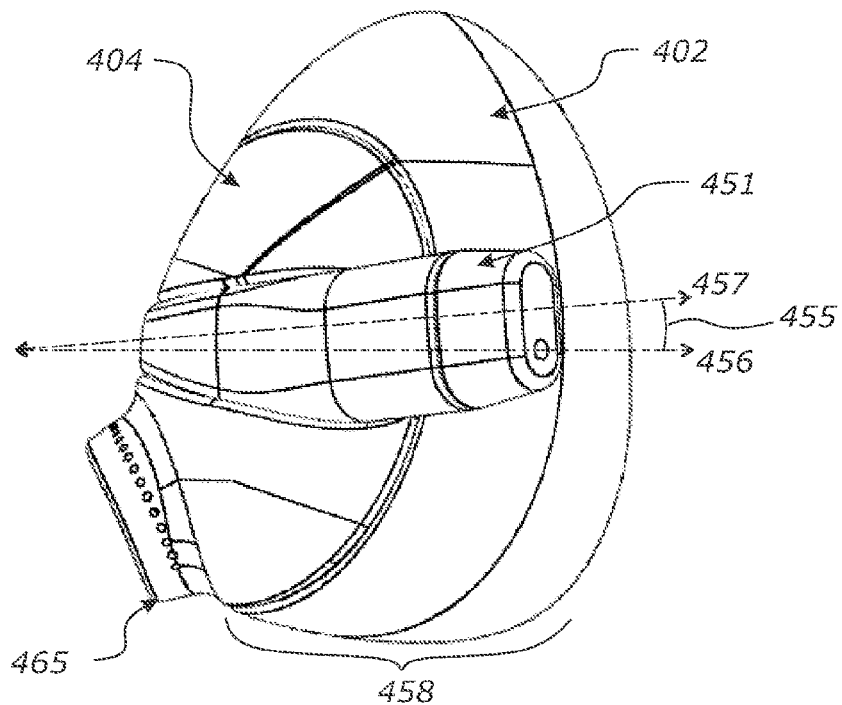
Figure 131:
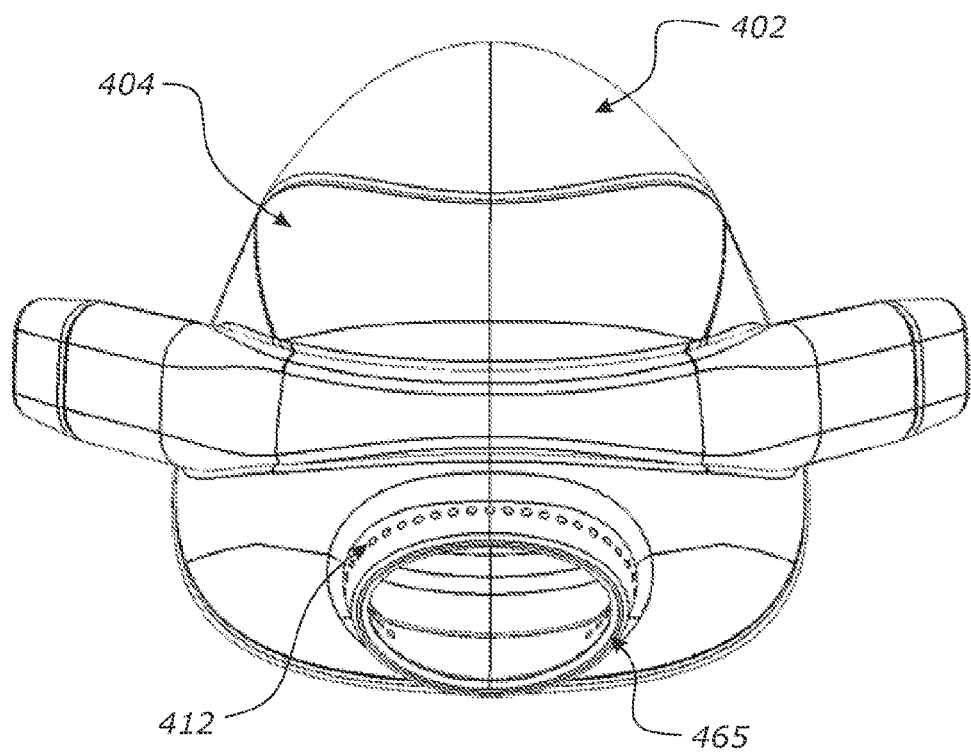
Figure 132:
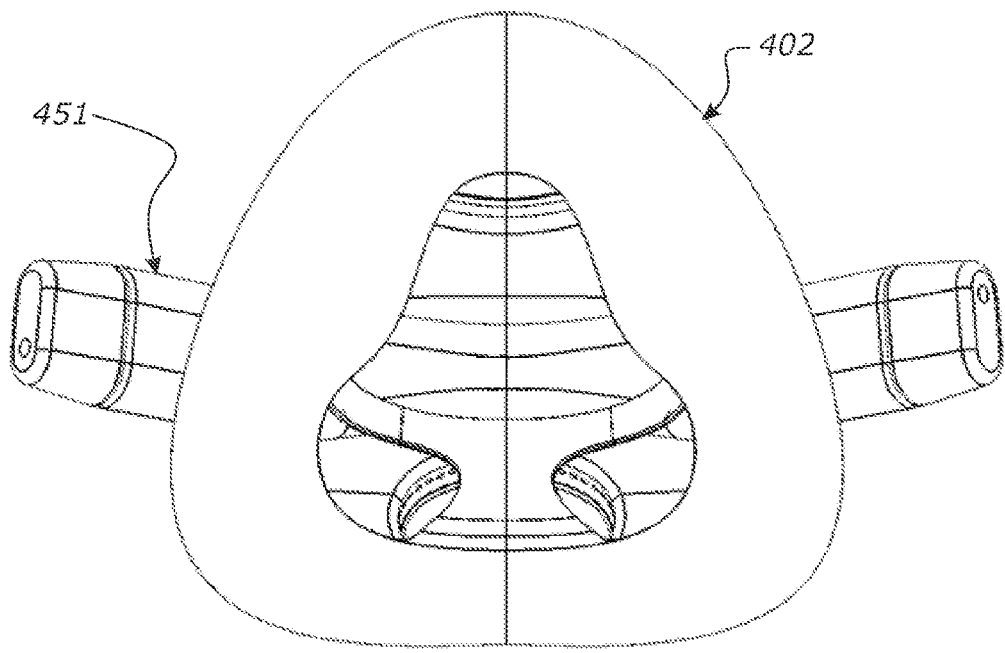
Figure 133:
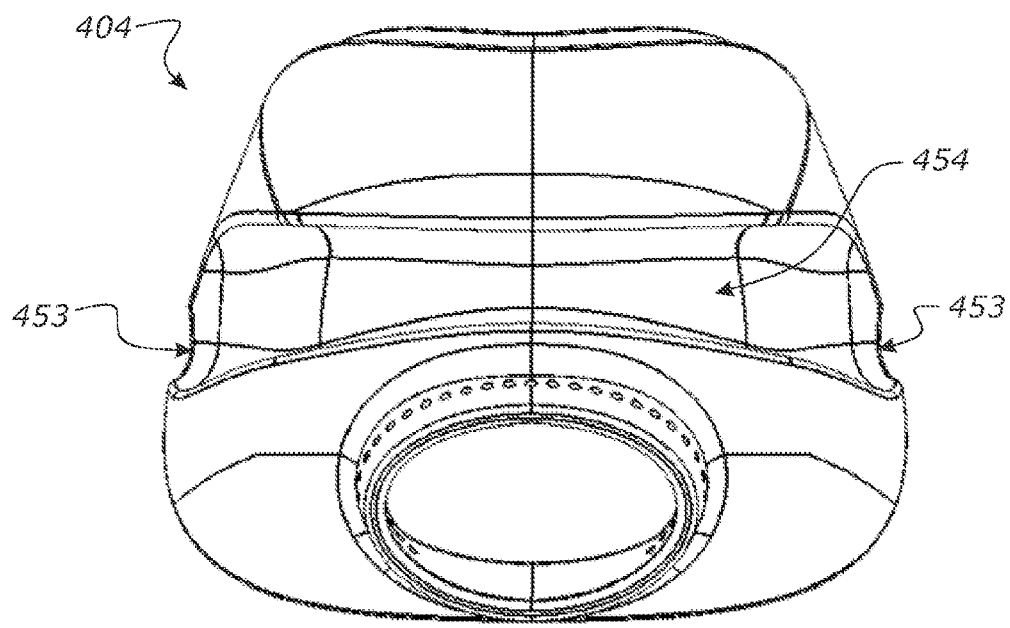
Figure 134:
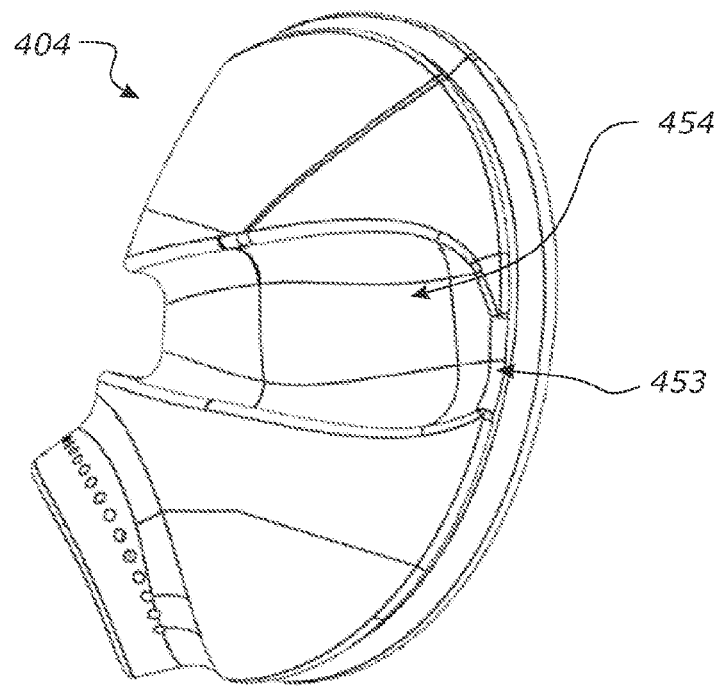

The third form nasal mask interface is similar to the first and second forms, and like components use like reference numerals. The third form nasal mask interface assembly utilises an interference fit to couple the yoke 451 into the yoke channel 454 of the seal housing 404 like in the second form nasal mask interface. However, the shape and configuration of the yoke channel 454 of the seal housing 454 in the third form is altered to angle the longitudinal axis of the yoke 451 upwardly to enable to provide an improved headgear vector. The angular offset or inclination of the yoke 451 upwardly is provided by the shape of the yoke channel 454 and the lateral cutout formations 453 provided at the side surfaces of the channel as shown on FIG. 133. Referring to FIG. 130, the horizontal orientation of the longitudinal axis of the yoke 451 is shown at 456 and this is the orientation of the first and second forms of the nasal mask interface. The inclination of the yoke angle is shown with the longitudinal axis 457 of the yoke 451 in the third form, with the angular inclination indicated at 455. In this form, the angle of inclination is approximately 5°, although it will be appreciated the angle may be varied as desired.

Referring to FIGS. 130 and 137-139, the nasal seal 402 of the third form also comprises variations relative to the previous forms. The third form nasal seal 402 has a thickened upper lip region as indicated 458 in FIG. 130 relative to the thinner upper lip region 459 of the second form embodiment shown in FIG. 119. This provides for more compression in the bottom or upper lip region of the nasal seal in use and generally a flatter smoother transition to the contacting surface of the nasal seal.

Figure 121:
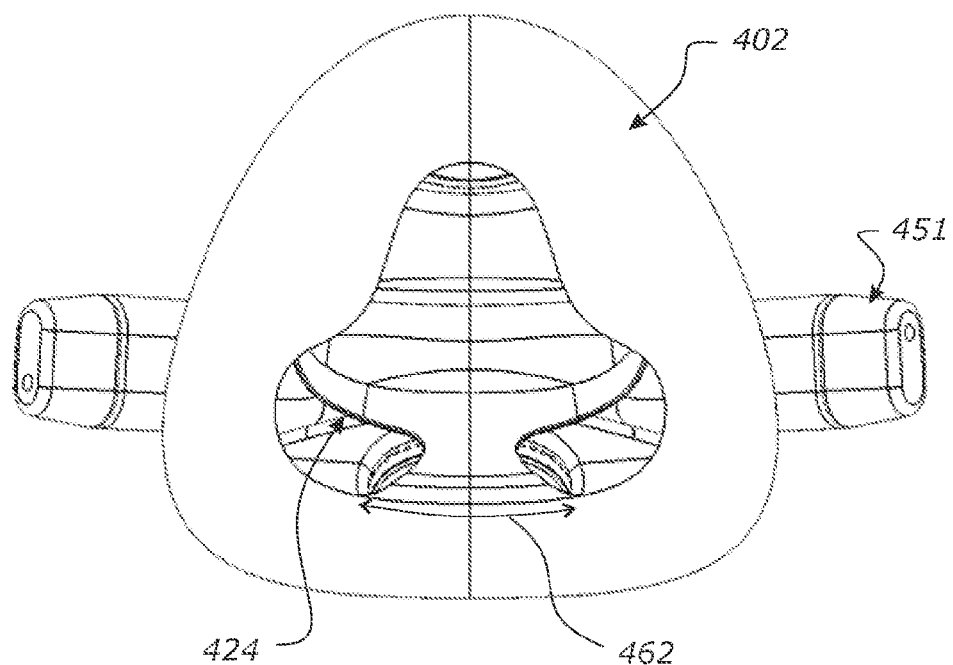
Figure 122:
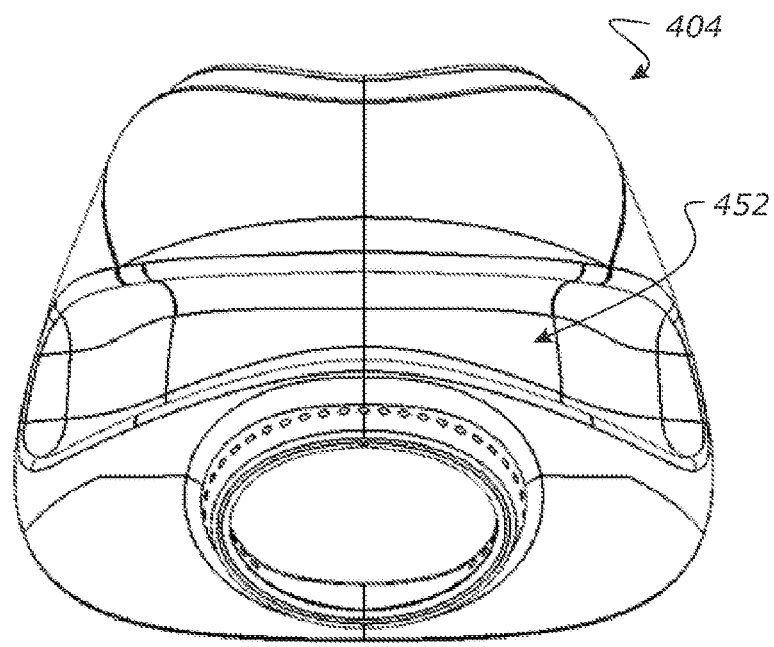
Figure 123:
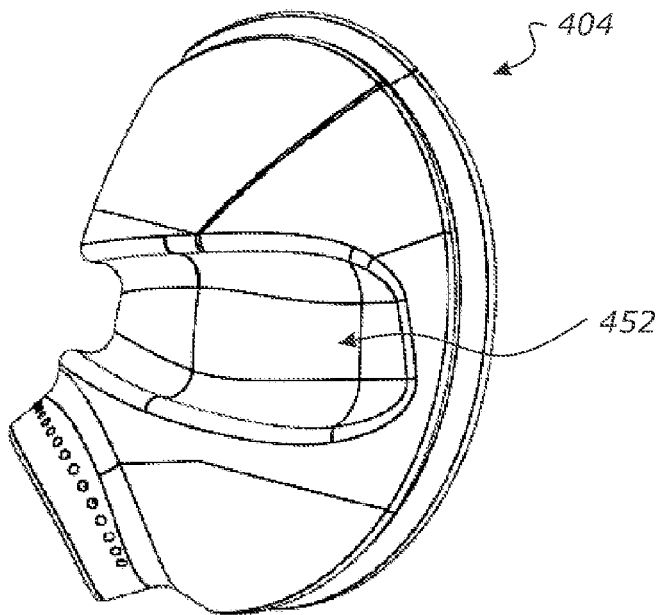
Figure 124:
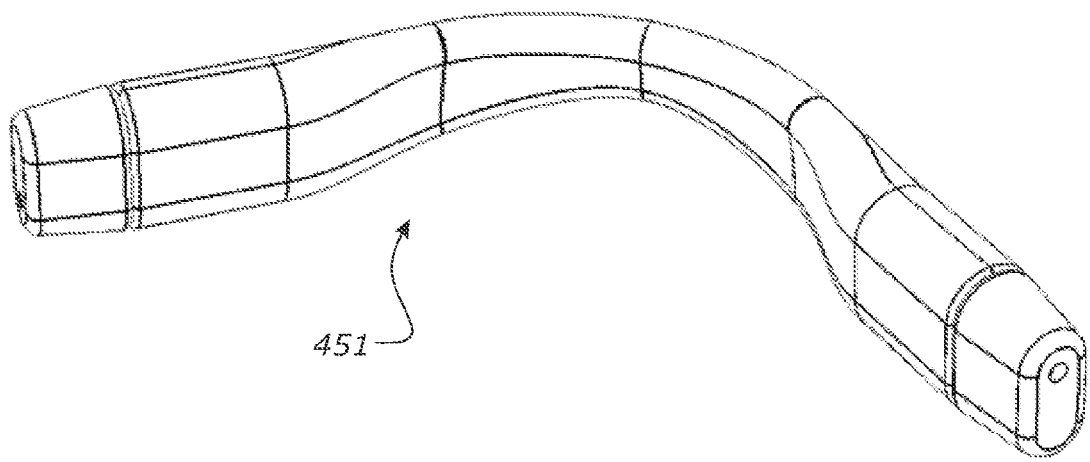
Figure 125:
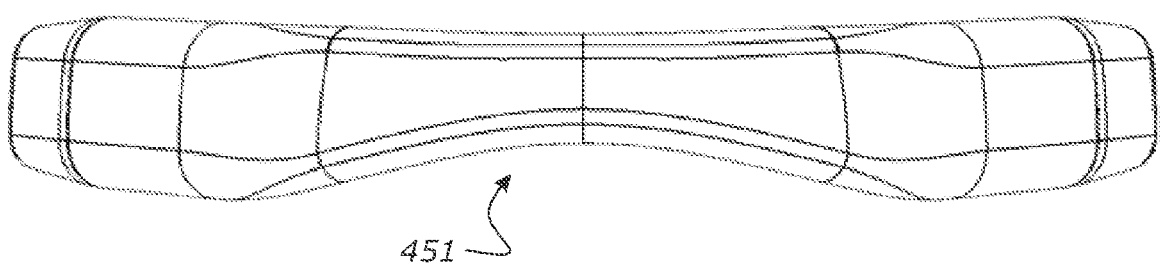
Figure 126:
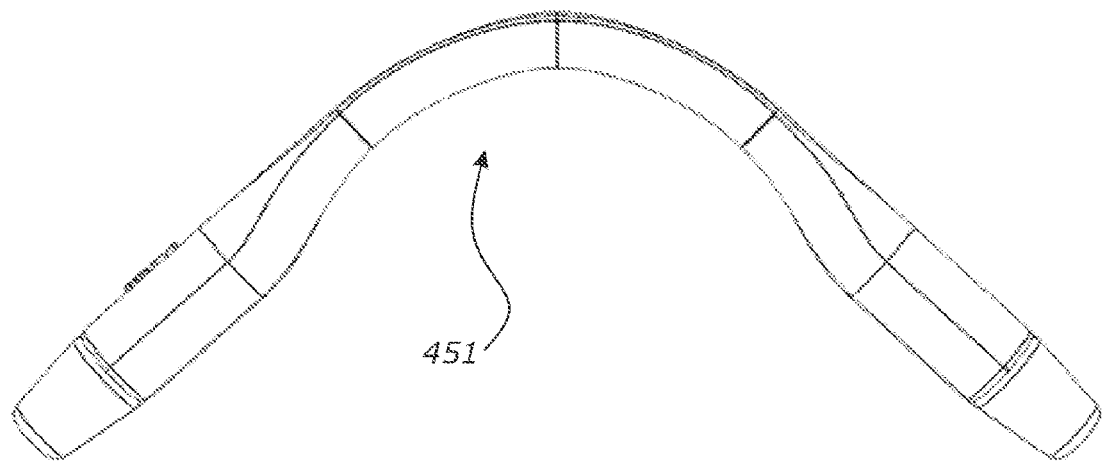
Figure 127:
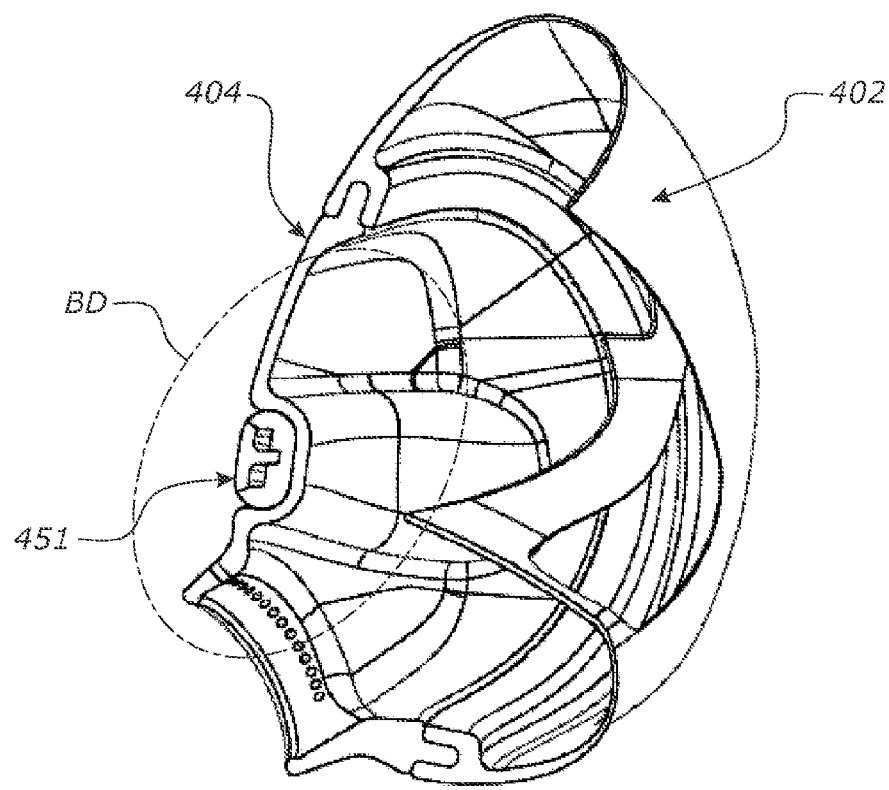
Figure 128:
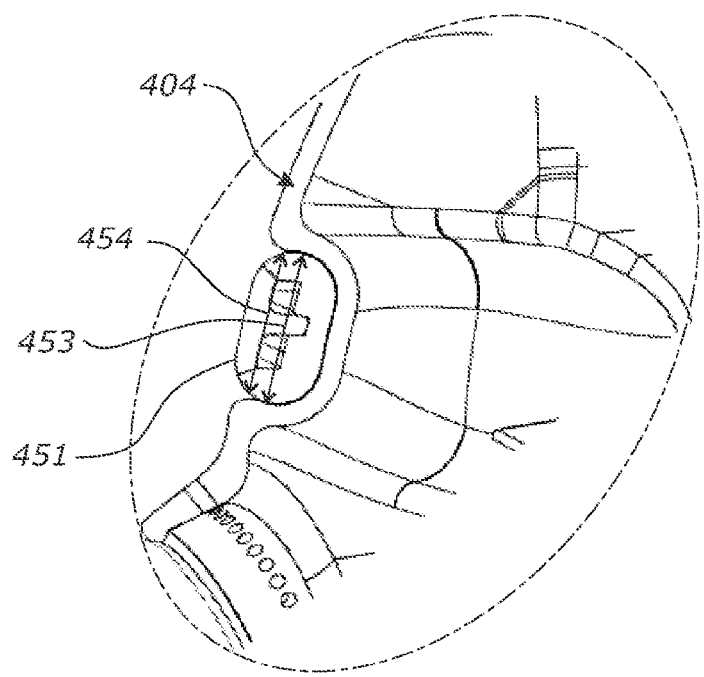

The lower connecting portion 460 of the under-nose support 424 is also thinner laterally at the connecting edge of the nasal aperture as indicated at 461 in FIG. 137 relative to the wider connection shown at 462 in FIG. 121 of the second form. The lateral connections 462 of the main lateral band of the under-nose support 424 are also thicker and extend further into the nasal seal from the connecting channel edge 464 as shown in FIG. 139. For example, the connections 462 may integrally couple to the channel connecting edge 464 of the nasal seal and a portion of the inner surface of the sidewall. In some embodiments, the lateral connections 462 may also couple with or extend to a portion of the inner surface of the contacting surface of the nasal seal.

In this third form, the length of the under-nose support 424 stemming from the connecting edge of the nasal aperture to the rear edge of the main lateral band 465 has been lengthened to accommodate longer noses. By way of example only, the length shown at 463 may be approximately 22.8 mm compared with, for example, 17.9 mm in the first and second forms of the fifth embodiment.

Fourth Form Nasal Mask Interface of the Fifth Embodiment

Referring to FIGS. 140-149, a fourth form nasal mask interface 470 will be described in further detail. The fourth form nasal mask interface 470 is substantially similar to the third form nasal mask interface 460 and like components have like reference numerals.

The first main difference in the fourth form as a mask interface 470 relative to a third form is that the bias flow vent 471 has been moved from the inlet aperture 465 to the upper central region of the seal housing 404 above the yoke channel. As shown, the bias flow vent comprises a cluster or arrangement of tightly spaced apertures or holes as indicated at 471.

Referring to FIGS. 146-149, the fourth form nasal mask interface comprises a nasal seal 402A having a modified geometry that provides a flatter contacting surface. In particular, with reference FIG. 149, a comparison between the third form nasal seal 402 and the fourth form nasal seal 402A is shown. As depicted, the upper region, including the nasal bridge region of the nasal seal, and the lower upper lip region of the nasal seal have been brought forward relative to the third form nasal seal 402 to provide an overall flatter sealing surface that provides more cushioning.

Additionally, the length of the under nose support extending from the central connector at the nasal aperture edge to the rear edge of the main lateral band as indicated at 474 in FIG. 148 has been further lengthened relative to the third form nasal seal to a length of approximately 26.49 mm, compared with 22.8 mm in the third form nasal seal.

Sixth Embodiment

Referring to FIGS. 150-154, a sixth embodiment of the nasal mask interface 500 will be described. The substantive configuration of the nasal mask interface 500 is similar to the previous embodiments and in particular to the fourth form 470 and like numerals represent like components. The following description will focus on the main differences, and it will be appreciated that the alternatives discussed with reference to the previous embodiments may also be applied to this sixth embodiment.

The primary difference with the nasal mask interface 500 compared with the fourth form 470 is that the seal housing 504 has been reconfigured by swapping the position of the yoke connection channel 454 and inlet aperture or conduit connector 465. In particular the conduit connector 465 is positioned in an upper central region of the seal housing above the yoke channel that receives the yoke 451. The yoke channel (not visible) is similar to the yoke channel 454 of the fourth form nasal mask assembly 470. In some embodiments, the lower yoke positioning on the seal housing may limit the amount of the frame rolling up on the user's face.

The nasal mask interface 500 also comprises an alternative bias event arrangement. In this embodiment, two bias event aperture clusters 501 are provided in the upper lateral regions on the seal housing on either side of the inlet conduit 465.

Seventh Embodiment

With reference to FIGS. 155-162, various alternative forms of a nasal seal for use in the nasal mask assembly will be described. As will be appreciated by a skilled person, the alternative forms of nasal seal of this seventh embodiment can be used with any of the embodiments of the nasal seal interface described, in particular any of the various forms of seal housing, yoke assembly and connection, and headgear assemblies.

First Form Nasal Seal of the Seventh Embodiment

Referring to FIGS. 155-157, a first form nasal seal 600 will be described. The first form nasal seal 600 of this embodiment is similar to the previous nasal seals described and includes an under-nose support indicated at 601. The primary difference with this nasal seal 600 is that it is provided with lateral wings or flaps 602 along at least a portion of the lateral sides of the contacting surface 603. In this embodiment, the winged portions 602 are located at approximately the midway or middle region of the lateral sides of the nasal seal. The wings 602 are shaped and configured to provide additional contacting surfaces that are configured to engage the cheekbone/nasal area of the user to increase stability, and the increased footprint of the contact surface of the nasal seal on the user's face assists in reducing rolling or rocking from occurring in use in some embodiments. With reference to FIG. 157, each of the wings 602 comprises a connecting portion 602A that couples to a side wall portion of the nasal seal rearward of the contacting surface 603, and an extension portion 602B that extends forwardly of the contacting surface 603 to provide the winged contacting surfaces on each lateral side of the nasal seal. The winged contacting portion 602 provide added support to prevent the nasal mask from rolling up the face of a user.

Second Form Nasal Seal of the Seventh Embodiment

The second form nasal seal 610 is similar to the first form 600 in that it comprises lateral winged portions 604 that extend from the lateral side of the nasal seal. Compared to the first form nasal seal 600, the wings 604 are longer and adapted to conform with the flat area of the cheekbone/nasal area. As shown, in FIG. 161 the curved or contoured profile of the winged regions is adapted to suit the contour of the user's face. As with the first form, the wings 604 comprise a connecting portion 604A that couples the wing to the lateral side of the nasal seal and an extension or contacting portion 604B that is configured to contact the cheekbone/nasal area of the user's face to stabilise the nasal mask on the user's face and prevent rolling as with the first form.

Referring to FIG. 162, a nasal mask interface comprising the second form nasal seal 610 with the wings 604 is shown secured to the head of a user via a headgear assembly of the type previously described. As shown, the winged regions 604 may be loosely coupled or tethered to a strap of the headgear assembly, such as the side or front strap 252 on each side of the nasal seal. In an embodiment, the wings may be provided with a coupling or connection mechanism at or towards the end of wing 604 for coupling to the side strap 252. In one form, the connector 606 may be a loop member or similar through which the side strap 252 extends to thereby loosely couple or tether the side strap to the winged portion 604 of the nasal seal. In other forms, the wings 604 may be de-coupled or untethered from the side straps 252.

Eighth Embodiment

With reference to FIGS. 163-170, various alternative forms of a nasal seal for use in the nasal mask assembly will be described. As will be appreciated by a skilled person, the alternative forms of nasal seal of this eighth embodiment can be used with any of the embodiments of the nasal seal interface described, in particular any of the various forms of seal housing, yoke assembly and connection, and headgear assemblies.

First Form Nasal Seal of the Eighth Embodiment

Referring to FIGS. 163 and 164, the first form nasal mask interface 700 is shown in FIG. 163 with the nasal seal 701, seal housing 702, and gases supply conduit 703. In this first form of the eighth embodiment, the nasal mask interface additionally comprises a forehead support component indicated at 704. The forehead support component is configured to engage with the user's forehead between or above their eyebrows should the mask roll or start to roll up the face and counteracts this rolling force. In particular, the dimension and angular orientation of the forehead support 704 is such that in rest or normal use the forehead support does not engage or is displaced from the user's forehead, and only engages so as to counteract any upward rolling of the nasal mask during use should that occur.

In this first form of the eighth embodiment, the forehead support 704 is centrally provided above the nasal bridge region of the nasal seal. In one form, the forehead support 704 may be coupled to extend exclusively from the seal housing 702, or exclusively from the nasal seal 701, or in yet a further alternative may be coupled to extend from both an upper region of the seal housing 702 and nasal seal 701.

The forehead support 704 may be an integral part of the seal housing 702 and/or nasal seal 701, or alternatively may be formed separately and coupled or connected to the seal housing 702 and/or nasal seal 701. FIG. 164 shows the forehead support 704 with a contacting region 704A located at or toward the end of the forehead support component, which in this form is substantially elongate. The first form nasal mask interface 700 can be seen worn by a user in FIG. 164 with a nasal mask interface being coupled via a headgear assembly of the type previously described coupled to the nasal mask interface by the yoke 706. The side strap 705 of the headgear assembly can be seen in FIG. 164.

Second Form Nasal Seal of the Eighth Embodiment

Referring to FIGS. 165-170, a second form 710 nasal seal for use in the nasal mask interface is shown. The nasal seal 710 is substantially similar in configuration to the previous nasal seals described. A primary difference is that the nasal seal is provided with a support protrusion 712 that extends upwardly from the apex of the seal. The second form nasal seal 710 is shorter in height than the first form nasal seal 700, and the support protrusion 712 is configured to counteract rolling up of the nasal mask in use by contacting the nasal bridge region of the user's face, rather than the forehead region like in the first form nasal seal 700.

As shown, the support protrusion 712 is integrally formed and extends from an outer upper side of the nasal seal up and over the apex of the nasal bridge region of the contacting surface indicated at 711. As shown in FIG. 167, the support protrusion in this embodiment generally tapers in thickness from the nasal seal connecting ends toward the upper extremity of the support protrusion.

Referring to FIGS. 169 and 170, the nasal seal is shown in place on a user with the remainder of the nasal mask interface assembly omitted from view for clarity. As shown, in rest and normal use the upper support protrusion 712 is configured to be offset or displaced from the user's nasal bridge. It is only if the nasal mask starts to roll or pivot up the user's face in use that the support protrusion 712 is rocked or pivoted inwardly toward the user's nasal bridge region to thereby counteracts the rolling force. In this embodiment, the in rest displacement of the support protrusion 712 may be approximately 3 mm from a user's nasal bridge.

Ninth Embodiment

With reference to FIGS. 171-185, various alternative forms of nasal seal for use of a nasal mask interface will be described. The various forms of nasal seal may be used with any of the described nasal mask interface assemblies, as will be appreciated by a skilled person.

First Form Nasal Seal of the Ninth Embodiment

Referring to FIGS. 171-174, the first form nasal seal 750 of the ninth embodiment is substantially similar to the previous nasal seals described and includes an under-nose support indicated at 752. The first form nasal seal 750 additionally comprises thickened regions in the upper lateral side portions of the contacting surface as indicated at 754 which add support to the upper region of the nasal seal or cushion 750. As shown, the thickened regions 754 are located proximal to or adjacent either side of the nasal bridge region of the contacting surface indicated at 751.

The first form nasal seal 750 further comprises a pair of support ribs 756 located within the thickened region 754. The support ribs 756 extend at an orientation that is substantially radial relative to the centre region or nasal aperture of the nasal seal, rather than horizontally or vertically. The support ribs 756 add support to the upper region of the nasal seal from the inner surface of the nasal seal within the mask cavity and assist in reducing the upwards roll of the nasal mask interface in use.

With reference to FIG. 174, the support ribs are located above the lateral connections 758 of the under nose support 752. In other words, the support ribs 756 in this form are isolated from the under nose support connections 758. As shown, the support ribs 756 are connected to a portion of the side wall of the nasal seal including a portion of the contacting surface but terminating prior to the thinned edge region at the periphery of the nasal aperture.

In this embodiment, the support ribs 756 on the inside of the nasal seal have an angular orientation relative to the vertical centre line extending through the nasal seal. In this embodiment, the angular orientation indicated at 760 may be in the range of approximately 50° to approximately 70°, preferably approximately 60°, in other words the ribs have an angular orientation of approximately 60° relative to the vertical centre line extending through the nasal seal.

Second Form Nasal Seal of the Ninth Embodiment

Referring to FIGS. 175-182, the second form of the nasal seal of the ninth embodiment will be described.

The second form nasal seal 770 of the ninth embodiment comprises an altered geometry relative to the first form nasal seal 750. In particular, the second form nasal seal 770 is shorter vertically, for example by approximately 10 mm. The nasal seal otherwise has similar configuration to the previous nasal seals described. Referring to FIG. 175, the overall height of the second form nasal seal 770 as indicated at 772 is approximately 47 mm, and the overall width of the nasal seal as indicated 774 is approximately 59 mm. Referring to FIG. 177, the overall depth of the second form nasal seal 770 as indicated 776 is approximately 39 mm. In this embodiment, the ratio of the overall height to width is in the range of approximately 1:1 to approximately 1:1.4, preferably approximately 1:1.3. In this embodiment, the ratio of the overall height to overall width to overall depth is in the range of approximately 1:1:0.6 to approximately 1:1.4:1, preferably approximately 1:1.3:0.8.

The contacting surface of the nasal seal is indicated at 771 and the outer side comprising the seal housing aperture is indicated at 773.

Referring to FIG. 179, the difference between the upper contacting point of the nasal seal of the first and second forms of the ninth embodiment on the user's nasal bridge can be seen. The nasal bridge contacting point for the second form nasal seal 770 is indicated at 777, and this is below the typical contacting point on the nasal bridge of the taller first form nasal seal as indicated at 778. The reduced vertical height of the second form nasal seal 770 enables it to contact the nasal bridge at a much lower point, for example to contact a portion of the nasal bridge within the area or region of the nasal bridge extending between the tip of the nose and halfway up or to the center of the nasal bridge. This lower contacting region relative to conventional nasal seals may be more uniform between multiple users and therefore increases the percentage of the population being able to successfully use the nasal mask.

Referring to FIGS. 181 and 182, the first form nasal seal 750 is shown overlaid onto the shorter second form nasal seal 770 to show the difference in geometry for comparison.

Third Form Nasal Seal of the Ninth Embodiment

With reference to FIGS. 183-185, a third form nasal seal 780 of the ninth embodiment will be described.

The third form nasal seal 780 in this embodiment is similar in size and shape to the shorter second form nasal seal 770. The main difference is that the third form nasal seal 780 additionally comprises support ribs 782 on the inner surface of the nasal seal. In particular, the main lateral portion of the under nose support 781 at each lateral end connects to a respective support rib 782. As shown, the support ribs 782 have a substantially vertical or near vertical orientation. The under nose support and its connection to the support ribs is similar in configuration to that described with reference to the nasal seal of the fourth embodiment.

In this third form nasal seal 780, the ribs 782 strengthen the connection of the under nose support within the nasal seal and also perform the dual function of providing structural support to the upper region of the nasal seal. In this third form, the under-nose support is more squarish in shape, rather than U-shaped. In particular, the main lateral portion comprises a substantially flat or horizontal central region 783 and two substantially vertical lateral portions 784 extending upwardly from a respective end of the central region.

Tenth Embodiment

With reference to FIGS. 186-205, various forms and configurations of seal housing and conduit frame of the nasal mask interface will be described. It will be appreciated that these various forms of seal housing and conduit frame variations may be incorporated into the various embodiments of the nasal mask assembly described to provide alternative configurations.

First Form Conduit Frame Configuration of the Tenth Embodiment

Referring to FIGS. 186-189, the first form conduit frame 800 is a hollow ovular body that extends between the housing connecting end 801 and a gases supply conduit connecting at 802. As shown, the main body has a curved surface profile that corresponds with the surface profile of the seal housing 804 about the periphery of the aperture 806 into which the conduit frame connects. In particular, the conduit frame has a surface profile that co-operates with the surface profile of the seal housing to provide a blended or continuous surface at the interface between the two components when assembled together.

The first form conduit frame 800 provides a pair of scalloped grip regions on the lateral sides of the main body toward the conduit connecting end 802 as indicated at 808 (only one visible). The seal housing connecting end 801 is provided with protrusions as indicated at 810 on the upper and lower surface for snap fit engagement with complementary recess or grooves 812 provided in the surfaces of the aperture of the seal housing 804 similar to the configuration described with respect of the fourth embodiment.

With reference to FIG. 188, the main body of the conduit frame 800 is configured to provide an approximately 30° decline angle as indicated at 814 relative to the horizontal. In particular, the axis at the conduit end at 802 is angled or offset relative to the axis of the aperture at the seal housing connecting end 801. It will be appreciated that the angle may be varied.

Second Form Conduit Frame Configuration of the Tenth Embodiment

With reference to FIGS. 190-193, the second form conduit frame 820 of the tenth embodiment will be described. In this embodiment, the conduit connecting end 821 of the conduit frame 820 is again provided with scalloped grip regions or portions 822.

The seal housing connecting end indicated at 823 is larger and comprises winged portions that overlap with portions of the external surface of the seal housing 824 adjacent the air inlet conduit protrusion 825 of the seal housing.

As shown in FIG. 191, the conduit frame comprises a complementary conduit portion having one or more protrusions or grooves 826 that complement for snap fit or interference engagement with complementary protrusions or grooves 827 provided on the conduit protrusion 825 of the seal housing 824.

As shown in FIG. 192, the winged lateral portions of the conduit frame at the seal housing connecting end 823 may comprise apertures 828. These apertures may provide a surface for diffuser mats to provide a bias vent if the seal housing is provided with aligned complementary apertures.

Third Form Conduit Frame Configuration of the Tenth Embodiment

With reference to FIGS. 194-197, a third form conduit frame 830 will be described. The third form conduit frame 830 is substantially similar to the second form conduit frame 820. The main difference is that the seal housing 835 is provided with a larger inlet aperture opening 833 that entirely receives the winged regions 832 of the conduit frame to provide a blended surface. In other words, there is no overlap with the winged region of the conduit frame onto the external surface of the seal housing like in the second form configuration.

As shown in FIGS. 194-197, the lateral edges of the winged regions of the conduit frame may be provided with protrusions or grooves 832 that are configured to snap fit or otherwise engage with complementary grooves or protrusions 833 provided within the inner peripheral surfaces of the aperture 831 of the seal housing 835.

Fourth Form Conduit Frame Configuration of the Tenth Embodiment

With reference to FIGS. 198-201, a fourth form conduit frame 840 will be described. The fourth form conduit frame 840 is provided with a conduit at the seal housing connecting end as indicated at 843 that is received within a complementary conduit 844 of the seal housing 842. The conduit portion 843 of the conduit frame comprises either protrusions or grooves 845 on the upper and/or lower surfaces or other surfaces that engage with complementary aligned protrusions or grooves 846 via the internal surface of the conduit aperture 844 of the seal housing 842.

Referring to FIG. 201, surrounding the lateral portions of the conduit portion 843 are winged regions 847 that extend from the lateral sides of the conduit frame on either side of the conduit portion 843. These winged regions or portions 847 are received within complementary recessed regions 848 provided on the lateral sides of the inlet of the seal housing 842. The external surface profile of the winged regions 846 and main body generally of the conduit frame at the seal housing connecting end is configured to marry or blend in with the surface profile of the seal housing in the regions surrounding the inlet aperture such that there is a seamless or blended surface at the interface of the two components when assembled together as shown in FIG. 198.

Opposite to the seal housing connecting end of the conduit frame is provided gripping tabs or protrusions 849 that extend laterally from the sides of the conduit frame at the gases supply conduit connecting end 850 of the conduit frame. These gripping tabs 849 allow the user to pull the conduit frame from the seal housing when desired. They also may assist in inserting the conduit frame into the seal housing during assembly.

Fifth Form Conduit Frame Configuration of the Tenth Embodiment

Referring to FIGS. 202-205, a fifth form conduit frame 850 of the tenth embodiment will be described.

The fifth form conduit frame 850 is similar to the fourth form conduit frame 840. The main differences are that the gripping tabs are replaced with a series or rows of gripping protrusions as indicated at 852 at the gases supply conduit connecting end the conduit frame 850. The winged regions 853 and conduit portion 855 at the seal housing connecting end is symmetrical relative to a horizontal plane extending through axis 856 indicated at FIG. 204.

The fifth form conduit frame 850 has an angular offset between the seal housing connecting end 858 and the gases supply conduit supply connecting end 859. In this embodiment, the axis extending from the conduit connecting end 859 is offset at a declined angle of approximately 40° relative to the axis extending from the seal housing connecting end 858, although this angle may be altered as appreciated.

With the symmetrical seal housing arrangement, the conduit frame 850 may be connected into the seal housing 862 in either of two orientations that are rotated 180° relative to each other. Additionally, the angled offset at the conduit connecting end 859 enables the conduit frame to be assembled into the seal housing 862 in a first orientation in which the conduit connecting end 859 is angled downwardly to allow the conduit to face or extend toward the user's feet, or an alternative may be installed in a second orientation such that the conduit connecting end 856 is angled upwardly such that the conduit can extend upwardly in the direction of the user's forehead.

Further Alternative Embodiments

The following describes various alternative embodiments or configurations of the interface. It will be appreciated that any one or more of these embodiments or configurations either alone or in combination may be applied to the general embodiments described above.

Full Face Embodiment

The embodiments described above with reference to FIGS. 2A-205 relate to nasal seal interfaces that are configured to seal about the nose of a user. However, it will be appreciated that such embodiments may also be adapted into full face or oronasal masks that are configured to seal about both the nose and mouth of a user such that therapy gases can be delivered to the user's airways via the nose and mouth. By way of example only, FIG. 206 shows an eleventh embodiment in the form of a full face interface 102E. The full face seal 102E is similar to that described in the third embodiment 102D of FIGS. 30-34 and comprises a single band under-nose support 124D configuration. The full-face seal 102E is substantially similar in configuration although has a larger contacting surface 120E. The enlarged contacting surface 120E is configured to seal about the users nose and mouth, i.e. is shaped to circumscribe about both the nose and mouth. The upper region 125 at or toward the nasal bridge region is substantially similar to that previously described, but the side cheek regions 123 extend further downwardly and are connected by a lower region 121E that is configured to seal below the users mouth, such as proximal to their chin. With this larger contacting surface, both the user's nose and mouth can be encapsulated within the seal 102E.

Under-Nose Support Formed of Different Material to the Seal

In the above embodiments described with reference to FIGS. 2A-205, the under-nose support is typically integrally formed and an integral part of the nasal seal. For example, the nasal seal and its under-nose support are integrally molded as a single unit from silicone or other suitable material. Alternatively, the nasal seal and under-nose support are molded as separate parts initially then permanently coupled or connected together, such as by adhesive or welding or similar, to form an unitary nasal seal component.

In alternative embodiments, the under-nose support may be formed of a material that is different to the nasal seal. For example, the nasal seal may be formed of silicone, but the under-nose support may be formed of a different material such as, but not limited to, a textile material, foam material, neoprene, Breath-o-Prene® material, thermoplastic polyurethane (TPU). The under-nose support can then be permanently coupled or connected into the nasal seal, such as by adhesive or welding or similar, to form a unitary nasal seal component.

Non-Fixedly Connected Under-Nose Support and Other Connection Configurations

In the above embodiments described with reference to FIGS. 2A-205, the under-nose support is typically fixedly connected within the nasal seal, such as being integrally formed or otherwise permanently connected into the nasal seal. In alternative embodiments, the under-nose support may be removably or releasably connected into the nasal seal by a releasable connection assemblies at the connection points or locations of the nasal seal previously described.

In further alternative configurations, the under-nose support may be fixedly or releasably connected or coupled to non-seal structures or components of the interface. For example, the under-nose support may be fixedly or releasably connected to the seal housing or rigid clip components or frame components, depending on the configuration. As previously mentioned, the under-nose support may be formed of any suitable material including, but not limited to, silicone, textile, foam material, neoprene, Breath-o-Prene® material, or TPU.

The foregoing description of the invention includes preferred forms thereof. Modifications may be made thereto without departing from the scope of the invention as described by the accompanying claims.

The invention claimed is:

1. A nasal mask interface assembly comprising:
    a seal housing;
    a flexible nasal seal connected or connectable to the seal housing to define a mask cavity, the nasal seal extending between a face-contacting side and an outer side, and comprising:
    a contacting surface comprising an edge that defines a nose-receiving opening into the mask cavity and which is configured to seal about the user's nose; and
    an under-nose support comprising an elongate main lateral portion non-removably connected to and suspended between opposing sidewall portions of the nasal seal such that it extends laterally within the mask cavity and the main lateral portion of the under-nose support having a contact surface that is oriented to contact at least a portion of the under-nose surface of the user, wherein the under-nose support comprises one or more extension or connecting portions that extend from the main lateral portion toward and connect to the nasal seal at an upper lip region of the nasal seal.

2. A nasal mask interface assembly according to claim 1, wherein the contacting surface seals about the user's nose including across a portion of the nasal bridge in an area extending between the tip of the user's nose and the center of their nasal bridge.

3. A nasal mask interface assembly according to claim 1, wherein connecting locations at opposing sidewall portions within the nasal seal are isolated or displaced from the edge of the contacting surface of the nasal seal.

4. A nasal mask interface assembly according to claim 1, wherein connecting locations at opposing sidewall portions within the nasal seal are displaced from the contacting surface of the nasal seal.

5. A nasal mask interface assembly according to claim 1, wherein the under-nose support comprises one or more extension or connecting portions that extend from within the mask cavity and connect to the edge of the contacting surface of the nasal seal in an upper lip region of the nasal seal.

6. A nasal mask interface assembly according to claim 1, wherein the under-nose support further comprises a central connecting portion that extends between the main lateral portion and a portion of the edge of the contacting surface in an upper lip region of the nasal seal.

7. A nasal mask interface assembly according to claim 6, wherein the central connecting portion of the under-nose support has a contacting surface that is primarily configured to contact with at least a portion of the columella of the nasal septum of the under-nose surface of the nose of a user.

8. A nasal mask interface assembly according to claim 6, wherein the central connecting portion of the under-nose support varies in thickness across its length from a thicker region at the end connecting to the main lateral portion and a thinner region at or toward the end connecting to the edge of the contacting surface.

9. A nasal mask interface assembly according to claim 6, wherein the central connecting portion of the under-nose support comprises a central region of reduced width relative to the width at its ends.

10. A nasal mask interface assembly according to claim 9, wherein the width of the central connecting portion progressively varies along its length such that it is substantially hour-glass in shape or profile.

11. A nasal mask interface assembly according to claim 1, wherein the main lateral portion of the under-nose support is integrally or fixedly connected at each end indirectly to inner surfaces of the nasal seal via a respective rib that extends from the inner surfaces of the nasal seal.

12. A nasal mask interface assembly according to claim 11, wherein each rib comprises a panel of flexible material having a first connecting edge portion that is connected to a portion of the inner surface of the nasal seal and a second connecting edge portion that is connected to a respective end of the main lateral portion of the under-nose support at another portion of its peripheral edge.

13. A nasal mask interface assembly according to claim 1, wherein the ratio of the overall height to overall depth of the seal housing and nasal seal when assembled together is in the range of approximately 1:0.8 to approximately 1:1.2.

14. A nasal mask interface assembly according to claim 1, wherein the ratio of the overall height to overall depth to overall lateral width of the seal housing and nasal seal when assembled together is in the range of approximately 1:0.8:1 to approximately 1:1.2:1.4.

15. A nasal mask interface assembly according to claim 1, further comprising:
    a yoke connected or connectable to the seal housing,
    headgear connected or connectable to the yoke, and
    an inlet opening in the seal housing for connecting to a gases supply conduit.

16. A nasal mask interface assembly according to claim 15, wherein the seal housing comprises a yoke channel extending lateral across the exterior surface of the seal housing that is configured to releasably receive and retain the yoke.

17. A nasal mask interface assembly according to claim 16, wherein the yoke is curved along its length between its ends, having a concave inner engagement surface with the yoke channel and a convex outer surface.

18. A nasal mask interface according to claim 15, further comprising a conduit frame that is releasably received and retained in the inlet opening of the seal housing, the conduit frame being connected or connectable to an end of the gases supply conduit.

19. A nasal mask interface according to claim 18, wherein the conduit frame is a hollow body that is ovular in shape, and wherein the conduit frame is symmetrical such that it can be releasably received and retained in the inlet opening of the seal housing in either of two orientations that are 180 degrees apart.

20. A nasal mask interface assembly according to claim 1, wherein at any location along the under-nose support, the under-nose support is substantially thinner in the transverse direction relative to its contact surface than the corresponding width of the contact surface at that location.

21. A nasal seal for a nasal mask or interface, the seal formed of a flexible material and extending between a face-contacting side and an outer side, comprising:
    a contacting surface comprising an edge that defines a nose-receiving opening and which is configured to seal about the user's nose; and an under-nose support comprising an elongate main lateral portion non-removably connected to and suspended between opposing sidewall portions of the nasal seal such that it extends laterally within a cavity of the nasal seal, wherein the under-nose support is located rearward of the nose-receiving opening and has a contact surface that is oriented to contact at least a portion of the under-nose surface of the user, wherein the under-nose support comprises one or more extension or connecting portions that extend from the main lateral portion toward and connect to the nasal seal at an upper lip region of the nasal seal.

22. A nasal mask interface assembly comprising:

a seal housing;

a flexible nasal seal connected or connectable to the seal housing to define a mask cavity, the nasal seal extending between a face-contacting side and an outer side, and comprising:

a contacting surface comprising an edge that defines a nose-receiving opening into the mask cavity and which is configured to seal about the user's nose; and an under-nose support comprising an elongate main lateral portion non-removably connected to and suspended between opposing sidewall portions of the nasal seal such that it extends laterally within the mask cavity, the main lateral portion of the under-nose support having a contact surface that is oriented to contact at least a portion of the under-nose surface of the user, wherein the under-nose support comprises one or more extension or connecting portions that extend from the main lateral portion toward and connect to the nasal seal at an upper lip region of the nasal seal, and headgear comprising single left and right side straps configured to extend over the user's ears and which connect to the seal housing.

23. A nasal mask interface assembly according to claim 22, wherein the left and right side straps connect to respective attachment locations at or toward respective sides of the seal housing.

24. A nasal seal for a nasal mask or interface, the seal formed of a flexible material and extending between a face-contacting side and an outer side, comprising:

a contacting surface comprising an edge that defines a nose-receiving opening and which is configured to seal about the user's nose; and an under-nose support comprising an elongate main lateral portion non-removably connected to and suspended between opposing sidewall portions of the nasal seal, wherein the under-nose support comprises one or more extension or connecting portions that extend from within the mask cavity and connect to the edge of the contacting surface of the nasal seal in an upper lip region of the nasal seal.

25. A nasal seal according to claim 24, wherein the contact surface of at least a central portion of the under-nose support is oriented at an angle relative to a seal axis that extends tangentially between outermost upper and lower contact points in a central region of the contacting surface of the nasal seal.

26. A nasal seal according to claim 25, wherein the contact surface of the central portion of the under-nose support is oriented at an angle in the range of approximately 40° to approximately 80° relative to the seal axis.

27. A nasal seal according to claim 24, wherein the nasal seal is defined by the contact surface at the face-contacting side and a sidewall portion that extends rearwardly from the contact surface to the outer side of the nasal seal and which terminates in an opening or connecting edge for coupling or connected to a complimentary seal housing.

* * * * *